US005127936A

United States Patent [19]

Selby

[11] Patent Number: 5,127,936

[45] Date of Patent: Jul. 7, 1992

[54] SUBSTITUTED PHENYLTRIAZOLOPYRIMIDINE HERBICIDES

[75] Inventor: Thomas P. Selby, Wilmington, Del.

[73] Assignee: E. I. Du Pont de Nemours and Company, Wilmington, Del.

[21] Appl. No.: 635,525

[22] Filed: Jan. 8, 1991

Related U.S. Application Data

[63] Continuation-in-part of Ser. No. 335,121, Apr. 7, 1989, abandoned, which is a continuation-in-part of Ser. No. 221,155, Jul. 19, 1988, abandoned.

[51] Int. Cl.$^5$ .................... A01N 43/54; C07D 487/02

[52] U.S. Cl. ........................................ 71/92; 544/236; 544/263; 544/281; 544/350

[58] Field of Search ............................ 544/263; 71/92

[56] References Cited

U.S. PATENT DOCUMENTS

| | | | |
|---|---|---|---|
| 4,036,233 | 7/1977 | O'Brien | 544/263 |
| 4,209,621 | 6/1980 | Dusza | 544/263 |
| 4,740,233 | 4/1986 | Kleschick et al. | 544/263 |
| 4,981,507 | 1/1991 | Jelich et al. | 544/263 |
| 5,041,157 | 8/1991 | Seiler et al. | 544/263 |

FOREIGN PATENT DOCUMENTS

| | | | |
|---|---|---|---|
| 0375076 | 6/1990 | European Pat. Off. | 544/263 |
| 90-01030 | 2/1990 | World Int. Prop. O. | |

OTHER PUBLICATIONS

Maekawa et al. Chem. Abstr. vol. 87, entry 17148y (1977).

Okabe et al. Chem. Abstr. Vol. 83 entry 127285r (1975).

*Primary Examiner*—Donald G. Daus

*Attorney, Agent, or Firm*—Susan B. Evans

[57] ABSTRACT

Novel substituted phenyltriazolopyrimidines and their preparation and method-of-use as preemergence and postemergence herbicides.

10 Claims, No Drawings

SUBSTITUTED PHENYLTRIAZOLOPYRIMIDINE HERBICIDES

RELATED APPLICATION

This application is a continuation-in-part of my co-pending application U.S. Ser. No. 07/335,121 filed Apr. 7, 1989, now abandoned which is a continuation-in-part of U.S. Ser. No. 07/221,155, filed Jul. 19, 1988 now abandoned.

BACKGROUND OF THE INVENTION

U.S. Pat. No. 4,209,621, issued Jun. 24, 1980, discloses substituted phenyl-1,2,4-triazolo[1,5-a]pyrimidines of the formula

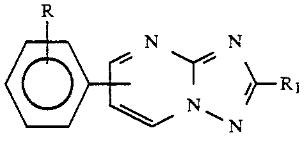

wherein $R_1$ is H or alkyl as anxiolytic agents.

French Patent 1,433,798, published Feb. 21, 1966, (U.S. priority May 1, 1964), discloses 7-hydroxy-5-methyl-1,2,4-triazolo[1,5-a]pyrimidine as a herbicide.

EP-A-220,458, published May 6, 1987 (German priority Sep. 28, 1985) and EP-A-217,218, published Apr. 8, 1987 (German priority. Sep. 28, 1985), disclose herbicidal triazolopyrimidines of the formula

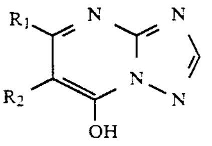

EP-A-215,382, published Mar. 25, 1987 (German priority Sep. 17, 1985), discloses herbicidal 7-aminoazolo[1,5-a]pyrimidines of the formula

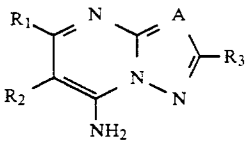

wherein

A is N, CH, C(alkyl) CBr or CCl.

U.S. Pat. No. 4,740,233, issued Apr. 26, 1988, discloses herbicidal triazolopyrimidines of the formula

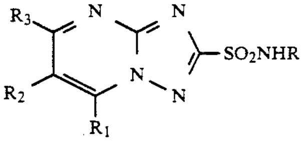

wherein $R_1$ includes phenyl and substituted phenyl.

J. Fac. Agric. Kyushu Univ. 1977, 21 (2-3), 99-105 discloses herbicidal triazolopyrimidines of the formula

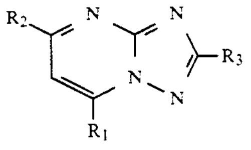

wherein $R_1$ is H, SCN, $SCH_3$, Ph or $CH_3$;

$R_2$ is H or CH3; and $R_3$ is SH, $SCH_2Ph$ or $SCH_2CO_2H$.

J. Fac. Agric. Kyushu Univ. 1975, 19(2-3), 91-102 discloses s-triazolo[1,5-a]pyrimidines with herbicidal activity.

The present invention is patentably distinguishable over the foregoing at least in the substitution on the azole and/or the pyrimidine functionality.

SUMMARY OF THE INVENTION

This invention comprises compounds of Formula I, agriculturally suitable compositions containing them, and their method-of-use as preemergence and/or post-emergence herbicides

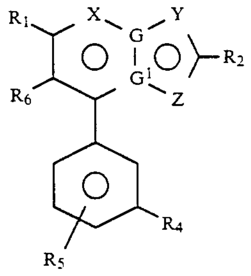

I wherein

G and $G^1$ are N or C;

$R_1$ is $C_1$-$C_4$ alkyl, $C_1$-$C_4$ haloalkyl, $C_2$-$C_4$ alkoxyalkyl, $C_2$-$C_4$ alkenyl, $C_2$-$C_4$ alkynyl, $C_1$-$C_4$ alkoxy, $C_1$-$C_4$ alkylthio, halogen, CN, $C_2$-$C_4$ alkylcarbonyl, $C_1$-$C_4$ alkylamino, $C_2$-$C_4$ dialkylamino or $C_2$-$C_4$ alkylthioalkyl;

$R_2$ is halogen, $NO_2$, $OR_3$, $S(O)_nR_3$, $OSO_2R_3$, $C_1$-$C_4$ haloalkyl, $C_3$-$C_4$ halocycloalkyl, $C_3$-$C_4$ haloalkynyl or $C_2$-$C_4$ haloalkenyl;

$R_3$ is $C_1$-$C_4$ alkyl, $C_1$-$C_4$ haloalkyl, $C_2$-$C_4$ alkenyl, $C_2$-$C_4$ haloalkenyl, $C_3$-$C_4$ alkynyl, $C_3$-$C_4$ haloalkynyl, or $C_3$-$C_4$ halocycloalkyl:

$R_4$ is H, halogen, $C_1$-$C_3$ alkoxy, $C_1$-$C_3$ alkyl or $CF_3$;

$R_5$ is H, halogen, $C_1$-$C_4$ alkyl, $C_1$-$C_4$ haloalkyl, $C_2$-$C_4$ alkoxyalkyl, $C_2$-$C_4$ alkenyl, $C_2$-$C_4$ alkynyl, $NO_2$, $OR_3$, $S(O)nR_3$, $OSO_2R_3$, phenyl, phenoxy, $C_2$-$C_4$ alkoxycarbonyl, $C_2$-$C_4$ alkylcarbonyl, CN, $NHSO_2CF_3$, $C_2$-$C_4$ haloalkenyl, $C_3$-$C_4$ haloalkynyl, $C_2$-$C_4$ dialkylamino, or $C_3$-$C_4$ halocycloalkyl;

n is 0, 1 or 2;

$R_6$ is H or F;

X, Y and Z are independently $CR_7$ or N; and $R_7$ is H, CN, halogen, $NO_2$, $CO_2R_3$, $C_1$-$C_3$ alkyl, $C_1$-$C_3$ haloalkyl or $CONH_2$;

provided that (a) G and $G^1$ are not the same, (b) $R_1$ is not CN when X is N and (c) only one of X, Y, Z can be $CR_7$.

In the above definitions, the term "alkyl," used either alone or in compound words such as "alkylthio" denotes straight chain or branched alkyl, e.g., methyl, ethyl, n-propyl, isopropyl or the different butyl isomers.

Alkoxy denotes methoxy, ethoxy, n-propoxy, isopropoxy and the different butoxy isomers.

Alkenyl denotes straight chain or branched alkenes, e.g., vinyl, 1-propenyl, 2-propenyl, 3-propenyl and the different butenyl isomers.

Alkynyl denotes straight chain or branched alkynes, e.g., ethynyl, 1-propynyl, 2-propynyl and the different butynyl isomers.

The term "halogen," denotes fluorine, chlorine, bromine or iodine.

The term haloalkyl or halocycloalkyl denotes mono to per-halogentaed alkyl isomers e.g. 1-fluroethyl, 1,1,2,2,2 pentafluro ethane, 2.2-diflurocyclopropane.

The total number of carbon atoms in a substitutent group is indicated by the $C_i$–$C_j$ prefix where i and j are numbers from 1 to 4. For example $C_3$–$C_4$ alkenyl would designate propenyl through butenyl.

Preferred Compounds

Preferred for reasons of increased ease of synthesis and/or greater herbicidal efficacy are:

1. Compound of Formula I wherein
   G is CH and $G^1$ is N (Formula Ia); or
   G is N and $G^1$ is CH (Formula Ib).

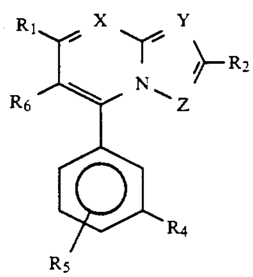

Ia

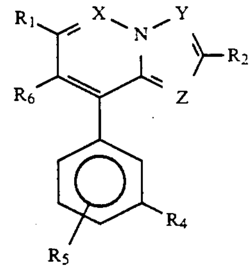

Ib

2. Compounds of Preferred 1 wherein
   Formula I is Ia;
   X is $CR_7$;
   Y is N; and
   Z is N.
3. Compounds of Preferred 1 wherein
   Formula I is Ib;
   X is $CR_7$;
   Y is N; and
   Z is N.
4. Compounds of Preferred 1 wherein
   Formula I is Ia;
   X is N;
   Y is $CR_7$; and
   Z is N.
5. Compounds of Preferred 1 wherein
   Formula I is Ib;
   X is N;
   Y is $CR_7$; and
   Z is N.
6. Compounds of Preferred 1 wherein
   Formula I is Ia;
   X is N;
   Y is N; and
   Z is $CR_7$.
7. Compounds of Preferred 1 wherein
   Formula I is Ib;
   X is N;
   Y is N; and
   Z is $CR_7$.
8. Compounds of Preferred 1 wherein
   Formula I is Ia;
   X is N;
   Y is N; and
   Z is N.
9 Compounds of Preferred 1 wherein
   Formula I is Ib;
   X is N;
   Y is N; and
   Z is N.
10. Compounds of Preferred 8 wherein
   $R_6$ is H; and
   $R_1$ is $C_1$–$C_3$ alkyl, $SCH_3$, $NHCH_3$, $CHO_2CH_3$ or $CH_2SCH_3$.
11. Compounds of Preferred 10 wherein
   $R_2$ is $CF_3$, $SCF_3$, $SCF_2H$, $OCF_3$, $OCH_2CHF_2$, $OCH_2CF_3$, $OCF_2H$, $CF_2CF_3$, $CF_2Cl$, $CHF_2$, $CH{=}CF_2$ or 2,2-difluorocyclopropane.
12. Compounds of Preferred 11 wherein
   $R_3$ is $CH_2CH_2F$, $CH_2CF_3$, $CH(CH_3)CF_3$, $CH_2CH_2CF_3$, $CH_2CHF_2$, $CF_3$ or $CF_2H$; and
   $R_4$ is H.
13. Compounds of Preferred 12 wherein
   $R_5$ is H, halogen, $OCH_3$, $OCF_2H$, $OCH_2CF_3$, $SCF_3$, $C_1$–$C_3$ alkyl, $OCF_3$, $OCH_2CHF_2$, $OCH_2CF_3$, $OCH_2CH_2F$, $SCHF_2$, $CF_3$, $CHF_2$, $CF_2Cl$, $CH_2CF_3$, $CH_2F$, $CCl_3$, $CH_2Cl$ or CN and $R_5$ is in the meta position.
14. Compounds of Preferred 13 wherein
   $R_1$ is $C_1$–$C_3$ alkyl.
5. Compounds of Preferred 9 wherein
   $R_1$ is $C_1$–$C_3$ alkyl;
   $R_2$ is $CF_3$, $SCF_3$, $SCF_2H$, $OCF_3$, $OCH_2CHF_2$, $OCH_2CF_3$, $OCF_2H$, $CF_2CF_3$, $CH_2Cl$, $CHF_2$, $CH{=}CF_2$ or 2,2-diflurocyclopropane;
   $R_3$ is $CH_2CH_2F$, $CH_2CF_3$, $CH(CH_3)CF_3$, $CH_2CH_2CF_3$, $CH_2CHF_2$, $CF_3$ or $CF_2H$;
   $R_4$ is H;
   $R_5$ is H, halogen, $OCH_3$, $OCF_2H$, $OCH_2CF_3$, $SCF_3$, $C_1$–$C_3$ alkyl, $OCF_3$, $OCH_2CHF_2$, $OCH_2CH_2F$, $SCHF_2$, $CF_3$, $CHF_2$, $CF_2Cl$, $CH_2CF_3$, $CH_2F$, $CCl_3$, $CH_2Cl$ or CN and $R_5$ is in the meta position; and
   $R_6$ is H.
6. Compounds of Preferred 4 wherein
   $R_1$ is $C_1$–$C_3$ alkyl;
   $R_2$ is $CF_3$, $SCF_3$, $SCF_2H$, $OCF_3$, $OCH_2CHF_2$, $OCH_2CF_3$, $OCF_2H$, $CF_2CF_3$, $CH_2Cl$, $CHF_2$, $CH{=}CF_2$ or 2.2-diflurocyclopropane;
   $R_3$ is $CH_2CH_2F$, $CH_2CF_3$, $CH(CH_3)CF_3$, $CH_2CH_2CF_3$, $CH_2CHF_2$, $CF_3$ or $CF_2H$;
   $R_4$ is H;
   $R_5$ is H, halogen, $OCH_3$, $OCF_2H$, $OCH_2CF_3$, $SCF_3$, $C_1$–$C_3$ alkyl, $OCF_3$, $OCH_2CHF_2$, $OCH_2CH_2F$, $SCHF_2$, $CF_3$, $CHF_2$, $CF_2Cl$, $CH_2CF_3$, $CH_2F$, $CCl_3$, $CH_2Cl$ or CN and $R_5$ is in the meta position;

$R_6$ is H; and
$R_7$ is CN.

17. Compounds of Preferred 5 wherein
$R_1$ is $C_1$–$C_3$ alkyl;
$R_2$ is $CF_3$, $SCF_3$, $SCF_2H$, $OCF_3$, $OCH_2CHF_2$, $OCH_2CF_3$, $OCF_2H$, $CF_2CF_3$, $CH_2Cl$, $CHF_2$, $CH{=}CF_2$ or 2,2-diflurocyclopropane;
$R_3$ is $CH_2CH_2F$, $CH_2CF_3$, $CH(CH_3)CF_3$, $CH_2CH_2CF_3$, $CH_2CHF_2$, $CF_3$ or $CF_2H$;
$R_4$ is H;
$R_5$ is H, halogen, $OCH_3$, $OCF_2H$, $OCH_2CF_3$, $SCF_3$, $C_1$–$C_3$ alkyl, $OCF_3$, $OCH_2CHF_2$, $OCH_2CH_2F$, $SCHF_2$, $CF_3$, $CHF_2$, $CF_2Cl$, $CH_2CF_3$, $CH_2F$, $CCl_3$, $CH_2Cl$ or CN and $R_5$ is in the meta position;
$R_6$ is H; and
$R_7$ is CN.

Specifically Preferred for reasons of greatest ease of synthesis and/or greatest herbicidal efficacy are:
5-methyl-2-(trifluoromethyl)-7-[3-(trifluoromethyl)-phenyl][1,2,4]triazolo[1,5-a]pyrimidine;
7-(3-chlorophenyl)-5-methyl-2-(trifluoromethyl)[1,2,4]-triazolo[1,5-a]pyrimidine;
5-methyl-2-(trifluoromethyl)-7-[3-(trifluoromethyl)-phenyl]-pyrazolo[1,5-a]pyrimidine-3-carbonitrile;
5-methyl-2-(2,2,2-trifluoroethoxy)-7-[3-(trifluoromethyl)-phenyl][1,2,4]triazolo[1,5-a]-pyrimidine;
2-(difluoromethoxy)-5-methyl-7-[3-(trifluoromethyl)-phenyl][1,2,4]triazolo[1,5-a]pyrimidine.

DETAILED DESCRIPTION OF THE INVENTION

Synthesis

Compounds of general Formula I can be prepared using one or more of the reactions and techniques described in Schemes 1–8 of this section as well as by following the specific procedures given in Examples 1–15.

Scheme-1 illustrates the reaction of aminoheterocycles of Formula II with an appropriately substituted diketone of Formula III to afford desired compounds of Formula Ia where $R_1$ is alkyl, alkenyl, alkoxyalkyl, alkyl substituted by halogen and $R_2$, $R_4$, $R_5$ and $R_6$ are defined as above. This reaction is carried out by heating the reactants neat or in an inert polar protic or aprotic solvent at temperatures between 50° and 130° C. Suitable solvents are glacial acetic acid, ethanol, methanol, dimethylformamide, and dimethylsulfoxide. Aminoheterocycles of Formula II can be prepared by synthetic methods reviewed in "The Chemistry of Heterocyclic Compounds" Volumes 6 (1953), 22 (1967), and 37 (1981), John Wiley & Sons. Beta-diketones of Formula III can be synthesized by standard Claisen acylation procedures such as those taught by C. R. Hauser et. al. in *Journal of American Chemical Society* 67. pg. 284 (1945), 68, pg. 2742 (1946), 69 pg. 2649 (1947) and 70 pg. 4023 (1948).

Scheme-1

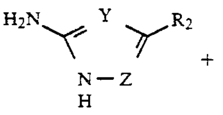

II

-continued

Scheme-1

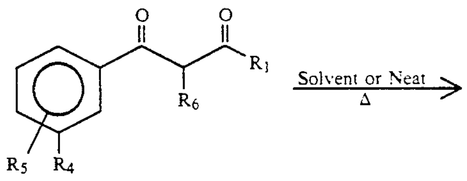

III

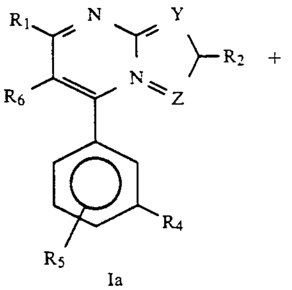

Ia

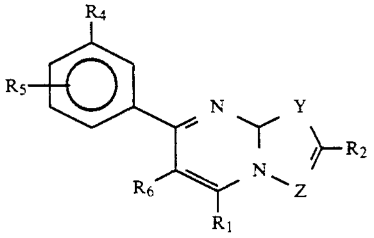

Ia'

A minor regio isomer Ia' can also be formed in the reaction shown in Scheme-1. Compounds of Formula Ia are isolated pure, however, after aqueous workup, trituration, and subsequent purification by recrystallization or silica gel column chromatography. Silica gel column chromatography can also be used to isolate products of Formula Ia directly from the crude reaction residue obtained after reaction work up. Scheme-2 illustrates the preparation of compounds of Formula Ia (where $R_1$ is hydrogen, alkylthio, or alkoxy and $R_2$, $R_4$, $R_5$ and $R_6$ are defined as above) by reaction of aminoheterocycles of Formula II with compounds of Formula IV where Q is a suitable leaving group such as dimethylamino, methylthio or methoxy. This reaction is carried out by heating reactants II and IV neat or in an inert polar protic or aprotic solvent such as glacial acetic acid, ethanol, methanol, dimethylformamide, or dimethylsufoxide at temperatures between 50° and 130° C. Compounds of Formula IV can readily be prepared by one skilled in the art by known methods.

Scheme-2

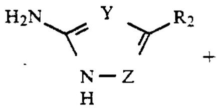

II

-continued

Scheme-2

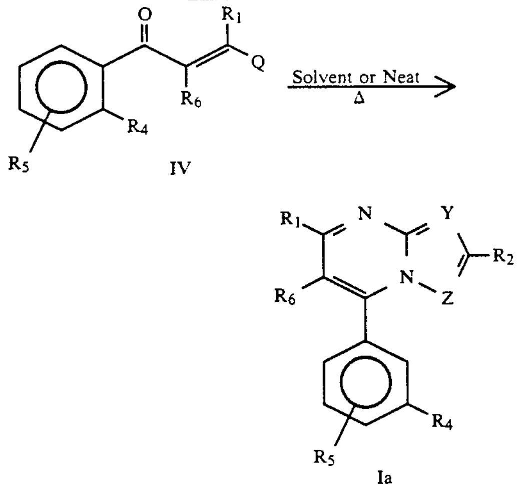

IV

Ia

Scheme-3 illustrates the diazotization of compounds of Formula V (Prepared by the method shown in Scheme-1 where $R_2=NH_2$) in an aqueous acid medium of Formula HL (where L is equal to halogen) to give compounds of Formula Ic where $R_2$ is halogen and G, G', X, Y, Z, $R_1$, $R_4$, $R_5$ and $R_6$ are defined as above. Acetic acid can be used as a solvent in this diazotization reaction to enhance the solubility of V in the acid medium. The diazotization is conducted intially at temperatures between 5° and 25° and subsequently heated at 30° to 100° C. or maintained throughout at room temperature.

Scheme-3

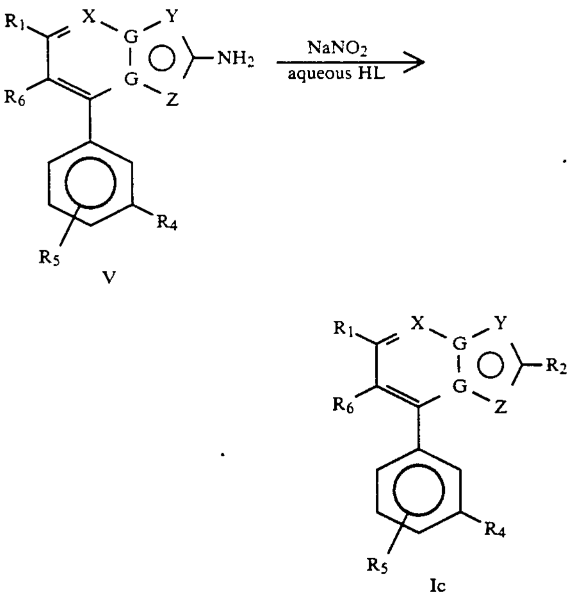

V

Ic

Scheme-4 illustrates the reaction of compounds of Formula VI (where K is O or S, G', X, Y, W, Z, $R_1$, $R_4$, $R_5$ and $R_6$ are defined as above) with an alkylating agent of formula $R_3$-Q' (where Q' is a suitable leaving group such as halogen and $R_3$ is defined as above) in a polar protic or aprotic solvent such as aqueous dioxane or dimethylformamide in the Presence of a base such as a metal carbonate, metal hydroxide or metal alkoxide (where the metal is sodium or potassium) at temperatures between 0° and 70° C. to give compounds of Formula Id. Compounds of Formula VI can be prepared by the method shown in Scheme-1 where $R_2$ equals mercapto or hydroxyl. Oxidation of compounds of Formula Id (K is S) with one equivalent of oxidizing agent such as 3-chloroperoxybenzoic acid, sodium periodate, or hydrogen peroxide in a suitable solvent such as methylene chloride (in the case when 3-chloroperoxybenzoic acid is used) at temperatures between 0° and 40° C. gives the corresponding sulfoxide derivatives of Formula Ie (where n is equal to one). Use of excess oxidizing agent under these same conditions gives the sulfone derivatives Ie (where n is equal to two). Substituents G, G', X, Y, Z, $R_1$, $R_4$, $R_5$ and $R_6$ on Id and Ie are as defined above.

Scheme-4

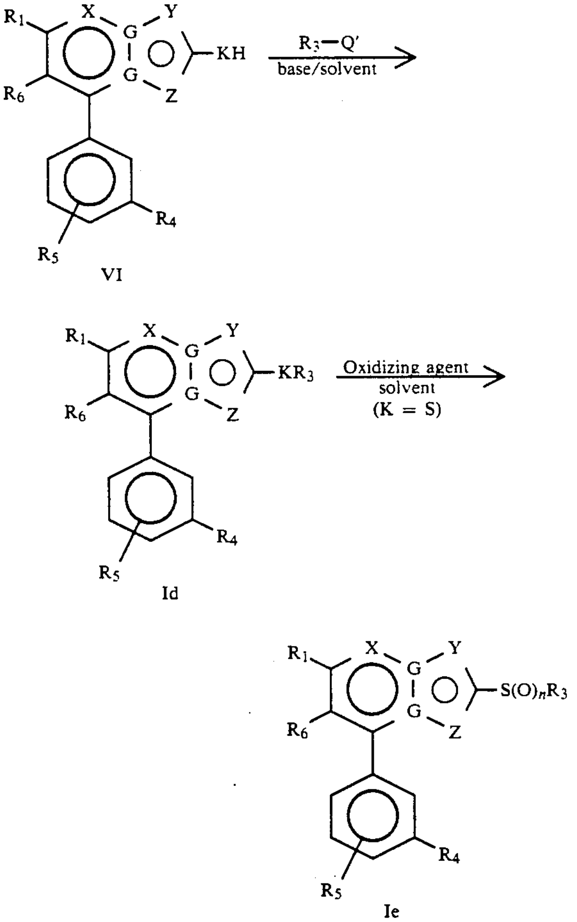

VI

Id

Ie n is 1 or 2

Scheme-5 illustrates the preparation of compounds of Formula If (where G, $G_1$, X, Y, Z, $R_1$, $R_4$, $R_5$ and $R_6$ are defined as above) by reaction of compounds of Formula Ic (where $R_2$=halogen) with metal alkoxides and metal haloalkoxides of formula $R_3O^-M^+$ (where M=Li, K, or Na and $R_3$ is defined as above) by heating in polar protic or aprotic solvents such as tetrahydrofuran or dimethylformamide at temperatures between 25° C. and 140° C.

Scheme-5

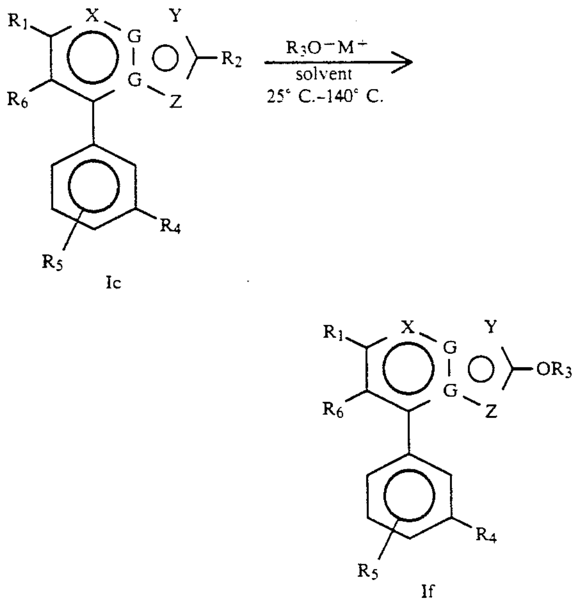

Ic

If

Scheme-6 illustrates the reaction of aminoheterocycles of Formula VII with an appropriately substituted ketone of Formula VIII (where Q' is a suitable leaving group such as halogen) to afford compounds of Formula Ig (where $R_2$ is alkyl or haloalkyl). The reaction is carried out by heating reactants VII and VIII neat or in an inert polar protic or aprotic solvent such as ethanol, methanol, dimethylformamide or dimethylsulfoxide at temperatures between 50° C. and 130° C. Aminoheterocycles of Formula VI where X=N can be prepared by methods such as that taught by H. G. O. Becker et al., *Tetrahedron,* 24, 2687 (1968).

Scheme-6

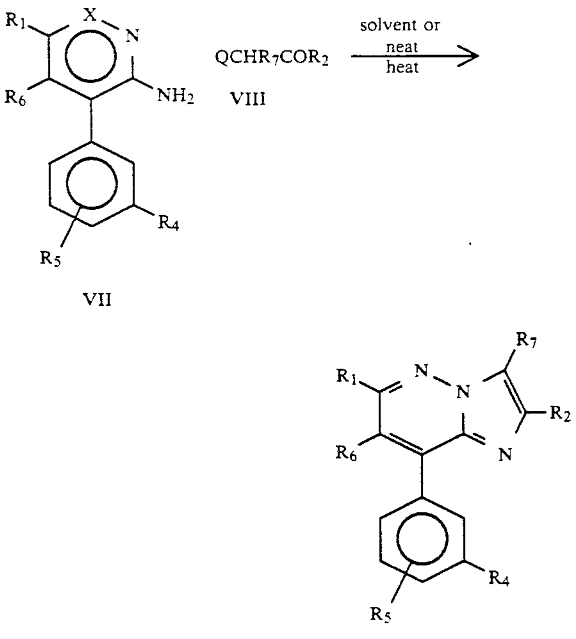

VII

Ig

Scheme-7 illustrates the preparation of compounds of Formula Ih by cyclization of compounds of Formula IX with an acid anhydride or an acid chloride (for $R_2$=haloalkyl) or an orthocarbonate (for $R_2=OR_3$) as taught by Y. Tamura et al., *J. Het. Chem,* 12, 107 (1975) and W. Kantlehner, *Synthesis,* 73 (1977).

Compounds of Formula IX can be prepared from compounds of Formula VII by reagents such as hydroxylamine-o-sulfonic acid, o-mesitylenesulfonyl hydroxylamine or o-diphenylphosphinylhydroxylamine as taught by K. T. Potts et al., *J. Org. Chem.* 31, 260 (1961) and Y. Tamura et al., *Tet. Lett.* 4133 (1972) and W. Klotzer et al., *Synthesis,* 592 (1982).

Compounds of Formula IX where $X=CR_7$ can be prepared by synthetic methods such as those reviewed in "The Chemistry of Heterocyclic Compounds", Volume 14, John Wiley and Sons, or known to one skilled in the art.

Scheme-7

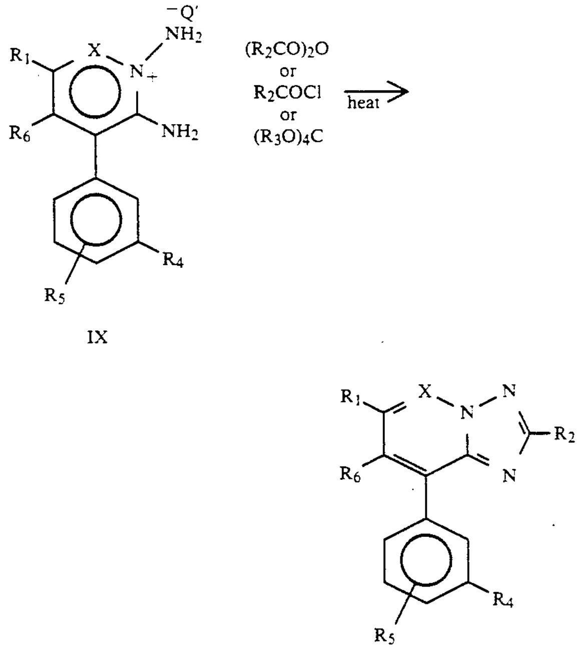

IX

Ih

Scheme-8 illustrates the preparation of compounds of Formula Ii from compounds of Formula X. The chemistry is analogous to that of Scheme-7.

Scheme-8

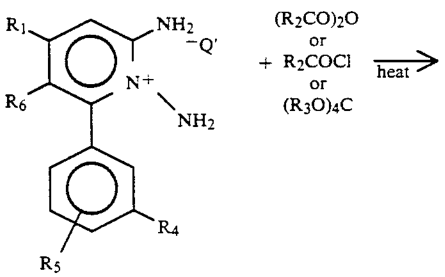

X

-continued

Scheme-8

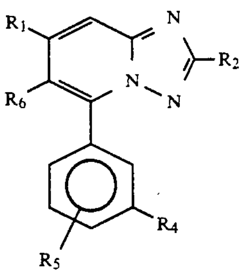

Ii

EXAMPLE 1

Preparation of 5-Methyl-7-phenyl-2-(trifluoromethyl)-1,2,4-triazolo[1,5-a]pyrimidine By the procedure reported by V. A. Lopyrev *Zh. Obshch. Khim.* 53 p. 1684, 1983 (*Chemical Abstracts* 139865y, 1983) a crude sample of 3-amino-5-trifluoromethyl-1,2,4-triazole was prepared by the cyclocondensation of aminoguanidine bicarbonate with trifluoroacetic acid in refluxing toluene. This material was used effectively without further purification in subsequent ring condensation reactions. To 30 ml. of glacial acetic acid stirring, 3.0 g (19.7 mmol) of 3-amino-5-trifluoromethyl-1,2,4-triazole and 3.5 g (21.6 mmol) of benzoylacetone were added and the mixture heated at reflux for 3 h. A solution soon formed after heating. The solvent was evaporated in vacuo and excess water added to the residue followed by extraction with 200 ml of ethyl acetate. The extract was washed with water, saturated sodium bicarbonate, brine, dried over magnesium sulfate and evaporated in vacuo to give an oily residue. Silica gel column chromatography (methylene chloride) afforded 3.09 g of the title compound which was present as the major component, m.p. 106°-108° C.

A minor regioisomer in which the phenyl and methyl groups on the desired product are reversed was also isolated (240 mg., m.p. 143°-144°) from the chromatography.

EXAMPLE 2

Preparation of 7-(3-Chlorophenyl)-5-methyl-2-(trifluoromethyl)-1,2,4-triazolo1,5-a]pyrimidine To 10.0 g (51.0 mmol) of 3'-chloroacetophenone stirring in 100 ml of tetrahydrofuran/100 ml of diethyl ether and 20 ml of ethyl acetate, 4.0 g of 50% sodium hydride oil dispersion was added portionwise with a certain amount of foaming. The reaction was stirred at ambient temperature overnight. Methanol (5.0 ml) was added followed by 150 ml of water and 150 ml of diethyl ether. The aqueous layer was separated and acidified with 10% HCl to pH ~2-3. The aqeuous mixture was re-extracted with 200 ml of diethyl ether, the ether extract was washed with water (2X), brine, dried over magnesium sulfate, and evaporated in vacuo to give 11.6 g of 3'-chlorobenzoylacetone isolated as an oil. This oil was used directly in the next step without further purification.

To 5.0 g (32.9 mmol) of 3-amino-5-trifluoromethyl-1,2,4-triazole and 7.0 g (36.0 mmol) 3'-chlorobenzoylacetone in a round bottom flask, 50 ml of glacial acetic acid was added and the reaction heated at reflux 3 h. The solvent was evaporated in vacuo to give a residue to which excess water and 200 ml of ethyl acetate was added. The organic layer was separated and washed with water, saturated sodium bicarbonate, brine, dried over magnesium sulfate, and evaporated in vacuo to give an oily residue to which a minimal amount of n-butylchloride was added. On standing, a solid precipitated which was filtered and washed with a small amount of n-butylchloride to give 2.2 g of the title compound. The filtrate was concentrated in vacuo to give an oil which was chromatographed on silica gel (methylene chloride followed by 3:1 ethyl acetate/methylene chloride) to afford another 2.42 g of the title compound, m.p. 115°-116° C.

The minor regio isomer formed in this reaction where the phenyl and methyl groups are reversed was also isolated from the chromatography in a yield of 690 mg (m.p. 126°-128° C.).

EXAMPLE 3

Preparation of 7-Phenyl-2-(trifluoromethyl)1,2,4-triazolo[1.-a]pyrimidine

A mixture of 3.0 ml of acetphenone and 4.0 ml of N,N-dimethylformamide dimethylacetal were heated neat at about 90° for 4 h. After cooling, 4.0 g (26.0 mmol) of 3-amino-5-trifluoromethyl-1,2,4-triazole and 70 ml of glacial acetic acid were added followed by heating at reflux 2 h. The reaction mixture was evaporated to dryness in vacuo and excess water and 200 ml of ethyl acetate added. The ethyl acetate layer was separated, washed with water (2X), saturated sodium bicarbonate, brine, dried over magnesium sulfate, and evaporated in vacuo to give an oil. Silica gel column chromotagraphy afforded 1.4 g of the title compound (m.p. 138°-142° C.). which was the major component present.

EXAMPLE 4

Preparation of 5-Methyl-2-(methylthio)-7phenyl-1,2,4-triazolo[1,5-a]pyrimidine

To 50 ml of stirring glacial acetic acid, 2.5 g (19.2 mmol) of 3-amino-5-methylthio-1,2,4-triazole and 3.1 g (19.1 mmol) of benzoylacetone was added followed by heating at reflux for 2 h. The solvent was evaporated in vacuo and excess water added to the residue followed by extraction with 200 ml of ethyl acetate. The extract was washed with water, saturated sodium bicarbonate, brine, dried over magnesium sulfate and evaporated in vacuo to give an oil. Addition of n-butyl chloride resulted in crystallization of a solid which was filtered and washed with n-butyl chloride to give 1.33 g of the pure title compound, m.p. 121°-123° C.

EXAMPLE 5

Preparation of 5-Methyl-2-(methylsulfonyl)-7-phenyl-1,2,4-triazolo[1,5-a]pyrimidine To 2.6 g (10.2 mmol) of 5-methyl-2-(methylthio)-7-phenyl-1,2,4-triazolo[1,5-a]pyrimidine stirring in 30 ml of methylene chloride, 4.7 g of 3-chloroperoxy benzoic acid was added portionwise. The mixture was then stirred at ambient temperature for 45 minutes. Methylene chloride (150 ml) was added and the solution washed with 10% sodium bisulfite, water, saturated sodium bicarbonate (2X), brine, dried over magnesium sulfate and evaporated in vacuo to give an oily foam. Addition of n-butyl chloride to the foam resulted in crystallization of a solid which was filtered and washed with the same solvent to give 1.4 g of the title compound, m.p. 158°–159° C.

EXAMPLE 6

Preparation of 2-Chloro-5-methyl-7-phenyl-1,2,4-triazolo[1,5-a]pyrimidine

A mixture of 14 g (141.4 mmol) of 3,5-diamino-1,2,4-triazole and 24.0 g (148.1 mmol) benzoylacetone was heated in 200 ml of glacial acetic acid at reflux for 2 hours. A solution soon formed after heating. The solvent was removed in vacuo and the residue dissolved in 400 ml of methylene chloride which was then washed with water (2X), brine and dried over magnesium sulfate. The solution was concentrated in vacuo (not to complete dryness) and ethyl acetate added to the residue. The precipitated solid was filtered and washed with ethyl acetate to give 16.0 g of reasonably pure intermediate 5-methyl-7-phenyl-1,2,4-triazolo[1,5-a]pyrimidin-2-amine which was able to be taken on directly to the next step without further purification m.p. 246°–250°.

To 2.0 g (8.9 mmol) of 5-methyl-7-phenyl-1,2,4triazolo[1,5-a]pyrimidin-2-amine stirring in 25 ml of concentrated hydrochloric acid, 1.2 g (17.4 mmol) of sodium nitrite dissolved in 4.0 ml of water was added dropwise at ambient temperature. After the addition, the reaction suspension was warmed at about 60° for 15 minutes followed by stirring another 10 minutes without heat. Ethyl acetate (150 ml) and excess water were added. The ethyl acetate layer was separated whereby a certain amount of insoluble material present was ignored and the extract washed with water (2X), saturated sodium bicarbonate, brine, dried over magnesium sulfate, and evaporated in vacuo to give a solid residue. Silica gel column chromatography (methylene chloride followed by 10:1 methylene chloride/ethyl acetate) afforded the title compound, m.p. 179°–181° C.

EXAMPLE 7

Preparation of 2-Bromo-5-methyl-7-phenyl-1,2,4-triazolo[1,5-a]pyrimidine

A mixture of 7.0 g (71 mmol) 3,5-diamino-1,2,4-triazole and 12.0 g (74 mmol) benzoylacetone in 100 ml of glacial acetic acid was heated at reflux 2 hours. After cooling, methylene chloride (200 ml) was added followed by the addition of excess water. The organic layer was separated, washed with water, brine, dried over magensium sulfate and evaporated in vacuo to give a solid residue to which ethyl acetate was added. Filtering gave 16.0 g of crude 5-methyl-7-phenyl-1,2,4-triazolo[1,5-a]pyrimidin-2-amine (m.p. 246°–250° C.) which was used directly in the next step.

To 2.0 g (8.9 mmol) of 5-methyl-7-phenyl-1,2,4-triazolo[1,5-a]pyrimidin-2-amine stirring in a mixture of 20 ml of 48% hydrobromic acid and 10 ml of glacial acetic acid, 2.0 g (29.0 mmol) of sodium nitrite was slowly added portionwise with good stirring at ambient temperature. The thick suspension was stirred at about 60° C. for 15 minutes followed by stirring another 10 minutes without heat. Ethyl acetate (150 ml) and excess water were added. The ethyl acetate layer was separated whereby a certain amount of insoluble material present was ignored and the extract washed with water (2X), saturated sodium bicarbonate, brine, dried over magnesium sulfate, and evaporated in vacuo to give a solid residue. Silica gel column chromatography (methylene chloride followed by 10:1 methylene chloride/ethyl acetate) afforded the title compound, 15 m.p. 178°–180° C.

EXAMPLE 8

Preparation of 5-methyl-7-phenyl-2-[(trifluoromethyl)thio]-1,2,4-triazolo[1,5-a]pyrimidine A mixture of 10.0 9 (86 mmol) 3-amino-5-mercapto-1,2,4-triazole and 14.0 g (86.5 mmol) of benzoylacetone in 100 ml of glacial acetic acid was heated at reflux 4 hours. Methylene chloride (500 ml) and excess water were added. The organic layer was separated and washed with water, brine, dried over magnesium sulfate and evaporated in vacuo to give a residue to which n-butyl chloride was added. Filtering gave 4.9 g of crude 5-methyl-7-phenyl-1,2,4-triazolo[1,5-a]pyrimidin-2-thiol which was used directly in the next step.

To 1.5 g (6.2 mmol) of 5-methyl-7-phenyl-1,2,4-triazolo[1,5-a]pyrimidin-2-thiol and 1.5 g (10.9 mmol) of powdered potassium carbonate stirring in 20 ml of dimethylformamide, 3 ml of condensed trifluoromethyl iodide was added dropwise at ambient temperature. Keeping the dry ice condenser on from the addition, the stirred mixture was warmed to 30° C. At three separate times during a 2 h period, 2.0 ml portions of trifluoromethyliodide were added. Excess water was added and the aqueous mixture was extracted with a 1:1 mixture of ethyl acetate/diethyl ether (200 ml) and the organic layer was washed with water, saturated sodium bicarbonate, brine, dried over magnesium sulfate and evaporated in vacuo to give an oil. Silica gel column chromatography (methylene chloride followed by 1:1 methylene chloride/ethyl acetate) afforded 0.4 g of the title compound (main component present), m.p. 91°–93° C.

EXAMPLE 9

5-methyl-7-(3-trifluoromethylphenyl)-2(trifluoromethyl)-1,2,4-triazolo[1,5-a]pyrimidine A mixture of 5.5 g (23.9 mmol) of 3'-trifluoromethylbenzoylacetone (prepared by the same procedure as that shown in the beginning of Example 2 for the preparation of 3'chlorobenzoylacetone) and 3.0 g (19.7 mmol) 3-amino-5-trifluoromethyltriazole (prepared as reported in Example 1) were heated at reflux in 50 ml of glacial acetic acid for 2.5 h. The solvent was removed in vacuo and the resulting residue diluted with excess water and the aqueous mixture extracted with 200 ml of ethyl acetate. The extract was washed with water, saturated sodium bicarbonate, and dried over magnesium sulfate and evaporated in vacuo to give an oily residue.

A solid was triturated on addition of n-butylchloride/hexane and was filtered and purified by silica gel column chromatography (methylene chloride) to give 0.7 g of the title compound, m.p. 133°–134° C.

EXAMPLE 10

Preparation of 5-methyl-7-phenyl-2-[(2,2,2-trifluoroethoxy]-1,2,4-triazolo[1.5-a]pyrimidine To 2.5 g (8.7 mmol) of 2-bromo-5-methyl-7-phenyl-1,2,4-triazolo[1,5-a]pyrimidine and 4.3 g of 2,2,2-trifluoroethanol stirring in 50 ml of THF, 0.4 g of sodium hydride (60% oil dispersion) was added portionwise with considerable foaming. The stirred reaction mixture was heated at reflux 16 hours. After cooling, 5.0 ml of methanol of was added followed by the addition of 200 ml of ethyl acetate and excess water. The organic layer was washed with water, brine, dried over magnesium sulfate and evaporated in vacuo to give an oil. Trituration with n-butyl chloride/hexane and filtering afforded 1.4 g of the title compound (m.p. 103°-104° C.).

EXAMPLE 11

Preparation of 7-(3-chlorophenyl)-5-methyl-2-(trifluoromethyl)thiol-1,2,4-triazolo[5-a]pyrimidine A mixture of 10.0 g (51 mmol) of 3'-chlorobenzoylacetone and 6.0 g (52 mmol) of 3-amino-5-mercapto-1,2,4-triazole in 100 ml of glacial acetic acid was heated at reflux 10 hours. The reaction mixture was concentrated in vacuo and 500 ml of methylene chloride and excess water added. The organic layer was separated and washed with water, brine, dried over magnesium sulfate and evaporated in vacuo to give a solid residue to which n-butyl chloride was added. Filtration gave 6.2 g of crude 7-(3-chlorophenyl)-5-methyl-1,2,4-triazolo[1,5-a]-pyrimidin-2-thiol which was used directly in the next step.

To 5.6 g (20 mmol) of crude 7-(3-chlorophenyl)-5-methyl-1,2,4-triazolo[1,5-a]pyrimidin-2-thiol and 2.0 g of potassium hydroxide in 100 ml of dioxane and 30 ml of water, 6.0 ml of trifluoromethyl iodide was added by way of a gas addition funnel equipped with a dry-ice condensor. The mixture was stirred at 60°-70° C. (keeping the dry-ice condensor on the reaction) under irradiation from a sunlamp for 2 hours. Ethyl acetate (300 ml) and excess water were added. The organic layer was separated and washed with water, brine, dried over magnesium sulfate, and evaporated in vacuo. The isolated residue was chromatographed on silica gel (3:1 followed by 1:1 hexane/ethyl acetate) to afford 2.5 g of the title compound, m.p. 95°-96° C.

EXAMPLE 12

Preparation of 7-(3-chlorophenyl)-difluoromethyl)-thiol]-5-methyl-1,2,4-triazolo[1,5-a]pyrimidine To 5.5 g (20.0 mmol) of crude 7-(3-chlorophenyl)-5-methyl-1,2,4-triazolo[1,5-a]pyrimidin-2-thio 1 and 2.7 g of potassium hydroxide stirring in a mixture of 150 ml of dioxane and 20 ml of water, 8.0 ml of chlorodifluoromethane was added by way of a gas addition funnel equipped with a dry-ice condensor. The mixture was heated at 60° C. for 1.5 hours. Excess water and a 1:1 mixture of ethyl acetate and ethyl ether was added. The organic layer was separated and washed with water, saturated sodium bicarbonate, brine, dried over magnesium sulfate, and evaporated in vacuo. The residue was chromatographed on silica gel (methylene chloride followed by 4:1 methylene chloride/ethyl acetate) to give 2.5 g of the title compound, m.p. 145°-146° C.

EXAMPLE 13

Preparation of 6-methyl-2-(trifluoromethyl)-8-((3-trifluoromethyl)phenyl)-imidazo[1,2-b]pyridazine A solution of 3 g (12 mmol) of 6-methyl-4((3-trifluoromethyl)phenyl)-3-pyridazinamine (prepared from 3'-trifluoromethylbenzoylacetone by the method of H. G. O. Becker et al., *Tetrahedron.* 24, 2687 (1968)) and 2.5 g (13 mmol) of 1-bromo-3,3,3-trifluoro-2-propanone in 75 ml of ethanol was refluxed for 16 hours. The solvent was removed with a rotary evaporator. The residue was dissolved in dichloromethane, was washed with saturated aqueous sodium bicarbonate and was dried (sodium sulfate). The solvent was removed with a rotary evaporator. The residue was purified by silica gel column chromatography to give 2.04 g of the title compound as a solid, m.p. 122°-123° C.

EXAMPLE 14

Preparation of 6-methyl-2-(trifluoromethyl)-8-((3-trifluoromethyl)-phenyl)-[1,2,4]triazolo[1,5-b]pyridazine To a slurry of 3.05 9 (13 mmol) of O-diphenylphosphinylhydroxylamine in 65 ml of chloroform was added 3.0 g (12 mmol) of 6-methyl-4-((3-trifluoromethyl)phenyl-3-pyridazinamine. The mixture was stirred for 4 hours at room temperature, was refluxed for 2 hours and then was stirred at room temperature for 16 hours.

The solvent was removed with a rotary evaporator. A 100 ml portion of water was added to the residue. The pH was adjusted to 2 with 50% HI. The reaction mixture was filtered and the water was removed from the filtrate with a rotary evaporator to give 2.5 g of solid.

A 1.4 g portion of this solid was placed in a teflon-capped test tube and 5 ml of trifluoroacetic anhydride was added. The test tube was placed in an oil bath heated to 200° C. for 15 minutes. After cooling, the residue was dissolved in dichloromethane and was washed with a saturated aqueous sodium bicarbonate solution and was dried (sodium sulfate). The solvent was removed with a rotary evaporator. The residue was purified by silica gel column chromatography to give 0.74 g of the title compound as a solid, m.p. 134°-135.5° C.

EXAMPLE 15

Preparation of 5-methyl-7-phenyl-2-(trifluoromethyl)pyrazolo[1,5-a]pyrimidin-3-carbonitrile To a solution of 30 g (0.17 mole) of 1,1-dicyano-2-chloro-2-trifluoromethylethylene (prepared as taught by V. I. Krokhtyak et al., *J. Org. Chem.* (U.S.S.R), 1441 (1981)) in 300 ml of ether at 0° C. was added 10.6 ml (0.33 mole) of hydrazine dropwise. The reaction waas stirred 30 minutes at room temperature. It was filtered and the solvent was removed with a rotary evaporator to give 28 g of a yellow semi-solid.

A 5.4 g (30 mmol) sample of this material was dissolved in 90 ml of ethanol and 5.0 g (30 mmol) of benzoylacetone was added. The reaction mixture was heated at reflux for 16 hours. It was cooled and the solvent was removed with a rotary evaporator. The residue was purified by silica gel column chromotography to give 4.7 g of the title compound as a solid, m.p. 143°-148° C.

Using the procedures outlined in Schemes 1-8 and Examples 1-15, the compounds of Tables I-VIII can be prepared.

TABLE I

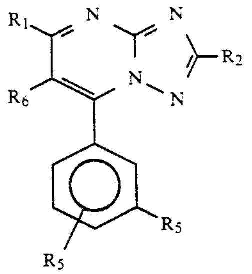

| $R_1$ | $R_2$ | $R_4$ | $R_5$ | $R_6$ |
|---|---|---|---|---|
| Me | $CF_3$ | H | $CF_3$ | H |
| Me | $CH_3$ | H | Cl | H |
| Me | $CF_3$ | H | Br | H |
| Me | $CF_3$ | H | CN | H |
| Me | $CF_3$ | H | $OCF_3$ | H |
| Me | $CF_3$ | H | $OCHF_2$ | H |
| Me | $CF_3$ | H | $OCH_2CF_3$ | H |
| Me | $CF_3$ | H | $SCF_3$ | H |
| Me | $CF_3$ | H | $SCHF_2$ | H |
| Me | $CF_3$ | H | $SO_2CF_3$ | H |
| Me | $CF_3$ | H | H | H |
| Me | $CF_3$ | H | OMe | H |
| Me | $CF_3$ | H | OEt | H |
| Me | $CF_3$ | H | Me | H |
| Me | $CF_3$ | H | $C_2F_5$ | H |
| Et | $CF_3$ | H | $CF_3$ | H |
| Et | $CH_3$ | H | Cl | H |
| Et | $CF_3$ | H | Br | H |
| Et | $CF_3$ | H | CN | H |
| Et | $CF_3$ | H | $OCF_3$ | H |
| Et | $CF_3$ | H | $OCHF_2$ | H |
| Et | $CF_3$ | H | $OCH_2CF_3$ | H |
| Et | $CF_3$ | H | $SCF_3$ | H |
| Et | $CF_3$ | H | $SCHF_2$ | H |
| Et | $CF_3$ | H | $SO_2CF_3$ | H |
| Et | $CF_3$ | H | H | H |
| Et | $CF_3$ | H | $SO_2CHF_2$ | H |
| Et | $CF_3$ | H | $SC_2F_5$ | H |
| Et | $CF_3$ | H | $SO_2C_2F_5$ | H |
| Et | $CF_3$ | H | $SO_2CF_3$ | H |
| Pr | $CF_3$ | H | $CF_3$ | H |
| Pr | $CH_3$ | H | Cl | H |
| Pr | $CF_3$ | H | Br | H |
| Pr | $CF_3$ | H | CN | H |
| Pr | $CF_3$ | H | $OCF_3$ | H |
| Pr | $CF_3$ | H | $OCHF_2$ | H |
| Pr | $CF_3$ | H | $OCH_2CF_3$ | H |
| Pr | $CF_3$ | H | $SCF_3$ | H |
| Pr | $CF_3$ | H | $SCHF_2$ | H |
| Pr | $CF_3$ | H | $SO_2CF_3$ | H |
| Pr | $CF_3$ | H | OH | H |
| Pr | $CF_3$ | H | $CONH_2$ | H |
| Et | $CF_3$ | H | $NHSO_2CF_3$ | H |
| Me | $CHF_2$ | H | $CF_3$ | H |
| Me | $CHF_2$ | H | Cl | H |
| Me | $CHF_2$ | H | Br | H |
| Me | $CHF_2$ | H | CN | H |
| Me | $CHF_2$ | H | $OCF_3$ | H |
| Me | $CHF_2$ | H | $OCHF_2$ | H |
| Me | $CHF_2$ | H | $OCH_2CF_3$ | H |
| Me | $CHF_2$ | H | $SCF_3$ | H |
| Me | $CHF_2$ | H | $SCHF_2$ | H |
| Me | $CHF_2$ | H | $SO_2CF_3$ | H |
| Me | $CHF_2$ | H | H | H |
| Et | $CHF_2$ | H | $CF_3$ | H |
| Et | $CHF_2$ | H | Cl | H |
| Et | $CHF_2$ | H | Br | H |
| Et | $CHF_2$ | H | CN | H |
| Et | $CHF_2$ | H | $OCF_3$ | H |
| Et | $CHF_2$ | H | $OCHF_2$ | H |
| Et | $CHF_2$ | H | $OCH_2CF_3$ | H |
| Et | $CHF_2$ | H | $SCF_3$ | H |
| Et | $CHF_2$ | H | $SCHF_2$ | H |
| Et | $CHF_2$ | H | $SO_2CF_3$ | H |
| Pr | $CHF_2$ | H | $CF_3$ | H |
| Pr | $CHF_2$ | H | Cl | H |
| Pr | $CHF_2$ | H | Br | H |

TABLE I-continued

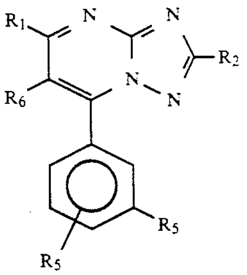

| $R_1$ | $R_2$ | $R_4$ | $R_5$ | $R_6$ |
|---|---|---|---|---|
| Pr | $CHF_2$ | H | CN | H |
| Pr | $CHF_2$ | H | $OCF_3$ | H |
| Pr | $CHF_2$ | H | $OCHF_2$ | H |
| Pr | $CHF_2$ | H | $OCH_2CF_3$ | H |
| Pr | $CHF_2$ | H | $SCF_3$ | H |
| Pr | $CHF_2$ | H | $SCHF_2$ | H |
| Pr | $CHF_2$ | H | $SO_2CF_3$ | H |
| Me | $OCH_2CF_3$ | H | $CF_3$ | H |
| Me | $OCH_2CF_3$ | H | Cl | H |
| Me | $OCH_2CF_3$ | H | Br | H |
| Me | $OCH_2CF_3$ | H | CN | H |
| Me | $OCH_2CF_3$ | H | $OCF_3$ | H |
| Me | $OCH_2CF_3$ | H | $OCHF_2$ | H |
| Me | $OCH_2CF_3$ | H | $OCH_2CF_3$ | H |
| Me | $OCH_2CF_3$ | H | $SCF_3$ | H |
| Me | $OCH_2CF_3$ | H | $SCHF_2$ | H |
| Me | $OCH_2CF_3$ | H | $SO_2CF_3$ | H |
| Et | $OCH_2CF_3$ | H | $CF_3$ | H |
| Et | $OCH_2CF_3$ | H | Cl | H |
| Et | $OCH_2CF_3$ | H | Br | H |
| Et | $OCH_2CF_3$ | H | CN | H |
| Et | $OCH_2CF_3$ | H | $OCF_3$ | H |
| Et | $OCH_2CF_3$ | H | $OCHF_2$ | H |
| Et | $OCH_2CF_3$ | H | $OCH_2CF_3$ | H |
| Et | $OCH_2CF_3$ | H | $SCF_3$ | H |
| Et | $OCH_2CF_3$ | H | $SCHF_2$ | H |
| Et | $OCH_2CF_3$ | H | $SO_2CF_3$ | H |
| Pr | $OCH_2CF_3$ | H | $CF_3$ | H |
| Pr | $OCH_2CF_3$ | H | Cl | H |
| Pr | $OCH_2CF_3$ | H | Br | H |
| Pr | $OCH_2CF_3$ | H | CN | H |
| Pr | $OCH_2CF_3$ | H | $OCF_3$ | H |
| Pr | $OCH_2CF_3$ | H | $OCHF_2$ | H |
| Pr | $OCH_2CF_3$ | H | $OCH_2CF_3$ | H |
| Pr | $OCH_2CF_3$ | H | $SCF_3$ | H |
| Pr | $OCH_2CF_3$ | H | $SCHF_2$ | H |
| Pr | $OCH_2CF_3$ | H | $SO_2CF_3$ | H |
| Me | $OCHF_2$ | H | $CF_3$ | H |
| Me | $OCHF_2$ | H | Cl | H |
| Me | $OCHF_2$ | H | Br | H |
| Me | $OCHF_2$ | H | CN | H |
| Me | $OCHF_2$ | H | $OCF_3$ | H |
| Me | $OCHF_2$ | H | $OCHF_2$ | H |
| Me | $OCHF_2$ | H | $OCH_2CF_3$ | H |
| Me | $OCHF_2$ | H | $SCF_3$ | H |
| Me | $OCHF_2$ | H | $SCHF_2$ | H |
| Me | $OCHF_2$ | H | $SO_2CF_3$ | H |
| Et | $OCHF_2$ | H | $CF_3$ | H |
| Et | $OCHF_2$ | H | Cl | H |
| Et | $OCHF_2$ | H | Br | H |
| Et | $OCHF_2$ | H | CN | H |
| Et | $OCHF_2$ | H | $OCF_3$ | H |
| Et | $OCHF_2$ | H | $OCHF_2$ | H |
| Et | $OCHF_2$ | H | $OCH_2CF_3$ | H |
| Et | $OCHF_2$ | H | $SCF_3$ | H |
| Et | $OCHF_2$ | H | $SCHF_2$ | H |
| Et | $OCHF_2$ | H | $SO_2CF_3$ | H |
| Pr | $OCHF_2$ | H | $CF_3$ | H |
| Pr | $OCHF_2$ | H | Cl | H |
| Pr | $OCHF_2$ | H | Br | H |
| Pr | $OCHF_2$ | H | CN | H |
| Pr | $OCHF_2$ | H | $OCF_3$ | H |
| Pr | $OCHF_2$ | H | $OCHF_2$ | H |
| Pr | $OCHF_2$ | H | $OCH_2CF_3$ | H |
| Pr | $OCHF_2$ | H | $SCF_3$ | H |
| Pr | $OCHF_2$ | H | $SCHF_2$ | H |
| Pr | $OCHF_2$ | H | $SO_2CF_3$ | H |

TABLE I-continued

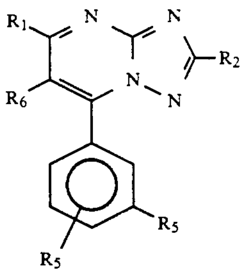

| $R_1$ | $R_2$ | $R_4$ | $R_5$ | $R_6$ |
|---|---|---|---|---|
| Me | $OCF_3$ | H | $CF_3$ | H |
| Me | $OCF_3$ | H | Cl | H |
| Me | $OCF_3$ | H | Br | H |
| Me | $OCF_3$ | H | CN | H |
| Me | $OCF_3$ | H | $OCF_3$ | H |
| Me | $OCF_3$ | H | $OCHF_2$ | H |
| Me | $OCF_3$ | H | $OCH_2CF_3$ | H |
| Me | $OCF_3$ | H | $SCF_3$ | H |
| Me | $OCF_3$ | H | $SCHF_2$ | H |
| Me | $OCF_3$ | H | $SO_2CF_3$ | H |
| Et | $OCF_3$ | H | $CF_3$ | H |
| Et | $OCF_3$ | H | Cl | H |
| Et | $OCF_3$ | H | Br | H |
| Et | $OCF_3$ | H | CN | H |
| Et | $OCF_3$ | H | $OCF_3$ | H |
| Et | $OCF_3$ | H | $OCHF_2$ | H |
| Et | $OCF_3$ | H | $OCH_2CF_3$ | H |
| Et | $OCF_3$ | H | $SCF_3$ | H |
| Et | $OCF_3$ | H | $SCHF_2$ | H |
| Et | $OCF_3$ | H | $SO_2CF_3$ | H |
| Pr | $OCF_3$ | H | $CF_3$ | H |
| Pr | $OCF_3$ | H | Cl | H |
| Pr | $OCF_3$ | H | Br | H |
| Pr | $OCF_3$ | H | CN | H |
| Pr | $OCF_3$ | H | $OCF_3$ | H |
| Pr | $OCF_3$ | H | $OCHF_2$ | H |
| Pr | $OCF_3$ | H | $OCH_2CF_3$ | H |
| Pr | $OCF_3$ | H | $SCF_3$ | H |
| Pr | $OCF_3$ | H | $SCHF_2$ | H |
| Pr | $OCF_3$ | H | $SO_2CF_3$ | H |
| Me | $SCF_3$ | H | $CF_3$ | H |
| Me | $SCF_3$ | H | Cl | H |
| Me | $SCF_3$ | H | Br | H |
| Me | $SCF_3$ | H | CN | H |
| Me | $SCF_3$ | H | $OCF_3$ | H |
| Me | $SCF_3$ | H | $OCHF_2$ | H |
| Me | $SCF_3$ | H | $OCH_2CF_3$ | H |
| Me | $SCF_3$ | H | $SCF_3$ | H |
| Me | $SCF_3$ | H | $SCHF_2$ | H |
| Me | $SCF_3$ | H | $SO_2CF_3$ | H |
| Et | $SCF_3$ | H | $CF_3$ | H |
| Et | $SCF_3$ | H | Cl | H |
| Et | $SCF_3$ | H | Br | H |
| Et | $SCF_3$ | H | CN | H |
| Et | $SCF_3$ | H | $OCF_3$ | H |
| Et | $SCF_3$ | H | $OCHF_2$ | H |
| Et | $SCF_3$ | H | $OCH_2CF_3$ | H |
| Et | $SCF_3$ | H | $SCF_3$ | H |
| Et | $SCF_3$ | H | $SCHF_2$ | H |
| Et | $SCF_3$ | H | $SO_2CF_3$ | H |
| Pr | $SCF_3$ | H | $CF_3$ | H |
| Pr | $SCF_3$ | H | Cl | H |
| Pr | $SCF_3$ | H | Br | H |
| Pr | $SCF_3$ | H | CN | H |
| Pr | $SCF_3$ | H | $OCF_3$ | H |
| Pr | $SCF_3$ | H | $OCHF_2$ | H |
| Pr | $SCF_3$ | H | $OCH_2CF_3$ | H |
| Pr | $SCF_3$ | H | $SCF_3$ | H |
| Pr | $SCF_3$ | H | $SCHF_2$ | H |
| Pr | $SCF_3$ | H | $SO_2CF_3$ | H |
| Me | $SCHF_2$ | H | $CF_3$ | H |
| Me | $SCHF_2$ | H | Cl | H |
| Me | $SCHF_2$ | H | Br | H |
| Me | $SCHF_2$ | H | CN | H |
| Me | $SCHF_2$ | H | $OCF_3$ | H |
| Me | $SCHF_2$ | H | $OCHF_2$ | H |
| Me | $SCHF_2$ | H | $OCH_2CF_3$ | H |

TABLE I-continued

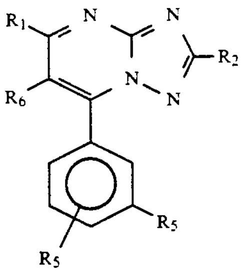

| $R_1$ | $R_2$ | $R_4$ | $R_5$ | $R_6$ |
|---|---|---|---|---|
| Me | $SCHF_2$ | H | $SCF_3$ | H |
| Me | $SCHF_2$ | H | $SCHF_2$ | H |
| Me | $SCHF_2$ | H | $SO_2CF_3$ | H |
| Et | $SCHF_2$ | H | $CF_3$ | H |
| Et | $SCHF_2$ | H | Cl | H |
| Et | $SCHF_2$ | H | Br | H |
| Et | $SCHF_2$ | H | CN | H |
| Et | $SCHF_2$ | H | $OCF_3$ | H |
| Et | $SCHF_2$ | H | $OCHF_2$ | H |
| Et | $SCHF_2$ | H | $OCH_2CF_3$ | H |
| Et | $SCHF_2$ | H | $SCF_3$ | H |
| Et | $SCHF_2$ | H | $SCHF_2$ | H |
| Et | $SCHF_2$ | H | $SO_2CF_3$ | H |
| Pr | $SCHF_2$ | H | $CF_3$ | H |
| Pr | $SCHF_2$ | H | Cl | H |
| Pr | $SCHF_2$ | H | Br | H |
| Pr | $SCHF_2$ | H | CN | H |
| Pr | $SCHF_2$ | H | $OCF_3$ | H |
| Pr | $SCHF_2$ | H | $OCHF_2$ | H |
| Pr | $SCHF_2$ | H | $OCH_2CF_3$ | H |
| Pr | $SCHF_2$ | H | $SCF_3$ | H |
| Pr | $SCHF_2$ | H | $SCHF_2$ | H |
| Pr | $SCHF_2$ | H | $SO_2CF_3$ | H |
| Me | SMe | H | H | H |
| Me | SMe | H | CN | H |
| Et | SMe | H | $CF_3$ | H |
| Pr | SMe | H | $CF_3$ | H |
| Pr | SMe | H | Cl | H |
| Me | $SO_2Me$ | H | H | H |
| Pr | $SO_2Me$ | H | $CF_3$ | H |
| Me | Cl | H | H | H |
| Me | Cl | H | $CF_3$ | H |
| Me | Cl | H | $CF_3$ | H |
| Me | Br | H | Br | H |
| Me | Br | H | $CF_3$ | H |
| Me | Br | H | $OCF_3$ | H |
| Et | Br | H | $CF_3$ | H |
| Et | Br | H | Cl | H |
| Et | Br | H | Br | H |
| Pr | Br | H | $CF_3$ | H |
| Me | $SO_2CF_3$ | H | H | H |
| Me | $SO_2CF_3$ | H | $CF_3$ | H |
| Et | $SO_2CF_3$ | H | Cl | H |
| Me | $CCl_3$ | H | H | H |
| Me | $CCl_3$ | H | Cl | H |
| Me | $CCl_3$ | H | $CF_3$ | H |
| Et | $CCl_3$ | H | Cl | H |
| Me | $OCH(CH_3)CF_3$ | H | $CF_3$ | H |
| Me | $OCH(CH_3)CF_3$ | H | Cl | H |
| Me | $CF_2Cl$ | H | $CF_3$ | H |
| Me | $CF_2Cl$ | H | Cl | H |
| H | $CF_3$ | H | H | H |
| H | $CF_3$ | H | Cl | H |
| H | Cl | H | $CF_3$ | H |
| i-Pr | $CF_3$ | H | Cl | H |
| i-Pr | $CF_3$ | H | $CF_3$ | H |
| n-Bu | $CF_3$ | H | Cl | H |
| n-Bu | $CF_3$ | H | $CF_3$ | H |
| $FCH_2$ | $CF_3$ | H | $CF_3$ | H |
| $C_2CH$ | $CF_3$ | H | $CF_3$ | H |
| $ClCH_2$ | $CF_3$ | H | Cl | H |
| MeS | $CF_3$ | H | Br | H |
| MeS | $CF_3$ | H | $CF_3$ | H |
| EtS | $CF_3$ | H | $CF_3$ | H |
| MeO | $CF_3$ | H | Cl | H |
| MeO | $CF_3$ | H | $CF_3$ | H |
| EtO | $CF_3$ | H | $CF_3$ | H |

TABLE I-continued

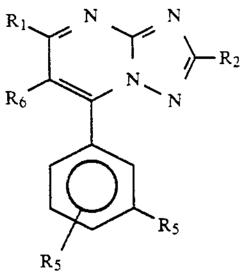

| $R_1$ | $R_2$ | $R_4$ | $R_5$ | $R_6$ |
|---|---|---|---|---|
| EtO | $CF_3$ | H | Br | H |
| MeNH | $CF_3$ | H | $CF_3$ | H |
| $Me_2N$ | $CF_3$ | H | Br | H |
| $CH_3CO$ | $CF_3$ | H | Br | H |
| $CH_3CO$ | $CF_3$ | H | Cl | H |
| $CH_3CO$ | $CF_3$ | H | $CF_3$ | H |
| $MeOCH_2$ | $CF_3$ | H | Cl | H |
| $EtOCH_2$ | $CF_3$ | H | $CF_3$ | H |
| $F_2CHO$ | $CF_3$ | H | Cl | H |
| $FCH_2CH_2O$ | $CF_3$ | H | Cl | H |
| $CH_3CH_2CHCl$ | $SCH_3$ | H | $CF_3$ | H |
| $CH_2{=}CH$ | $CF_3$ | H | $CF_3$ | H |
| $CH_2{=}CH$ | $CF_3$ | H | Cl | H |
| $CH_2{=}CH$ | $CHF_2$ | H | Br | H |
| $CH_2{=}CH$ | $OCF_3$ | H | $CF_3$ | H |
| $CH_2{=}CH$ | $OCHF_2$ | H | $SCF_3$ | H |
| $CH_2{=}CH$ | $OCH_2CF_3$ | H | $OCF_3$ | H |
| $CH_2{=}CH$ | $SCF_3$ | H | CN | H |
| $CH{\equiv}C$ | $CF_3$ | H | $CF_3$ | H |
| $CH{\equiv}C$ | $CHF_2$ | H | Cl | H |
| $CH{\equiv}C$ | $OCF_3$ | H | CN | H |
| $CH{\equiv}C$ | $OCHF_2$ | H | $OCF_3$ | H |
| $CH{\equiv}C$ | $OCH_2CF_3$ | H | Br | H |
| $CH{\equiv}C$ | $SCF_3$ | H | $SCF_3$ | H |
| $CH{\equiv}C$ | $SCHF_2$ | H | $OCHF_2$ | H |
| $CH_3CH{=}CH$ | $CF_3$ | H | Cl | H |
| $CH_3CH{=}CH$ | $CF_3$ | H | CN | H |
| $CH_3CH{=}CH$ | $SCF_3$ | H | Br | H |
| $CH_3CH{=}CH$ | $CHF_2$ | H | $OCF_3$ | H |
| $CH_3CH{=}CH$ | $OCF_3$ | H | $SCF_3$ | H |
| $CH_3CH{=}CH$ | $OCH_2CF_3$ | H | $SCHF_2$ | H |
| Me | $CF_3$ | H | 4-Cl | H |
| Me | $CF_3$ | H | 2-Cl | H |
| Me | $CF_3$ | H | 4-OMe | H |
| Me | $CF_3$ | H | 2-Me | H |
| Me | $CF_3$ | H | 2-F | H |
| Me | $CF_3$ | H | 4-F | H |
| Me | $CF_3$ | OMe | 5-OMe | H |
| Me | $CF_3$ | OMe | 2-OMe | H |
| Me | $CF_3$ | Me | 4-Me | H |
| Me | $CF_3$ | Cl | 5-Cl | H |
| Me | $CF_3$ | Cl | 2-Cl | H |
| Me | $CF_3$ | Cl | 5-OMe | H |
| Me | $CF_3$ | F | 5-F | H |
| Me | $CF_3$ | Cl | 2-OMe | H |
| Me | $CF_3$ | $CF_3$ | 5-F | H |
| Et | $CF_3$ | Cl | 5-Cl | H |

TABLE II

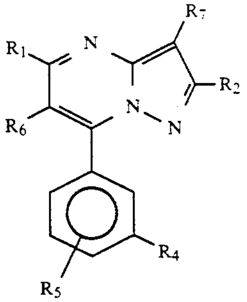

| $R_1$ | $R_2$ | $R_4$ | $R_5$ | $R_6$ | $R_7$ |
|---|---|---|---|---|---|
| Me | $CF_3$ | $CF_3$ | H | H | H |
| Me | $CF_3$ | Cl | H | H | H |
| Et | $CF_3$ | Cl | H | H | H |
| Et | $CF_3$ | $CF_3$ | H | H | H |
| H | $CF_3$ | $CF_3$ | H | H | CN |
| Me | SMe | Cl | H | H | H |
| Me | Cl | $CF_3$ | H | H | H |
| Me | SEt | $CF_3$ | H | H | H |
| Me | $CF_3$ | H | 3-$SCF_3$ | H | H |
| Me | $OCH_2CF_3$ | $CF_3$ | H | H | CN |
| Me | $OCH_2CF_3$ | $CF_3$ | H | H | H |
| Me | $CF_3$ | $CF_3$ | H | H | CN |
| Me | $CF_3$ | Cl | H | H | CN |
| Me | $CF_3$ | $CF_3$ | H | F | CN |
| Me | $CF_3$ | $CF_3$ | H | H | Br |
| Et | $CF_3$ | $CF_3$ | H | H | CN |
| n-propyl | $CF_3$ | $CF_3$ | H | H | CN |
| Me | $CF_3$ | $CF_3$ | H | H | F |
| Et | $CF_3$ | Cl | H | H | CN |
| n-propyl | $CF_3$ | $CF_3$ | H | H | H |
| Me | $CF_3$ | H | 3-CN | H | H |
| MeO | $CF_3$ | $CF_3$ | H | H | H |
| $F_2CH$ | $CF_3$ | Cl | H | H | H |
| Et | SMe | OMe | H | H | H |
| Me | $CF_3$ | $CF_3$ | H | F | H |
| Me | Cl | OMe | H | H | H |
| Me | $CF_3$ | Cl | H | F | H |
| isopropyl | $CF_3$ | Cl | H | H | H |
| MeS | $CF_3$ | Cl | H | H | H |
| $MeOCH_2$ | $CF_3$ | Cl | H | H | H |
| Me | $CF_3$ | H | 3-$SO_2CF_3$ | H | H |
| Me | $CF_3$ | H | 3-$SO_2Me$ | H | H |
| Et | Br | Cl | H | H | H |
| Me | $OCH_2CF_3$ | $CF_3$ | H | H | Cl |
| Me | $CF_3$ | Cl | H | H | $NO_2$ |
| Me | $CF_3$ | $CF_3$ | H | F | H |
| Me | Cl | $CF_3$ | H | H | CN |
| Et | Cl | $CF_3$ | H | H | CN |
| Et | Cl | $CF_3$ | H | H | H |
| Me | $SCHF_2$ | $CF_3$ | H | H | H |
| Et | $CF_3$ | H | 3-CN | H | H |
| Me | $SCHF_2$ | $CF_3$ | H | H | CN |
| Et | $CF_3$ | H | 3-$OCHF_2$ | H | H |
| Me | $CF_3$ | H | 3-$OCHF_2$ | H | CN |
| n-propyl | $CF_3$ | H | 3-$OCF_3$ | H | CN |
| $MeOCH_2$ | $CF_3$ | $CF_3$ | H | H | CN |
| Et | Br | $CF_3$ | H | H | H |
| Et | $CF_3$ | OMe | H | H | CN |
| Me | $CF_3$ | $CF_3$ | H | H | Me |
| Et | $CF_3$ | Cl | H | H | $CO_2Me$ |
| Me | $CF_3$ | H | 3-$OCH_2CF_3$ | H | CN |
| Me | $CF_3$ | H | 3-$SCF_3$ | H | CN |
| Et | $CF_3$ | H | 3-$SCHF_2$ | H | CN |
| $MeSCH_2$ | $CF_3$ | $CF_3$ | H | H | CN |
| Me | Cl | $CF_3$ | H | H | Cl |
| ET | $OCH_2CHF_2$ | $CF_3$ | H | H | CN |
| Me | Cl | $CF_3$ | H | H | $CF_3$ |
| MeNH | $CF_3$ | $CF_3$ | H | H | CN |
| $Me_2N$ | $CF_3$ | $CF_3$ | H | H | CN |
| Me | $SO_2CHF_2$ | $CF_3$ | H | H | CN |
| Me | $SO_2CH_3$ | $CF_3$ | H | H | CN |
| Me | $CF_3$ | H | 3-CN | H | CN |
| n-propyl | $CF_3$ | H | 3-CN | H | CN |
| Et | $CF_3$ | H | 3-SMe | H | CN |
| Et | Cl | H | 3-CN | H | H |
| Me | $SCHF_2$ | $CF_3$ | H | H | H |

TABLE II-continued

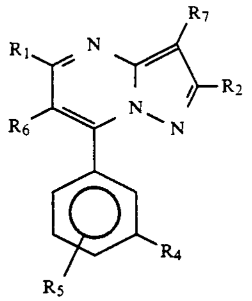

| $R_1$ | $R_2$ | $R_4$ | $R_5$ | $R_6$ | $R_7$ |
|---|---|---|---|---|---|
| Me | $CF_3$ | Br | H | H | CN |
| $HC\equiv C$ | $CF_3$ | $CF_3$ | H | H | CN |
| Me | $CF_3$ | H | 3-$SO_2CHF_2$ | H | CN |
| Me | $CF_3$ | Cl | 3-Cl | H | CN |
| Me | $CF_3$ | $CF_3$ | H | H | CN |
| Me | $CF_2Cl$ | $CF_3$ | H | H | CN |
| Et | $CHF_2$ | $CF_3$ | H | H | CN |
| $FCH_2CH_2$ | $CF_3$ | $CF_3$ | H | H | CN |
| Me | $OCHF_2$ | $CF_3$ | H | H | CN |
| Me | $OCH_2CF_3$ | H | H | H | H |
| Me | $CF_3$ | $CF_3$ | H | H | $CONH_2$ |
| Me | $CF_3$ | Cl | H | H | $CONH_2$ |
| Me | $CF_3$ | $CF_3$ | H | H | $NO_2$ |
| Me | $CF_3$ | $CF_3$ | H | H | $CO_2Et$ |
| Me | $CF_3$ | Cl | H | H | $CO_2Et$ |
| Me | $OCF_2H$ | $CF_3$ | H | H | CN |
| Me | $OCF_2H$ | $CF_3$ | H | H | H |
| Me | $OCF_2H$ | Cl | H | H | CN |
| Me | $OCF_2H$ | Cl | H | H | H |
| Me | $OCF_3$ | $CF_3$ | H | H | CN |
| Me | $OCF_3$ | $CF_3$ | H | H | H |

TABLE III

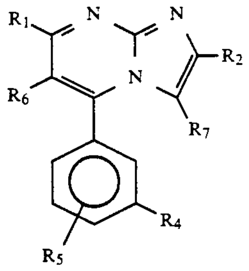

| $R_1$ | $R_2$ | $R_4$ | $R_5$ | $R_6$ | $R_7$ |
|---|---|---|---|---|---|
| Me | $CF_3$ | $CF_3$ | H | H | H |
| Me | $CF_3$ | Cl | H | H | H |
| Et | $CF_3$ | Cl | H | H | H |
| Et | $CF_3$ | $CF_3$ | H | H | H |
| H | $CF_3$ | $CF_3$ | H | H | CN |
| Me | SMe | Cl | H | H | H |
| Me | Cl | $CF_3$ | H | H | H |
| Me | SEt | $CF_3$ | H | H | H |
| Me | $CF_3$ | H | 3-$SCF_3$ | H | H |
| Me | $OCH_2CF_3$ | $CF_3$ | H | H | CN |
| Me | $OCH_2CF_3$ | $CF_3$ | H | H | H |
| Me | $CF_3$ | $CF_3$ | H | H | CN |
| Me | $CF_3$ | Cl | H | H | CN |
| Me | $CF_3$ | $CF_3$ | H | F | CN |
| Me | $CF_3$ | $CF_3$ | H | H | Br |
| Et | $CF_3$ | $CF_3$ | H | H | CN |
| n-propyl | $CF_3$ | $CF_3$ | H | H | CN |
| Me | $CF_3$ | $CF_3$ | H | H | F |
| Et | $CF_3$ | Cl | H | H | CN |
| n-propyl | $CF_3$ | $CF_3$ | H | H | H |
| Me | $CF_3$ | H | 3-CN | H | H |
| MeO | $CF_3$ | $CF_3$ | H | H | H |
| $F_2CH$ | $CF_3$ | Cl | H | H | H |
| Et | SMe | OMe | H | H | H |
| Me | $CF_3$ | $CF_3$ | H | F | H |

TABLE III-continued

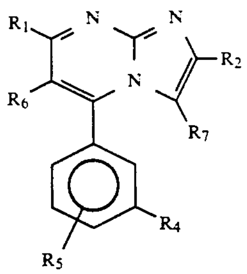

| $R_1$ | $R_2$ | $R_4$ | $R_5$ | $R_6$ | $R_7$ |
|---|---|---|---|---|---|
| Me | Cl | OMe | H | H | H |
| Me | $CF_3$ | Cl | H | F | H |
| isopropyl | $CF_3$ | Cl | H | H | H |
| MeS | $CF_3$ | Cl | H | H | H |
| $MeOCH_2$ | $CF_3$ | Cl | H | H | H |
| Me | $CF_3$ | H | 3-$SO_2CF_3$ | H | H |
| Me | $CF_3$ | H | 3-$SO_2Me$ | H | H |
| Et | Br | Cl | H | H | H |
| Me | $OCH_2CF_3$ | $CF_3$ | H | H | Cl |
| Me | $CF_3$ | Cl | H | H | $NO_2$ |
| Me | $CF_3$ | $CF_3$ | H | F | H |
| Me | Cl | $CF_3$ | H | H | CN |
| Et | Cl | $CF_3$ | H | H | CN |
| Et | Cl | $CF_3$ | H | H | N |
| Me | $SCHF_2$ | $CF_3$ | H | H | H |
| Et | $CF_3$ | H | 3-CN | H | H |
| Me | $SCHF_2$ | $CF_3$ | H | H | CN |
| Et | $CF_3$ | H | 3-$OCHF_2$ | H | H |
| Me | $CF_3$ | H | 3-$OCHF_2$ | H | CN |
| n-propyl | $CF_3$ | H | 3-$OCF_3$ | H | CN |
| $MeOCH_2$ | $CF_3$ | $CF_3$ | H | H | CN |
| Et | Br | $CF_3$ | H | H | H |
| Et | $CF_3$ | OMe | H | H | CN |
| Me | $CF_3$ | $CF_3$ | H | H | Me |
| Et | $CF_3$ | Cl | H | H | $CO_2Me$ |
| Me | $CF_3$ | H | 3-$OCH_2CF_3$ | H | CN |
| Me | $CF_3$ | H | 3-$SCF_3$ | H | CN |
| Et | $CF_3$ | H | 3-$SCHF_2$ | H | CN |
| $MeSCH_2$ | $CF_3$ | $CF_3$ | H | H | CN |
| Me | Cl | $CF_3$ | H | H | Cl |
| Et | $OCH_2CHF_2$ | $CF_3$ | H | H | CN |
| Me | Cl | $CF_3$ | H | H | $CF_3$ |
| MeNH | $CF_3$ | $CF_3$ | H | H | CN |
| $Me_2N$ | $CF_3$ | $CF_3$ | H | H | CN |
| Me | $SO_2CHF_2$ | $CF_3$ | H | H | CN |
| Me | $SO_2CH_3$ | $CF_3$ | H | H | CN |
| Me | $CF_3$ | H | 3-CN | H | CN |
| n-propyl | $CF_3$ | H | 3-CN | H | CN |
| Et | $CF_3$ | H | 3-SMe | H | CN |
| Et | Cl | H | 3-CN | H | H |
| Me | $SCHF_2$ | $CF_3$ | H | H | H |
| Me | $CF_3$ | Br | H | H | CN |
| $HC\equiv C$ | $CF_3$ | $CF_3$ | H | H | CN |
| Me | $CF_3$ | H | 3-$SO_2CHF_2$ | H | CN |
| Me | $CF_3$ | Cl | 3-Cl | H | CN |
| Me | $CF_3$ | $CF_3$ | H | H | CN |
| Me | $CF_2Cl$ | $CF_3$ | H | H | CN |
| Et | $CHF_2$ | $CF_3$ | H | H | CN |
| $FCH_2CH_2$ | $CF_3$ | $CF_3$ | H | H | CN |
| Me | $OCHF_2$ | $CF_3$ | H | H | CN |
| Me | $OCH_2CF_3$ | H | H | H | H |
| Me | $CF_3$ | $CF_3$ | H | H | $CONH_2$ |
| Me | $CF_3$ | Cl | H | H | $CONH_2$ |
| Me | $CF_3$ | $CF_3$ | H | H | $NO_2$ |
| Me | $CF_3$ | $CF_3$ | H | H | $CO_2Et$ |
| Me | $CF_3$ | Cl | H | H | $CO_2Et$ |
| Me | $OCF_2H$ | $CF_3$ | H | H | CN |
| Me | $OCF_2H$ | $CF_3$ | H | H | H |
| Me | $OCF_2H$ | Cl | H | H | CN |
| Me | $OCF_2H$ | Cl | H | H | H |
| Me | $OCF_3$ | $CF_3$ | H | H | CN |
| Me | $OCF_3$ | $CF_3$ | H | H | H |

TABLE IV

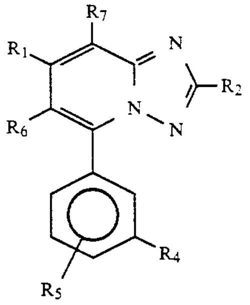

| $R_1$ | $R_2$ | $R_4$ | $R_5$ | $R_6$ | $R_7$ |
|---|---|---|---|---|---|
| Me | $CF_3$ | $CF_3$ | H | H | H |
| Me | $CF_3$ | Cl | H | H | H |
| Et | $CF_3$ | Cl | H | H | H |
| Et | $CF_3$ | $CF_3$ | H | H | H |
| H | $CF_3$ | $CF_3$ | H | H | CN |
| Me | SMe | Cl | H | H | H |
| Me | Cl | $CF_3$ | H | H | H |
| Me | SEt | $CF_3$ | H | H | H |
| Me | $CF_3$ | H | 3-$SCF_3$ | H | H |
| Me | $OCH_2CF_3$ | $CF_3$ | H | H | CN |
| Me | $OCH_2CF_3$ | $CF_3$ | H | H | H |
| Me | $CF_3$ | $CF_3$ | H | H | CN |
| Me | $CF_3$ | Cl | H | H | CN |
| Me | $CF_3$ | $CF_3$ | H | F | CN |
| Me | $CF_3$ | $CF_3$ | H | H | Br |
| Et | $CF_3$ | $CF_3$ | H | H | CN |
| n-propyl | $CF_3$ | $CF_3$ | H | H | CN |
| Me | $CF_3$ | $CF_3$ | H | H | F |
| Et | $CF_3$ | Cl | H | H | CN |
| n-propyl | $CF_3$ | $CF_3$ | H | H | H |
| Me | $CF_3$ | H | 3-CN | H | H |
| MeO | $CF_3$ | $CF_3$ | H | H | H |
| $F_2CH$ | $CF_3$ | Cl | H | H | H |
| Et | SMe | OMe | H | H | H |
| Me | $CF_3$ | $CF_3$ | H | F | H |
| Me | Cl | OMe | H | H | H |
| Me | $CF_3$ | Cl | H | F | H |
| isopropyl | $CF_3$ | Cl | H | H | H |
| MeS | $CF_3$ | Cl | H | H | H |
| $MeOCH_2$ | $CF_3$ | Cl | H | H | H |
| Me | $CF_3$ | H | 3-$SO_2CF_3$ | H | H |
| Me | $CF_3$ | H | 3-$SO_2Me$ | H | H |
| Et | Br | Cl | H | H | H |
| Me | $OCH_2CF_3$ | $CF_3$ | H | H | Cl |
| Me | $CF_3$ | Cl | H | H | $NO_2$ |
| Me | $CF_3$ | $CF_3$ | H | F | H |
| Me | Cl | $CF_3$ | H | H | CN |
| Et | Cl | $CF_3$ | H | H | CN |
| Et | Cl | $CF_3$ | H | H | N |
| Me | $SCHF_2$ | $CF_3$ | H | H | H |
| Et | $CF_3$ | H | 3-CN | H | H |
| Me | $SCHF_2$ | $CF_3$ | H | H | CN |
| Et | $CF_3$ | H | 3-$OCHF_2$ | H | H |
| Me | $CF_3$ | H | 3-$OCHF_2$ | H | CN |
| n-propyl | $CF_3$ | H | 3-$OCF_3$ | H | CN |
| $MeOCH_2$ | $CF_3$ | $CF_3$ | H | H | CN |
| Et | Br | $CF_3$ | H | H | H |
| Et | $CF_3$ | OMe | H | H | CN |
| Me | $CF_3$ | $CF_3$ | H | H | Me |
| Et | $CF_3$ | Cl | H | H | $CO_2Me$ |
| Me | $CF_3$ | H | 3-$OCH_2CF_3$ | H | CN |
| Me | $CF_3$ | H | 3-$SCF_3$ | H | CN |
| Et | $CF_3$ | H | 3-$SCHF_2$ | H | CN |
| $MeSCH_2$ | $CF_3$ | $CF_3$ | H | H | CN |
| Me | Cl | $CF_3$ | H | H | Cl |
| Et | $OCH_2CHF_2$ | $CF_3$ | H | H | CN |
| Me | Cl | $CF_3$ | H | H | $CF_3$ |
| MeNH | $CF_3$ | $CF_3$ | H | H | CN |
| $Me_2N$ | $CF_3$ | $CF_3$ | H | H | CN |
| Me | $SO_2CHF_2$ | $CF_3$ | H | H | CN |
| Me | $SO_2CH_3$ | $CF_3$ | H | H | CN |
| Me | $CF_3$ | H | 3-CN | H | CN |
| n-propyl | $CF_3$ | H | 3-CN | H | CN |
| Et | $CF_3$ | H | 3-SMe | H | CN |
| Et | Cl | H | 3-CN | H | H |
| Me | $SCHF_2$ | $CF_3$ | H | H | H |

TABLE IV-continued

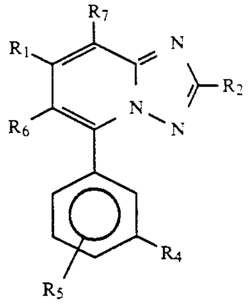

| $R_1$ | $R_2$ | $R_4$ | $R_5$ | $R_6$ | $R_7$ |
|---|---|---|---|---|---|
| Me | $CF_3$ | Br | H | H | CN |
| HC≡C | $CF_3$ | $CF_3$ | H | H | CN |
| Me | $CF_3$ | H | 3-$SO_2CHF_2$ | H | CN |
| Me | $CF_3$ | Cl | 3-Cl | H | CN |
| Me | $CF_3$ | $CF_3$ | H | H | CN |
| Me | $CF_2Cl$ | $CF_3$ | H | H | CN |
| Et | $CHF_2$ | $CF_3$ | H | H | CN |
| $FCH_2CH_2$ | $CF_3$ | $CF_3$ | H | H | CN |
| Me | $OCHF_2$ | $CF_3$ | H | H | CN |
| Me | $OCH_2CF_3$ | H | H | H | H |
| Me | $CF_3$ | $CF_3$ | H | H | $CONH_2$ |
| Me | $CF_3$ | Cl | H | H | $CONH_2$ |
| Me | $CF_3$ | $CF_3$ | H | H | $NO_2$ |
| Me | $CF_3$ | $CF_3$ | H | H | $CO_2Et$ |
| Me | $CF_3$ | Cl | H | H | $CO_2Et$ |
| Me | $OCF_2H$ | $CF_3$ | H | H | CN |
| Me | $OCF_2H$ | $CF_3$ | H | H | H |
| Me | $OCF_2H$ | Cl | H | H | CN |
| Me | $OCF_2H$ | Cl | H | H | H |
| Me | $OCF_3$ | $CF_3$ | H | H | CN |
| Me | $OCF_3$ | $CF_3$ | H | H | H |

TABLE V

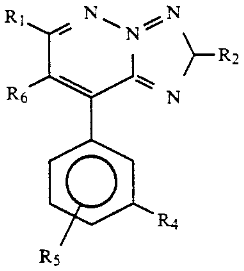

| $R_1$ | $R_2$ | $R_4$ | $R_5$ | $R_6$ |
|---|---|---|---|---|
| Me | $CF_3$ | H | H | H |
| Me | SMe | H | H | H |
| Me | $SO_2Me$ | H | H | H |
| Me | Cl | H | H | H |
| Me | Br | H | H | H |
| Me | $SCF_3$ | H | H | H |
| H | $CF_3$ | H | H | H |
| Me | $SO_2CF_3$ | H | H | H |
| Me | $CCl_3$ | H | H | H |
| Me | $CF_3$ | H | 4-Cl | H |
| Me | $CF_3$ | OMe | H | H |
| Me | $OCH_2CF_3$ | $CF_3$ | H | H |
| Me | $OCH_2CHF_2$ | $CF_3$ | H | H |
| Me | $OCH_2CF_3$ | Cl | H | H |
| Me | $OCH(CH_3)CF_3$ | $CF_3$ | H | H |
| Et | $OCH_2CF_3$ | $CF_3$ | H | H |
| n-propyl | $OCH_2CF_3$ | $CF_3$ | H | H |
| Et | $OCH_2CF_3$ | Cl | H | H |
| $MeSCH_2$ | $CF_3$ | $CF_3$ | H | H |
| Me | $OCH_2CF_3$ | H | 3-CN | H |
| Me | $CF_3$ | H | 2-Cl | H |
| Et | $CF_3$ | H | H | H |
| Me | $CF_3$ | F | H | H |
| Me | $CF_3$ | Cl | H | H |
| Me | $CF_3$ | H | 4-OMe | H |

TABLE V-continued

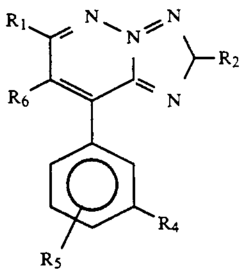

| $R_1$ | $R_2$ | $R_4$ | $R_5$ | $R_6$ |
|---|---|---|---|---|
| Me | $CF_3$ | Me | H | H |
| Me | $CF_3$ | $CF_3$ | H | H |
| Me | $CF_3$ | H | 2-Me | H |
| Me | $CF_3$ | Br | H | H |
| Me | $CF_3$ | OMe | 5-OMe | H |
| Me | $CF_3$ | OMe | 2-OMe | H |
| Me | $CF_3$ | Me | 4-Me | H |
| Me | $OCH_2CF_3$ | H | H | H |
| Me | $CF_3$ | H | 3-SMe | H |
| Me | $CF_3$ | H | 3-$SO_2Me$ | H |
| Me | $CF_3$ | H | 3-$SCF_3$ | H |
| Me | $CF_3$ | H | 3-$SO_2CF_3$ | H |
| Me | $CF_3$ | OEt | H | H |
| Me | $CF_3$ | H | 3-Ph | H |
| Me | $CF_3$ | H | 3-OPh | H |
| Me | $CF_3$ | H | 3-$CO_2Me$ | H |
| Me | $CF_3$ | H | 3-$OCHF_2$ | H |
| Me | $CF_3$ | H | 3-CN | H |
| Me | $CF_3$ | H | 3-$CH_2Br$ | H |
| Me | $CF_3$ | H | 3-n-propyl | H |
| Me | $CF_3$ | H | 3-isopropyl | H |
| Me | $CF_3$ | H | 3-SEt | H |
| Me | $CF_3$ | H | 3-$OCH_2CF_3$ | H |
| Me | $CF_3$ | Cl | 3-Cl | H |
| Me | $OCF_3$ | $CF_3$ | H | H |
| Me | $OCF_3$ | Cl | H | H |
| Me | $OCHF_2$ | H | 3-CN | H |
| Me | $SCHF_2$ | H | 3-CN | H |
| Me | $CF_3$ | H | 3-$OCF_2CF_3$ | H |
| Me | $CF_3$ | H | 3-$OCF_3$ | H |
| Me | $CF_3$ | H | 3-$NO_2$ | H |
| Me | SEt | Cl | H | H |
| Me | Cl | $CF_3$ | H | H |
| Me | Cl | H | 3-SMe | H |
| Me | Br | $CF_3$ | H | H |
| Me | $SCF_3$ | $CF_3$ | H | H |
| Me | $SCF_3$ | Cl | H | H |
| Me | $SO_2CF_3$ | $CF_3$ | H | H |
| Me | $CCl_3$ | Cl | H | H |
| Me | $OCHF_2$ | Cl | H | H |
| H | $CF_3$ | Cl | H | H |
| Me | $CF_3$ | H | 3-$CH_2OMe$ | H |
| Me | $CF_3$ | H | 3-$COCH_3$ | H |
| H | Cl | $CF_3$ | H | H |
| Et | $CF_3$ | $CF_3$ | H | H |
| Et | $CCl_3$ | Cl | H | H |
| Et | $CF_3$ | Cl | H | H |
| Et | $SCF_3$ | $CF_3$ | H | H |
| Et | $SCF_3$ | Cl | H | H |
| Et | $SO_2CF_3$ | Cl | H | H |
| n-propyl | $CF_3$ | $CF_3$ | H | H |
| isopropyl | $CF_3$ | Cl | H | H |
| n-butyl | $CF_3$ | $CF_3$ | H | H |
| $FCH_2$ | $CF_3$ | $CF_3$ | H | H |
| $F_2CH$ | $CF_3$ | Cl | H | H |
| $ClCH_2$ | $CF_3$ | Cl | H | H |
| MeO | $CF_3$ | Cl | H | H |
| EtO | $CF_3$ | $CF_3$ | H | H |
| Me | $OCHF_2$ | $CF_3$ | H | H |
| Me | $SCHF_2$ | $CF_3$ | H | H |
| Me | $SCHF_2$ | Cl | H | H |
| Me | $CHF_2$ | $CF_3$ | H | H |
| Me | $CF_2Cl$ | $CF_3$ | H | H |
| Me | $CF_2Cl$ | Cl | H | H |
| $MeOCH_2$ | $CF_3$ | Cl | H | H |
| $EtOCH_2$ | $CF_3$ | $CF_3$ | H | H |
| $F_2CHO$ | $CF_3$ | Cl | H | H |

TABLE V-continued

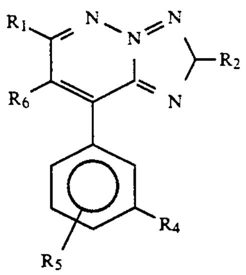

| $R_1$ | $R_2$ | $R_4$ | $R_5$ | $R_6$ |
|---|---|---|---|---|
| $FCH_2O$ | $CF_3$ | $CF_3$ | H | H |
| EtO | $CF_3$ | Br | H | H |
| Et | SMe | $CF_3$ | H | H |
| Et | $CF_3$ | H | 3-$NHSO_2CF_3$ | H |
| Et | $CF_3$ | H | 3-$NO_2$ | H |
| $FCH_2CH_2O$ | $CF_3$ | Cl | H | H |
| MeS | $CF_3$ | Br | H | H |
| EtS | $CF_3$ | $CF_3$ | H | H |
| n-butyl | $CF_3$ | Cl | H | H |
| C≡CH | $CF_3$ | Cl | H | H |
| $HC{=}CH_2$ | $CF_3$ | $CF_3$ | H | H |
| allyl | $CF_3$ | Cl | H | H |
| Me | $CF_3$ | Cl | H | F |
| Me | $CF_3$ | $CF_3$ | H | F |
| Et | $CF_3$ | H | 3-CN | F |
| Et | $CF_3$ | H | 3-$SO_2CF_3$ | H |
| n-propyl | $CF_3$ | H | 3-$SCF_3$ | H |
| n-propyl | Cl | $CF_3$ | H | H |
| Me | $CF_3$ | H | 2-F | H |
| Me | $CF_3$ | H | 4-F | H |
| Me | $CF_3$ | H | 3-$SO_2CH_2CH_3$ | H |
| Me | $CF_3$ | Cl | 3-Cl | H |
| Me | $CF_3$ | Cl | 2-Cl | H |
| n-propyl | $CF_3$ | Cl | H | H |
| Et | $SCHF_2$ | $CF_3$ | H | H |
| n-propyl | $SCHF_2$ | $CF_3$ | H | H |
| MeNH | $CF_3$ | $CF_3$ | H | H |
| $Me_2N$ | $CF_3$ | $CF_3$ | H | H |
| Me | $OCH_2CF_3$ | $CF_3$ | H | F |
| n-propyl | $CF_3$ | H | 3-CN | H |
| Et | $CF_3$ | H | 3-CN | H |
| Me | $OCF_2H$ | $CF_3$ | H | H |
| Me | $OCF_2H$ | Cl | H | H |
| Me | $OCF_3$ | $CF_3$ | H | H |
| Me | $OCF_3$ | Cl | H | H |

TABLE VI

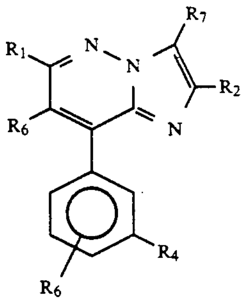

| $R_1$ | $R_2$ | $R_4$ | $R_5$ | $R_6$ | $R_7$ |
|---|---|---|---|---|---|
| Me | $CF_3$ | $CF_3$ | H | H | H |
| Me | $CF_3$ | Cl | H | H | H |
| Et | $CF_3$ | Cl | H | H | H |
| Et | $CF_3$ | $CF_3$ | H | H | H |
| H | $CF_3$ | $CF_3$ | H | H | CN |
| Me | SMe | Cl | H | H | H |
| Me | Cl | $CF_3$ | H | H | H |
| Me | SEt | $CF_3$ | H | H | H |
| Me | $CF_3$ | H | 3-$SCF_3$ | H | H |
| Me | $OCH_2CF_3$ | $CF_3$ | H | H | CN |
| Me | $OCH_2CF_3$ | $CF_3$ | H | H | H |

TABLE VI-continued

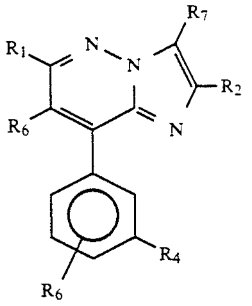

| $R_1$ | $R_2$ | $R_4$ | $R_5$ | $R_6$ | $R_7$ |
|---|---|---|---|---|---|
| Me | $CF_3$ | $CF_3$ | H | H | CN |
| Me | $CF_3$ | Cl | H | H | CN |
| Me | $CF_3$ | $CF_3$ | H | F | CN |
| Me | $CF_3$ | $CF_3$ | H | H | Br |
| Et | $CF_3$ | $CF_3$ | H | H | CN |
| n-propyl | $CF_3$ | $CF_3$ | H | H | CN |
| Me | $CF_3$ | $CF_3$ | H | H | F |
| Et | $CF_3$ | Cl | H | H | CN |
| n-propyl | $CF_3$ | $CF_3$ | H | H | H |
| Me | $CF_3$ | H | 3-CN | H | H |
| MeO | $CF_3$ | $CF_3$ | H | H | H |
| $F_2CH$ | $CF_3$ | Cl | H | H | H |
| Et | SMe | OMe | H | H | H |
| Me | $CF_3$ | $CF_3$ | H | F | H |
| Me | Cl | OMe | H | H | H |
| Me | $CF_3$ | Cl | H | F | H |
| isopropyl | $CF_3$ | Cl | H | H | H |
| MeS | $CF_3$ | Cl | H | H | H |
| $MeOCH_2$ | $CF_3$ | Cl | H | H | H |
| Me | $CF_3$ | H | 3-$SO_2CF_3$ | H | H |
| Me | $CF_3$ | H | 3-$SO_2Me$ | H | H |
| Et | Br | Cl | H | H | H |
| Me | $OCH_2CF_3$ | $CF_3$ | H | H | Cl |
| Me | $CF_3$ | Cl | H | H | $NO_2$ |
| Me | $CF_3$ | $CF_3$ | H | F | H |
| Me | Cl | $CF_3$ | H | H | CN |
| Et | Cl | $CF_3$ | H | H | CN |
| Et | Cl | $CF_3$ | H | H | N |
| Me | $SCHF_2$ | $CF_3$ | H | H | H |
| Et | $CF_3$ | H | 3-CN | H | H |
| Me | $SCHF_2$ | $CF_3$ | H | H | CN |
| Et | $CF_3$ | H | 3-$OCHF_2$ | H | H |
| Me | $CF_3$ | H | 3-$OCHF_2$ | H | CN |
| n-propyl | $CF_3$ | H | 3-$OCF_3$ | H | CN |
| $MeOCH_2$ | $CF_3$ | $CF_3$ | H | H | CN |
| Et | Br | $CF_3$ | H | H | H |
| Et | $CF_3$ | OMe | H | H | CN |
| Me | $CF_3$ | $CF_3$ | H | H | Me |
| Et | $CF_3$ | Cl | H | H | $CO_2Me$ |
| Me | $CF_3$ | H | 3-$OCH_2CF_3$ | H | CN |
| Me | $CF_3$ | H | 3-$SCF_3$ | H | CN |
| Et | $CF_3$ | H | 3-$SCHF_2$ | H | CN |
| $MeSCH_2$ | $CF_3$ | $CF_3$ | H | H | CN |
| Me | Cl | $CF_3$ | H | H | Cl |
| Et | $OCH_2CHF_2$ | $CF_3$ | H | H | CN |
| Me | Cl | $CF_3$ | H | H | $CF_3$ |
| MeNH | $CF_3$ | $CF_3$ | H | H | CN |
| $Me_2N$ | $CF_3$ | $CF_3$ | H | H | CN |
| Me | $SO_2CHF_2$ | $CF_3$ | H | H | CN |
| Me | $SO_2CH_3$ | $CF_3$ | H | H | CN |
| Me | $CF_3$ | H | 3-CN | H | CN |
| n-propyl | $CF_3$ | H | 3-CN | H | CN |
| Et | $CF_3$ | H | 3-SMe | H | CN |
| Et | Cl | H | 3-CN | H | H |
| Me | $SCHF_2$ | $CF_3$ | H | H | H |
| Me | $CF_3$ | Br | H | H | CN |
| HC≡C | $CF_3$ | $CF_3$ | H | H | CN |
| Me | $CF_3$ | H | 3-$SO_2CHF_2$ | H | CN |
| Me | $CF_3$ | Cl | 3-Cl | H | CN |
| Me | $CF_3$ | $CF_3$ | H | H | CN |
| Me | $CF_2Cl$ | $CF_3$ | H | H | CN |
| Et | $CHF_2$ | $CF_3$ | H | H | CN |
| $FCH_2CH_2$ | $CF_3$ | $CF_3$ | H | H | CN |
| Me | $OCH_2CF_3$ | H | H | H | H |
| Me | $CF_3$ | $CF_3$ | H | H | $CONH_2$ |
| Me | $CF_3$ | Cl | H | H | $CONH_2$ |

TABLE VI-continued

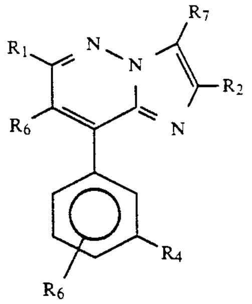

| $R_1$ | $R_2$ | $R_4$ | $R_5$ | $R_6$ | $R_7$ |
|---|---|---|---|---|---|
| Me | $CF_3$ | $CF_3$ | H | H | $NO_2$ |
| Me | $CF_3$ | $CF_3$ | H | H | $CO_2Et$ |
| Me | $CF_3$ | Cl | H | H | $CO_2Et$ |
| Me | $OCF_2H$ | $CF_3$ | H | H | CN |
| Me | $OCF_2H$ | $CF_3$ | H | H | H |
| Me | $OCF_2H$ | Cl | H | H | CN |
| Me | $OCF_2H$ | Cl | H | H | H |
| Me | $OCF_3$ | $CF_3$ | H | H | CN |
| Me | $OCF_3$ | $CF_3$ | H | H | H |

TABLE VII

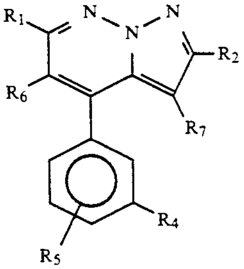

| $R_1$ | $R_2$ | $R_4$ | $R_5$ | $R_6$ | $R_7$ |
|---|---|---|---|---|---|
| Me | $CF_3$ | $CF_3$ | H | H | H |
| Me | $CF_3$ | Cl | H | H | H |
| Et | $CF_3$ | Cl | H | H | H |
| Et | $CF_3$ | $CF_3$ | H | H | H |
| H | $CF_3$ | $CF_3$ | H | H | CN |
| Me | SMe | Cl | H | H | H |
| Me | Cl | $CF_3$ | H | H | H |
| Me | SEt | $CF_3$ | H | H | H |
| Me | $CF_3$ | H | 3-$SCF_3$ | H | H |
| Me | $OCH_2CF_3$ | $CF_3$ | H | H | CN |
| Me | $OCH_2CF_3$ | $CF_3$ | H | H | H |
| Me | $CF_3$ | $CF_3$ | H | H | CN |
| Me | $CF_3$ | Cl | H | H | CN |
| Me | $CF_3$ | $CF_3$ | H | F | CN |
| Me | $CF_3$ | $CF_3$ | H | H | Br |
| Et | $CF_3$ | $CF_3$ | H | H | CN |
| n-propyl | $CF_3$ | $CF_3$ | H | H | CN |
| Me | $CF_3$ | $CF_3$ | H | H | F |
| Et | $CF_3$ | Cl | H | H | CN |
| n-propyl | $CF_3$ | $CF_3$ | H | H | H |
| Me | $CF_3$ | H | 3-CN | H | H |
| MeO | $CF_3$ | $CF_3$ | H | H | H |
| $F_2CH$ | $CF_3$ | Cl | H | H | H |
| Et | SMe | OMe | H | H | H |
| Me | $CF_3$ | $CF_3$ | H | F | H |
| Me | Cl | OMe | H | H | H |
| Me | $CF_3$ | Cl | H | F | H |
| isopropyl | $CF_3$ | Cl | H | H | H |
| MeS | $CF_3$ | Cl | H | H | H |
| $MeOCH_2$ | $CF_3$ | Cl | H | H | H |
| Me | $CF_3$ | H | 3-$SO_2CF_3$ | H | H |
| Me | $CF_3$ | H | 3-$SO_2Me$ | H | H |
| Et | Br | Cl | H | H | H |
| Me | $OCH_2CF_3$ | $CF_3$ | H | H | Cl |
| Me | $CF_3$ | Cl | H | H | $NO_2$ |
| Me | $CF_3$ | $CF_3$ | H | F | H |
| Me | Cl | $CF_3$ | H | H | CN |

TABLE VII-continued

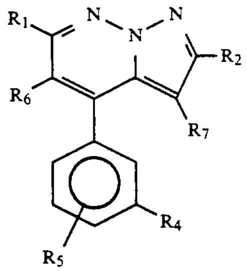

| $R_1$ | $R_2$ | $R_4$ | $R_5$ | $R_6$ | $R_7$ |
|---|---|---|---|---|---|
| Et | Cl | $CF_3$ | H | H | CN |
| Et | Cl | $CF_3$ | H | H | N |
| Me | $SCHF_2$ | $CF_3$ | H | H | H |
| Et | $CF_3$ | H | 3-CN | H | H |
| Me | $SCHF_2$ | $CF_3$ | H | H | CN |
| Et | $CF_3$ | H | 3-$OCHF_2$ | H | H |
| Me | $CF_3$ | H | 3-$OCHF_2$ | H | CN |
| n-propyl | $CF_3$ | H | 3-$OCF_3$ | H | CN |
| $MeOCH_2$ | $CF_3$ | $CF_3$ | H | H | CN |
| Et | Br | $CF_3$ | H | H | H |
| Et | $CF_3$ | OMe | H | H | CN |
| Me | $CF_3$ | $CF_3$ | H | H | Me |
| Et | $CF_3$ | Cl | H | H | $CO_2Me$ |
| Me | $CF_3$ | H | 3-$OCH_2CF_3$ | H | CN |
| Me | $CF_3$ | H | 3-$SCF_3$ | H | CN |
| Et | $CF_3$ | H | 3-$SCHF_2$ | H | CN |
| $MeSCH_2$ | $CF_3$ | $CF_3$ | H | H | CN |
| Me | Cl | $CF_3$ | H | H | Cl |
| Et | $OCH_2CHF_2$ | $CF_3$ | H | H | CN |
| Me | Cl | $CF_3$ | H | H | $CF_3$ |
| MeNH | $CF_3$ | $CF_3$ | H | H | CN |
| $Me_2N$ | $CF_3$ | $CF_3$ | H | H | CN |
| Me | $SO_2CHF_2$ | $CF_3$ | H | H | CN |
| Me | $SO_2CH_3$ | $CF_3$ | H | H | CN |
| Me | $CF_3$ | H | 3-CN | H | CN |
| n-propyl | $CF_3$ | H | 3-CN | H | CN |
| Et | $CF_3$ | H | 3-SMe | H | CN |
| Et | Cl | H | 3-CN | H | H |
| Me | $SCHF_2$ | $CF_3$ | H | H | H |
| Me | $CF_3$ | Br | H | H | CN |
| HC≡C | $CF_3$ | $CF_3$ | H | H | CN |
| Me | $CF_3$ | H | 3-$SO_2CHF_2$ | H | CN |
| Me | $CF_3$ | Cl | 3-Cl | H | CN |
| Me | $CF_3$ | $CF_3$ | H | H | CN |
| Me | $CF_2Cl$ | $CF_3$ | H | H | CN |
| Et | $CHF_2$ | $CF_3$ | H | H | CN |
| $FCH_2CH_2$ | $CF_3$ | $CF_3$ | H | H | CN |
| Me | $OCH_2CF_3$ | H | H | H | H |
| Me | $CF_3$ | $CF_3$ | H | H | $CONH_2$ |
| Me | $CF_3$ | Cl | H | H | $CONH_2$ |
| Me | $CF_3$ | $CF_3$ | H | H | $NO_2$ |
| Me | $CF_3$ | $CF_3$ | H | H | $CO_2Et$ |
| Me | $CF_3$ | Cl | H | H | $CO_2Et$ |
| Me | $OCF_2H$ | $CF_3$ | H | H | CN |
| Me | $OCF_2H$ | $CF_3$ | H | H | H |
| Me | $OCF_2H$ | Cl | H | H | CN |
| Me | $OCF_2H$ | Cl | H | H | H |
| Me | $OCF_3$ | $CF_3$ | H | H | CN |
| Me | $OCF_3$ | $CF_3$ | H | H | H |

TABLE VIII

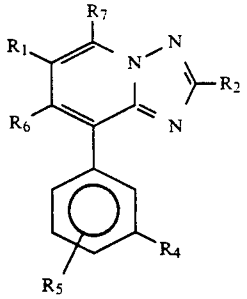

| $R_1$ | $R_2$ | $R_4$ | $R_5$ | $R_6$ | $R_7$ |
|---|---|---|---|---|---|
| Me | $CF_3$ | $CF_3$ | H | H | H |
| Me | $CF_3$ | Cl | H | H | H |
| Et | $CF_3$ | Cl | H | H | H |
| Et | $CF_3$ | $CF_3$ | H | H | H |
| H | $CF_3$ | $CF_3$ | H | H | CN |
| Me | SMe | Cl | H | H | H |
| Me | Cl | $CF_3$ | H | H | H |
| Me | SEt | $CF_3$ | H | H | H |
| Me | $CF_3$ | H | 3-$SCF_3$ | H | H |
| Me | $OCH_2CF_3$ | $CF_3$ | H | H | CN |
| Me | $OCH_2CF_3$ | $CF_3$ | H | H | H |
| Me | $CF_3$ | $CF_3$ | H | H | CN |
| Me | $CF_3$ | Cl | H | H | CN |
| Me | $CF_3$ | $CF_3$ | H | F | CN |
| Me | $CF_3$ | $CF_3$ | H | H | Br |
| Et | $CF_3$ | $CF_3$ | H | H | CN |
| n-propyl | $CF_3$ | $CF_3$ | H | H | CN |
| Me | $CF_3$ | $CF_3$ | H | H | F |
| n-propyl | $CF_3$ | $CF_3$ | H | H | H |
| Me | $CF_3$ | H | 3-CN | H | H |
| MeO | $CF_3$ | $CF_3$ | H | H | H |
| $F_2CH$ | $CF_3$ | Cl | H | H | H |
| Et | SMe | OMe | H | H | H |
| Me | $CF_3$ | $CF_3$ | H | F | H |
| Me | Cl | OMe | H | H | H |
| Me | $CF_3$ | Cl | H | F | H |
| isopropyl | $CF_3$ | Cl | H | H | H |
| MeS | $CF_3$ | Cl | H | H | H |
| $MeOCH_2$ | $CF_3$ | Cl | H | H | H |
| Me | $CF_3$ | H | 3-$SO_2CF_3$ | H | H |
| Me | $CF_3$ | H | 3-$SO_2Me$ | H | H |
| Et | Br | Cl | H | H | H |
| Me | $OCH_2CF_3$ | $CF_3$ | H | H | Cl |
| Me | $CF_3$ | Cl | H | H | $NO_2$ |
| Me | $CF_3$ | $CF_3$ | H | F | H |
| Me | Cl | $CF_3$ | H | H | CN |
| Et | Cl | $CF_3$ | H | H | CN |
| Et | Cl | $CF_3$ | H | H | N |
| Me | $SCHF_2$ | $CF_3$ | H | H | H |
| Et | $CF_3$ | H | 3-CN | H | H |
| Me | $SCHF_2$ | $CF_3$ | H | H | CN |
| Et | $CF_3$ | H | 3-$OCHF_2$ | H | H |
| Me | $CF_3$ | H | 3-$OCHF_2$ | H | CN |
| n-propyl | $CF_3$ | H | 3-$OCF_3$ | H | CN |
| $MeOCH_2$ | $CF_3$ | $CF_3$ | H | H | CN |
| Et | Br | $CF_3$ | H | H | H |
| Et | $CF_3$ | OMe | H | H | CN |
| Me | $CF_3$ | $CF_3$ | H | H | Me |
| Et | $CF_3$ | Cl | H | H | $CO_2Me$ |
| Me | $CF_3$ | H | 3-$OCH_2CF_3$ | H | CN |
| Me | $CF_3$ | H | 3-$SCF_3$ | H | CN |
| Et | $CF_3$ | H | 3-$SCHF_2$ | H | CN |
| $MeSCH_2$ | $CF_3$ | $CF_3$ | H | H | CN |
| Me | Cl | $CF_3$ | H | H | Cl |
| Et | $OCH_2CHF_2$ | $CF_3$ | H | H | CN |
| Me | Cl | $CF_3$ | H | H | $CF_3$ |
| MeNH | $CF_3$ | $CF_3$ | H | H | CN |
| $Me_2N$ | $CF_3$ | $CF_3$ | H | H | CN |
| Me | $SO_2CHF_2$ | $CF_3$ | H | H | CN |
| Me | $SO_2CH_3$ | $CF_3$ | H | H | CN |
| Me | $CF_3$ | H | 3-CN | H | CN |
| n-propyl | $CF_3$ | H | 3-CN | H | CN |
| Et | $CF_3$ | H | 3-SMe | H | CN |
| Et | Cl | H | 3-CN | H | H |
| Me | $SCHF_2$ | $CF_3$ | H | H | H |
| Me | $CF_3$ | Br | H | H | CN |

TABLE VIII-continued

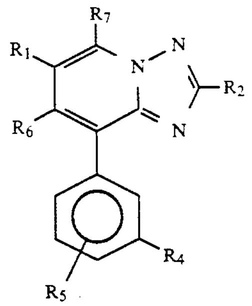

| $R_1$ | $R_2$ | $R_4$ | $R_5$ | $R_6$ | $R_7$ |
|---|---|---|---|---|---|
| HC≡C | $CF_3$ | $CF_3$ | H | H | CN |
| Me | $CF_3$ | H | 3-$SO_2CHF_2$ | H | CN |
| Me | $CF_3$ | Cl | 3-Cl | H | CN |
| Me | $CF_3$ | $CF_3$ | H | H | CN |
| Me | $CF_2Cl$ | $CF_3$ | H | H | CN |
| Et | $CHF_2$ | $CF_3$ | H | H | CN |
| $FCH_2CH_2$ | $CF_3$ | $CF_3$ | H | H | CN |
| Me | $OCH_2CF_3$ | H | H | H | H |
| Me | $CF_3$ | $CF_3$ | H | H | $CONH_2$ |
| Me | $CF_3$ | Cl | H | H | $CONH_2$ |
| Me | $CF_3$ | $CF_3$ | H | H | $NO_2$ |
| Me | $CF_3$ | $CF_3$ | H | H | $CO_2Et$ |
| Me | $CF_3$ | Cl | H | H | $CO_2Et$ |
| Me | $OCF_2H$ | $CF_3$ | H | H | CN |
| Me | $OCF_2H$ | $CF_3$ | H | H | H |
| Me | $OCF_2H$ | Cl | H | H | CN |
| Me | $OCF_2H$ | Cl | H | H | H |
| Me | $OCF_3$ | $CF_3$ | H | H | CN |
| Me | $OCF_3$ | $CF_3$ | H | H | H |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

| | Weight Percent* | | |
|---|---|---|---|
| | Active Ingredient | Diluent(s) | Surfactant(s) |
| Wettable Powders | 20-90 | 0-74 | 1-10 |
| Oil Suspensions, Emulsions, Solutions, (including Emulsifiable Concentrates) | 3-50 | 40-95 | 0-15 |
| Aqueous Suspension | 10-50 | 40-84 | 1-20 |
| Dusts | 1-25 | 70-99 | 0-5 |
| Granules and Pellets | 0.1-95 | 5-99.9 | 0-15 |
| High Strength Compositions | 90-99 | 0-10 | 0-2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138-140, 162-164, 166, 167 and 169-182;

H. Gysin and E. Knusli, U.S. Pat. No. 2,891,855, Jun. 23, 1959, Col. 3, line 66 through Col. 5, line 17 and Examples 1-4;

G. C. Klingman, "Weed Control as a Science", John Wiley and Sons, Inc., New York, 1961, pp. 81-96; and J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE A

| Wettable Powder | |
|---|---|
| 7-(3-chlorophenyl)-5-methyl-2-(trifluoromethyl)-1,2,4-triazolo[1,5-a]pyrimidine | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE B

| Wettable Powder | |
|---|---|
| 7-(3-chlorophenyl)-5-methyl-2-(trifluoromethyl)-1,2,4-triazolo[1,5-a]pyrimidine | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE C

| Granule | |
|---|---|
| Wettable Powder of Example 11 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE D

| Extruded Pellet | |
|---|---|
| 7-(3-chlorophenyl)-5-methyl-2-(trifluoromethyl)-1,2,4-triazolo[1,5-a]pyrimidine | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE E

| Low Strength Granule | |
|---|---|
| 7-(3-chlorophenyl)-5-methyl-2-(trifluoromethyl)-1,2,4-triazolo[1,5-a]Pyrimidine | 1% |
| N,N-dimethylformamide | 9% |
| attapulgite granules (U.S.S. 20 to 40 sieve) | 90% |

The active ingredient is dissolved in the solvent and the solution is sprayed upon dedusted granules in a double-cone blender. After spraying of the solution has been completed, the blender is allowed to run for a short period and then the granules are packaged.

EXAMPLE F

| Granule | |
|---|---|
| 7-(3-chlorophenyl)-5-methyl-2-(trifluoromethyl)-1, 2,4-triazolo[1,5-a]pyrimidine | 80% |
| wetting agent | 1% |
| crude ligninsulfonate salt (containing 5–20 of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE G

| Aqueous Suspension | |
|---|---|
| 7-(3-chlorophenyl)-5-methyl-2-(trifluoromethyl)-1,2,4-triazolo[1,5-a]pyrimidine | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE H

| High Strength Concentrate | |
|---|---|
| 7-(3-chlorophenyl)-5-methyl-2-(trifluoromethyl)-1,2,4-triazolo[1,5-a]Pyrimidine | 99% |
| silica aerogel | 0.5% |
| synthetic amorphous silica | 0.5% |

The ingredients are blended and ground in a hammermill to produce a material essentially all passing a U.S.S. No. 50 screen (0.3 mm opening). The concentrate may be formulated further if necessary.

EXAMPLE I

| Wettable Powder | |
|---|---|
| 7-(3-chlorophenyl)-5-methyl-2-(trifluoromethyl)-1,2,4-triazolo[1,5-a]pyrimidine | 90% |
| dioctyl sodium sulfosuccinate | 0.1% |
| synthetic fine silica | 9.9% |

The ingredients are blended and ground in a hammermill to produce particles essentially all below microns. The material is sifted through a U.S.S. No. 50 screen and then packaged.

EXAMPLE J

| Wettable Powder | |
|---|---|
| 7-(3-chlorophenyl)-5-methyl-2-(trifluoromethyl)-1,2,4-triazolo[1,5-a]pyrimidine | 40% |
| sodium ligninsulfonate | 20% |

-continued

| Wettable Powder | |
|---|---|
| montmorillonite clay | 40% |

The ingredients are thoroughly blended, coarsely hammer-milled and then air-milled to produce particles essentially all below 10 microns in size. The material is reblended and then packaged.

EXAMPLE K

| Oil Suspension | |
|---|---|
| 7-(3-chlorophenyl)-5-methyl-2-(trifluoromethyl)-1,2,4-triazolo[1,5-a]pyrimidine | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE L

| Dust | |
|---|---|
| 7-(3-chlorophenyl)-5-methyl-2-(trifluoromethyl)-1,2,4-triazolo[1,5-a]pyrimidine | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE M

| Oil Suspension | |
|---|---|
| 7-(3-chlorophenyl)-5-methyl-2-(trifluoromethyl)-1,2,4-triazolo[1,5-a]pyrimidine | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

Utility

Test results indicate that compounds of the present invention are highly active preemergent and/or postemergent herbicides or plant growth regulants. Many of the compounds have utility for pre- and/or postemergence broad-spectrum grass and broadleaf weed control in areas where complete control of all vegetation is desired, such as around storage tanks, industrial storage areas, parking lots, drive-in theaters, around billboards, highways, and railroad structures, and in fallow crop areas. Some compounds have utility in crops such as barley (Hordeum spp.), corn (Zea spp.), cotton (Gossypium spp.), pea (Pisum spp.), peanut (Arachis spp.), rape (Brassica spp.), rice (Oryza spp.), sorghum (Sorghum spp.), soybean (Glycine spp.), sugar beet (Beta spp ), sunflower (Helianthus spp.), triticale (Triticum-Secale spp.), and wheat (Triticum spp.). Some compounds are particularly useful for preemergence control of troublesome grass and selected small-seeded broadleaf weeds in barley, corn, cotton, rice, soybean, and wheat. In cereal crops such as barley, triticale, and wheat, some compounds are particularly useful for preemergence control of grass weeds such as blackgrass (*Alopecurus myosuroides*), foxtail (Setaria spp.), and wild oat (*Avena fatua*), and selected broadleaf weeds such as kochia (*Kochia scoparia*), lambsquarters (*Chenopodium album*), and wild buckwheat (*Polygonum convolvulus*). In rice, some compounds are particularly useful for the control of barnyardgrass (*Echinochloa crus-galli*). In cotton, some compounds are particularly useful for the control of barnyardgrass (*Echinochloa crus-galli*), bermudagrass (*Cynodon dactylon*), panicum (Panicum spp.), goosegrass (Eleusine spp.), crabgrass (Digitaria spp.), and pigweed (Amaranthus spp.).

In addition, many compounds of this invention are useful for the control of weeds in plantation crops such as banana, citrus crops, cocoa, coffee, palm, rubber, sugar cane, etc. Several of these compounds are also useful for weed control in fruit crops such as cranberries, apples, pears, cherries, etc. Several compounds of this invention are particularly useful for the control of troublesome grass weeds in sugar cane (Saccharum spp.). Alternatively, the subject compounds are useful to modify plant growth.

The rates of application for compounds of this invention are determined by a number of factors, including their use as plant growth modifiers or as herbicides, the crop species involved, the types of weeds to be controlled, weather and climate, formulations selected, mode of application, amount of foliage present, etc. In general terms, the subject compounds should be applied at levels of around 0.004 to 20 kg/ha, the lower rates being suggested for use on lighter soils and/or those having a low organic matter content, for plant growth modification or for situations where only short-term persistence is required, such as a herbicide for fallow land. Preferred rates of application are from 0.025 to 2.0 kg/ha. One skilled in the art can easily determine the application rate needed for the desired level of weed control.

The compounds of the invention may be used in combination with any other commercial herbicide, representative examples of which are those of the sulfonylurea, triazine, triazole, uracil, urea, amide, diphenyl ether, carbamate, imidazolinone, cineole and bipyridylium types. A partial listing follows:

| Common Name | Chemical Name |
|---|---|
| acetochlor | 2-chloro-N-(ethoxymethyl)-N-(2-ethyl-6-methylphenyl)acetamide |
| acifluorfen | 5-[2-chloro-4-(trifluoromethyl) phenoxy]-2-nitrobenzoic acid |
| acrolein | 2-propenal |
| alachlor | 2-chloro-N-(2,6-diethylphenyl)-N-(methoxy-methyl)acetamide |
| ametryn | N-ethyl-N'-(1-methylethyl)-6-(methylthio)-1,3,5-triazine-2,4-diamine |
| amitrole | 1H-1,2,4-triazol-3-amine |
| AMS | ammonium sulfamate |
| asulam | methyl [(4-aminophenyl)sulfonyl] carbamate |
| atrazine | 6-chloro-N-ethyl-N'-(1-methyl ethyl)-1,3,5-triazine-2,4-diamine |
| barban | 4-chloro-2-butynyl 3-chloro |

-continued

| Common Name | Chemical Name |
|---|---|
| | carbamate |
| benefin | N-butyl-N-ethyl-2,6-dinitro-4-(tri-fluoromethyl)benzenamine |
| bensulfuron methyl | 2-[[[[[(4,6-dimethoxy-2-pyrimi dinyl)amino]-methylcarbonyl]amino] sulfonyl]methyl]benzoic acid, methyl ester |
| bensulide | O,O-bis(1-methylethyl) S-[2-[(phenylsulfonyl)amino]ethyl] phosphorodithioate |
| bentazon | 3-(1-methylethyl)-(1H)-2,1,3-benzothia-diazin-4(3H)-one, 2,2-dioxide |
| benzofluor | N-[4-(ethylthio)-2-(trifluoro methyl)-phenyl]methanesulfonamide |
| benzoylprop | N-benzoyl-N-(3,4-dichlorophenyl)-DL-alanine |
| bifenox | methyl 5-(2,4-dichlorophenoxy)-2-nitrobenzoate |
| bromacil | 5-bromo-6-methyl-3-(1-methyl propyl)-2,4(1H,3H)pyrimidinedione |
| bromoxynil | 3,5-dibromo-4-hydroxybenzonitrile |
| butachlor | N-(butoxymethyl)-2-chloro-N-(2,6-diethyl-phenyl)acetamide |
| buthidazole | 3-[5-(1,1-dimethylethyl)-1,3,4-thia-diazol-2-yl]-4-hydroxy-1-methyl-2-imidazolidinone |
| butralin | 4-(1,1-dimethylethyl)-N-(1-methyl-propyl)-2,6-dinitrobenzenamine |
| butylate | S-ethyl bis(2-methylpropyl)-carbamothioate |
| cacodylic acid | dimethyl arsinic oxide |
| CDAA | 2-chloro-N,N-di-2-propenylacetamide |
| CDEC | 2-chloroallyl diethyldithiocarbamate |
| chloramben | 3-amino-2,5-dichlorobenzoic acid |
| chlorbromuron | 3-(4-bromo-3-chlorophenyl)-1-methoxy-1-methylurea |
| chlorimuron ethyl | 2-[[[[(4-chloro-6-methoxy-2-pyrimidinyl)amino]carbonyl]amino]-sulfonyl]benzoic acid, ethyl ester |
| chloroxuron | N'-[4-(4-Chlorophenoxy)phenyl]-N,N-dimethylurea |
| chlorpropham | 1-methylethyl 3-chlorophenylcarbamate |
| chlorsulfuron | 2-chloro-N-[[(4-methoxy-6-methyl-1,3,5-triazin-2-yl)amino]carbonyl]benzene-sulfonamide |
| chlortoluron | N'-(3-chloro-4-methylphenyl)-N,N-dimethylurea |
| cinmethylin | exo-1-methyl-4-(1-methylethyl)-2-[(2-methylphenyl)methoxy]-7-oxabicyclo-[2.2.1]heptane |
| clethodim | (E,E)-(±)-2-[1-[[(3-chloro-2-propenyl)-oxy]imino]propyl]-5-[2-(ethylthio)-propyl]-3-hydroxy-2-cyclohexen-1-one |
| clomazone | 2-[(2-chlorophenyl)methyl]-4,4-dimethyl-3-isoxazolidinone |
| cloproxydim | (E,E)-2-[1-[[(3-chloro-2-propenyl)oxy)-imino]butyl]-5-[2-(ethylthio)propyl]-3-hydroxy-2-cyclohexen-1-one |
| clopyralid | 3,6-dichloro-2-pyridinecarboxylic acid |
| CMA | calcium salt of MAA |
| cyanazine | 2-[[4-chloro-6-(ethylamino)-1,3,5-tri-azin-2-yl]amino]-2-methylpropanenitrile |
| cycloate | S-ethyl cyclohexylethylcarbamothioate |
| cycluron | 3-cyclooctyl-1,1-dimethylurea |
| cyperquat | 1-methyl-4-phenylpyridinium |
| cyprazine | 2-chloro-4-(cyclopropylamino)-6-(iso-propylamino)-s-triazine |
| cyprazole | N-[5-(2-chloro-1,1-dimethylethyl)-1,3,4-thiadiazol-2-yl]cyclopropanecarbox-amide |
| cypromid | 3',4'-dichlorocyclopropanecarboxanilide |
| dalapon | 2,2-dichloropropanoic acid |
| dazomet | tetrahydro-3,5-dimethyl-2H-1,3,5-thia-diazine-2-thione |
| DCPA | dimethyl 2,3,5,6-tetrachloro-1,4-benzene-dicarboxylate |
| desmediphan | ethyl [3-[[(phenylamino)carbonyl]oxy]-phenyl]carbamate |
| desmetryn | 2-(isopropylamino)-4-(methylamino)-6- |

-continued

| Common Name | Chemical Name |
|---|---|
| | (methylthio)-s-triazine |
| diallate | S-(2,3-dichloro-2-propenyl)bis(1-methylethyl)carbamothioate |
| dicamba | 3,6-dichloro-2-methoxybenzoic acid |
| dichlobenil | 2,6-dichlorobenzonitrile |
| dichlorprop | (±)-2-(2,4-dichlorophenoxy)-propanoic acid |
| dichlofop | (±)-2-[4-(2,4-dichlorophenoxy)-phenoxy]propanoic acid |
| diethatyl | N-(chloroacetyl)-N-(2,6-diethylphenyl)-glycine |
| difenzoquat | 1,2-dimethyl-3,5-diphenyl-1H-pyrazolium |
| dinitramine | $N^3$,$N^3$-diethyl-2,4-dinitro-6-(trifluoro-methyl)-1,3-benzenediamine |
| dinoseb | 2-(1-methylpropyl)-4,6-dinitrophenol |
| diphenamid | N,N-dimethyl-α-phenylbenzene-acetamide |
| dipropetryn | 6-(ethylthio)-N,N'-bis(1-methylethyl)-1,3,5-triazine-2,4-diamine |
| diquat | 6,7-dihydrodipyrido[1,2-a:2',1'-c]-pyrazinedium ion |
| diuron | N'-(3,4-dichlorophenyl)-N,N-dimethylurea |
| DNOC | 2-methyl-4,6-dinitrophenol |
| DPX-M6316 | 3-[[[[(4-methoxy-6-methyl-1,3,5-triazin-2-yl)amino]carbonyl]amino]sulfonyl]-2-thiophenecarboxylic acid, methyl ester |
| DSMA | disodium salt of MAA |
| endothall | 7-oxabicyclo[2.2.1]heptane-2,3-dicarbox-ylic acid |
| EPTC | S-ethyl dipropylcarbamothioate |
| ethalfluralin | N-ethyl-N-(2-methyl-2-propenyl)-2,6-dinitro-4-(trifluoromethyl)-benzenamin |
| ethofumesate | (±)-2-ethoxy-2,3-dihydro-3,3-dimethyl-5-benzofuranyl methanesulfonate |
| Express ® | 2-[[[N-(4-methoxy-6-methyl-1,3,5-triazine-2-yl)-N-methylamino]carbonyl]-amino]sulfonyl]benzoic acid, methyl ester |
| fenac | 2,3,6-trichlorobenzeneacetic acid |
| fenoxaprop | (±)-2-[4-[(6-chloro-2-benzoxazolyl)oxy]-phenoxy]propanoic acid |
| fenuron | N,N-dimethyl-N'-phenylurea |
| fenuron TCA | Salt of fenuron and TCA |
| flamprop | N-benzoyl-N-(3-chloro-4-fluorophenyl)-DL-alanine |
| fluazifop | (±)-2-[4-[[5-(trifluoromethyl)-2-pyri-dinyl]oxy]phenoxy]propanoic acid |
| fluazifop-P | (R)-2-[4-[[5-(trifluoromethyl)-2-pyri-dinyl]oxy]phenoxy]propanoic acid |
| fluchloralin | N-(2-chloroethyl)-2,6-dinitro-N-propyl-4-(trifluoromethyl)benzenamine |
| fluometuron | N,N-dimethyl-N'-[3-(trifluoromethyl)-phenyl]urea |
| fluorochlor-idone | 3-chloro-4-(chloromethyl)-1-[3-(tri-fluoromethyl)phenyl]-2-pyrrolidinone |
| fluorodifen | p-nitrophenyl α, α,α-trifluoro-2-nitro-p-tolyl ether |
| fluoroglycofen | carboxymethyl 5-[2-chloro-4-(tri-fluoromethyl)phenoxy]-2-nitrobenzoate |
| fluridone | 1-methyl-3-phenyl-5-[3-(trifluoro-methyl)phenyl]-4(1H)-pyridinone |
| fomesafen | 5-[2-chloro-4-(trifluoromethyl)phenoxy]-N-(methylsulfonyl)-2-nitrobenzamide |
| fosamine | ethyl hydrogen (aminocarbonyl)-phosphate |
| glyphosate | N-(phosphonomethyl)glycine |
| haloxyfop | 2-[4-[[3-chloro-5-(trifluoromethyl)-2-pyridinyl]oxy]phenoxy]propanoic acid |
| hexaflurate | potassium hexafluoroarsenate |
| hexazinone | 3-cyclohexyl-6-(dimethylamino)-1-methyl-1,3,5-triazine-2,4(1H,3H)-dione |
| imazamethabenz | 6-(4-isopropyl-4-methyl-5-oxo-2-imidazolin-2-yl)-m-toluic acid, methyl ester and 6-(4-isopropyl-4-methyl-5-oxo-2-imidazolin-2-yl)-p-toluic acid, methyl ester |
| imazapyr | (±)-2-[4,5-dihydro-4-methyl-4-(1- |

-continued

| Common Name | Chemical Name |
|---|---|
| | methylethyl)-5-oxo-1H-imidazol-2-yl]-3-pyridinecarboxylic acid |
| imazaquin | 2-[4,5-dihydro-4-methyl-4-(1-methylethyl)-5-oxo-1H-imidazol-2-yl]-3-quinolinecarboxylic acid |
| imazethapyr | (±)-2-[4,5-dihydro 4-methyl-4-(1-methylethyl)-5-oxo-1H-imidazol-2-yl]-5-ethyl-3-pyridinecarboxylic acid |
| ioxynil | 4-hydroxy-3,5-diiodobenzonitrile |
| isopropalin | 4-(1-methylethyl)-2,6-dinitro-N,N-dipropylbenzenamine |
| isoproturon | N-(4-isopropylphenyl)-N',N'-dimethylurea |
| isouron | N'-[5-(1,1-dimethylethyl)-3-isoxazolyl]-N,N-dimethylurea |
| isoxaben | N-[3-(1-ethyl-1-methylpropyl)-5-isoxazolyl]-2,6-dimethoxybenzamide |
| karbutilate | 3-[[(dimethylamino)carbonyl]amino]9 -phenyl-(1,1-dimethylethyl)carbamate |
| lactofen | (±)-2-ethoxy-1-methyl-2-oxoethyl 5-[2-chloro-4-(trifluoromethyl)phenoxy]-2-nitrobenzoate |
| lenacil | 3-cyclohexyl-6,7-dihydro-1H-cyclopenta-Pyrimidine-2,4(3H,5H)-dione |
| linuron | N'-(3,4-dichlorophenyl)-N-methoxy-N-methylurea |
| MAA | methylarsonic acid |
| MAMA | monoammonium salt of MAA |
| MCPA | (4-chloro-2-methylphenoxy)acetic acid |
| MCPB | 4-(4-chloro-2-methylphenoxy)butanoic acid |
| mecoprop | (±)-2-(4-chloro-2-methylphenoxy)-propanoic acid |
| mefluidide | N-[2,4-dimethyl-5-[[(trifluoromethyl)-sulfonyl]amino]phenyl]acetamide |
| methal-propalin | N-(2-methyl-2-propenyl)-2,6-dinitro-N-propyl-4-(trifluoromethyl)benzenamide |
| methabenz-thiazuron | 1,3-dimethyl-3-(2-benzothiazolyl)urea |
| metham | methylcarbamodithioic acid |
| methazole | 2-(3,4-dichlorophenyl)-4-methyl-1,2,4-oxadiazolidine-3,5-dione |
| methoxuron | N'-(3-chloro-4-methoxyphenyl)-N,N-dimethylurea |
| metolachlor | 2-chloro-N-(2-ethyl-6-methylphenyl)-N-(2-methoxy-1-methylethyl)acetamide |
| metribuzin | 4-amino-6-(1,1-dimethylethyl)-3-(methylthio)-1,2,4-triazin-5(4H)-one |
| metsulfuron methyl | 2-[[[[(4-methoxy-6-methyl-1,3,5-triazin-2-yl)amino]carbonyl]-amino]sulfonyl]benzoic acid, methyl ester |
| MH | 1,2-dihydro-3,6-pyridazinedione |
| molinate | S-ethyl hexahydro-1H-azepine-1-carbothioate |
| monolinuron | 3-(p-chlorophenyl)-1-methoxy-1-methylurea |
| monuron | N'-(4-chlorophenyl)-N,N-dimethylurea |
| monuron TCA | Salt of monuron and TCA |
| MSMA | monosodium salt of MAA |
| napropamide | N,N-diethyl-2-(1-naphthalenyloxy)-propanamide |
| naptalam | 2-[(1-naphthalenylamino)carbonyl]-benzoic acid |
| neburon | 1-butyl-3-(3,4-dichlorophenyl)-1-methylurea |
| nitralin | 4-(methylsulfonyl)-2,6-dinitro-N,N-dipropylaniline |
| nitrofen | 2,4-dichloro-1-(4-nitrophenoxy)benzene |
| nitrofluorfen | 2-chloro-1-(4-nitrophenoxy)-4-(trifluoromethyl)benzene |
| norea | N,N-dimethyl-N'-(octahydro-4,7-methano-1H-inden-5-yl)urea 3aα,-4α,5α,7α,7aα-isomer |
| norflurazon | 4-chloro-5-(methylamino)-2-[3-(trifluromethyl)phenyl]-3(2H)-pyridazinon |
| oryzalin | 4-(dipropylamino)-3,5-dinitrobenzenesulfonamide |
| oxadiazon | 3-[2,4-dichloro-5-(1-methylethoxy)-phenyl]-5-(1,1-dimethylethyl)-1,3,4-oxadiazol-2(3H)-one |

-continued

| Common Name | Chemical Name |
|---|---|
| oxyfluorfen | 2-chloro-1-(3-ethoxy-4-nitrophenoxy)-4-(trifluoromethyl)benzene |
| paraquat | 1,1'-dimethyl-4,4'-dipyridinium ion |
| pebulate | S-propyl butylethylcarbamothioate |
| pendimethalin | N-(1-ethylpropyl)-3,4-dimethyl-2,6-dinitrobenzenamine |
| perfluidone | 1,1,1-trifluoro-N-[2-methyl-4-(phenylsulfonyl)phenyl]methanesulfonamide |
| phenmedipham | 3-[(methoxycarbonyl)amino]phenyl (3-methylphenyl)carbamate |
| picloram | 4-amino-3,5,6-trichloro-2-pyridinecarboxylic acid |
| PPG-1013 | 5-[2-chloro-4-(trifluoromethyl)-phenoxy]-2-nitroacetophenone oxime-O-acetic acid, methyl ester |
| procyazine | 2-[[4-chloro-6-(cyclopropylamino)-1,3,5-triazine-2-yl]amino]-2-methylpropanenitrile |
| profluralin | N-(cyclopropylmethyl)-2,6-dinitro-N-propyl-4-(trifluoromethyl)benzenamine |
| prometon | 6-methoxy-N,N'-bis(1-methylethyl)-1,3,5-triazine-2,4-diamine |
| Prometryn | N,N'-bis(1-methylethyl)-6-(methylthio)-1,3,5-triazine-2,4-diamine |
| pronamide | 3,5-dichloro-N-(1,1-dimethyl-2-propynyl)benzamide |
| propachlor | 2-chloro-N-(1-methylethyl)-N-phenylacetamide |
| propanil | N-(3,4-dichlorophenyl)propanamide |
| propazine | 6-chloro-N,N'-bis(1-methylethyl)-1,3,5-triazine-2,4-diamine |
| propham | 1-methylethyl phenylcarbamate |
| prosulfalin | N-[[4-(dipropylamino)-3,5-dinitrophenyl]sulfonyl]-S,S-dimethylsulfilimine |
| prynachlor | 2-chloro-N-(1-methyl-2-propynyl)acetanilide |
| pyrazon | 5-amino-4-chloro-2-phenyl-3(2H)-pyridazinone |
| quizalofop ethyl | (±)-2-[4-[(6-chloro-2-quinoxalinyl)-oxy]phenoxy]propanoic acid, ethyl ester |
| secbumeton | N-ethyl-6-methoxy-N'-(1-methylpropyl)-1,3,5-triazine-2,4-diamine |
| sethoxydim | 2-[1-(ethoxyimino)butyl]-5-[2-(ethylthio)propyl]-3-hydroxy-2-cyclohexen-1-one |
| siduron | N-(2-methylcyclohexyl)-N'-phenylurea |
| simazine | 6-chloro-N,N'-diethyl-1,3,5-triazine-2,4-diamine |
| sulfometuron methyl | 2-[[[[(4,6-dimethyl-2-pyrimidinyl)-amino]carbonyl]amino]sulfonyl]-benzoic acid, methyl ester |
| TCA | trichloroacetic acid |
| tebuthiuron | N-[5-(1,1-dimethylethyl)-1,3,4-thiadiazol-2-yl]-N,N'-dimethylurea |
| terbacil | 5-chloro-3-(1,1-dimethylethyl)-6-methyl-2,4(1H,3H)-pyrimidinedione |
| terbuchlor | N-(butoxymethyl)-2-chloro-N-[2-(1,1-dimethylethyl)-6-methylphenyl]-acetamide |
| terbuthyl-azine | 2-(tert-butylamino)-4-chloro-6-(ethylamino)-s-triazine |
| terbutol | 2,6-di-tert-butyl-p-tolyl methylcarbamate |
| terbutryn | N-(1,1-dimethylethyl)-N'-ethyl-6-(methylthio)-1,3,5-triazine-2,4-diamine |
| thiobencarb | S-[(4-chlorophenyl)methyl] diethylcarbamothioate |
| triallate | S-(2,3,3-trichloro-2-propenyl) bis(1-methylethyl)carbamothioate |
| triclopyr | [(3,5,6-trichloro-2-pyridinyl)-oxy]acetic acid |
| tridiphane | 2-(3,5-dichlorophenyl)-2-(2,2,2-trichloroethyl)oxirane |
| trifluralin | 2,6-dinitro-N,N-dipropyl-4-(trifluoromethyl)benzenamine |
| trimeturon | 1-(p-chlorophenyl)-2,3,3-trimethylpseudourea |
| 2,4-D | (2,4-dichlorophenoxy)acetic acid |

-continued

| Common Name | Chemical Name |
|---|---|
| 2,4-DB | 4-(2,4-dichlorophenoxy)butanoic acid |
| vernolate | S-propyl dipropylcarbamothioate |
| xylachlor | 2-chloro-N-(2,3-dimethylphenyl)-N- |

-continued

| Common Name | Chemical Name |
|---|---|
| | (1-methylethyl)acetamide |

The herbicidal properties of the subject compounds were discovered in a number of greenhouse tests. The test procedures and results follow.

TABLE OF COMPOUNDS

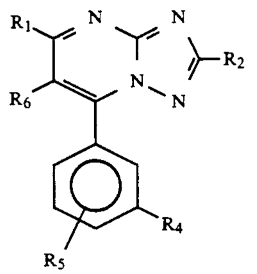

| CMPD | $R_1$ | $R_2$ | $R_4$ | $R_5$ | $R_6$ | m.p. °C. |
|---|---|---|---|---|---|---|
| 1 | Me | SMe | H | H | H | 76–79 |
| 2 | Me | $SO_2Me$ | H | H | H | 158–159 |
| 3 | Me | $CF_3$ | H | H | H | 106–108 |
| 4 | Me | $CF_3$ | H | 4-Cl | H | 147–148 |
| 5 | Me | $CF_3$ | OMe | H | H | 102–104 |
| 6 | $BrCH_2$ | $CF_3$ | OMe | H | H | 94–98 |
| 7 | $Br_2CH$ | $CF_3$ | OMe | H | H | 123–128 |
| 8 | Me | $CHF_2$ | $CF_3$ | H | H | 113–115 |
| 9 | Me | $CF_3$ | H | 2-Cl | H | 149–150 |
| 10 | $CF_3$ | $CF_3$ | H | H | H | 120–121 |
| 11 | Et | $CF_3$ | H | H | H | 99–101 |
| 12 | H | $CF_3$ | H | H | H | 138–142 |
| 13 | Me | $CF_3$ | F | H | H | 113 |
| 14 | Me | SOMe | H | H | H | 136–137 |
| 15 | Me | $CF_3$ | Cl | H | H | 115–116 |
| 16 | Me | $SCF_3$ | H | H | H | 91–93 |
| 17 | Me | $CF_2Cl$ | $CF_3$ | H | H | 115–117 |
| 18 | Me | $CF_3$ | H | 4-OMe | H | 102–104 |
| 19 | Me | Cl | H | H | H | 179–181 |
| 20 | Me | $CF_3$ | Me | H | H | 110–111 |
| 21 | Me | Br | H | H | H | 178–180 |
| 22 | Me | OMe | H | H | H | 136–137 |
| 23 | Me | $CF_3$ | $CF_3$ | H | H | 133–134 |
| 24 | Me | $CF_3$ | H | 2-Me | H | 109–110 |
| 25 | Me | $CF_3$ | Br | H | H | 110–112 |
| 26 | Me | $CF_3$ | OMe | 5-OMe | H | 137–139 |
| 27 | Me | $CF_3$ | OMe | 2-OMe | H | 152–153 |
| 28 | Me | $OCH_2CF_3$ | H | H | H | 103–104 |
| 29 | Me | $CF_3$ | Me | 4-Me | H | 149–150 |
| 30 | Me | SMe | Cl | H | H | 140–142 |
| 31 | Me | $SO_2Me$ | Cl | H | H | 162–163 |
| 32 | Me | $OCH_2CF_3$ | Cl | H | H | 156–157 |
| 33 | Me | $SCF_3$ | Cl | H | H | 90–93 |
| 34 | Me | Br | $CF_3$ | H | H | 129–130 |
| 35 | Me | $C_2F_5$ | $CF_3$ | H | H | 103–104 |
| 36 | Me | $OCH_2CF_3$ | $CF_3$ | H | H | 157–159 |
| 37 | Me | $C_2F_5$ | Cl | H | H | 107–108 |
| 38 | Me | $SCH_2CF_3$ | Cl | H | H | 98–99 |
| 39 | Me | $SO_2CH_2CF_3$ | Cl | H | H | 141–142 |
| 40 | Me | $OCH_2C_2F_5$ | $CF_3$ | H | H | 159–160 |
| 41 | OMe | $CF_3$ | H | H | H | 157–158 |
| 42 | Me | $OCH_2CCl_3$ | Cl | H | H | 155–157 |
| 43 | Me | $SCHF_2$ | Cl | H | H | 145–146 |
| 44 | Me | Cl | $CF_3$ | H | H | 140–141 |
| 45 | Me | Br | Cl | H | H | 166–167 |
| 46 | Me | $SCHF_2$ | $CF_3$ | H | H | 140–141 |
| 47 | Me | $SO_2CHF_2$ | $CF_3$ | H | H | 96–98 |
| 48 | Me | $SCF_3$ | $CF_3$ | H | H | 144–145 |
| 49 | Me | $OSO_2CF_3$ | Cl | H | H | 131–133 |
| 50 | Et | $CF_3$ | Cl | H | H | 96–98 |
| 51 | Me | $CF_3$ | H | 3-$NO_2$ | H | 206–208 |
| 52 | n-butyl | $CF_3$ | Cl | H | H | 66–69 |
| 53 | Et | $CF_3$ | $CF_3$ | H | H | 91–94 |
| 54 | n-butyl | $CF_3$ | $CF_3$ | H | H | 54–56 |
| 55 | Et | $CF_3$ | Br | H | H | 95–99 |
| 56 | Me | $CF_3$ | H | 3-CN | H | 185–189 |
| 57 | n-propyl | $CF_3$ | $CF_3$ | H | H | 66–69 |

TABLE OF COMPOUNDS-continued

| | | | | | | |
|---|---|---|---|---|---|---|
| 58 | Me | $CF_3$ | H | H | F | 99.5-100.5 |
| 59 | iso-propyl | $CF_3$ | $CF_3$ | H | H | 72-74 |
| 60 | SMe | $CF_3$ | $CF_3$ | H | H | 120-124 |
| 61 | Me | $CF_3$ | H | 3-$OCF_3$ | H | 115-117 |
| 62 | $NMe_2$ | $CF_3$ | $CF_3$ | H | H | 183-185 |
| 63 | OEt | $CF_3$ | $CF_3$ | H | H | 158-160 |
| 64 | OMe | $CF_3$ | $CF_3$ | H | H | 142-145 |
| 65 | SMe | $CF_3$ | Br | H | H | 116-118 |
| 66 | Me | SMe | $CF_3$ | H | H | 173-175 |
| 67 | Me | $CF_3$ | H | 3-$(CF_2)_3CF_3$ | H | 93-95 |
| 68 | Me | $OCH_2CHF_2$ | $CF_3$ | H | H | 136-137 |
| 69 | Me | $OCH(Me)CF_3$ | $CF_3$ | H | H | 177-178 |
| 70 | Et | $CF_3$ | Cl | 3-Cl | H | 185-190 |
| 71 | n-propyl | $CF_3$ | Cl | H | H | 86-88 |
| 72 | Me | $CF_3$ | H | 3-OPh | H | 167-170 |
| 73 | n-propyl | $CF_3$ | H | 3-CN | H | 109-110 |
| 74 | Et | $CF_3$ | H | 3-CN | H | 164-167 |
| 83 | Et | $CF_3$ | H | 3-$NMe_2$ | H | 88-90 |
| 84 | Et | $CF_3$ | H | 3-$OCHF_2$ | H | 103-105 |
| 85 | Me | $CF_3$ | H | 3-SMe | H | 95-100 |
| 86 | Me | $CF_3$ | H | 3-Ph | H | 165-173 |
| 87 | Me | $CF_3$ | H | 3-$OCHF_2$ | H | 96-99 |
| 88 | Me | $CF_3$ | H | 2-F | H | 112-115 |
| 89 | MeNH | $CF_3$ | $CF_3$ | H | H | 191-194 |
| 90 | MeNH | $CF_3$ | Br | H | H | 215-218 |
| 91 | Me | $CF_3$ | F | 2-F | H | 103-106 |
| 92 | n-butyl | $CF_3$ | H | H | H | 77-79 |
| 96 | $CF_3$ | $CF_3$ | $SCH_2Cl$ | H | H | 96-99 |
| 97 | $CH_3$ | $SCH_3$ | CN | H | H | 202-204 |
| 98 | $CH_2CH_3$ | $CF_3$ | $SCHF_2$ | H | H | oil |
| 99 | $CH_3$ | $CF_3$ | I | H | H | 93-95 |
| 100 | $CH_2CH3$ | $CF_3$ | $SCF_3$ | H | H | 63-68 |
| 101 | $CH_2CH_2CH_3$ | Br | $CF_3$ | H | H | 90-92 |
| 102 | $CH_2CH_3$ | $CF_3$ | $SO_2CHF_2$ | H | H | 136-140 |
| 103 | $CH_2CH_2CH_3$ | $OCH_2CF_3$ | $CF_3$ | H | H | 77-80 |
| 104 | $CH_3$ | $CF_3$ | $CF_2CF_3$ | H | H | 146-149 |
| 105 | $CH_2CH_3$ | $CF_3$ | $SCF_2CF_3$ | H | H | oil |
| 106 | $CH_2CH_3$ | $CF_3$ | $SO_2CF_2CF_3$ | H | H | wax |
| 109 | $CH_2CH_3$ | Br | Br | H | H | 132-135 |
| 110 | $CH_2CH_3$ | $OCH_2CF_3$ | Br | H | H | 93-95 |
| 111 | $CH_3$ | $CF_3$ | Cl | 2-$OCH_3$ | H | 102-105 |
| 112 | $CH_3$ | $CF_3$ | $CF_3$ | 6-F | H | 85-89 |
| 113 | $CH_3$ | Br | $OCF_3$ | H | H | 126-129 |
| 114 | $CH_2CH_3$ | Br | Cl | H | H | 130-133 |
| 115 | $CH_3$ | $OCH_2CF_3$ | $OCF_3$ | H | H | 141-143 |
| 116 | $CH_2CH_3$ | $OCH_2CF_3$ | Cl | H | H | oil |
| 117 | $CH_3$ | $OCH_3$ | $CF_3$ | H | H | 173-174 |
| 118 | $CH_3$ | $OCHF_2$ | $CF_3$ | H | H | 102 |

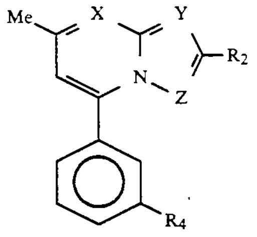

| CMPD | X | Y | Z | $R_2$ | $R_4$ | m.p. °C. |
|---|---|---|---|---|---|---|
| 75 | N | C—CN | N | $CF_3$ | H | 110-115 |
| 76 | N | C—CN | N | $CF_3$ | $CF_3$ | 125-126.5 |
| 94 | N | CH | N | $OCH_2CF_3$ | H | 101-103 |
| 95 | N | C—CN | N | $CF_3$ | Cl | 178-179 |
| 120 | CH | N | N | $CF_3$ | $CF_3$ | 83-84 |

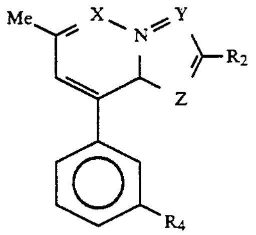

| | | | | | | |
|---|---|---|---|---|---|---|
| 77 | N | CH | N | $CF_3$ | H | 114-117.5 |
| 78 | N | C—Br | N | $CF_3$ | H | 132-135 |

TABLE OF COMPOUNDS-continued

| | | | | | | |
|---|---|---|---|---|---|---|
| 79 | N | CH | N | $CF_3$ | $CF_3$ | 122-123 |
| 80 | N | N | N | $CF_3$ | H | 108-110 |
| 81 | N | C—F | N | $CF_3$ | H | 120-123.5 |
| 82 | N | N | N | $CF_3$ | $CF_3$ | 134-135.5 |
| 107 | N | N | N | $CF_3$ | Cl | 123-126 |
| 108 | N | C—$CO_2Et$ | N | $CF_3$ | Cl | 92-94 |
| 119 | N | C—$CONH_2$ | N | $CF_3$ | Cl | 225-228 |

TEST A

Seeds of barley (*Hordeum vulgare*), barnyardgrass (*Echinochloa crus-galli*), cheatgrass, (*Bromus secalinus*), cocklebur (*Xanthium pensylvanicum*), corn (*Zea mays*), cotton, (*Gossypium hirsutum*), crabgrass (Digitaria spp.), giant foxtail (*Setaria faberi*), morningglory (Ipomoea spp.), rice (*Oryza sativa*), sorghum (*Sorghum bicolor*), soybean (*Glycine max*), sugar beet (*Beta volgaris*), velvetleaf (pi Abutilon theophrasti), wheat (*Triticum aestivum*), and wild oat (*Avena fatua*) and purple nutsedge (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated plants and controls were maintained in a greenhouse for approximately sixteen days, after which all species were compared to controls and visually evaluated. The ratings, summarized in Table A, are based on a scale of 0 to 10 where 0 is no effect and 10 is complete control. A dash (-) response means no test result.

TABLE A

POSTEMERGENCE

| | COMPOUND (2000 g/ha) | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 |
| Barley | — | — | 4 | 0 | 3 | 0 | 0 | 9 | 0 | 0 | 2 | 0 | 1 | 0 | 8 | 1 | 7 | 0 | 0 | 2 | 0 | 0 | 8 | 0 | 3 | 0 | 0 | 0 | 0 | 0 | 0 | 5 | — | 4 | 4 | 0 | 7 |
| Barnyardgrass | 0 | 0 | 6 | 0 | 9 | 0 | 0 | — | 0 | 0 | 9 | 2 | 8 | 1 | 9 | 5 | — | 0 | 0 | 7 | 0 | 0 | 9 | 2 | 9 | 0 | 0 | 9 | 0 | 2 | 0 | 9 | — | 9 | 9 | 4 | 9 |
| Cheatgrass | 0 | 0 | 0 | 0 | 7 | 0 | 0 | 8 | 0 | 0 | 2 | 0 | 2 | 0 | 8 | 2 | 8 | 0 | 0 | 2 | 0 | 0 | 8 | 0 | 8 | 0 | 0 | 2 | 0 | 0 | 2 | 9 | — | 3 | 5 | 0 | 4 |
| Cocklebur | 2 | 3 | 5 | 1 | 8 | 3 | 2 | 8 | 2 | 0 | 6 | 1 | 7 | 3 | 6 | 4 | 8 | 0 | 1 | 6 | 1 | 2 | 9 | 1 | 6 | 1 | 1 | 5 | 0 | 2 | 2 | 9 | — | 6 | 8 | 5 | 9 |
| Corn | 0 | 0 | 4 | 0 | 6 | 0 | 0 | 9 | 0 | 0 | 7 | 0 | 7 | 0 | 8 | 6 | 7 | 0 | 0 | 6 | 0 | 0 | 9 | 0 | 7 | 0 | 0 | 8 | 0 | 0 | 5 | 8 | — | 5 | 5 | 2 | 7 |
| Cotton | 2 | 6 | 7 | 2 | 9 | 9 | 7 | 10 | 4 | 0 | 7 | 1 | 10 | 7 | 10 | 9 | 10 | 0 | 1 | 9 | 0 | 0 | 9 | 5 | 10 | 1 | 1 | 5 | 0 | 1 | 7 | 10 | — | 10 | 10 | 9 | — |
| Crabgrass | 0 | 6 | 7 | 3 | 7 | 2 | 2 | 9 | 0 | 0 | 10 | 0 | 8 | 2 | 9 | 8 | — | 0 | 0 | 8 | 1 | 0 | 9 | 8 | 9 | 8 | 1 | 9 | 0 | 5 | 7 | 9 | — | 10 | 10 | 5 | 9 |
| Giant Foxtail | — | — | 7 | 0 | 9 | 0 | 0 | 9 | 0 | 0 | 8 | 0 | 8 | 2 | 9 | 6 | 9 | 0 | 0 | 5 | 2 | 0 | 9 | 9 | 9 | 7 | 2 | 9 | 1 | 6 | 8 | 9 | — | 9 | 9 | 3 | 10 |
| Morningglory | 5 | 5 | 7 | 5 | 8 | 3 | 6 | 9 | 5 | 0 | 7 | 2 | 9 | 3 | 9 | 8 | 9 | 1 | 2 | 3 | 6 | 1 | 9 | 9 | 9 | 1 | 3 | 8 | 1 | 5 | 7 | 9 | — | 8 | 9 | 7 | 10 |
| Nutsedge | 0 | 0 | 4 | 0 | 7 | 0 | 0 | 9 | 0 | 0 | 2 | 0 | 5 | 0 | 6 | 3 | 7 | 0 | 0 | — | 0 | 0 | 9 | — | 8 | 0 | 0 | 5 | 0 | 0 | 4 | 5 | — | 8 | 3 | 0 | 5 |
| Rice | 0 | 0 | 3 | 1 | 8 | 1 | 0 | 9 | 0 | 0 | 5 | 2 | 8 | 0 | 8 | 3 | 8 | 0 | 0 | 5 | 1 | 0 | 9 | 0 | 8 | 3 | 2 | 2 | 0 | 0 | 0 | 5 | — | 3 | 4 | 0 | 6 |
| Sorghum | 0 | 0 | 2 | 0 | 7 | 1 | 0 | 9 | 0 | 0 | 2 | 0 | 5 | 0 | 7 | 0 | 7 | 0 | 0 | 2 | 0 | 0 | 8 | 0 | 8 | 0 | 0 | 5 | 0 | 3 | 2 | 7 | — | 6 | 7 | 1 | 7 |
| Soybean | 3 | 8 | 7 | 3 | 8 | 8 | 2 | 9 | 7 | 3 | 9 | 2 | 9 | 4 | 9 | 9 | 9 | 0 | 6 | 9 | 6 | 6 | 9 | 6 | 9 | 4 | 2 | 9 | 3 | 5 | 8 | 9 | — | 10 | 10 | 7 | 9 |
| Sugar beet | 5 | 2 | 7 | 3 | 9 | 8 | 3 | 9 | 5 | 0 | 8 | 2 | 9 | 3 | 10 | 8 | 9 | 0 | 7 | 9 | 8 | 5 | 10 | 7 | 9 | 2 | 3 | 5 | 0 | 6 | 8 | 9 | — | 8 | 8 | 3 | 10 |
| Velvetleaf | 2 | 1 | 4 | 1 | 8 | 2 | 0 | 9 | 1 | 0 | 8 | 0 | 8 | 2 | 7 | 1 | 7 | 0 | 1 | 7 | 3 | 1 | 9 | 0 | 9 | 0 | 0 | 9 | 1 | 2 | 2 | 9 | — | 8 | — | 1 | 8 |
| Wheat | 0 | 0 | 3 | 0 | 3 | 0 | 0 | 8 | 0 | 0 | 0 | 0 | 1 | 0 | 7 | 1 | 7 | 0 | 0 | 1 | 0 | 0 | 8 | 0 | 8 | 0 | 0 | 1 | 0 | 0 | 0 | 3 | — | 2 | 3 | 0 | 6 |
| Wild oat | 0 | 0 | 3 | 0 | 7 | 0 | 0 | 9 | 0 | 0 | 3 | 0 | 6 | 0 | 9 | 4 | 7 | 0 | 0 | 6 | 0 | 0 | 9 | 2 | 9 | 0 | 0 | 8 | 0 | 0 | 0 | 9 | — | 10 | 10 | 3 | 9 |

| | COMPOUND (2000 g/ha) | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 |
| Barley | 1 | 0 | 4 | 0 | — | 3 | 4 | 1 | 6 | 1 | 3 | 1 | 7 | 0 | 0 | 8 | 1 | 6 | 1 | 5 | 0 | 0 | 3 | 7 | 2 | 1 | 0 | 0 | 1 | 0 | 8 | 8 | 0 |
| Barnyardgrass | 5 | 2 | 7 | 0 | — | 8 | 9 | 9 | 9 | 4 | 9 | 9 | 9 | 2 | 1 | 9 | 4 | 9 | 9 | 10 | 4 | 4 | 9 | 9 | 7 | 7 | 9 | 9 | 8 | 1 | 9 | 9 | 6 |
| Cheatgrass | 0 | 0 | 2 | 0 | — | 1 | 6 | 0 | 8 | 0 | 4 | 1 | 6 | 0 | 0 | 4 | 0 | 1 | 2 | 9 | 0 | 0 | 5 | 7 | 1 | 2 | 0 | 2 | 5 | 0 | 9 | 9 | 0 |
| Cocklebur | 5 | 1 | 7 | 1 | — | 8 | 8 | 5 | 8 | 7 | 7 | 7 | 8 | 0 | 5 | 8 | 5 | 3 | 8 | 9 | 3 | 1 | 8 | 8 | 2 | 8 | 6 | 7 | 5 | 0 | 9 | 8 | 3 |
| Corn | 4 | 1 | 5 | 0 | — | 4 | 8 | 5 | 7 | 1 | 5 | 6 | 8 | 0 | 0 | 8 | 1 | 6 | 7 | 7 | 3 | 0 | 4 | 7 | 4 | 2 | 1 | 4 | 6 | 0 | 8 | 7 | 0 |
| Cotton | 9 | 7 | 10 | 0 | — | 10 | 10 | 10 | 10 | 5 | 10 | 10 | 10 | 2 | 8 | 10 | 10 | 10 | 10 | 10 | 7 | 6 | 10 | 10 | 10 | 8 | 9 | 10 | 4 | 0 | 10 | 7 | 6 |
| Crabgrass | 8 | 0 | 9 | 0 | — | 10 | 10 | 9 | 9 | 8 | 9 | 9 | 9 | 5 | 2 | 9 | 3 | 9 | 10 | 10 | 9 | 5 | 10 | 9 | 8 | 9 | 8 | 9 | 10 | 5 | — | 9 | 3 |
| Giant Foxtail | 9 | 3 | 9 | 2 | — | 9 | 10 | 8 | 9 | 7 | 9 | 9 | 9 | 9 | 4 | 9 | 5 | 9 | 9 | 10 | 8 | 0 | 9 | 9 | 8 | 6 | 8 | 9 | 9 | 0 | 9 | 9 | 2 |
| Morningglory | 8 | 3 | 9 | 1 | — | 9 | 10 | 7 | 8 | 5 | 8 | 7 | 9 | 2 | 5 | 9 | 3 | 8 | 9 | 10 | 5 | 1 | 8 | 9 | 4 | 9 | 7 | 7 | 2 | 1 | 9 | 8 | 2 |
| Nutsedge | 0 | 0 | 2 | 0 | — | 3 | 8 | 3 | 7 | 0 | 5 | 4 | 7 | 0 | 0 | 7 | 0 | 5 | 7 | 7 | 1 | 0 | — | 7 | 3 | — | 0 | 0 | 0 | — | 8 | — | 0 |
| Rice | 1 | 0 | 5 | 0 | — | 1 | 5 | 4 | 8 | 2 | 5 | 4 | 6 | 0 | 0 | 8 | 1 | 3 | 6 | 9 | 1 | 0 | 2 | 8 | 3 | 2 | 0 | 3 | 4 | 0 | 8 | 6 | 0 |
| Sorghum | 1 | 0 | 4 | 0 | — | 5 | 7 | 3 | 8 | 2 | 6 | 5 | 9 | 0 | 0 | 8 | 5 | 6 | 8 | 9 | 0 | 0 | 4 | 9 | 4 | 1 | 0 | 3 | 2 | 0 | 8 | 7 | 0 |
| Soybean | 6 | 3 | 7 | 2 | — | 9 | 9 | 8 | 9 | 2 | 7 | 8 | 8 | 4 | 3 | 9 | 6 | 9 | 9 | 8 | 3 | 1 | 7 | 9 | 5 | 7 | 3 | 4 | 9 | 0 | 9 | 9 | 5 |
| Sugar beet | 9 | 3 | 9 | 2 | — | 10 | 10 | ·10 | 9 | 7 | 8 | 8 | 9 | 4 | 5 | 9 | 5 | 9 | 9 | 10 | 7 | 5 | 9 | 9 | 6 | 9 | 8 | 9 | 8 | 0 | 9 | 8 | 3 |
| Velvetleaf | 5 | 1 | 7 | 0 | — | 6 | 8 | 4 | 8 | 5 | 8 | 7 | 8 | 0 | 1 | 9 | 1 | 6 | 6 | 10 | 3 | 0 | 7 | 9 | 7 | 5 | 1 | 7 | 1 | 0 | 7 | 7 | 0 |
| Wheat | 0 | 0 | 1 | 0 | — | 1 | 4 | 2 | 5 | 2 | 2 | 2 | 7 | 0 | 0 | 8 | 0 | 5 | 1 | 5 | 0 | 0 | 3 | 7 | 1 | 1 | 0 | 2 | 0 | 0 | 5 | 5 | 0 |
| Wild oat | 4 | 1 | 6 | 0 | — | 6 | 8 | 2 | 9 | 1 | 8 | 7 | 9 | 0 | 0 | 9 | 3 | 8 | 7 | 9 | 2 | 1 | 7 | 10 | 4 | 7 | 5 | 8 | 5 | 0 | 9 | 8 | 2 |

| | COMPOUND (2000 g/ha) | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 94 | 95 | 96 | 97 | 98 | 99 | 100 | 101 | 102 | 103 | 104 |
| Barley | 5 | 1 | 9 | 9 | 5 | 5 | 0 | 0 | 1 | 1 | 0 | 6 | 0 | 6 | 0 | 0 | 8 | 0 | 7 | 6 | 1 | 0 | 0 | 1 | — | 0 | 2 | 2 | 5 | 4 | 0 | 3 | 2 |
| Barnyardgrass | 9 | 5 | 9 | 9 | 9 | 9 | 1 | 7 | 7 | 6 | 7 | 9 | 4 | 9 | 6 | 0 | 9 | 8 | 8 | 8 | 0 | 0 | 0 | 6 | — | 0 | 9 | 8 | 9 | 9 | 2 | 9 | 7 |
| Cheatgrass | 7 | 0 | 9 | 9 | 0 | 7 | 0 | 0 | 1 | 0 | 0 | 7 | 0 | 9 | 1 | 0 | 9 | 0 | 5 | 5 | 0 | 0 | 0 | 1 | — | 0 | 5 | 2 | 8 | 3 | 0 | 8 | 2 |
| Cocklebur | 7 | 5 | 9 | 8 | 6 | 10 | 1 | 2 | 5 | 4 | 2 | 8 | 6 | 9 | 6 | 3 | 9 | 5 | 7 | 7 | 4 | 3 | 1 | 6 | — | 1 | 7 | 8 | 9 | 8 | 7 | 8 | 6 |
| Corn | 6 | 2 | 10 | 9 | 6 | 7 | 0 | 0 | 1 | 3 | 1 | 4 | 3 | 9 | 3 | 0 | 9 | 6 | 7 | 7 | 2 | 1 | 0 | 4 | — | 2 | 7 | 7 | 7 | 5 | 2 | 4 | 3 |
| Cotton | 10 | 9 | 10 | 10 | 8 | 10 | 0 | 9 | 7 | 9 | 8 | 10 | 5 | 10 | 10 | 6 | 8 | 5 | 7 | 10 | 10 | 4 | 0 | 10 | — | 0 | 10 | 9 | 10 | 10 | 6 | 10 | 9 |
| Crabgrass | 9 | 4 | 10 | 10 | 10 | 10 | 3 | 3 | 9 | 9 | 9 | 9 | 4 | 10 | — | 1 | 10 | 9 | 9 | 9 | 10 | 5 | 2 | 9 | — | 5 | 9 | 9 | 10 | 9 | 4 | 9 | 8 |
| Giant Foxtail | 9 | 2 | 10 | 9 | 9 | 9 | 3 | 7 | 8 | 7 | 9 | 9 | 4 | 9 | 9 | 0 | 9 | 9 | 9 | 9 | 7 | 1 | 1 | 5 | — | 2 | 9 | 9 | 9 | 9 | 1 | 9 | 5 |
| Morningglory | 10 | 9 | 10 | 10 | 9 | 10 | 1 | 5 | 7 | 7 | 1 | 9 | 6 | 10 | 9 | 5 | 9 | 7 | 10 | 7 | 7 | 3 | 2 | 8 | — | 1 | 7 | 9 | 10 | 7 | 4 | 7 | 4 |

TABLE A-continued

| | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| Nutsedge | — | — | 9 | 9 | 2 | 3 | 0 | 0 | 0 | 0 | 0 | 1 | 1 | 9 | 2 | 0 | 9 | 5 | 5 | 5 | 0 | 0 | 0 | 3 | — | 0 | 3 | 7 | 3 | 8 | 0 | 5 | — |
| Rice | 3 | 1 | 9 | 8 | 3 | 5 | 0 | 0 | 1 | 0 | 1 | 5 | 1 | 10 | 4 | 0 | 9 | 1 | 7 | 6 | 0 | 0 | 0 | 1 | — | 0 | 3 | 2 | 4 | 4 | 0 | 3 | 3 |
| Sorghum | 6 | 1 | 9 | 9 | 6 | 7 | 0 | 0 | 1 | 2 | 2 | 6 | 1 | 9 | 1 | 0 | 9 | 0 | 6 | 6 | 0 | 0 | 0 | 4 | — | 0 | 6 | 2 | 7 | 4 | 0 | 5 | 2 |
| Soybean | 10 | 6 | 9 | 9 | 6 | 6 | 1 | 2 | 5 | 5 | 2 | 8 | 4 | 10 | 10 | 4 | 9 | 8 | 8 | 7 | 9 | 7 | 3 | 5 | — | 2 | 8 | 8 | 9 | 8 | 5 | 8 | 4 |
| Sugar beet | 9 | 8 | 10 | 10 | 9 | 10 | 0 | 6 | 9 | 9 | 9 | 10 | 7 | 10 | 10 | 6 | 9 | 8 | 9 | 9 | 7 | 5 | 0 | 8 | — | 3 | 9 | 10 | 10 | 9 | 7 | 9 | 9 |
| Velvetleaf | 8 | 5 | 7 | 5 | 2 | 7 | 2 | 2 | 2 | 1 | 5 | 8 | 5 | 9 | 2 | 2 | 9 | 2 | 7 | 7 | 2 | 2 | 0 | 4 | — | 0 | 7 | 8 | 9 | 7 | 1 | 9 | 3 |
| Wheat | 6 | 2 | 9 | 9 | 5 | 2 | 0 | 0 | 0 | 0 | 0 | 3 | 0 | 8 | 0 | 0 | 7 | 0 | 4 | 4 | 0 | 0 | 0 | 3 | — | 0 | 3 | 3 | 2 | 2 | 0 | 3 | 1 |
| Wild oat | 10 | 2 | 10 | 9 | 8 | 9 | 0 | 2 | 2 | 5 | 4 | 10 | 1 | 10 | 2 | 0 | 9 | 2 | 6 | 8 | 0 | 0 | 0 | 8 | — | 1 | 6 | 4 | 9 | 4 | 2 | 8 | 5 |

| | COMPOUND (2000 g/ha) | | | | | | | | | | | | | | COMPOUND (400 g/ha) | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|
| | 105 | 106 | 107 | 108 | 109 | 110 | 111 | 112 | 113 | 114 | 115 | 116 | 117 | 118 | 8 | 15 | 16 | 17 | 18 | 19 | 20 | 21 | 22 | 23 | 24 | 25 | 26 | 27 | 28 | 29 | 30 | 31 | 32 | 33 | 34 |
| Barley | 2 | 0 | 3 | — | 3 | 6 | 1 | 1 | 2 | — | — | — | 6 | 9 | 5 | 3 | 0 | 2 | 0 | 0 | 0 | 0 | 0 | 6 | 0 | 0 | 0 | 0 | 0 | 0 | 0 | 0 | 0 | 1 | 0 |
| Barnyardgrass | 8 | 2 | 9 | — | 9 | 9 | 7 | 7 | 9 | — | — | — | 9 | 9 | — | 6 | 1 | — | 0 | 0 | 1 | 0 | 0 | 9 | 0 | 7 | 0 | 0 | 5 | 0 | 1 | 1 | 8 | 3 | 6 |
| Cheatgrass | 2 | 0 | 0 | — | 6 | 4 | 4 | 2 | 9 | — | — | — | 1 | 9 | 3 | 3 | 0 | 1 | 0 | 0 | 0 | 0 | 0 | 6 | 0 | 1 | 0 | 0 | 0 | 0 | 0 | 0 | 2 | 5 | 2 |
| Cocklebur | 9 | 6 | 5 | — | 9 | 5 | 6 | 7 | 9 | — | — | — | 7 | 9 | 8 | 4 | 2 | 7 | 0 | 1 | 6 | 2 | 2 | 7 | 1 | 5 | 0 | 0 | 4 | 0 | 2 | 3 | 8 | 5 | 5 |
| Corn | 2 | 1 | 2 | — | 5 | 3 | 6 | 5 | 7 | — | — | — | 6 | 8 | 9 | 3 | 1 | 6 | 0 | 0 | 1 | 0 | 0 | 7 | 0 | 5 | 0 | 0 | 2 | 0 | 0 | 2 | 5 | 4 | 3 |
| Cotton | 10 | 10 | 9 | — | 9 | 9 | 9 | 10 | 10 | — | — | — | 8 | 10 | 4 | 9 | 4 | 10 | 0 | 0 | 8 | 0 | 0 | 9 | 1 | 9 | 0 | 0 | — | 0 | 1 | 4 | 4 | 6 | 5 |
| Crabgrass | 6 | 4 | 9 | — | 8 | 9 | 4 | 9 | 10 | — | — | — | 9 | 9 | — | 9 | 0 | — | 0 | 0 | 4 | 0 | 0 | 9 | 1 | 9 | 0 | 0 | 5 | 0 | 1 | 5 | 9 | 9 | 9 |
| Giant Foxtail | 2 | 1 | 5 | — | 8 | 4 | 3 | 7 | 9 | — | — | — | 9 | 9 | 9 | 5 | 0 | 9 | 0 | 0 | 1 | 0 | 0 | 9 | 0 | 9 | 1 | 0 | 7 | 0 | 3 | 6 | 9 | 9 | 9 |
| Morningglory | 7 | 1 | 8 | — | 8 | 8 | 9 | 9 | 9 | — | — | — | 8 | 10 | 8 | 9 | 7 | 7 | 0 | 1 | 2 | 4 | — | 9 | 2 | 8 | 0 | 1 | 7 | 0 | 2 | 7 | 9 | 8 | 7 |
| Nutsedge | — | 2 | 0 | — | — | 3 | 1 | 1 | 5 | — | — | — | 8 | 9 | 5 | 5 | 0 | 4 | 0 | 0 | — | 0 | 0 | 5 | 0 | 6 | 1 | 0 | 0 | 0 | 0 | 0 | 3 | 2 | 2 |
| Rice | 3 | 0 | 1 | — | 7 | 2 | 3 | 2 | 8 | — | — | — | 7 | 9 | 7 | 3 | 0 | 5 | 0 | 0 | 0 | 0 | 0 | 7 | 0 | 3 | — | 0 | 0 | 0 | 0 | 0 | 2 | 1 | 1 |
| Sorghum | 2 | 0 | 1 | — | 8 | 3 | 1 | 2 | 5 | — | — | — | 5 | 10 | 7 | 2 | 0 | 4 | 0 | 0 | 1 | 0 | 0 | 4 | 0 | 3 | 0 | 0 | 1 | 0 | 0 | 0 | 7 | 2 | 4 |
| Soybean | 6 | 4 | 5 | — | 8 | 7 | 8 | 8 | 9 | — | — | — | 8 | 9 | 9 | 9 | 8 | 9 | 0 | 5 | 7 | 5 | 2 | 9 | 3 | 7 | 0 | 3 | 7 | 1 | 5 | 5 | 9 | 8 | 10 |
| Sugar beet | 9 | 6 | 10 | — | 9 | 9 | 10 | 9 | 10 | — | — | — | 8 | 10 | 9 | 9 | 6 | 9 | 0 | 3 | 5 | 5 | 3 | 8 | 4 | 9 | 3 | 1 | 1 | 0 | 2 | 5 | 8 | 8 | 8 |
| Velvetleaf | 8 | 1 | 6 | — | 7 | 5 | 7 | 4 | 9 | — | — | — | 7 | 9 | 7 | 4 | 0 | 5 | 0 | 1 | 4 | — | 2 | — | 0 | 7 | 0 | 0 | 2 | 0 | 1 | — | 8 | 7 | 7 |
| Wheat | 2 | 0 | 3 | — | 3 | 3 | 0 | 1 | 1 | — | — | — | 1 | 9 | 1 | 4 | 0 | 1 | 0 | 0 | 0 | 0 | 0 | 4 | 0 | 2 | 0 | 0 | 0 | 0 | 0 | 0 | 0 | 1 | 0 |
| Wild oat | 6 | 2 | 5 | — | 7 | 9 | 3 | 5 | 7 | — | — | — | 4 | 10 | 8 | 6 | 1 | 6 | 0 | 0 | 2 | 0 | 0 | 8 | 0 | 7 | 0 | 0 | 2 | 0 | 0 | 0 | 7 | 2 | 4 |

| | COMPOUND (400 g/ha) | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 |
| Barley | 2 | 0 | 0 | 1 | 0 | 0 | 0 | 1 | 0 | 1 | 0 | 2 | 0 | 2 | 0 | 2 | 0 | 0 | 3 | 0 | 2 | 0 | 3 | 0 | 0 | 1 | 6 | 1 | 0 | 0 | 1 | 0 | 0 | 4 | 3 | 0 |
| Barnyardgrass | 9 | 3 | 8 | 2 | 0 | 3 | 0 | 4 | 3 | 6 | 4 | 9 | 0 | 9 | 9 | 8 | 0 | 2 | 9 | 4 | 7 | 8 | 9 | 0 | 1 | 7 | 9 | 5 | 5 | 0 | 7 | 2 | 0 | 9 | 9 | 2 |
| Cheatgrass | 4 | 0 | 0 | 0 | 0 | 1 | 0 | 0 | 0 | 2 | 0 | 1 | 0 | 2 | 0 | 3 | 0 | 0 | 2 | 0 | 0 | 0 | 5 | 0 | 0 | 1 | 1 | 0 | 0 | 0 | 0 | 0 | 0 | 8 | 3 | 0 |
| Cocklebur | 8 | 4 | 6 | 3 | 1 | 6 | 0 | 7 | 5 | 5 | 3 | 5 | 5 | 7 | 6 | 5 | 1 | 2 | 7 | 2 | 5 | 7 | 8 | 0 | 1 | 7 | 7 | 4 | 5 | 0 | 5 | 5 | 0 | 8 | 8 | 2 |
| Corn | 3 | 2 | 4 | 1 | 0 | 4 | 0 | 2 | 2 | 4 | 1 | 5 | 1 | 4 | 1 | 3 | 0 | 0 | 6 | 0 | 3 | 4 | 4 | 0 | 0 | 1 | 5 | 2 | 1 | 0 | 1 | 1 | 0 | 7 | 7 | 1 |
| Cotton | 10 | 5 | 9 | 7 | 2 | 8 | 0 | 10 | 10 | 9 | 8 | 10 | 5 | 10 | 7 | 10 | 0 | — | 10 | 10 | 10 | 9 | 10 | 3 | 7 | 10 | 10 | 9 | 9 | 5 | 9 | 3 | 0 | 4 | 8 | — |
| Crabgrass | 9 | 3 | 9 | 5 | 0 | 7 | 0 | 6 | 9 | 9 | 8 | 10 | 3 | 9 | 9 | 8 | 0 | 0 | 8 | 4 | 8 | 8 | 10 | 0 | 2 | 8 | 9 | 9 | 4 | 1 | 8 | 5 | 0 | 9 | 9 | 2 |
| Giant Foxtail | 9 | 5 | 9 | 5 | 0 | 9 | 0 | 8 | 8 | 9 | 5 | 9 | 2 | 9 | 9 | 9 | 3 | 2 | 9 | 6 | 9 | 8 | 9 | 0 | 0 | 5 | 9 | 8 | 2 | 0 | 6 | 6 | 0 | 9 | 9 | 2 |
| Morningglory | 8 | 6 | 9 | 7 | 1 | 7 | 1 | 8 | 6 | 10 | 8 | 7 | 2 | 7 | 7 | 8 | 1 | 2 | 7 | 2 | 7 | 8 | 10 | 1 | 1 | 7 | 8 | 1 | 4 | 2 | 5 | 2 | 1 | 8 | 8 | 4 |
| Nutsedge | 1 | 0 | 2 | 0 | 0 | 0 | 0 | 0 | 0 | 3 | 1 | — | 0 | 0 | 3 | — | 0 | 0 | 4 | 0 | 2 | 3 | 3 | 0 | 0 | 0 | 3 | 0 | — | 0 | 0 | 0 | — | 3 | 0 | 0 |
| Rice | 1 | 0 | 2 | 1 | 0 | 1 | 0 | 0 | 0 | 3 | 2 | 2 | 1 | 4 | 1 | 2 | 0 | 0 | 3 | 0 | 2 | 1 | 7 | 0 | 0 | 3 | 5 | 0 | 0 | 0 | 1 | 0 | 0 | 8 | 3 | 0 |
| Sorghum | 4 | 0 | 2 | 1 | 0 | 1 | 0 | 2 | 1 | 2 | 1 | 7 | 0 | 5 | 4 | 5 | 0 | 0 | 6 | 1 | 5 | 4 | 5 | 0 | 0 | 4 | 8 | 0 | 0 | 0 | 1 | 0 | 0 | 7 | 5 | 0 |
| Soybean | 10 | 4 | 8 | 5 | 1 | 6 | 0 | 6 | 7 | 9 | 8 | 8 | 1 | 6 | 6 | 8 | 2 | 3 | 9 | 2 | 8 | 9 | 8 | 2 | 1 | 5 | 9 | 2 | 7 | 1 | 5 | 6 | 0 | 9 | 10 | 3 |
| Sugar beet | 8 | 2 | 9 | 5 | 1 | 8 | 1 | 8 | 8 | 9 | 8 | 9 | 3 | 9 | 7 | 8 | 1 | 2 | 9 | 5 | 8 | 8 | 10 | 3 | 2 | 8 | 9 | 8 | 7 | 2 | 6 | 6 | 0 | 9 | 8 | 6 |
| Velvetleaf | 7 | 1 | 7 | 1 | 0 | 5 | 0 | 5 | 2 | 7 | 2 | 7 | 3 | 7 | 6 | 5 | 0 | 1 | 6 | 1 | 5 | 4 | 8 | 0 | 0 | 5 | 8 | 4 | 2 | 0 | 5 | 2 | 0 | 2 | 2 | 0 |
| Wheat | 1 | 0 | 0 | 0 | 0 | 0 | 0 | 0 | 0 | 2 | 0 | 2 | 0 | 1 | 0 | 1 | 0 | 0 | 3 | 0 | 1 | 0 | 2 | 0 | 0 | 1 | 2 | 0 | 0 | 0 | 2 | 0 | 0 | 2 | 4 | 0 |
| Wild oat | 5 | 3 | 6 | 3 | 0 | 3 | 0 | 3 | 2 | 3 | 2 | 7 | 1 | 8 | 7 | 8 | 0 | 0 | 8 | 1 | 6 | 4 | 6 | 0 | 0 | 5 | 8 | 3 | 3 | 0 | 6 | 2 | 0 | 7 | 9 | 2 |

| | COMPOUND (400 g/ha) | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 94 | 95 | 96 | 97 | 98 | 99 | 100 | 101 | 102 | 103 | 104 | 105 | 106 | 107 |
| Barley | 4 | 0 | 6 | 5 | — | 2 | 0 | 0 | 0 | 0 | 0 | 1 | 0 | 3 | 0 | 0 | 5 | 0 | 2 | 1 | 0 | 0 | 0 | 0 | 0 | 0 | 1 | 0 | 2 | — | 0 | 4 | 2 | 0 | 0 | 3 |
| Barnyardgrass | 8 | 5 | 9 | 9 | — | 9 | 0 | 5 | 3 | 1 | 4 | 9 | 3 | 9 | 1 | 0 | 9 | 0 | 6 | 7 | 0 | 0 | 0 | 5 | 0 | 0 | 3 | 1 | 7 | — | 1 | 4 | 2 | 7 | 0 | 3 |

TABLE A-continued

| | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| Cheatgrass | 4 | 0 | 5 | 0 | — | 2 | 0 | 0 | 0 | 0 | 0 | 2 | 0 | 7 | 0 | 0 | 3 | 0 | 4 | 0 | 0 | 0 | 0 | 0 | 0 | 0 | 2 | 0 | 6 | — | 0 | 7 | 0 | 0 | 0 | 2 |
| Cocklebur | 5 | 3 | 6 | 7 | — | 7 | 0 | 2 | 4 | 0 | 1 | 5 | 5 | 8 | 3 | 2 | 8 | 2 | 7 | 7 | 3 | 2 | 0 | 7 | 2 | 0 | 6 | 5 | 6 | — | 1 | 6 | 6 | 7 | 1 | 3 |
| Corn | 3 | 1 | 8 | 8 | — | 4 | 0 | 0 | 1 | 1 | 0 | 3 | 0 | 7 | 1 | 0 | 7 | 0 | 7 | 5 | 0 | 0 | 0 | 3 | 0 | 0 | 4 | 3 | 3 | — | 0 | 2 | 1 | 1 | 1 | 2 |
| Cotton | 10 | 5 | 10 | 9 | — | 10 | 0 | 2 | 5 | 1 | 1 | 10 | 5 | 10 | 8 | 5 | 8 | 2 | 10 | 9 | 4 | 4 | 0 | 8 | 3 | 0 | 9 | 8 | 0 | — | 3 | 8 | 9 | 10 | 6 | 8 |
| Crabgrass | 8 | 2 | 10 | 9 | — | — | 0 | 2 | 2 | 1 | 7 | 10 | 2 | 9 | — | 1 | 9 | 0 | 8 | 7 | 2 | 3 | 0 | 7 | 1 | 0 | 5 | 5 | 7 | — | 0 | 9 | 1 | 4 | 0 | 7 |
| Giant Foxtail | 3 | 1 | 9 | 9 | — | 9 | 0 | 5 | 3 | 1 | 2 | 9 | 2 | 9 | 2 | 0 | 9 | 0 | 9 | 8 | 0 | 0 | 0 | 3 | 1 | 0 | 4 | 0 | 3 | — | 0 | 3 | 0 | 0 | 0 | 2 |
| Morningglory | 10 | 3 | 10 | 7 | — | 9 | 0 | 2 | 4 | 1 | 0 | 10 | 4 | 9 | 8 | 3 | 9 | 5 | 7 | 6 | 2 | 2 | 1 | 6 | 2 | 1 | 7 | 8 | 9 | — | 2 | 5 | 4 | 4 | 1 | 5 |
| Nutsedge | 3 | 5 | 7 | 5 | — | 1 | 0 | 0 | 0 | 0 | 0 | — | 0 | 6 | 0 | 0 | — | 0 | 4 | 3 | 0 | 0 | 0 | 0 | 0 | 0 | 0 | 0 | 2 | — | 0 | 1 | 0 | 0 | — | 0 |
| Rice | 0 | 1 | 7 | 5 | — | 3 | 0 | 0 | 0 | 0 | 0 | 3 | 0 | 9 | 0 | 0 | 7 | 0 | 5 | 2 | 0 | 0 | 0 | 0 | 1 | 0 | 3 | 0 | 2 | — | 0 | 1 | 0 | 2 | 0 | 1 |
| Sorghum | 1 | 1 | 7 | 6 | — | 6 | 0 | 0 | 0 | 0 | 0 | 3 | 0 | 8 | 1 | 0 | 7 | 0 | 5 | 3 | 0 | 0 | 0 | 3 | 0 | 0 | 1 | 0 | 2 | — | 0 | 1 | 0 | 1 | 0 | 2 |
| Soybean | 9 | 4 | 9 | 9 | — | 4 | 0 | 1 | 3 | 1 | 2 | 5 | 2 | 9 | 5 | 2 | 9 | 7 | 6 | 6 | 6 | 3 | 1 | 6 | 2 | 2 | 8 | 7 | 7 | — | 3 | 8 | 4 | 4 | 2 | 5 |
| Sugar beet | 6 | 7 | 9 | 9 | — | 10 | 0 | 1 | 6 | 1 | 3 | 10 | 5 | 10 | 9 | 2 | 9 | 4 | 8 | 8 | 4 | 2 | 0 | 7 | 3 | 1 | 9 | 8 | 9 | — | 3 | 8 | 9 | 8 | 5 | 9 |
| Velvetleaf | 3 | 1 | 5 | 2 | — | 6 | 0 | 1 | 1 | 0 | 0 | 7 | 2 | 9 | 2 | 1 | 7 | 1 | 6 | 5 | 1 | 1 | 0 | 2 | 1 | 0 | 7 | 5 | 7 | — | 0 | 9 | 2 | 5 | 1 | 2 |
| Wheat | 1 | 0 | 2 | 7 | — | 1 | 0 | 0 | 0 | 0 | 0 | 2 | 0 | 1 | 0 | 0 | 3 | 0 | 4 | 1 | 0 | 0 | 0 | 1 | 1 | 0 | 1 | 0 | 1 | — | 0 | 0 | 0 | 0 | 0 | 0 |
| Wild oat | 8 | 3 | 7 | 8 | — | 8 | 0 | 0 | 2 | 0 | 2 | 7 | 0 | 9 | 0 | 0 | 7 | 0 | 6 | 5 | 0 | 0 | 0 | 5 | 1 | 0 | 3 | 3 | 6 | — | 0 | 5 | 2 | 3 | 0 | 5 |

| | COMPOUND (400 g/ha) | | | | | | | | | | |
|---|---|---|---|---|---|---|---|---|---|---|---|
| | 108 | 109 | 110 | 111 | 112 | 113 | 114 | 115 | 116 | 117 | 118 |
| Barley | 0 | 2 | 3 | 0 | 0 | 0 | — | — | — | 2 | 9 |
| Barnyardgrass | 0 | 3 | 6 | 2 | 3 | 3 | — | — | — | 9 | 9 |
| Cheatgrass | 0 | 0 | 2 | 1 | 1 | 5 | — | — | — | 1 | 9 |
| Cocklebur | 0 | 2 | 3 | 5 | 7 | 8 | — | — | — | 7 | 9 |
| Corn | 0 | 1 | 1 | 1 | 2 | 2 | — | — | — | 3 | 7 |
| Cotton | 0 | 8 | 9 | 9 | 9 | 8 | — | — | — | 7 | 10 |
| Crabgrass | 0 | 1 | 3 | 2 | 9 | 9 | — | — | — | 9 | 10 |
| Giant Foxtail | 0 | 2 | 1 | 1 | 6 | 8 | — | — | — | 9 | 9 |
| Morningglory | 0 | 4 | 3 | 8 | 7 | 8 | — | — | — | 3 | 10 |
| Nutsedge | — | 0 | 0 | 0 | 0 | 2 | — | — | — | 1 | — |
| Rice | 0 | 1 | 0 | 0 | 1 | 2 | — | — | — | 2 | 7 |
| Sorghum | 0 | 1 | 2 | 0 | 1 | 0 | — | — | — | 1 | 9 |
| Soybean | 0 | 7 | 6 | 7 | 7 | 8 | — | — | — | 9 | 9 |
| Sugar beet | 0 | 7 | 6 | 7 | 9 | 9 | — | — | — | 7 | 10 |
| Velvetleaf | 0 | 1 | 3 | 2 | 6 | 5 | — | — | — | 4 | 9 |
| Wheat | 0 | 0 | 0 | 0 | 0 | 0 | — | — | — | 0 | 4 |
| Wild oat | 0 | 1 | 5 | 1 | 2 | 3 | — | — | — | 2 | 9 |

PREEMERGENCE

| | COMPOUND (2000 g/ha) | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 |
| Barley | — | — | 0 | 0 | 9 | 0 | 0 | 8 | 0 | 0 | 8 | 0 | 8 | 0 | 7 | 4 | 7 | 0 | 0 | 0 | 0 | 0 | 7 | 1 | 8 | 1 | 1 | 2 | 0 | 1 | 2 | 6 | — |
| Barnyardgrass | 9 | 8 | 9 | 0 | 9 | 0 | 0 | 10 | 7 | 0 | 10 | 0 | 10 | 0 | 10 | 9 | 10 | 0 | 8 | 10 | 4 | 0 | 10 | 5 | 10 | 5 | 1 | 10 | 0 | 9 | 9 | 10 | — |
| Cheatgrass | 5 | 2 | 7 | 0 | 3 | 0 | 0 | 9 | 2 | 0 | 8 | 0 | 10 | 0 | 9 | 2 | 9 | 0 | 0 | 3 | 0 | 0 | 9 | 1 | 7 | 2 | 0 | 2 | 0 | 0 | 0 | 9 | — |
| Cocklebur | 2 | 3 | 0 | 0 | 0 | 0 | 2 | 8 | 1 | 0 | 3 | 0 | 6 | 0 | 5 | 2 | 4 | 0 | 0 | 0 | 1 | 0 | 2 | 3 | 1 | 0 | 1 | 4 | 0 | 0 | 4 | 5 | — |
| Corn | 4 | 6 | 5 | 0 | 9 | 0 | 0 | 9 | 4 | 0 | 8 | 0 | 7 | 0 | 7 | 5 | 7 | 0 | 0 | 2 | 0 | 0 | 8 | 6 | 7 | 2 | 4 | 9 | 0 | 0 | 6 | 8 | — |
| Cotton | 0 | 0 | 0 | 0 | 2 | 0 | 0 | 6 | 0 | 0 | 0 | 0 | 0 | 0 | 7 | 2 | 5 | 0 | 0 | 0 | 0 | 0 | 9 | 2 | 3 | 0 | 0 | 2 | 0 | 0 | 0 | 0 | — |
| Crabgrass | 9 | 8 | 10 | 3 | 9 | 8 | 0 | 10 | 9 | 0 | 10 | 0 | 10 | 0 | 10 | 10 | 10 | 3 | 9 | 10 | 9 | 5 | 9 | 8 | 10 | 9 | 9 | 10 | 0 | 9 | 9 | 9 | — |
| Giant Foxtail | — | — | 10 | 3 | 9 | 2 | 0 | 10 | 10 | 0 | 10 | 5. | 10 | 0 | 10 | 10 | 10 | 0 | 10 | 8 | 10 | 6 | 10 | 9 | 10 | 9 | 9 | 10 | 0 | 8 | 8 | 10 | — |
| Morningglory | 9 | 10 | 10 | 0 | 10 | 8 | 8 | 10 | 10 | 0 | 10 | 1 | 10 | 1 | 10 | 10 | 10 | 0 | 9 | 7 | 10 | 8 | 10 | 10 | 10 | 2 | 9 | 8 | 0 | 9 | 10 | 10 | — |
| Nutsedge | 2 | 3 | 0 | 0 | 3 | 0 | 0 | 7 | 4 | 0 | 5 | 0 | 9 | — | 8 | — | 3 | 0 | 0 | 0 | 0 | 0 | 6 | 2 | 4 | 0 | 0 | 3 | 0 | 0 | 7 | 5 | — |
| Rice | 2 | 3 | 7 | 0 | 5 | 0 | 0 | 9 | 1 | 0 | 5 | 0 | 4 | 0 | 6 | 5 | 7 | 0 | 0 | 4 | 0 | 0 | 8 | 3 | 6 | 0 | 0 | 5 | 0 | 0 | 5 | 4 | — |
| Sorghum | 1 | 2 | 7 | 0 | 9 | 0 | 0 | 10 | 3 | 0 | 9 | 0 | 10 | 0 | 8 | 6 | 9 | 0 | 0 | 5 | 0 | 0 | 10 | 5 | 9 | 2 | 1 | 7 | 0 | 0 | 7 | 9 | — |
| Soybean | 5 | 7 | 9 | 0 | 9 | 0 | 0 | 9 | 8 | 3 | 8 | 1 | 9 | 2 | 9 | 9 | 8 | 0 | 8 | 8 | 8 | 8 | 9 | 8 | 8 | 1 | 7 | 9 | 0 | 8 | 8 | 8 | — |
| Sugar beet | 5 | 10 | 10 | 0 | 10 | 3 | 4 | 10 | 10 | 0 | 10 | 5 | 10 | 0 | 10 | 9 | 10 | 0 | 9 | 10 | 9 | 8 | 10 | 10 | 10 | 2 | 8 | 10 | 0 | 9 | 9 | 10 | — |

TABLE A-continued

| | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| Velvetleaf | 2 | 4 | 10 | 0 | 10 | 6 | 1 | 10 | 9 | 0 | 7 | 0 | 10 | 0 | 10 | 9 | 10 | 0 | 5 | 10 | 7 | 3 | 10 | 9 | 10 | 0 | 0 | 7 | 0 | 2 | 8 | 10 | — |
| Wheat | 1 | 0 | 2 | 0 | 5 | 0 | 0 | 9 | 0 | 0 | 5 | 0 | 3 | 0 | 6 | 3 | 7 | 0 | 0 | 1 | 0 | 0 | 8 | 0 | 5 | 2 | 1 | 0 | 0 | 0 | 0 | 1 | — |
| Wild oat | 8 | 2 | 7 | 0 | 6 | 0 | 0 | 9 | 1 | 0 | 7 | 0 | 10 | 0 | 10 | 3 | 10 | 0 | 0 | 7 | 0 | 0 | 9 | 2 | 10 | 0 | 2 | 4 | 0 | 3 | 2 | 9 | — |

| | COMPOUND (2000 g/ha) | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 |
| Barley | 2 | 9 | 7 | 5 | 0 | 0 | 4 | 0 | — | 2 | 6 | 0 | 7 | 0 | 6 | 0 | 9 | 3 | 0 | 9 | 1 | 8 | 2 | 9 | 0 | 0 | 3 | 9 | 1 | 1 |
| Barnyardgrass | 10 | 10 | 10 | 10 | 9 | 0 | 9 | 1 | — | 9 | 10 | 9 | 10 | 0 | 10 | 10 | 10 | 9 | 5 | 10 | 8 | 10 | 10 | 10 | 9 | 6 | 10 | 10 | 7 | 8 |
| Cheatgrass | 4 | 10 | 8 | 9 | 2 | 0 | 5 | 0 | — | 7 | 6 | 2 | 9 | 0 | 10 | 2 | 9 | 5 | 3 | 10 | 2 | 10 | 10 | 10 | 0 | 0 | 7 | 10 | 4 | 3 |
| Cocklebur | 3 | 3 | 1 | 1 | 0 | 0 | 2 | 0 | — | 2 | 6 | 0 | — | — | 3 | 7 | 5 | 3 | 1 | 8 | 0 | 1 | 6 | 5 | 0 | 0 | 2 | 9 | 3 | 2 |
| Corn | 5 | 7 | 4 | 6 | 0 | 0 | 4 | 0 | — | 5 | 5 | 1 | 8 | 0 | 4 | 4 | 9 | 3 | 0 | 9 | 2 | 7 | 8 | 8 | 5 | 0 | 2 | 9 | 0 | 2 |
| Cotton | 1 | 9 | 6 | 9 | 0 | 7 | 8 | 0 | — | 4 | 5 | 4 | 1 | 0 | 8 | 1 | 10 | 6 | 3 | 8 | 0 | 5 | 10 | 8 | 0 | 0 | — | 7 | 2 | 9 |
| Crabgrass | 10 | 10 | 10 | 10 | 10 | 2 | 10 | 8 | — | 10 | 10 | 10 | 10 | 5 | 7 | 10 | 9 | 9 | 9 | 9 | 9 | 10 | 10 | 10 | 10 | 9 | 10 | 9 | 10 | 10 |
| Giant Foxtail | 10 | 10 | 9 | 10 | 9 | 7 | 10 | 9 | — | 10 | 10 | 10 | 10 | 4 | 7 | 10 | 10 | 9 | 8 | 10 | 9 | 10 | 10 | 10 | 10 | 9 | 10 | 9 | 9 | 10 |
| Morningglory | 10 | 10 | 10 | 9 | 9 | 0 | 7 | 1 | — | 9 | 10 | 10 | 9 | 5 | 10 | 10 | 10 | 10 | 5 | 10 | 6 | 10 | 10 | 10 | 10 | 5 | 10 | 10 | 9 | 6 |
| Nutsedge | 1 | 1 | 2 | 7 | 2 | 0 | 1 | 0 | — | 0 | 8 | 0 | 0 | 0 | 0 | 5 | 7 | 4 | 0 | 6 | 0 | 0 | 7 | 4 | 1 | 0 | 0 | 5 | 2 | 1 |
| Rice | 1 | 5 | 2 | 6 | 0 | 0 | 5 | 0 | — | 1 | 4 | 2 | 1 | 5 | 2 | 3 | 7 | 5 | 0 | 7 | 0 | 6 | 9 | 9 | 2 | 0 | 3 | 7 | 2 | 0 |
| Sorghum | 9 | 8 | 7 | 8 | 5 | 1 | 4 | 0 | — | 9 | 8 | 4 | 9 | 5 | 7 | 7 | 9 | 3 | 0 | 10 | 3 | 8 | 9 | 10 | 3 | 0 | 7 | 9 | 4 | 3 |
| Soybean | 8 | 7 | 7 | 5 | 1 | 0 | 5 | 0 | — | 7 | 8 | 8 | 4 | 4 | 6 | 8 | 9 | 8 | 0 | 9 | 1 | 7 | 10 | 8 | 8 | 0 | 2 | 8 | 6 | 0 |
| Sugar beet | 10 | 10 | 10 | 10 | 10 | 0 | 10 | 0 | — | 9 | 10 | 10 | 10 | 9 | 10 | 10 | 10 | 10 | 0 | 10 | 7 | 10 | 10 | 10 | 10 | 5 | 10 | 10 | 10 | 9 |
| Velvetleaf | 10 | 10 | 10 | 10 | 7 | 0 | 9 | 0 | — | 9 | 10 | 10 | 10 | 0 | 10 | 8 | 10 | 7 | 2 | 10 | 4 | 10 | 10 | 10 | 10 | 3 | 9 | 10 | 10 | 6 |
| Wheat | 1 | 4 | 3 | 5 | 0 | 0 | 1 | 0 | — | 3 | 2 | 1 | 7 | 0 | 2 | 0 | 9 | 1 | 0 | 7 | 0 | 6 | 9 | 9 | 1 | 0 | 2 | 9 | 1 | 0 |
| Wild oat | 4 | 10 | 7 | 9 | 1 | 0 | 9 | 0 | — | 8 | 7 | 4 | 9 | 1 | 9 | 2 | 9 | 2 | 0 | 9 | 7 | 9 | 8 | 10 | 3 | 0 | 10 | 10 | 2 | 8 |

| | COMPOUND (2000 g/ha) | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 94 | 95 | 96 |
| Barley | 1 | 3 | 2 | 0 | 9 | 6 | 0 | 9 | 0 | 9 | 6 | 4 | 5 | 0 | 0 | 0 | 2 | 0 | 7 | 0 | 6 | 0 | 0 | 8 | 1 | 2 | 3 | 0 | 0 | 0 | 4 | — |
| Barnyardgrass | 9 | 9 | 8 | 0 | 10 | 9 | 3 | 10 | 5 | 10 | 10 | 9 | 9 | 3 | 3 | 8 | 9 | 7 | 10 | 3 | 10 | 9 | 0 | 10 | 10 | 8 | 9 | 4 | 0 | 0 | 8 | — |
| Cheatgrass | 5 | 4 | 7 | 0 | 10 | 9 | 3 | 10 | 4 | 9 | 9 | 0 | 8 | 0 | 0 | 2 | 1 | 0 | 9 | 3 | 10 | 2 | 0 | 10 | 0 | 5 | 5 | 0 | 0 | 0 | 6 | — |
| Cocklebur | 2 | 3 | 1 | 0 | 7 | 8 | 0 | 0 | 0 | 8 | 9 | 1 | 5 | 0 | 0 | — | 1 | 7 | 0 | 0 | 7 | 2 | 0 | 5 | 3 | 6 | 2 | 1 | 4 | 0 | 1 | — |
| Corn | 0 | 2 | 6 | 0 | 8 | 6 | 1 | 7 | 0 | 9 | 7 | 6 | 5 | 0 | 0 | 2 | 3 | 1 | 3 | 0 | 7 | 3 | 0 | 9 | 7 | 7 | 4 | 3 | 0 | 0 | 2 | — |
| Cotton | 1 | 9 | 0 | 0 | 3 | 8 | 0 | 9 | 1 | 10 | 10 | 0 | 8 | 0 | 0 | 1 | 0 | 0 | 1 | 0 | 10 | 1 | 1 | 9 | — | 2 | 6 | — | 0 | 0 | 2 | — |
| Crabgrass | 9 | 9 | 9 | 4 | 10 | 10 | 8 | 10 | 5 | 10 | 10 | 10 | 10 | 7 | 9 | 10 | 9 | 10 | 10 | 5 | 10 | 9 | 4 | 10 | 10 | 10 | 10 | 9 | 7 | 8 | 9 | — |
| Giant Foxtail | 10 | 10 | 9 | 5 | 9 | 9 | 6 | 10 | 5 | 10 | 10 | 10 | 10 | 9 | 9 | 10 | 10 | 9 | 10 | 4 | 10 | 10 | 2 | 10 | 10 | 9 | 9 | 10 | 8 | 9 | 10 | — |
| Morningglory | 9 | 10 | 10 | 1 | 10 | 10 | 8 | 10 | 7 | 10 | 10 | 9 | 9 | 0 | 0 | 8 | 10 | 3 | 10 | 2 | 10 | 10 | 6 | 10 | 10 | 10 | 10 | 10 | 0 | 0 | 8 | — |
| Nutsedge | 0 | 3 | 0 | 0 | 5 | 1 | 0 | 3 | 0 | 5 | 6 | 3 | 2 | 0 | 0 | 2 | 0 | 0 | 1 | 0 | 5 | 3 | 0 | 5 | 5 | 5 | — | 1 | 0 | 0 | 10 | — |
| Rice | 0 | 4 | 1 | 0 | 6 | 2 | 0 | 5 | 1 | 8 | 7 | 1 | 0 | 0 | 0 | 1 | 2 | 0 | 3 | 0 | 6 | 2 | 0 | 8 | 4 | 5 | 4 | 2 | 0 | 0 | 1 | — |
| Sorghum | 2 | 5 | 4 | 0 | 10 | 8 | 2 | 9 | 1 | 10 | 10 | 7 | 8 | 0 | 0 | 3 | 1 | 5 | 7 | 1 | 8 | 5 | 0 | 10 | 7 | 8 | 7 | 3 | 0 | 0 | 7 | — |
| Soybean | 1 | 4 | 8 | 0 | 9 | 7 | 1 | 8 | 1 | 9 | 9 | 6 | 3 | 0 | 0 | 0 | 7 | 0 | 3 | 0 | 8 | 8 | 2 | 9 | 8 | 7 | 7 | 9 | 0 | 0 | 5 | — |
| Sugar beet | 10 | 8 | 10 | 0 | 10 | 10 | 5 | 10 | 7 | 10 | 10 | 10 | 10 | 0 | 0 | 8 | 9 | 6 | 10 | 5 | 10 | 10 | 10 | 10 | 10 | 10 | 10 | 9 | 0 | 0 | 9 | — |
| Velvetleaf | 9 | 9 | 8 | 0 | 10 | 10 | 2 | 10 | 7 | 10 | 10 | 10 | 10 | 0 | 2 | 4 | 8 | 0 | 10 | 0 | 10 | 5 | 5 | 10 | 10 | 10 | 10 | 10 | 1 | 0 | 3 | — |
| Wheat | 0 | 1 | 0 | 0 | 7 | 3 | 0 | 7 | 0 | 10 | 7 | 1 | 5 | 0 | 0 | 0 | 1 | 0 | 4 | 0 | 7 | 0 | 0 | 9 | 0 | 3 | 5 | 0 | 0 | 0 | 0 | — |
| Wild oat | 6 | 6 | 5 | 0 | 9 | 9 | 0 | 10 | 0 | 10 | 10 | 8 | 9 | 0 | 2 | 3 | 4 | 2 | 8 | 0 | 10 | 2 | 1 | 9 | 2 | 6 | 7 | 3 | 0 | 0 | 5 | — |

| | COMPOUND (2000 g/ha) | | | | | | | | | | | | | | | | | | | | | COMPOUND (400 g/ha) | | | | | | | | |
|---|---|---|---|---|---|---|---|---|---|---|---|---|---|---|---|---|---|---|---|---|---|---|---|---|---|---|---|---|---|---|
| | 97 | 98 | 99 | 100 | 101 | 102 | 103 | 104 | 105 | 106 | 107 | 108 | 109 | 110 | 111 | 112 | 113 | 114 | 115 | 116 | 117 | 118 | 8 | 15 | 16 | 17 | 18 | 19 | 20 | 21 | 22 |
| Barley | 0 | 4 | 4 | 7 | 5 | 0 | 5 | 0 | 2 | 0 | 7 | — | 7 | 9 | 1 | 5 | 2 | — | — | — | 2 | 9 | 6 | 4 | 0 | 2 | 0 | 0 | 0 | 0 | 0 |
| Barnyardgrass | 0 | 10 | 9 | 10 | 10 | 5 | 10 | 9 | 9 | 8 | 10 | — | 10 | 10 | 10 | 9 | 10 | — | — | — | 10 | 10 | 10 | 9 | 2 | 9 | 0 | 0 | 4 | 0 | 0 |
| Cheatgrass | 0 | 5 | 7 | 9 | 8 | 2 | 10 | 4 | 6 | 0 | 9 | — | 9 | 10 | 1 | 8 | 6 | — | — | — | 5 | 10 | 2 | 1 | 0 | 1 | 0 | 0 | 0 | 0 | 0 |
| Cocklebur | 0 | 1 | 0 | 2 | 2 | 1 | 2 | 0 | 2 | 0 | 0 | — | 9 | 8 | 5 | 1 | 10 | — | — | — | 6 | 10 | 1 | 0 | 0 | — | 0 | 0 | 0 | 0 | 0 |
| Corn | 0 | 5 | 2 | 3 | 5 | 1 | 3 | 1 | 1 | 4 | 5 | — | 6 | 6 | 2 | 5 | 7 | — | — | — | 6 | 7 | 7 | 3 | 2 | 2 | 0 | 0 | 1 | 0 | 0 |
| Cotton | 0 | 1 | 1 | 8 | 1 | 0 | 9 | 1 | — | 0 | 1 | — | 8 | 10 | 1 | 0 | 1 | — | — | — | 0 | 10 | 0 | 0 | 0 | 1 | 0 | 0 | 0 | 0 | 0 |
| Crabgrass | 6 | 10 | 10 | 10 | 10 | 10 | 10 | 10 | 10 | 8 | 10 | — | 10 | 10 | 10 | 10 | 10 | — | — | — | 9 | 10 | 10 | 10 | 9 | 10 | 0 | 5 | 8 | 8 | 0 |

TABLE A-continued

| | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| Giant Foxtail | 4 | 10 | 10 | 10 | 10 | 10 | 10 | 10 | 10 | 9 | 10 | — | 10 | 10 | 10 | 10 | 10 | — | — | — | 10 | 10 | 10 | 10 | 10 | 10 | 0 | 1 | 2 | 7 | 0 |
| Morningglory | 5 | 10 | 10 | 10 | 10 | 10 | 9 | 9 | 8 | 4 | 8 | — | 10 | 10 | 10 | 10 | 10 | — | — | — | 10 | 10 | 10 | 10 | 8 | 9 | 0 | 0 | 5 | 1 | 3 |
| Nutsedge | 0 | 0 | 1 | 2 | 3 | 2 | 1 | 0 | 0 | 0 | 2 | — | 10 | 2 | 5 | 0 | 3 | — | — | — | 5 | 3 | 4 | 0 | 0 | 1 | 0 | 0 | 0 | 0 | 0 |
| Rice | 0 | 5 | 1 | 1 | 6 | 0 | 0 | 2 | 2 | 0 | 1 | — | 7 | 6 | 5 | 4 | 4 | — | — | — | 4 | 7 | 7 | 5 | 0 | 3 | 0 | 0 | 0 | 0 | 0 |
| Sorghum | 0 | 7 | 8 | 7 | 7 | 4 | 7 | 3 | 5 | 0 | 7 | — | 8 | 8 | 5 | 5 | 10 | — | — | — | 9 | 9 | 8 | 5 | 0 | 7 | 0 | 0 | 0 | 0 | 0 |
| Soybean | 7 | 8 | 6 | 8 | 8 | 7 | 7 | 2 | 2 | 0 | 4 | — | 9 | 7 | 9 | 5 | 9 | — | — | — | 9 | 9 | 9 | 4 | 2 | 2 | 0 | 3 | 2 | 2 | 1 |
| Sugar beet | 9 | 10 | 10 | 10 | 10 | 10 | 10 | 10 | 10 | 9 | 10 | — | 10 | 10 | 10 | 10 | 10 | — | — | — | 10 | 10 | 9 | 10 | 8 | 9 | 0 | 2 | 4 | 0 | 1 |
| Velvetleaf | 1 | 10 | 9 | 10 | 10 | 7 | 9 | 10 | 7 | 6 | 10 | — | 10 | 10 | 10 | 8 | 10 | — | — | — | 10 | 10 | 10 | 10 | 0 | 8 | 0 | 0 | 6 | 1 | 0 |
| Wheat | 0 | 1 | 1 | 3 | 3 | 0 | 5 | 0 | 0 | 0 | 1 | — | 4 | 6 | 0 | 5 | 2 | — | — | — | 7 | 10 | 5 | 3 | 0 | 2 | 0 | 0 | 0 | 0 | 0 |
| Wild oat | 0 | 7 | 8 | 9 | 8 | 0 | 10 | 5 | 6 | 0 | 9 | — | 9 | 10 | 2 | 7 | 7 | — | — | — | 9 | 10 | 6 | 3 | 0 | 5 | 0 | 0 | 1 | 0 | 0 |

| | COMPOUND (400 g/ha) | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| | 23 | 24 | 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 |
| Barley | 1 | 0 | 2 | 0 | 0 | 0 | 0 | 0 | 0 | 4 | 1 | 0 | 6 | 1 | 3 | 0 | 0 | 1 | 0 | 0 | 0 | 1 | 0 | 6 | 0 | 3 | 0 | 7 | 0 | 0 | 7 | 0 | 6 |
| Barnyardgrass | 10 | 0 | 9 | 0 | 0 | 9 | 0 | 1 | 2 | 9 | 9 | 9 | 9 | 7 | 10 | 4 | 0 | 8 | 0 | 5 | 9 | 9 | 2 | 10 | 0 | 10 | 7 | 9 | 2 | 3 | 10 | 3 | 9 |
| Cheatgrass | 5 | 0 | 3 | 0 | 0 | 0 | 0 | 0 | 0 | 3 | 3 | 0 | 5 | 0 | 7 | 0 | 0 | 2 | 0 | 6 | 1 | 0 | 0 | 7 | 0 | 6 | 0 | 7 | 2 | 0 | 9 | 0 | 5 |
| Cocklebur | 0 | 0 | 0 | 0 | 0 | 1 | 0 | 0 | 0 | 2 | 2 | 0 | 0 | 0 | 0 | 0 | 0 | 0 | 0 | 0 | 0 | 2 | 2 | — | 0 | 3 | 0 | 0 | 0 | 0 | 2 | 0 | 0 |
| Corn | 5 | 0 | 6 | 0 | 0 | 1 | 0 | 0 | 2 | 5 | 3 | 1 | 3 | 0 | 1 | 0 | 0 | 1 | 0 | 0 | 2 | 3 | 0 | 3 | 0 | 2 | 3 | 8 | 0 | 0 | 8 | 0 | 6 |
| Cotton | 3 | 0 | 0 | 0 | 0 | — | 0 | 0 | 0 | 0 | 1 | 0 | 3 | 1 | 0 | 0 | 0 | 5 | 0 | 0 | 1 | 0 | 0 | — | 0 | 4 | 0 | 0 | 1 | 0 | 3 | 0 | 0 |
| Crabgrass | 9 | 5 | 10 | 6 | 0 | 9 | 0 | 5 | 8 | 9 | 9 | 9 | 10 | 10 | 10 | 9 | 0 | 9 | 3 | 8 | 10 | 10 | 10 | 10 | 2 | 10 | 10 | 9 | 9 | 8 | 9 | 5 | 9 |
| Giant Foxtail | 10 | 8 | 10 | 7 | 4 | 10 | 0 | 5 | 4 | 9 | 10 | 9 | 10 | 9 | 10 | 9 | 1 | 10 | 7 | 9 | 9 | 10 | 10 | 10 | 2 | 10 | 9 | 10 | 8 | 8 | 10 | 5 | 10 |
| Morningglory | 10 | 3 | 10 | 0 | 0 | 5 | 0 | 3 | 3 | 10 | 8 | 6 | 9 | 10 | 8 | 7 | 0 | 7 | 0 | 7 | 8 | 10 | 10 | 10 | 0 | 8 | 9 | 10 | 3 | 1 | 10 | 0 | 10 |
| Nutsedge | 3 | 0 | 0 | 0 | 0 | 0 | 0 | 0 | 0 | 2 | 1 | 0 | 0 | 0 | 4 | — | 0 | 0 | 0 | 0 | 0 | 1 | 0 | 0 | 0 | 0 | 1 | 3 | 0 | 0 | 3 | 0 | 0 |
| Rice | 5 | 0 | 5 | 0 | 0 | 0 | 0 | 0 | 1 | 1 | 0 | 0 | 1 | — | 1 | 0 | 0 | 2 | 0 | 1 | 1 | 1 | 1 | 0 | 2 | 0 | 0 | 2 | 0 | 0 | 5 | 0 | 4 |
| Sorghum | 8 | 0 | 5 | 0 | 0 | 3 | 0 | 0 | 2 | 8 | 3 | 4 | 6 | 1 | 6 | 0 | 0 | 2 | 0 | 5 | 6 | 2 | 0 | 8 | 1 | 3 | 3 | 8 | 0 | 0 | 8 | 0 | 7 |
| Soybean | 8 | 5 | 4 | 0 | 0 | 3 | 0 | 0 | 6 | 7 | 2 | 3 | 7 | 3 | 1 | 0 | 0 | 2 | 0 | 0 | 5 | 6 | 7 | 3 | 0 | 2 | 2 | 4 | 0 | 0 | 5 | 0 | 3 |
| Sugar beet | 10 | 8 | 10 | 0 | 0 | 5 | 0 | 0 | 0 | 8 | 10 | 10 | 10 | 6 | 9 | 1 | 0 | 10 | 0 | 2 | 2 | 10 | 8 | 10 | 6 | 10 | 9 | 9 | 7 | 0 | 10 | 0 | 10 |
| Velvetleaf | 10 | 1 | 7 | 0 | 0 | 2 | 0 | 0 | 0 | 8 | 5 | 8 | 9 | 4 | 7 | 0 | 0 | 5 | 0 | 6 | 7 | 10 | 9 | 9 | 0 | 10 | 0 | 10 | 2 | 0 | 10 | 0 | 8 |
| Wheat | 3 | 0 | 1 | 0 | 0 | 0 | 0 | 0 | 0 | 1 | 0 | 0 | 1 | 0 | 0 | 0 | 0 | 0 | 0 | 0 | 0 | 0 | 0 | 2 | 0 | 0 | 0 | 6 | 0 | 0 | 2 | 0 | 1 |
| Wild oat | 9 | 0 | 7 | 0 | 0 | 0 | 0 | 1 | 0 | 6 | 4 | 0 | 9 | 1 | 5 | 0 | 0 | 5 | 0 | 0 | 0 | 3 | 0 | 7 | 0 | 8 | 0 | 8 | 0 | 0 | 8 | 0 | 7 |

| | COMPOUND (400 g/ha) | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
| Barley | 0 | 6 | 0 | 0 | 2 | 7 | 0 | 0 | 0 | 0 | 0 | 0 | 3 | 4 | 0 | 3 | 0 | 5 | 4 | — | 3 | 0 | 0 | 0 | 0 | 0 | 3 | 0 | 4 | 0 | 0 | 2 | 0 |
| Barnyardgrass | 10 | 10 | 0 | 0 | 8 | 10 | 4 | 8 | 1 | 8 | 2 | 0 | 9 | 9 | 2 | 10 | 3 | 10 | 10 | — | 9 | 0 | 0 | 5 | 3 | 1 | 9 | 0 | 10 | 1 | 0 | 10 | 2 |
| Cheatgrass | 0 | 9 | 0 | 0 | 7 | 8 | 0 | 2 | 2 | 1 | 1 | 0 | 7 | 8 | 0 | 10 | 0 | 4 | 8 | — | 5 | 0 | 0 | 0 | 0 | 0 | 5 | 0 | 8 | 0 | 0 | 3 | 0 |
| Cocklebur | 3 | 2 | 0 | 0 | 0 | 2 | — | 0 | 0 | — | 0 | 0 | 5 | 5 | 0 | 0 | 1 | 2 | 2 | — | 5 | 0 | 0 | 0 | 0 | 0 | 0 | 0 | 1 | 0 | 0 | 0 | 0 |
| Corn | 5 | 4 | 0 | 0 | 1 | 4 | 1 | 1 | 1 | 0 | 3 | 0 | 5 | 4 | 1 | 4 | 0 | 6 | 6 | — | 2 | 0 | 0 | 1 | 0 | 0 | 2 | 0 | 5 | 0 | 0 | 7 | 0 |
| Cotton | 1 | 0 | 0 | 0 | 0 | 4 | 1 | 0 | 0 | — | 0 | 0 | 2 | 10 | 0 | 2 | 0 | 9 | 3 | — | 6 | 0 | 0 | 0 | 0 | 0 | 0 | 0 | 3 | 0 | 0 | 3 | 0 |
| Crabgrass | 10 | 10 | 9 | 5 | 10 | 9 | 9 | 10 | 9 | 9 | — | 1 | 10 | 10 | 9 | 10 | 1 | 10 | 10 | — | 10 | 2 | 6 | 9 | 9 | 9 | 10 | 0 | 10 | 3 | 2 | 10 | 9 |
| Giant Foxtail | 10 | 10 | 8 | 1 | 9 | 10 | 8 | 10 | 9 | — | 8 | 2 | 9 | 9 | 4 | 10 | 1 | 10 | 10 | — | 10 | 3 | 6 | 9 | 9 | 9 | 10 | 0 | 10 | 2 | 0 | 9 | 10 |
| Morningglory | 10 | 8 | 5 | 0 | 9 | 9 | 3 | 5 | 0 | 7 | 5 | 0 | 10 | 9 | 5 | 9 | 3 | 10 | 10 | — | 8 | 0 | 0 | 2 | 2 | 0 | 7 | 0 | 10 | 9 | 1 | 10 | 6 |
| Nutsedge | — | 0 | 0 | 0 | 0 | 3 | 0 | 0 | 0 | 0 | 0 | 0 | 2 | 0 | 0 | 1 | 0 | 3 | 2 | — | 0 | 0 | 0 | 0 | 0 | 0 | 0 | 0 | 4 | 0 | 0 | 3 | 0 |
| Rice | 1 | 4 | 0 | 0 | 0 | 2 | 1 | 0 | 0 | 0 | 0 | 0 | 2 | 3 | 0 | 4 | 0 | 6 | 3 | — | 0 | 0 | 0 | 0 | 0 | 0 | 0 | 0 | 3 | 0 | 0 | 4 | 1 |
| Sorghum | 2 | 7 | 0 | 0 | 7 | 7 | 3 | 2 | 1 | 2 | 1 | 0 | 8 | 8 | 0 | 6 | 0 | 8 | 7 | — | 5 | 0 | 0 | 1 | 0 | 0 | 7 | 0 | 8 | 0 | 0 | 8 | 0 |
| Soybean | 8 | 6 | 2 | 0 | 0 | 7 | 4 | 0 | 0 | 1 | 1 | 0 | 7 | 7 | 0 | 1 | 0 | 8 | 9 | — | 4 | 0 | 0 | 0 | 1 | 0 | 0 | 0 | 6 | 2 | 2 | 7 | 4 |
| Sugar beet | 10 | 10 | 3 | 0 | 9 | 10 | 10 | 8 | 5 | 5 | 6 | 0 | 10 | 10 | 3 | 6 | 4 | 10 | 10 | — | 9 | 0 | 0 | 0 | 0 | 7 | 10 | 0 | 10 | 5 | 3 | 10 | 9 |
| Velvetleaf | 10 | 9 | 4 | 0 | 5 | 10 | 5 | 6 | 0 | 3 | 1 | 0 | 9 | 9 | 3 | 10 | 5 | 10 | 7 | — | 7 | 0 | 0 | 0 | 3 | 0 | 7 | 0 | 10 | 0 | 2 | 10 | 0 |
| Wheat | 0 | 3 | 0 | 0 | 0 | 4 | 0 | 0 | 0 | 0 | 0 | 0 | 2 | 2 | 0 | 5 | 0 | 5 | 1 | — | 0 | 0 | 0 | 0 | 0 | 0 | 1 | 0 | 1 | 0 | 0 | 3 | 0 |
| Wild oat | 2 | 10 | 0 | 0 | 6 | 9 | 2 | 3 | 0 | 2 | 2 | 0 | 7 | 9 | 0 | 10 | 0 | 4 | 3 | — | 6 | 0 | 0 | 0 | 0 | 0 | 9 | 0 | 10 | 0 | 0 | 5 | 0 |

| | COMPOUND (400 g/ha) | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| | 89 | 90 | 91 | 92 | 94 | 95 | 96 | 97 | 98 | 99 | 100 | 101 | 102 | 103 | 104 | 105 | 106 | 107 | 108 | 109 | 110 | 111 | 112 | 113 | 114 | 115 | 116 | 117 | 118 |

TABLE A-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Barley | 2 | 0 | 0 | 0 | 0 | 2 | 0 | 0 | 0 | 1 | 3 | — | 0 | 4 | 0 | 0 | 0 | 1 | 0 | 2 | 3 | 0 | 0 | 0 | — | — | — | 0 | 9 |
| Barnyardgrass | 8 | 5 | 0 | 0 | 0 | 5 | 0 | 0 | 7 | 5 | 9 | — | 0 | 9 | 7 | 5 | 2 | 9 | 0 | 9 | 9 | 1 | 9 | 10 | — | — | — | 8 | 10 |
| Cheatgrass | 1 | 0 | 0 | 0 | 0 | 4 | 0 | 0 | 2 | 0 | 5 | — | 0 | 7 | 0 | 3 | 0 | 2 | 0 | 0 | 10 | 0 | 1 | 2 | — | — | — | 0 | 10 |
| Cocklebur | 1 | 1 | 0 | 0 | 0 | 0 | 0 | 1 | 1 | 0 | — | — | 0 | 1 | 0 | 0 | 0 | 0 | 0 | 2 | 2 | 0 | 0 | 1 | — | — | — | 1 | 7 |
| Corn | 6 | 1 | 0 | 0 | 0 | 1 | 0 | 0 | 2 | 2 | 2 | — | 0 | 1 | 1 | 0 | 0 | 0 | 0 | 2 | 2 | 0 | 1 | 2 | — | — | — | 1 | 8 |
| Cotton | 9 | 0 | 0 | 0 | 0 | 0 | 0 | 0 | 0 | 0 | 1 | — | 0 | 1 | 0 | 0 | 0 | 0 | 0 | 1 | 8 | 0 | 0 | 1 | — | — | — | 0 | 4 |
| Crabgrass | 10 | 10 | 8 | — | 0 | 10 | 0 | 1 | 9 | 9 | 10 | — | 7 | 10 | 10 | 10 | 7 | 10 | 9 | 10 | 10 | 9 | 9 | 10 | — | — | — | 9 | 10 |
| Giant Foxtail | 9 | 9 | 6 | 2 | 0 | 10 | 0 | 0 | 10 | 8 | 10 | — | 5 | 10 | 9 | 8 | 6 | 10 | 0 | 9 | 10 | 9 | 10 | 9 | — | — | — | 9 | 10 |
| Morningglory | 9 | 10 | 3 | 0 | 0 | 8 | 0 | 0 | 9 | 7 | 9 | — | — | 10 | 0 | 4 | 0 | 0 | 0 | 8 | 9 | 10 | 8 | 10 | — | — | — | 10 | 10 |
| Nutsedge | 0 | 0 | 0 | 0 | 0 | 2 | 0 | 0 | 0 | 0 | — | — | 0 | 0 | 0 | 0 | 0 | 0 | 0 | 0 | 0 | 0 | 0 | 2 | — | — | — | 0 | 2 |
| Rice | 3 | 0 | 0 | 0 | 0 | 0 | 0 | 0 | 0 | 1 | 1 | — | 0 | 0 | 0 | 0 | 0 | 0 | 0 | 1 | 2 | — | 0 | 2 | — | — | — | 0 | 4 |
| Sorghum | 7 | 1 | 0 | 0 | 0 | 7 | 0 | 0 | 2 | 2 | 7 | — | 0 | 5 | 1 | 2 | 0 | 1 | 0 | 5 | 5 | 0 | 1 | 6 | — | — | — | 2 | 8 |
| Soybean | 3 | 1 | 2 | 0 | 0 | 1 | 0 | 0 | 5 | 1 | 4 | — | 0 | 2 | 1 | 0 | 0 | 0 | 0 | 2 | 2 | 5 | 2 | 3 | — | — | — | 7 | 9 |
| Sugar beet | 10 | 10 | 4 | 0 | 0 | 9 | 0 | 3 | 10 | 7 | 9 | — | 7 | 9 | 9 | 7 | 6 | 9 | 0 | 10 | 9 | 9 | 10 | 10 | — | — | — | 10 | 10 |
| Velvetleaf | 10 | 10 | 3 | 0 | 0 | 1 | 0 | 0 | 7 | 6 | 7 | — | 0 | 9 | 8 | 5 | 0 | 5 | 0 | 7 | 10 | 8 | 7 | 9 | — | — | — | 9 | 10 |
| Wheat | 0 | 1 | 0 | 0 | 0 | 1 | 0 | 0 | 0 | 0 | 0 | — | 0 | 2 | 0 | 0 | 0 | 0 | 0 | 0 | 1 | 0 | 0 | 0 | — | — | — | 0 | 4 |
| Wild oat | 4 | 5 | 0 | 0 | 0 | 4 | 0 | 0 | 1 | 0 | 9 | — | 0 | 8 | 2 | 2 | 0 | 4 | 0 | 5 | 9 | 0 | 1 | 2 | — | — | — | 0 | 10 |

(Compound 89 tested at 1000 grams/ha.)

TEST B

Seeds of barley (*Hordeum vulgare*), barnyardgrass (*Echinochloa crus-galli*), blackgrass (*Alopecurus myosuroides*), chickweed (*Stellaria media*), cocklebur (*Xanthium pensylvanicum*), corn (*Zea mays*), cotton (*Gossypium hirsutum*), crabgrass (Digitaria spp.), downy brome (*Bromus tectorum*), giant foxtail (*Setaria faberi*), green foxtail (*Setaria viridis*), jimsonweed (*Datura stramonium*), johnsongrass (*Sorghum halepense*), lambsquarters (*Chenopodium album*), morningglory (Ipomoea spp.), rape (*Brassica napus*), rice (*Oryza sativa*), sicklepod (*Cassia obtusifolia*), soybean (*Glycine max*), sugar beet (*Beta vulgaris*), teaweed (*Sida spinosa*), velvetleaf (*Abutilon theophrasti*), wheat (*Triticum aestivum*), wild buckwheat (*Polygonum convolvulus*), and wild oat (*Avena fatua*) and purple nutsedge (*Cyperus rotundus*), tubers were planted and treated preemergence with test chemicals dissolved in a non-phytotoxic solvent. At the same time, these crop and weed species were also treated with postemergence applications of test chemicals. Plants ranged in height from two to eighteen cm (two to three leaf stage) for postemergence treatments. Treated plants and controls were maintained in a greenhouse for approximately 24 days, after which all species were compared to controls and visually evaluated. Preemergence and postemergence application rates for each compound are listed in Table B. Plant response ratings, summarized in Table B, are based on a scale of 0 to 10 where 0 is no effect and 10 is complete control. A dash (-) response means no test result.

TABLE B

| | COMPOUND | | | | | | | | | |
|---|---|---|---|---|---|---|---|---|---|---|
| | (1000 g/ha) | | | | | | | | | |
| | 3 | 5 | 9 | 13 | 28 | 43 | 44 | 45 | 75 | 104 |
| | POSTEMERGENCE | | | | | | | | | |
| Barley | 3 | 3 | 0 | 4 | 2 | 0 | 4 | 0 | 3 | 0 |
| Barnyardgrass | 0 | 10 | 0 | 10 | 10 | 10 | 10 | 5 | 10 | 1 |
| Blackgrass | 5 | 9 | 0 | 10 | 7 | 10 | 10 | 3 | 10 | 3 |
| Chickweed | 3 | 9 | 5 | 10 | 3 | 8 | 10 | 5 | 10 | 10 |
| Cocklebur | 3 | 5 | 0 | 3 | 2 | 6 | 5 | 0 | 8 | 8 |
| Corn | 0 | 0 | 0 | 4 | 4 | 3 | 3 | 0 | 3 | 2 |
| Cotton | 8 | 8 | 2 | 7 | — | 4 | 4 | 3 | — | 8 |
| Crabgrass | 0 | 4 | 0 | 10 | 10 | 10 | 10 | 9 | 10 | 1 |
| Downy brome | 0 | 5 | 0 | 5 | 3 | 0 | 6 | 0 | 0 | 4 |
| Giant foxtail | 0 | 4 | 0 | 10 | 10 | — | 10 | 6 | 10 | 1 |
| Green foxtail | 0 | 4 | 0 | 9 | 10 | 6 | 10 | 7 | 9 | 1 |
| Jimsonweed | 9 | 10 | 4 | 10 | 10 | 10 | 10 | 10 | 10 | 10 |
| Johnsongrass | 3 | 4 | 0 | 7 | 3 | 10 | 10 | 0 | 8 | 4 |
| Lambsquarters | 8 | 10 | 8 | 10 | 10 | 10 | 10 | 10 | 9 | 10 |
| Morningglory | 6 | 8 | 5 | 10 | 8 | 5 | 10 | 7 | 8 | 9 |
| Nutsedge | 0 | 0 | 9 | 4 | 5 | 6 | — | — | 0 | 0 |
| Rape | 6 | 10 | 3 | 10 | 7 | 10 | 10 | 5 | 9 | 9 |
| Rice | 0 | 1 | 0 | 4 | 3 | 3 | 5 | 3 | 4 | 1 |
| Sicklepod | 2 | 6 | 0 | 4 | 9 | 3 | 7 | — | 9 | 7 |
| Soybean | 5 | 6 | 3 | 10 | 5 | 10 | 10 | 0 | — | 6 |
| Sugar beet | 5 | 10 | 9 | 10 | 5 | 10 | 10 | 10 | 10 | 10 |
| Teaweed | 0 | 4 | 0 | 7 | 5 | 5 | 8 | 5 | 2 | — |
| Velvetleaf | 6 | — | 3 | 4 | — | 7 | 6 | 3 | 6 | 8 |
| Wheat | 0 | 1 | 0 | 0 | 0 | 0 | 0 | 0 | 2 | 0 |
| Wild buckwheat | 8 | 10 | 7 | 10 | 5 | 10 | 10 | — | 10 | 8 |
| Wild Oat | 0 | 5 | 0 | 7 | 3 | 5 | 8 | 0 | 5 | 4 |

| | COMPOUND | | | | | | | | | | | | | | | | | | | |
|---|---|---|---|---|---|---|---|---|---|---|---|---|---|---|---|---|---|---|---|---|
| | (500 g/ha) | | | | | | | | | | | | | | | | | | | |
| | 3 | 5 | 8 | 9 | 13 | 15 | 16 | 17 | 23 | 25 | 28 | 33 | 34 | 35 | 36 | 37 | 40 | 43 | 44 | 45 |
| | POSTEMERGENCE | | | | | | | | | | | | | | | | | | | |
| Barley | 2 | 2 | 6 | 0 | 2 | 2 | 0 | 2 | 6 | 3 | 0 | 1 | 0 | 3 | 5 | 5 | 1 | 0 | 3 | 0 |
| Barnyardgrass | 0 | 10 | 9 | 0 | 9 | 10 | 0 | 7 | 10 | 10 | 2 | 10 | 4 | 10 | 10 | 10 | 4 | 10 | 7 | 3 |
| Blackgrass | 2 | 6 | 10 | 0 | 5 | 10 | 4 | 10 | 10 | 10 | 5 | 3 | 5 | 8 | 5 | 9 | 1 | 7 | 9 | 0 |
| Chickweed | 2 | 7 | 9 | 3 | 6 | 9 | 3 | 10 | 10 | 10 | 2 | 7 | 10 | 10 | 10 | 10 | 10 | 7 | 7 | 3 |
| Cocklebur | 2 | 3 | 6 | 0 | 0 | 2 | 0 | 5 | 6 | 5 | 2 | 5 | 6 | 6 | 7 | 8 | 6 | 5 | 3 | 0 |
| Corn | 0 | 0 | 6 | 0 | 2 | 5 | 0 | 2 | 5 | 4 | 2 | 0 | 0 | 3 | 8 | 4 | 2 | 3 | 0 | 0 |
| Cotton | 5 | 4 | 2 | 0 | 5 | 8 | 2 | 5 | 5 | 4 | 0 | 3 | 0 | 10 | 5 | 8 | 7 | 3 | 4 | 3 |
| Crabgrass | 0 | — | 8 | 0 | 4 | 10 | 7 | 7 | 10 | 10 | 3 | 9 | 5 | 10 | 10 | 10 | 9 | 10 | 10 | 6 |
| Downy brome | 0 | 3 | 3 | 0 | 0 | 4 | 0 | 3 | 8 | 3 | 0 | 0 | 2 | 3 | 3 | 0 | 0 | 0 | 4 | 0 |
| Giant foxtail | 0 | 3 | 10 | 0 | 9 | 10 | 2 | 3 | 10 | 10 | 8 | 10 | 0 | 10 | 10 | 10 | 6 | — | 7 | 0 |
| Green foxtail | 0 | 0 | 9 | 0 | 6 | 10 | 0 | 5 | 10 | 9 | 7 | 8 | 4 | 10 | 10 | 9 | 5 | 6 | 10 | 0 |
| Jimsonweed | 7 | 10 | 8 | 3 | 10 | 10 | 2 | 7 | 10 | 10 | 8 | 10 | 8 | 10 | 10 | 10 | 10 | 10 | 10 | 7 |
| Johnsongrass | 0 | 3 | 6 | 0 | 4 | 5 | 0 | 0 | 8 | 8 | 2 | 10 | 0 | 8 | 10 | 9 | 3 | — | 5 | 0 |
| Lambsquarters | 8 | 9 | 9 | 7 | 10 | 10 | 7 | 9 | 10 | 10 | 10 | 10 | 10 | 10 | 10 | 10 | 10 | 10 | 10 | 9 |
| Morningglory | 5 | 4 | — | 3 | 10 | 8 | 7 | 9 | 5 | 8 | 2 | 5 | 1 | 9 | 10 | 6 | 5 | 5 | 10 | 3 |
| Nutsedge | 0 | 0 | 7 | 6 | 0 | 2 | 0 | 4 | 8 | 7 | 2 | 3 | 2 | 0 | 1 | 0 | 0 | 0 | — | — |
| Rape | 4 | 9 | 10 | 0 | 10 | 10 | 10 | 10 | 10 | 10 | 3 | 7 | 9 | 10 | 10 | 10 | 9 | 10 | 10 | 4 |
| Rice | 0 | 0 | 4 | 0 | 3 | 3 | 0 | 4 | 7 | 4 | 2 | 0 | 0 | 4 | 8 | 5 | 3 | 0 | 4 | 0 |
| Sicklepod | 0 | — | 5 | 0 | 0 | 6 | 3 | 5 | 10 | 5 | 5 | 6 | 0 | 8 | 10 | 5 | 9 | — | 6 | 6 |
| Soybean | 5 | 5 | 8 | 2 | 9 | 10 | 5 | 5 | 8 | 10 | 3 | 4 | 5 | 4 | 10 | 10 | 5 | 8 | 7 | 0 |
| Sugar beet | 4 | 10 | 10 | 8 | 10 | 10 | 7 | 10 | 10 | 10 | 2 | 10 | 10 | 10 | 10 | 10 | 10 | 10 | 10 | 10 |
| Teaweed | 0 | — | 3 | 0 | 4 | 7 | 4 | 7 | 10 | 7 | 2 | 5 | 5 | 6 | 4 | 10 | 4 | 3 | 7 | 4 |
| Velvetleaf | 2 | 6 | 8 | 0 | 2 | 7 | 5 | 6 | 9 | 9 | 8 | 3 | 0 | 4 | 5 | 7 | 6 | 6 | 4 | 2 |
| Wheat | 0 | 0 | 1 | 0 | 0 | 1 | 1 | 1 | 2 | 0 | 0 | 0 | 0 | 0 | 3 | 1 | 0 | 0 | 0 | 0 |
| Wild buckwheat | 3 | 9 | 9 | 0 | 7 | — | — | 8 | 10 | 10 | 2 | 10 | 7 | 9 | 10 | 10 | 10 | 10 | 10 | 3 |
| Wild Oat | 0 | 3 | 6 | 0 | 3 | 7 | 3 | 4 | 8 | 5 | 2 | 0 | 2 | 3 | 5 | 3 | 1 | 5 | 3 | 0 |

| | COMPOUND | | | | | | | | | | | | | | | | | | | | |
|---|---|---|---|---|---|---|---|---|---|---|---|---|---|---|---|---|---|---|---|---|---|
| | (500 g/ha) | | | | | | | | | | | | | | | | | | | | |
| | 46 | 48 | 53 | 55 | 56 | 57 | 61 | 68 | 69 | 71 | 73 | 74 | 75 | 76 | 82 | 84 | 87 | 90 | 104 | 107 | 117 |
| | POSTEMERGENCE | | | | | | | | | | | | | | | | | | | | |
| Barley | 4 | 1 | 4 | 3 | 0 | 5 | 5 | 3 | 3 | 3 | 6 | 4 | 0 | 3 | 3 | 7 | 7 | 2 | 0 | 3 | 3 |
| Barnyardgrass | 5 | 10 | 10 | 10 | 0 | 10 | — | 8 | 7 | 10 | 10 | 10 | 8 | 4 | 3 | 10 | 9 | 6 | 1 | — | 9 |
| Blackgrass | 10 | 6 | 10 | — | 6 | 10 | 8 | 10 | 7 | 10 | 10 | 10 | 7 | — | 8 | 10 | 10 | 7 | 1 | 5 | 10 |
| Chickweed | 9 | 9 | 10 | 10 | 5 | 10 | 7 | 10 | 7 | 10 | 10 | 10 | 10 | 10 | 8 | 10 | 10 | 9 | 9 | 9 | 10 |
| Cocklebur | 6 | 6 | 8 | 8 | 3 | 7 | — | — | — | 7 | 3 | 4 | 7 | 9 | 3 | 10 | 3 | 5 | 8 | — | 2 |
| Corn | 6 | 6 | 5 | 3 | 0 | 4 | — | 3 | 3 | 5 | 8 | 5 | 3 | 2 | 3 | 7 | 6 | 5 | 1 | 3 | 4 |
| Cotton | 5 | 8 | 10 | 8 | 8 | 10 | — | 8 | 7 | 10 | 8 | 5 | 3 | 7 | 3 | 10 | 9 | 3 | 7 | 4 | 6 |
| Crabgrass | 6 | 10 | 10 | 10 | 8 | 10 | — | 10 | 10 | 10 | 10 | 10 | 10 | 10 | 10 | 10 | 10 | 7 | 1 | 8 | 7 |
| Downy brome | 3 | 0 | 1 | 0 | 0 | 7 | 4 | 3 | 2 | 6 | 8 | 9 | 0 | 4 | 3 | 7 | 6 | 2 | 0 | 1 | 2 |
| Giant foxtail | 10 | 9 | — | — | 10 | 10 | — | 8 | 6 | 9 | 9 | 10 | 8 | 3 | 10 | 10 | 9 | 3 | 1 | 5 | 10 |
| Green foxtail | 7 | 10 | 10 | 10 | 9 | 10 | — | 9 | 7 | 10 | 8 | 10 | 9 | 6 | 6 | 10 | 9 | 6 | 0 | 4 | 5 |
| Jimsonweed | 10 | 10 | 10 | 10 | 9 | 10 | — | 10 | 10 | 10 | 10 | 10 | 10 | 8 | 10 | 10 | 10 | 7 | 10 | — | 10 |
| Johnsongrass | 9 | 8 | 10 | 9 | 0 | 9 | — | 7 | 5 | 8 | 8 | 7 | 5 | 4 | 7 | 10 | 9 | 3 | 1 | 3 | 7 |
| Lambsquarters | 10 | 10 | 10 | 10 | 9 | 10 | — | 10 | 10 | 10 | 10 | 10 | — | 10 | 10 | 10 | 10 | 5 | 10 | 10 | 8 |
| Morningglory | 7 | 6 | 7 | 7 | 8 | 10 | — | 8 | 7 | 10 | 9 | 9 | 4 | 8 | 5 | 10 | 10 | 8 | 8 | 8 | 3 |
| Nutsedge | 5 | 0 | 4 | — | — | — | — | 7 | 3 | 0 | 7 | 7 | 0 | 3 | 0 | 6 | 3 | 3 | 0 | 5 | — |

| | COMPOUND | | | | | | | |
|---|---|---|---|---|---|---|---|---|
| | (250 g/ha) | | | | | | | |
| | 3 | 5 | 8 | 13 | 15 | 16 | 17 | 23 |
| | POSTEMERGENCE | | | | | | | |
| Barley | 0 | 0 | 3 | 0 | 2 | 0 | 1 | 4 |
| Barnyardgrass | 0 | 4 | 9 | 5 | 10 | 0 | 7 | 5 |
| Blackgrass | 0 | 2 | 5 | 3 | 9 | 2 | 5 | 10 |
| Chickweed | 0 | 4 | 7 | 3 | 7 | 0 | 8 | 10 |
| Cocklebur | 0 | 2 | 4 | 0 | 0 | 0 | 3 | 5 |
| Corn | 0 | 0 | 3 | 0 | 3 | 0 | 2 | 2 |
| Cotton | 4 | 2 | 1 | 3 | 5 | 0 | 3 | 3 |
| Crabgrass | 0 | 0 | 7 | 0 | 9 | 5 | 4 | 9 |
| Downy brome | 0 | 0 | 2 | 0 | 3 | 0 | 2 | 5 |
| Giant foxtail | 0 | 0 | 5 | 0 | 8 | 0 | 2 | 10 |
| Green foxtail | 0 | 0 | 9 | 0 | 9 | 0 | 3 | 10 |
| Jimsonweed | 5 | 8 | 6 | 9 | 10 | — | 2 | 10 |
| Johnsongrass | 0 | 0 | 2 | 0 | 4 | 0 | 0 | 4 |
| Lambsquarters | 8 | 8 | 8 | 9 | 10 | 7 | 7 | 9 |
| Morningglory | 3 | 4 | 9 | 9 | 7 | 7 | 3 | 2 |
| Nutsedge | 0 | 0 | 5 | 0 | 0 | 0 | 3 | 3 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Rape | 10 | 9 | 10 | 10 | 6 | 10 | 9 | 10 | 9 | 10 | 8 | 9 | 8 | 10 | 10 | 10 | 10 | 4 | 9 | 8 | 7 | 2 | 7 | 9 | 6 | 9 | 7 | 8 | 10 |
| Rice | 7 | 8 | 5 | 7 | 0 | 5 | — | 3 | 3 | 8 | 8 | 8 | 3 | 3 | 4 | 7 | 3 | 1 | 0 | 4 | 2 | 0 | 0 | 3 | 0 | 2 | 0 | 2 | 5 |
| Sicklepod | 10 | 6 | 8 | 8 | 6 | 10 | — | 7 | 7 | 10 | 8 | 8 | 4 | 8 | 8 | 10 | 10 | 5 | 5 | 6 | 3 | 0 | 5 | 5 | 0 | 4 | 2 | 5 | 8 |
| Soybean | 8 | 6 | 7 | 10 | 7 | 7 | — | 9 | 7 | 7 | 9 | 10 | 5 | — | 6 | 10 | 10 | 5 | 6 | 6 | 3 | 4 | 4 | 8 | 7 | 7 | 4 | 5 | 4 |
| Sugar beet | 10 | 10 | 10 | 10 | 10 | 10 | 10 | 10 | 10 | 10 | 10 | 10 | 10 | 10 | 9 | 10 | 10 | 10 | 10 | 10 | 10 | 0 | 9 | 9 | 10 | 10 | 3 | 10 | 10 |
| Teaweed | 3 | 7 | 8 | 6 | 7 | 10 | — | 7 | 8 | 10 | 2 | 4 | 2 | 7 | 3 | 7 | 9 | 2 | 6 | 5 | 3 | 0 | 3 | 2 | 0 | 4 | 2 | 2 | 5 |
| Velvetleaf | 10 | — | 10 | — | 4 | 10 | — | 6 | 7 | 7 | 3 | 4 | — | 8 | 3 | 8 | 10 | 0 | 5 | 6 | 3 | 0 | 5 | 8 | 0 | 3 | 4 | 5 | 7 |
| Wheat | 2 | 1 | 1 | 0 | 0 | 3 | 6 | 4 | 3 | 3 | 6 | 4 | 0 | 4 | 0 | 7 | 4 | 2 | 0 | 2 | 2 | 0 | 0 | 0 | 0 | 1 | 0 | 0 | 0 |
| Wild buckwheat | 9 | 10 | 10 | 10 | 5 | 10 | 8 | 10 | 9 | 10 | 10 | 10 | 10 | 10 | 8 | 10 | 10 | 9 | 7 | 10 | 3 | 0 | 9 | 9 | 4 | — | — | 5 | 10 |
| Wild Oat | 5 | 4 | 10 | 1 | 0 | 9 | 7 | 5 | 5 | 8 | 8 | 10 | 4 | 8 | 3 | 10 | 7 | 3 | 0 | 2 | 3 | 0 | 3 | 4 | 0 | 4 | 2 | 2 | 7 |

| | COMPOUND (250 g/ha) | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | 25 | 28 | 32 | 33 | 34 | 35 | 36 | 37 | 40 | 43 | 44 | 45 | 46 | 48 | 50 | 53 | 55 | 56 | 57 | 61 | 68 | 69 | 71 | 73 | 74 | 75 | 76 | 82 |
| | POSTEMERGENCE | | | | | | | | | | | | | | | | | | | | | | | | | | | |
| Barley | 2 | 0 | 0 | 0 | 0 | 0 | 2 | 5 | 0 | 0 | 3 | 0 | 4 | 0 | 1 | 3 | 0 | 0 | 4 | 4 | 2 | 2 | 2 | 5 | 4 | 0 | 3 | 2 |
| Barnyardgrass | 10 | 0 | 10 | 10 | 2 | 2 | 10 | 4 | 3 | 9 | 5 | 0 | 5 | 9 | 3 | 10 | 7 | 0 | 7 | 9 | 7 | 6 | 10 | 6 | 10 | 6 | 4 | 3 |
| Blackgrass | 10 | 2 | 8 | 3 | 3 | 0 | 5 | 1 | 0 | 2 | 7 | 0 | 8 | 6 | 9 | 9 | 8 | 5 | 10 | 7 | 10 | 5 | 10 | 9 | 10 | 3 | 10 | 3 |
| Chickweed | 9 | 0 | 10 | 3 | 5 | 6 | 10 | 10 | 9 | 4 | 5 | 0 | 7 | 9 | 10 | 10 | 10 | 4 | 10 | 6 | 10 | 7 | 10 | 10 | 10 | 2 | 10 | 8 |
| Cocklebur | 3 | 2 | 7 | 4 | 2 | 5 | 7 | 6 | 6 | 5 | 0 | 0 | 5 | 5 | 5 | 6 | 7 | 0 | 6 | 7 | — | — | 5 | 2 | 4 | 5 | 9 | 3 |
| Corn | 2 | 0 | 1 | 0 | 0 | 0 | 4 | 2 | 2 | 0 | 0 | 0 | 3 | 1 | 3 | 4 | 3 | 0 | 3 | 4 | 2 | 1 | 4 | 6 | 4 | 2 | 2 | 2 |
| Cotton | 2 | 0 | 5 | — | 0 | 6 | 4 | 8 | 7 | 2 | 4 | 3 | 3 | 8 | 0 | 4 | 1 | 4 | 7 | 9 | 6 | 7 | 10 | 5 | 5 | 2 | 7 | 2 |
| Crabgrass | 9 | 2 | 8 | 9 | 5 | 2 | 10 | 10 | 9 | 9 | 7 | 3 | 5 | 10 | 10 | 10 | 10 | 5 | 9 | 10 | 10 | 10 | 10 | 8 | 10 | 9 | 5 | 10 |
| Downy brome | 2 | 0 | 0 | 0 | 0 | 0 | 1 | 0 | 0 | 0 | 0 | 0 | 3 | 0 | 3 | 0 | 0 | 0 | 6 | 3 | 2 | 1 | 4 | 5 | 3 | 0 | 2 | 2 |
| Giant foxtail | 10 | 2 | 10 | 10 | 0 | 0 | 10 | 10 | 4 | — | 6 | 0 | 10 | 8 | — | — | — | 0 | 7 | 9 | 8 | 6 | 9 | 9 | 10 | 6 | 3 | 7 |
| Green foxtail | 9 | 2 | 10 | 6 | 3 | 5 | 10 | 9 | 4 | 5 | 5 | 0 | 7 | 7 | 6 | 7 | 9 | 3 | 7 | 10 | 8 | 6 | 9 | 7 | 10 | 3 | 5 | 2 |
| Jimsonweed | 10 | 7 | 10 | 10 | 7 | 10 | 10 | 9 | 9 | 7 | 6 | 6 | 10 | 10 | 8 | 10 | 10 | 8 | 10 | 10 | 10 | 7 | 10 | 9 | 10 | 7 | 7 | 9 |
| Johnsongrass | 3 | 0 | 8 | 4 | 0 | 0 | 10 | 1 | 1 | — | 3 | 0 | 7 | 5 | 8 | 10 | — | 0 | 6 | 8 | 6 | 5 | 7 | 6 | 7 | 2 | 4 | — |
| Lambsquarters | 10 | 5 | 10 | 7 | 3 | 10 | 10 | 10 | 10 | 10 | 9 | 9 | 10 | 10 | 8 | 10 | 10 | 8 | 10 | 10 | 10 | 10 | 10 | 10 | 10 | 6 | 9 | 9 |
| Morningglory | 8 | 2 | 7 | 5 | 0 | 5 | 8 | 4 | 2 | 5 | 7 | 0 | 7 | 6 | — | 7 | 7 | 7 | 10 | 10 | 7 | 7 | 9 | 8 | 8 | 3 | 8 | 5 |
| Nutsedge | 5 | 0 | 3 | 3 | 0 | 0 | 0 | 0 | 0 | 0 | — | — | 4 | 0 | 0 | 3 | 2 | — | — | 3 | 6 | 0 | 0 | 5 | 5 | 0 | 0 | 0 |
| Rape | 9 | 2 | 10 | 6 | 6 | 10 | 10 | 10 | 9 | 5 | 6 | 3 | 10 | 8 | 8 | 10 | 8 | 4 | 10 | 8 | 10 | 7 | 10 | 7 | 8 | 5 | 9 | 8 |
| Rice | 3 | 1 | 0 | 0 | 0 | 0 | 4 | 4 | 1 | 0 | 3 | 0 | 5 | 8 | 3 | 5 | 2 | 0 | 3 | 5 | 3 | 3 | 7 | 6 | 7 | 2 | 2 | 3 |
| Sicklepod | 5 | 2 | 10 | 4 | 0 | 4 | 8 | 4 | — | 2 | 5 | 4 | 10 | 6 | 4 | 8 | 6 | 5 | 8 | 8 | 6 | 7 | 8 | 5 | 4 | 3 | 8 | 7 |
| Soybean | 9 | 2 | 6 | 3 | 5 | 4 | 8 | 7 | 5 | 6 | 6 | 0 | 8 | 6 | — | 7 | 5 | 6 | 7 | 9 | 9 | 6 | 7 | 9 | 10 | 5 | 5 | 5 |
| Sugar beet | 10 | 0 | 10 | 10 | 10 | 10 | 10 | 10 | 10 | 9 | 10 | 10 | 10 | 10 | 10 | 10 | 10 | 10 | 10 | 10 | 10 | 9 | 10 | 10 | 10 | 10 | 10 | 9 |
| Teaweed | 5 | 0 | 5 | 4 | 4 | — | — | 5 | 4 | 2 | 6 | 4 | 3 | 6 | 3 | 6 | 4 | 3 | 10 | 10 | 7 | 7 | 8 | 0 | 0 | 0 | 6 | 2 |
| Velvetleaf | 9 | — | 2 | 1 | 0 | 3 | 5 | 5 | 6 | 3 | 3 | 0 | 8 | 9 | — | 8 | — | 2 | 8 | 10 | 4 | 6 | 7 | 0 | — | 5 | 7 | 3 |
| Wheat | 0 | 0 | 0 | 0 | 0 | 0 | 1 | 0 | 0 | 0 | 0 | 0 | 1 | 1 | 0 | 0 | 0 | 0 | 0 | 3 | 3 | 2 | 2 | 2 | 2 | 0 | 3 | 0 |
| Wild buckwheat | 9 | 0 | 10 | 10 | 6 | 0 | 10 | 10 | 9 | 10 | 6 | 0 | 9 | 4 | 10 | 10 | 10 | 3 | 10 | 7 | 10 | 9 | 10 | 10 | 10 | 10 | — | 7 |
| Wild Oat | 5 | 0 | 1 | 0 | 0 | 2 | 4 | 2 | 0 | 0 | 0 | 0 | 4 | 2 | 3 | 5 | 1 | 0 | 6 | 6 | 4 | 3 | 4 | 6 | 3 | 0 | 4 | 2 |

| | COMPOUND (250 g/ha) | | | | | | COMPOUND (125 g/ha) | | | | | | | | | | | | | | | | | | | | | |
|---|---|---|---|---|---|---|---|---|---|---|---|---|---|---|---|---|---|---|---|---|---|---|---|---|---|---|---|---|
| | 84 | 87 | 90 | 104 | 107 | 117 | 3 | 8 | 15 | 16 | 17 | 23 | 25 | 28 | 32 | 33 | 34 | 35 | 36 | 37 | 40 | 43 | 44 | 46 | 48 | 50 | 53 | 55 |
| | POSTEMERGENCE | | | | | | | | | | | | | | | | | | | | | | | | | | | |
| Barley | 6 | 4 | 1 | 0 | 3 | 2 | 0 | 2 | 0 | 0 | 0 | 2 | 1 | 0 | 0 | 0 | 0 | 0 | 2 | 1 | 0 | 0 | 0 | 2 | 0 | 0 | 0 | 0 |
| Barnyardgrass | 10 | 6 | 5 | 1 | 4 | 5 | 0 | 7 | 8 | 0 | 3 | 5 | 8 | 0 | 3 | 3 | 0 | 2 | 9 | 1 | 0 | 0 | 3 | 3 | 9 | 3 | 7 | 7 |
| Blackgrass | 9 | 10 | 4 | 0 | 3 | 5 | 0 | 2 | 8 | 0 | 2 | 8 | 9 | 0 | 2 | 0 | 0 | 0 | 3 | 0 | 0 | 0 | 3 | 3 | 2 | 9 | 7 | 7 |
| Chickweed | 10 | 9 | 8 | 8 | 9 | 8 | 0 | 3 | 2 | 0 | 2 | 9 | 5 | 0 | 6 | 2 | 0 | — | 10 | 6 | 7 | 0 | 3 | 3 | 7 | 6 | 9 | 5 |
| Cocklebur | 6 | 3 | 2 | 5 | 6 | 0 | 0 | 2 | 0 | 0 | 2 | 3 | 2 | 0 | 6 | 3 | 0 | 3 | 7 | 5 | 6 | 4 | 0 | 3 | 5 | 5 | 5 | 5 |
| Corn | 5 | 5 | 3 | 0 | 1 | 2 | 0 | 2 | 1 | 0 | 2 | 0 | 0 | 0 | 0 | 0 | 0 | 0 | 2 | 2 | 2 | 0 | 0 | 2 | 1 | 2 | 2 | 3 |

TABLE B-continued

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| Cotton | 9 | 4 | 3 | 6 | 3 | 2 | 0 | 1 | 4 | 0 | 3 | 2 | 0 | 0 | 5 | 0 | 0 | 4 | 4 | 8 | 7 | 1 | 4 | 3 | 8 | 0 | 2 | 1 |
| Crabgrass | 10 | 10 | 2 | 0 | 8 | 7 | 0 | 3 | 9 | 2 | 0 | 8 | 8 | 10 | 3 | 3 | 2 | 1 | 8 | 6 | 6 | 6 | 5 | 3 | 2 | 9 | 8 | 9 |
| Downy brome | 6 | 5 | 0 | 0 | 1 | 2 | 0 | 0 | 2 | 0 | 0 | 2 | 0 | 0 | 0 | 0 | 0 | 0 | 0 | 0 | 0 | 0 | 0 | 2 | 0 | 2 | 0 | 0 |
| Giant foxtail | 10 | 8 | 2 | 0 | 2 | 5 | 0 | 5 | 7 | 0 | 0 | 7 | 9 | 0 | 7 | 6 | 0 | 0 | 10 | 3 | 0 | — | 3 | 9 | 6 | — | — | — |
| Green foxtail | 10 | 8 | 2 | 0 | 2 | 2 | 0 | 6 | 9 | 0 | 2 | 8 | 8 | 0 | — | 5 | 0 | 3 | 9 | 3 | 1 | 0 | 0 | 5 | 5 | 4 | — | 8 |
| Jimsonweed | 10 | 10 | 5 | 9 | 9 | 10 | 0 | 5 | 10 | 0 | 0 | 10 | 10 | 2 | 10 | 5 | 3 | 10 | 10 | 8 | 9 | 5 | 5 | 10 | 10 | 8 | 9 | 10 |
| Johnsongrass | 10 | 7 | 0 | 0 | 2 | 2 | 0 | 2 | 2 | 0 | 0 | 3 | 2 | 0 | — | 0 | 0 | 0 | 2 | 0 | 0 | 4 | 3 | — | 2 | — | — | — |
| Lambsquarters | 10 | 10 | 2 | 10 | 10 | 3 | 0 | 8 | 10 | 2 | 5 | 9 | 9 | 2 | 10 | 6 | 3 | 10 | 10 | 10 | 10 | 6 | 7 | 10 | 10 | 8 | 10 | 10 |
| Morningglory | 10 | 10 | 3 | 8 | 7 | 1 | 0 | — | 7 | 2 | 2 | 0 | 8 | 2 | 5 | 5 | 0 | 5 | 2 | 2 | 1 | — | 3 | 7 | 5 | 8 | 5 | 6 |
| Nutsedge | 5 | 2 | 0 | 0 | 0 | — | 0 | 2 | 0 | 0 | 0 | 2 | 3 | 0 | 0 | 2 | 0 | 0 | 0 | 0 | 0 | 0 | — | 0 | 0 | 0 | 0 | 0 |
| Rape | 10 | 9 | 3 | 8 | 8 | 5 | 0 | 7 | 8 | 0 | 2 | 9 | 9 | 2 | — | 6 | 2 | 10 | 10 | 8 | 8 | 5 | 4 | 10 | 6 | 7 | 8 | 6 |
| Rice | 4 | 2 | 1 | 0 | 4 | 1 | 0 | 2 | 2 | 0 | 0 | 2 | 2 | 0 | 0 | 0 | 0 | 0 | 2 | 3 | 1 | — | 0 | 4 | 2 | 3 | 3 | 1 |
| Sicklepod | 10 | 9 | 5 | 5 | 4 | 3 | 0 | 3 | 3 | 0 | 3 | 2 | 3 | 0 | 9 | 2 | 0 | 4 | 8 | 2 | 8 | 2 | 3 | 9 | 5 | 4 | 6 | 4 |
| Soybean | 7 | 7 | 3 | 5 | 5 | 3 | 3 | 7 | 7 | 4 | 3 | 3 | 9 | 0 | 5 | 3 | 2 | 4 | 5 | 7 | 5 | 4 | 4 | 6 | 5 | — | 6 | 5 |
| Sugar beet | 10 | 10 | 8 | 10 | 10 | 10 | 0 | 8 | 10 | 0 | 9 | 10 | 9 | 0 | 9 | 10 | 8 | 10 | 10 | 10 | 10 | 8 | 8 | 10 | 10 | 10 | 10 | 10 |
| Teaweed | 6 | 7 | 0 | 5 | 4 | 2 | 0 | 0 | 3 | 0 | 0 | 2 | 5 | 0 | 3 | 3 | 0 | 4 | 4 | 4 | — | 0 | 3 | 0 | 6 | 3 | 4 | 4 |
| Velvetleaf | 7 | 9 | 0 | 5 | 5 | 3 | 0 | 3 | 2 | 2 | 5 | 6 | 7 | — | 0 | 0 | 0 | 1 | 4 | 5 | 6 | 0 | 3 | 8 | 5 | — | 7 | 9 |
| Wheat | 5 | 3 | 2 | 0 | 1 | 0 | 0 | 0 | 1 | 0 | 0 | 0 | 0 | 0 | 0 | 0 | 0 | 0 | 0 | 0 | 0 | 0 | 0 | 0 | 1 | 0 | 0 | 0 |
| Wild buckwheat | 10 | 9 | 7 | 7 | 10 | 3 | 0 | 5 | — | — | 3 | 10 | 9 | 0 | 10 | 9 | 0 | — | 10 | 10 | 6 | 10 | 4 | 7 | 0 | — | 10 | 10 |
| Wild Oat | 7 | 7 | 0 | 0 | 2 | 2 | 0 | 1 | 2 | 0 | 1 | 3 | 3 | 0 | 0 | 0 | 0 | 0 | 2 | 1 | 0 | 0 | 0 | 3 | 1 | 2 | 2 | 0 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | (125 g/ha) | | | | | | | | | | | | | | | | | (62 g/ha) | | | | | | | | | | |
| | 56 | 57 | 61 | 68 | 69 | 71 | 73 | 74 | 75 | 76 | 82 | 84 | 87 | 90 | 104 | 107 | 117 | 5 | 8 | 15 | 16 | 17 | 23 | 25 | 32 | 33 | 34 | 35 |
| | POSTEMERGENCE | | | | | | | | | | | | | | | | | | | | | | | | | | | |
| Barley | 0 | 0 | 3 | 1 | 2 | 1 | 5 | 0 | 0 | 1 | 0 | 5 | 2 | 1 | 0 | 2 | 2 | 0 | 0 | 0 | 0 | 0 | 0 | 0 | 0 | 0 | 0 | 0 |
| Barnyardgrass | 0 | 6 | 6 | 6 | 6 | — | 5 | 6 | 4 | 3 | 2 | 8 | 6 | 0 | 0 | 4 | 4 | 0 | 0 | 0 | 0 | 0 | 0 | 0 | 0 | 0 | 0 | 0 |
| Blackgrass | 0 | 7 | 6 | 8 | 4 | 10 | 9 | 10 | 2 | 7 | 3 | 8 | 8 | 2 | 0 | 0 | 2 | 0 | 0 | 4 | 0 | 0 | 5 | 5 | 0 | 0 | 0 | 0 |
| Chickweed | 3 | 8 | 6 | 9 | 5 | 9 | 5 | 10 | 0 | 10 | 5 | 10 | 7 | 2 | 5 | 8 | 6 | 2 | 0 | 1 | 0 | 0 | 8 | 3 | 6 | 0 | 0 | 0 |
| Cocklebur | 0 | 5 | 5 | — | — | 5 | 2 | 3 | 4 | 7 | 2 | 6 | 3 | 2 | 4 | 5 | 0 | 2 | 0 | 0 | 0 | 0 | 3 | 2 | 4 | 3 | 0 | 0 |
| Corn | 0 | 2 | 3 | 0 | 0 | 3 | 5 | 3 | 0 | — | 0 | 4 | 4 | 2 | 0 | 1 | 0 | 0 | 2 | 0 | 0 | 1 | 0 | 0 | 0 | 0 | 0 | 0 |
| Cotton | 3 | 6 | 6 | 6 | 7 | 3 | 5 | 3 | 1 | 6 | 2 | 5 | 4 | 2 | 6 | 2 | 2 | 0 | 1 | 3 | 0 | 1 | 0 | 0 | 4 | 0 | 0 | 3 |
| Crabgrass | 2 | 7 | 10 | 10 | 10 | — | 8 | 10 | 4 | — | 7 | 7 | 6 | 0 | 0 | 4 | 6 | 0 | 0 | 4 | 0 | 0 | 4 | 5 | 3 | 3 | 0 | 0 |
| Downy brome | 0 | 0 | 0 | 1 | 1 | 3 | 5 | 1 | 0 | 0 | 0 | 5 | 4 | 0 | 0 | 0 | 0 | 0 | 0 | 0 | 0 | 0 | 2 | 0 | 0 | 0 | 0 | 0 |
| Giant foxtail | 0 | 6 | 7 | 7 | 5 | 5 | 7 | 7 | 0 | 0 | 2 | 7 | 5 | 0 | 0 | 0 | 2 | 0 | 2 | 2 | 0 | 0 | 2 | 8 | 0 | 6 | 0 | 0 |
| Green foxtail | 0 | 6 | 7 | 7 | 4 | 9 | 7 | 10 | 2 | 2 | 0 | 5 | 6 | 0 | 0 | 0 | 0 | 0 | 2 | 4 | 0 | 0 | 5 | 4 | 7 | 0 | 0 | 0 |
| Jimsonweed | 6 | 10 | 10 | 10 | 6 | 10 | 9 | 5 | 6 | 7 | 7 | 10 | 10 | 2 | 8 | 9 | 8 | — | 5 | 9 | 0 | 0 | 8 | 9 | 10 | 3 | 0 | 4 |
| Johnsongrass | 0 | 4 | 6 | 5 | 4 | 1 | 6 | 3 | 0 | 3 | — | 6 | 4 | 0 | 0 | 0 | 2 | 0 | 1 | 0 | 0 | 0 | 0 | 0 | 8 | 0 | 0 | 0 |
| Lambsquarters | 7 | 10 | 10 | 10 | 10 | 10 | 9 | 10 | 6 | 8 | 9 | 10 | 10 | 0 | 9 | 7 | 2 | 8 | 5 | 8 | 0 | 2 | 8 | 8 | 10 | 5 | 0 | 8 |
| Morningglory | 7 | 10 | 8 | 7 | 7 | 5 | 8 | 7 | 2 | 7 | 3 | 10 | 9 | 3 | 4 | 5 | 0 | — | — | 7 | 2 | 0 | — | 8 | 5 | 5 | 0 | 3 |
| Nutsedge | — | — | 0 | 3 | 0 | 0 | 0 | 1 | 0 | 0 | 0 | 4 | 0 | 0 | 0 | 0 | — | 0 | 0 | 0 | 0 | 0 | 0 | 2 | 0 | 0 | 0 | 0 |
| Rape | 3 | 10 | 7 | 10 | 7 | 7 | 5 | 8 | 3 | 9 | 3 | 10 | 8 | 3 | 8 | 8 | 3 | 4 | 3 | 7 | 0 | 0 | 8 | 9 | 10 | 5 | 0 | 6 |
| Rice | 0 | 2 | 4 | 2 | 2 | 4 | 3 | 5 | 0 | 1 | 2 | 3 | 2 | 1 | 0 | 4 | 1 | 0 | 0 | 0 | 0 | 0 | 0 | 0 | 0 | 0 | 0 | 0 |
| Sicklepod | 4 | 7 | 7 | 5 | 7 | 7 | 2 | — | 3 | 6 | 2 | 10 | 6 | 5 | 4 | 4 | 2 | 4 | 0 | 0 | 0 | 2 | 2 | 3 | 6 | — | 0 | 2 |
| Soybean | 5 | 7 | 7 | 7 | 6 | 7 | 8 | 10 | 4 | 5 | 5 | 6 | 6 | 3 | 5 | 4 | 3 | 4 | 7 | 6 | 3 | 2 | 3 | 9 | 5 | 2 | 0 | 4 |
| Sugar beet | 7 | 10 | 10 | 10 | 9 | 10 | 8 | 10 | 9 | 10 | 9 | 10 | 10 | 7 | 10 | 10 | 10 | 7 | 6 | 10 | 0 | 8 | 10 | 9 | 4 | 10 | 5 | 10 |
| Teaweed | 3 | 9 | 8 | 7 | 6 | 7 | 0 | 0 | 0 | 5 | 0 | 5 | 6 | 0 | 4 | 4 | 1 | 3 | 0 | 0 | 0 | 0 | 0 | 2 | 3 | 3 | 0 | 4 |
| Velvetleaf | 0 | 7 | 10 | 3 | 6 | 4 | 0 | — | 5 | — | 0 | 6 | 8 | 0 | 0 | — | 2 | 3 | 3 | 0 | 0 | 3 | 4 | 5 | 0 | 0 | 0 | 0 |
| Wheat | 0 | 0 | 0 | 2 | 1 | 0 | 0 | 0 | 0 | 0 | 0 | 4 | 2 | 1 | 0 | 1 | 0 | 0 | 0 | 0 | 0 | 0 | 0 | 0 | 0 | 0 | 0 | 0 |
| Wild buckwheat | 0 | 9 | 7 | 10 | 9 | 9 | 9 | 10 | — | — | 3 | 10 | 9 | 5 | 5 | 6 | 0 | 5 | 3 | — | — | 0 | 8 | 5 | 5 | 3 | 0 | 0 |
| Wild Oat | 0 | 3 | 5 | 3 | 2 | 3 | 5 | 3 | 0 | 2 | 0 | 5 | 5 | 0 | 0 | 2 | 0 | 0 | 0 | 1 | 0 | 0 | 2 | 0 | 0 | 0 | 0 | 0 |

COMPOUND

TABLE B-continued

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | (62 g/ha) | | | | | | | | | | | | | | | | | | | | | | | | (31 g/ha) | | | |
| | 36 | 37 | 40 | 46 | 48 | 50 | 53 | 55 | 56 | 57 | 61 | 68 | 69 | 71 | 73 | 74 | 76 | 82 | 84 | 87 | 90 | 104 | 107 | 117 | 8 | 17 | 23 | 25 |
| | POSTEMERGENCE | | | | | | | | | | | | | | | | | | | | | | | | | | | |
| Barley | 0 | 0 | 0 | 2 | 0 | 0 | 0 | 0 | 0 | 0 | 0 | 1 | 1 | 0 | 0 | 0 | 1 | 0 | 3 | 0 | 0 | 0 | 2 | 0 | 0 | 0 | 0 | 0 |
| Barnyardgrass | 9 | 0 | 0 | 0 | 5 | 0 | 5 | 5 | 0 | 5 | 3 | 3 | 5 | 4 | 2 | 0 | — | 2 | 6 | 5 | 0 | 0 | 0 | 0 | 0 | 0 | 2 | 2 |
| Blackgrass | 0 | 0 | 0 | 0 | 0 | 4 | 7 | 1 | 0 | 5 | 4 | 5 | 2 | 7 | 5 | 8 | 4 | 2 | 7 | 8 | 0 | 0 | 0 | 2 | 0 | 0 | 3 | 2 |
| Chickweed | 9 | 3 | 3 | 0 | 5 | 5 | 6 | 3 | 0 | 7 | 5 | 6 | 5 | 6 | 4 | 4 | 8 | 2 | 10 | 7 | 0 | 4 | 4 | 3 | 0 | 0 | 5 | 0 |
| Cocklebur | 7 | 4 | 6 | 3 | — | 4 | — | 5 | 0 | 4 | 3 | — | — | 5 | 2 | 3 | 6 | 2 | 5 | 2 | 0 | 3 | 4 | 0 | 0 | 0 | 2 | 0 |
| Corn | 0 | 1 | 2 | 0 | 1 | 2 | 1 | 3 | 0 | 0 | 2 | 0 | 0 | 0 | 0 | 0 | 1 | 0 | 3 | 3 | 0 | 0 | 1 | 0 | 0 | 0 | 0 | 0 |
| Cotton | — | 8 | 7 | 2 | 7 | 0 | 2 | 0 | 3 | 5 | 3 | 5 | 6 | 3 | 4 | 0 | — | 0 | 4 | 2 | 2 | 6 | 1 | 0 | 1 | 1 | 0 | 0 |
| Crabgrass | 1 | 4 | 4 | 2 | — | 7 | 8 | 7 | 0 | 6 | 10 | 10 | 10 | 10 | 3 | 2 | 5 | 2 | 6 | 5 | 0 | 0 | 4 | 6 | 0 | 0 | 2 | 2 |
| Downy brome | 0 | 0 | 0 | 0 | 0 | 0 | 0 | 0 | 0 | 0 | 0 | 1 | 1 | 2 | 0 | 0 | 0 | 0 | 4 | 3 | 0 | 0 | 0 | 0 | 0 | 0 | 0 | 0 |
| Giant foxtail | 3 | 0 | 0 | 3 | 4 | — | — | — | 0 | 5 | 6 | 6 | 4 | 3 | 4 | 5 | 0 | 0 | 5 | 3 | 0 | 0 | 0 | 2 | 0 | 0 | 0 | 0 |
| Green foxtail | 4 | 1 | 0 | 3 | 3 | 3 | 6 | 1 | 0 | 4 | 5 | 5 | 3 | 6 | 6 | 9 | — | 0 | 3 | 4 | 0 | 0 | 0 | 0 | 0 | 0 | 2 | 3 |
| Jimsonweed | 9 | 7 | 8 | 5 | 9 | 6 | 9 | 6 | 5 | 10 | 10 | 6 | 6 | 10 | 7 | 4 | 7 | 7 | 10 | 9 | 0 | 8 | 7 | 6 | 3 | 0 | 8 | 8 |
| Johnsongrass | — | 0 | 0 | — | 0 | 8 | 8 | 5 | 0 | 3 | 3 | 3 | 3 | 0 | 2 | 0 | — | 2 | 3 | 3 | 0 | 0 | 0 | 0 | 0 | 0 | 0 | 0 |
| Lambsquarters | 10 | 9 | 10 | 9 | 9 | 7 | 10 | 8 | 6 | 10 | 9 | 10 | 9 | 9 | 5 | 7 | 6 | 9 | 10 | 9 | 0 | 9 | 5 | 2 | 5 | 0 | 7 | 5 |
| Morningglory | 0 | — | 1 | 5 | — | 6 | 5 | 5 | 6 | 10 | 6 | 7 | 7 | 5 | 5 | 6 | 7 | 0 | 10 | 9 | 3 | — | 5 | 0 | — | 0 | 0 | 7 |
| Nutsedge | 0 | — | 0 | 0 | 0 | 0 | 0 | 0 | — | — | 0 | 0 | 0 | 0 | 0 | 0 | 0 | 0 | 3 | 0 | 0 | 0 | 0 | — | 0 | 0 | 0 | 0 |
| Rape | 10 | 8 | 8 | 5 | — | 7 | 5 | 5 | 3 | 8 | 6 | 8 | 7 | 4 | 2 | 2 | 6 | 3 | 4 | 7 | 0 | 4 | 6 | 2 | 0 | 0 | 7 | 8 |
| Rice | 0 | 3 | 1 | 2 | 1 | 0 | 3 | — | 0 | 2 | 3 | 0 | 0 | 2 | 2 | 0 | 1 | 0 | 2 | 0 | 1 | 0 | 3 | 0 | 0 | 0 | 0 | 0 |
| Sicklepod | 5 | 1 | — | 8 | 5 | 3 | 3 | 4 | 3 | 6 | 7 | 4 | 6 | 6 | 0 | 4 | 5 | 0 | 7 | 5 | 4 | 4 | 3 | 2 | 0 | 0 | 0 | 0 |
| Soybean | 4 | 6 | 5 | 4 | 4 | 6 | 4 | 4 | 4 | 6 | 6 | 6 | 5 | 3 | 5 | 10 | 5 | 3 | 4 | 5 | 3 | 4 | 4 | 3 | 6 | 0 | 3 | 9 |
| Sugar beet | 10 | 10 | 10 | 10 | 10 | 9 | 10 | 10 | 6 | 10 | 9 | 8 | 7 | 10 | 3 | 10 | 10 | 5 | 10 | 10 | 7 | 10 | 9 | 8 | 6 | 7 | 10 | 8 |
| Teaweed | 3 | 3 | 4 | 0 | 5 | 0 | 3 | 3 | 0 | 9 | 8 | 6 | 4 | 5 | 0 | 0 | 2 | 0 | 4 | 5 | 0 | 4 | 2 | 1 | 0 | 0 | 0 | 0 |
| Velvetleaf | 0 | 4 | 6 | 3 | 4 | — | 6 | 8 | 0 | 7 | 6 | 3 | 6 | — | 0 | — | 7 | 0 | 5 | 8 | 0 | 0 | 3 | 1 | 3 | 0 | 0 | 2 |
| Wheat | 0 | 0 | 0 | 0 | 0 | 0 | 0 | 0 | 0 | 0 | 0 | 1 | 0 | 0 | 0 | 0 | 0 | 0 | 3 | 0 | 0 | 0 | 1 | 0 | 0 | 0 | 0 | 0 |
| Wild buckwheat | 8 | 9 | 3 | 7 | 0 | 10 | — | 10 | 0 | 8 | 6 | 7 | 7 | 6 | 7 | 8 | — | 0 | 8 | 9 | 0 | 4 | 5 | 0 | 0 | 0 | 7 | 5 |
| Wild Oat | 0 | 0 | 0 | 2 | 1 | 0 | 0 | 0 | 0 | 0 | 3 | 1 | 1 | 2 | 4 | 0 | 2 | 0 | 4 | 3 | 0 | 0 | 1 | 0 | 0 | 0 | 0 | 0 |

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | (31 g/ha) | | | | | | | | | | | | | | | | (1000 g/ha) | | | | | | | | (500 g/ha) | | | |
| | 32 | 33 | 34 | 35 | 36 | 37 | 40 | 50 | 53 | 55 | 57 | 68 | 69 | 76 | 84 | 117 | 3 | 5 | 9 | 13 | 28 | 43 | 75 | 104 | 3 | 5 | 8 | 9 |
| | POSTEMERGENCE | | | | | | | | | | | | | | | | PREEMERGENCE | | | | | | | | | | | |
| Barley | 0 | 0 | 0 | 0 | 0 | 0 | 0 | 0 | 0 | 0 | 0 | 1 | 1 | 0 | 0 | 0 | 0 | 3 | 0 | 5 | 2 | 0 | 0 | 2 | 0 | 3 | 2 | 0 |
| Barnyardgrass | 0 | 0 | 0 | 0 | 9 | 0 | 0 | 0 | 2 | 3 | 3 | 0 | 3 | 0 | 3 | 0 | 10 | 10 | 3 | 10 | 10 | 10 | 9 | 8 | 2 | 10 | 10 | 0 |
| Blackgrass | 0 | 0 | 0 | 0 | 0 | 0 | 0 | 2 | 4 | 1 | 3 | 4 | 0 | 4 | 6 | 2 | 5 | 10 | 5 | 10 | 8 | 10 | 8 | 7 | 3 | 10 | 10 | 3 |
| Chickweed | 3 | 0 | 0 | 0 | 8 | 0 | 0 | 4 | 3 | 1 | 5 | 0 | 3 | 7 | 8 | 0 | 9 | 10 | 9 | 10 | 5 | 9 | 9 | 6 | 2 | 9 | 10 | 7 |
| Cocklebur | 1 | 1 | 0 | 0 | 4 | 3 | 6 | 4 | 5 | 4 | 3 | — | — | 4 | 0 | 0 | 3 | 8 | 3 | 4 | 2 | 5 | 7 | 3 | 0 | 7 | 3 | 0 |
| Corn | 0 | 0 | 0 | 0 | 0 | 1 | 1 | 1 | 1 | 0 | 0 | 0 | 0 | 1 | 0 | 0 | 2 | 8 | 0 | 4 | 8 | 3 | 3 | 4 | 0 | 2 | 10 | 0 |
| Cotton | 2 | 0 | 0 | — | — | 8 | 7 | 0 | 1 | 0 | 4 | 4 | 6 | 5 | 3 | 0 | 5 | 4 | 0 | 0 | 0 | 0 | 0 | 2 | 3 | — | 0 | 0 |
| Crabgrass | 0 | 0 | 0 | 0 | 1 | 4 | — | 3 | 2 | 1 | 3 | 10 | 5 | 0 | 0 | 0 | 10 | 10 | 10 | 10 | 10 | 10 | 10 | 10 | 10 | 10 | 10 | 10 |
| Downy brome | 0 | 0 | 0 | 0 | 0 | 0 | 0 | 0 | 0 | 0 | 0 | 1 | 1 | 0 | 3 | 0 | 4 | 3 | 0 | 10 | 2 | 0 | 4 | 2 | 3 | 2 | 3 | 0 |
| Giant foxtail | 0 | 0 | 0 | 0 | 0 | 0 | 0 | — | — | — | 3 | 6 | 3 | 0 | 2 | 0 | 10 | 10 | 10 | 10 | 10 | 10 | 10 | 10 | 1 | 10 | 10 | 10 |
| Green foxtail | 0 | 0 | 0 | 0 | 3 | 1 | 0 | 1 | 1 | 0 | 3 | 3 | 0 | 0 | 0 | 0 | 10 | 10 | 10 | 10 | 10 | 10 | 10 | 10 | 10 | 10 | 10 | 8 |
| Jimsonweed | 9 | 0 | 0 | — | 9 | 7 | 8 | — | 6 | 6 | 10 | 6 | 5 | 6 | 6 | 5 | 9 | 10 | 8 | 10 | 10 | 10 | 6 | 7 | 8 | 10 | 10 | 5 |
| Johnsongrass | 0 | 0 | 0 | 0 | 0 | 0 | 0 | 5 | 0 | 0 | 0 | 0 | 0 | 0 | 0 | 0 | 8 | 10 | 0 | 10 | 10 | 8 | 7 | 7 | 6 | 5 | 10 | 0 |
| Lambsquarters | 8 | 3 | 0 | 3 | 10 | 9 | 9 | 4 | 4 | 4 | 10 | 10 | 7 | 4 | 9 | 0 | 10 | 10 | 10 | 10 | 10 | 10 | 9 | 10 | 9 | 10 | 10 | 10 |
| Morningglory | 0 | 0 | 0 | 0 | — | — | — | 6 | 3 | 3 | 10 | 6 | 7 | 5 | 4 | 0 | 9 | 10 | 7 | 10 | 10 | 9 | 5 | 4 | 3 | 9 | 10 | 3 |
| Nutsedge | 0 | 0 | 0 | 0 | 0 | 0 | 0 | 0 | 0 | 0 | — | 0 | 0 | 0 | 0 | — | 5 | 4 | 3 | 5 | 5 | 0 | 3 | 7 | 0 | — | 5 | 2 |
| Rape | 9 | 3 | 0 | 5 | 10 | 6 | 4 | 2 | 5 | 3 | 4 | 7 | 7 | 4 | 3 | 0 | 10 | 10 | 9 | 10 | 10 | 10 | 7 | 5 | 5 | 10 | 10 | 6 |
| Rice | 0 | 0 | 0 | 0 | 0 | 0 | 1 | 0 | 0 | 0 | 2 | 0 | 0 | 1 | 0 | 0 | 3 | 5 | 0 | 10 | 4 | 0 | 4 | 0 | 0 | 2 | 0 | 0 |

TABLE B-continued

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Sicklepod | 4 | — | 0 | 0 | 5 | 1 | 4 | 3 | 3 | — | 6 | 3 | 5 | 4 | 4 | 1 | 6 | 10 | 7 | 10 | 9 | 0 | 7 | 9 | 0 | 10 | 9 | 3 |
| Soybean | 2 | 2 | 0 | 3 | 3 | 5 | 4 | 4 | 4 | 3 | 3 | 6 | 5 | 5 | 0 | 2 | 4 | 7 | 3 | 4 | 6 | 4 | 0 | 4 | 0 | 4 | 8 | 2 |
| Sugar beet | 0 | 9 | 5 | 10 | 10 | 10 | 9 | 8 | 10 | 5 | 10 | 6 | 7 | 10 | 10 | 2 | 8 | 10 | 10 | 10 | 10 | 9 | 6 | 9 | 5 | 10 | 10 | 6 |
| Teaweed | 2 | 0 | 0 | 0 | 3 | 3 | 4 | 0 | 0 | 0 | 8 | 5 | 3 | 0 | 3 | 0 | 9 | 10 | 8 | 10 | 3 | 5 | 7 | 7 | 8 | 10 | 10 | 5 |
| Velvetleaf | 0 | 0 | 0 | 0 | 0 | — | 4 | 0 | 6 | 5 | 5 | 3 | 6 | 3 | 3 | 1 | 5 | 10 | 9 | 10 | 10 | 10 | 6 | 8 | 0 | 10 | 10 | 5 |
| Wheat | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 |
| Wild buckwheat | 4 | 3 | 0 | 0 | 5 | 2 | 0 | 4 | 10 | 7 | 3 | 7 | 6 | — | 4 | 0 | 9 | 10 | 9 | 10 | 9 | 6 | 7 | 7 | 9 | 9 | 10 | 8 |
| Wild Oat | 0 | 0 | 0 | 0 | 0 | 0 | 0 | 0 | 0 | 0 | 0 | 1 | 1 | 0 | 2 | 0 | 2 | 9 | 0 | 7 | 5 | 3 | 5 | 5 | 0 | 8 | 8 | 0 |

| | COMPOUND (500 g/ha) | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | 13 | 15 | 16 | 17 | 23 | 25 | 28 | 33 | 34 | 35 | 36 | 37 | 40 | 43 | 44 | 45 | 46 | 48 | 50 | 53 | 55 | 56 | 57 | 61 | 68 | 69 | 71 | 73 |
| PREEMERGENCE | | | | | | | | | | | | | | | | | | | | | | | | | | | | |
| Barley | 3 | 3 | 0 | 3 | 3 | 0 | 0 | 0 | 0 | 1 | 7 | 7 | 4 | 0 | 5 | 0 | 2 | 2 | 0 | 5 | 4 | 4 | 5 | — | 3 | 1 | 5 | 5 |
| Barnyardgrass | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | — | 10 | 10 | 10 | 10 |
| Blackgrass | 8 | 10 | 9 | 10 | 10 | 10 | 6 | 10 | 6 | 7 | 10 | 10 | 10 | 10 | 10 | 8 | 10 | 10 | — | 10 | 10 | 10 | 10 | — | 8 | 10 | 10 | 10 |
| Chickweed | 7 | 10 | 2 | 10 | 10 | 10 | 2 | 8 | 8 | 5 | 10 | 5 | 8 | 8 | 10 | 8 | 10 | 8 | 8 | 10 | 10 | 7 | 8 | — | 9 | 10 | 10 | 10 |
| Cocklebur | 0 | 0 | 0 | 4 | 2 | 0 | 0 | — | 5 | 5 | 10 | 2 | 0 | 3 | 0 | 0 | 3 | 0 | 10 | 10 | 7 | 8 | 10 | — | 6 | 0 | 3 | 3 |
| Corn | 3 | 5 | 3 | 7 | 8 | 3 | 6 | 3 | 2 | 4 | 8 | 3 | 3 | 0 | 10 | 2 | 5 | 6 | 3 | 7 | 6 | 7 | 8 | — | 4 | 2 | 7 | 9 |
| Cotton | 0 | 0 | 2 | 0 | 2 | 5 | 0 | 0 | 0 | 2 | 3 | 0 | 7 | 0 | 0 | 0 | 1 | 1 | 2 | 3 | 3 | 0 | 8 | — | 4 | 9 | 8 | 2 |
| Crabgrass | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 |
| Downy brome | 3 | 4 | 0 | 3 | 7 | — | 0 | 0 | 0 | 1 | 5 | 4 | 4 | 0 | 3 | 0 | 5 | 4 | 4 | 10 | 6 | 5 | 10 | — | 4 | 5 | 10 | 6 |
| Giant foxtail | 10 | 10 | 10 | 10 | 10 | 10 | 10 | 10 | 10 | 10 | 10 | 10 | 10 | 10 | 10 | 8 | 10 | 10 | 10 | 10 | 10 | 10 | 10 | — | 10 | 10 | 10 | 10 |
| Green foxtail | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | — | 10 | 10 | 10 | 10 |
| Jimsonweed | 10 | 10 | 3 | 10 | 10 | 10 | 8 | 6 | 10 | 10 | 10 | 10 | 9 | 9 | 10 | 0 | 7 | 10 | 9 | 10 | 10 | 2 | 10 | 10 | 10 | 10 | 10 | 10 |
| Johnsongrass | 8 | 10 | 9 | 9 | 10 | 10 | 10 | 10 | 10 | 10 | 10 | 10 | 9 | 7 | 10 | 10 | 10 | 8 | 9 | 10 | 9 | 10 | 10 | — | 4 | 4 | 9 | 10 |
| Lambsquarters | 10 | 10 | 9 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 |
| Morningglory | 10 | 9 | 3 | 6 | 10 | 10 | 10 | 10 | 7 | 9 | 10 | 10 | 10 | 8 | 10 | 7 | 7 | 8 | 9 | 10 | 9 | 10 | 10 | — | 10 | 9 | 4 | 9 |
| Nutsedge | 2 | 5 | 0 | 6 | 10 | 0 | 2 | 3 | 0 | 0 | 7 | 10 | 6 | 0 | — | — | 3 | 0 | 3 | 5 | 3 | — | — | 9 | 3 | 10 | 4 | 6 |
| Rape | 10 | 10 | 5 | 10 | 10 | 10 | 6 | 10 | 6 | 10 | 10 | 10 | 10 | 9 | 10 | 10 | 10 | 10 | — | 10 | 10 | 10 | 10 | — | 10 | 10 | 10 | 10 |
| Rice | 3 | 3 | 3 | 2 | 8 | 2 | 2 | 0 | 5 | 1 | 5 | 2 | 0 | 0 | 9 | 1 | 2 | 6 | 0 | 3 | 3 | 3 | 8 | 8 | 2 | 3 | 3 | 4 |
| Sicklepod | 7 | 4 | 0 | 7 | 8 | 8 | 9 | 9 | 3 | 8 | 10 | 5 | 8 | 0 | 3 | 2 | 3 | 4 | 3 | 10 | 9 | 0 | 3 | 10 | 10 | 10 | 9 | — |
| Soybean | 3 | 4 | 0 | 4 | 5 | 3 | 4 | 10 | 3 | 1 | 7 | 3 | 4 | 3 | 9 | 0 | 4 | 5 | 2 | 6 | 4 | 10 | 6 | — | 6 | 4 | 7 | 9 |
| Sugar beet | 10 | 10 | 10 | 10 | 10 | 10 | 2 | 9 | 10 | 10 | 10 | 10 | 10 | 7 | 10 | 10 | 9 | 10 | — | 10 | 10 | 10 | 10 | — | 10 | 10 | 10 | 10 |
| Teaweed | 5 | 8 | 0 | 7 | 10 | 8 | 2 | 3 | 10 | 3 | 10 | 10 | 8 | 4 | 8 | 0 | 8 | 10 | 9 | 10 | 9 | 2 | 8 | 10 | 10 | 9 | 9 | 3 |
| Velvetleaf | 10 | 10 | 8 | 10 | 10 | 10 | 9 | 9 | 10 | 10 | 10 | 10 | 10 | 9 | 10 | 8 | 10 | 10 | 10 | 10 | 10 | 10 | 10 | 10 | 10 | 9 | 10 | 7 |
| Wheat | 0 | 2 | 0 | 0 | 2 | 0 | 0 | 0 | 0 | 0 | 3 | 0 | 0 | 0 | 2 | 0 | 1 | 1 | 0 | 3 | 3 | 0 | 1 | — | 0 | 2 | 4 | 0 |
| Wild buckwheat | 9 | 10 | 0 | 8 | 9 | 10 | 5 | 10 | 4 | 0 | 10 | 9 | 8 | 5 | 9 | 8 | 10 | 9 | 3 | 10 | 5 | 10 | 10 | — | 10 | 10 | 9 | 9 |
| Wild Oat | 3 | 9 | 0 | 5 | 10 | 4 | 3 | 1 | 1 | 0 | — | 7 | 7 | 3 | 3 | 2 | 7 | 8 | 6 | 10 | 10 | 4 | 10 | — | 5 | 7 | 9 | 10 |

| | COMPOUND (500 g/ha) | | | | | | | | | | COMPOUND (250 g/ha) | | | | | | | | | | | | | | | | |
|---|---|---|---|---|---|---|---|---|---|---|---|---|---|---|---|---|---|---|---|---|---|---|---|---|---|---|---|
| | 74 | 75 | 76 | 82 | 84 | 87 | 90 | 104 | 107 | 117 | 5 | 8 | 9 | 13 | 15 | 16 | 17 | 23 | 25 | 28 | 32 | 33 | 34 | 35 | 36 | 37 | 40 |
| PREEMERGENCE | | | | | | | | | | | | | | | | | | | | | | | | | | | |
| Barley | 6 | 0 | 4 | 4 | 5 | 2 | 7 | 2 | 3 | 0 | 0 | 0 | 0 | 0 | 2 | 0 | 0 | 2 | 0 | 0 | 0 | 0 | 0 | 0 | 3 | 3 | 2 |
| Barnyardgrass | 10 | 8 | 8 | 10 | 10 | 10 | 8 | 6 | 10 | 10 | 6 | 10 | 0 | 5 | 10 | 8 | 8 | 10 | 10 | 10 | 10 | 10 | 10 | 10 | 10 | 10 | 10 |
| Blackgrass | 10 | 8 | 8 | 10 | 10 | 10 | 9 | 6 | 10 | 10 | 5 | 9 | 0 | 3 | 9 | 4 | 8 | 10 | 10 | 5 | 10 | 8 | 5 | 3 | 10 | 10 | 9 |
| Chickweed | 10 | 8 | 9 | 10 | 10 | 10 | 10 | 4 | 7 | 9 | 8 | 10 | 5 | 3 | 7 | 0 | 10 | 8 | 10 | 0 | 7 | 8 | 6 | 5 | 10 | 3 | 6 |
| Cocklebur | 10 | 0 | 0 | 0 | 5 | 5 | 2 | 3 | 0 | 4 | 4 | 3 | 0 | 0 | 0 | 0 | 4 | 0 | 0 | 0 | 0 | 9 | 0 | — | 0 | — | 0 |
| Corn | 5 | 2 | 3 | 5 | 6 | 4 | 7 | 2 | 2 | 4 | 2 | 5 | 0 | 2 | 3 | 1 | 4 | 7 | 2 | 5 | 2 | 1 | 2 | 3 | 7 | 2 | 2 |
| Cotton | 3 | 0 | 4 | 1 | 4 | 2 | 0 | 0 | 0 | 0 | 2 | 0 | 0 | 0 | 0 | 0 | 0 | 1 | 0 | 0 | 0 | 0 | 0 | 2 | 2 | 0 | 0 |
| Crabgrass | 10 | 10 | 10 | 10 | 10 | 10 | 10 | 10 | 10 | 10 | 10 | 10 | 8 | 10 | 10 | 10 | 10 | 10 | 10 | 10 | 10 | 10 | 10 | 10 | 10 | 10 | 10 |

TABLE B-continued

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| Downy brome | 4 | 3 | 5 | 6 | 10 | 5 | 3 | 2 | 0 | 3 | 1 | 0 | 0 | 0 | 2 | 0 | 0 | 3 | 1 | 0 | 0 | 0 | 0 | 0 | 1 | 2 | 2 |
| Giant foxtail | 10 | 10 | 10 | 10 | 10 | 10 | 9 | 10 | 10 | 10 | 7 | 10 | 7 | 10 | 10 | 10 | 10 | 10 | 10 | 10 | 10 | 10 | 10 | 10 | 10 | 10 | 10 |
| Green foxtail | 10 | 10 | 10 | 10 | 10 | 10 | 9 | 10 | 10 | 10 | 5 | 10 | 3 | 10 | 10 | 10 | 10 | 10 | 10 | 10 | 10 | 10 | 10 | 10 | 10 | 10 | 10 |
| Jimsonweed | 9 | 3 | 6 | 9 | 10 | 10 | 10 | 5 | 6 | 10 | 5 | 10 | 3 | 5 | 10 | 0 | 10 | 10 | 10 | 2 | 5 | 5 | 9 | 5 | 10 | 9 | 8 |
| Johnsongrass | 8 | 6 | 7 | 10 | 10 | 10 | 7 | 6 | 0 | 9 | 2 | 10 | 0 | 3 | 10 | 2 | 7 | 10 | 10 | 10 | 10 | 10 | 10 | 10 | 10 | 9 | 8 |
| Lambsquarters | 9 | 9 | 9 | 10 | 10 | 10 | 10 | 9 | 9 | 10 | 9 | 10 | 10 | 10 | 10 | 9 | 10 | 10 | 10 | 8 | 10 | 10 | 10 | 10 | 10 | 10 | 10 |
| Morningglory | 10 | 3 | 7 | 9 | 10 | 10 | 8 | 4 | 6 | 9 | 5 | 10 | 0 | 0 | 9 | 0 | 3 | 10 | 7 | 5 | 7 | 4 | 7 | 8 | 9 | 9 | 10 |
| Nutsedge | 5 | 3 | 3 | 3 | 3 | 5 | 2 | 3 | 6 | 8 | 0 | 3 | 0 | 0 | 2 | 0 | 2 | 8 | 0 | 0 | 0 | 3 | 0 | 0 | 5 | 6 | 4 |
| Rape | 10 | 6 | 10 | 5 | 10 | 10 | 10 | 5 | 6 | 10 | 8 | 10 | 4 | 8 | 10 | 3 | 9 | 10 | 10 | 4 | 10 | 0 | 3 | 10 | 10 | 10 | 10 |
| Rice | 0 | 3 | 0 | 2 | 6 | 7 | 3 | 0 | 0 | 5 | 1 | 0 | 0 | 0 | 2 | 0 | 0 | 7 | 10 | 0 | 1 | 0 | 5 | 1 | 1 | 0 | 0 |
| Sicklepod | 10 | 7 | 9 | 7 | 10 | 10 | 3 | 6 | 3 | 4 | 9 | 9 | 0 | 3 | 2 | 0 | 3 | 8 | 0 | 0 | 0 | — | — | 3 | 10 | 0 | 5 |
| Soybean | 9 | 0 | 4 | 1 | 9 | 7 | 4 | 3 | 3 | 4 | 2 | 5 | 0 | 2 | 3 | 0 | 2 | 4 | 0 | 2 | 3 | 0 | 2 | 0 | 4 | 0 | 3 |
| Sugar beet | 10 | 3 | 10 | 10 | 10 | 10 | 8 | 7 | 6 | 10 | 8 | 10 | 3 | 5 | 10 | 2 | 10 | 10 | 10 | 0 | 9 | 9 | 10 | — | 10 | 10 | 10 |
| Teaweed | 7 | 5 | 7 | 9 | 10 | 10 | 6 | 5 | 5 | 10 | 8 | 7 | 3 | 0 | 8 | 0 | 5 | 5 | 7 | 0 | 4 | 3 | 4 | 3 | 3 | 9 | 8 |
| Velvetleaf | 8 | 4 | 7 | 8 | 10 | 10 | 10 | 7 | 6 | 10 | 8 | 10 | 3 | 4 | 10 | 8 | 10 | 10 | 8 | 8 | 10 | 8 | 10 | 10 | 10 | 10 | 10 |
| Wheat | 3 | 0 | 4 | 1 | 2 | 0 | 0 | 0 | 0 | 0 | 0 | 0 | 0 | 0 | 0 | 0 | 0 | 0 | 0 | 0 | 0 | 0 | 0 | 0 | 2 | 0 | 0 |
| Wild buckwheat | 4 | 3 | 5 | 10 | 9 | 9 | 8 | 4 | 8 | 10 | 9 | 9 | 5 | 6 | 10 | 0 | 8 | 7 | 10 | 2 | 4 | 3 | 0 | 0 | 9 | 7 | 5 |
| Wild Oat | 5 | 4 | 7 | 9 | 10 | 6 | 4 | 4 | 4 | 0 | 5 | 2 | 0 | 0 | 4 | 0 | 2 | 10 | 3 | 0 | 0 | 0 | 0 | 0 | 3 | 5 | 3 |

| | COMPOUND (250 g/ha) | | | | | | | | | | | | | | | | | | | | | | | | | (125 g/ha) | |
|---|---|---|---|---|---|---|---|---|---|---|---|---|---|---|---|---|---|---|---|---|---|---|---|---|---|---|---|
| | 43 | 44 | 45 | 46 | 48 | 50 | 53 | 55 | 56 | 57 | 61 | 68 | 69 | 71 | 73 | 74 | 75 | 76 | 82 | 84 | 87 | 90 | 104 | 107 | 117 | 8 | 13 |
| PREEMERGENCE | | | | | | | | | | | | | | | | | | | | | | | | | | | |
| Barley | 0 | 2 | 0 | 0 | 2 | 0 | 4 | 3 | 0 | 4 | 1 | 3 | 0 | 4 | 4 | 0 | 0 | 3 | 3 | 2 | 2 | 3 | 0 | 2 | 0 | 0 | 0 |
| Barnyardgrass | 8 | 10 | 8 | 9 | 10 | 10 | 10 | 10 | 8 | 10 | 10 | 10 | 10 | 10 | 10 | 10 | 6 | 7 | 9 | 10 | 10 | 6 | 4 | 8 | 6 | 10 | 5 |
| Blackgrass | 7 | 10 | 4 | 10 | 10 | 10 | 10 | 10 | 10 | 10 | 10 | 4 | — | 10 | 10 | 10 | 7 | 8 | 10 | 9 | 9 | 7 | 6 | 7 | 10 | 7 | 3 |
| Chickweed | 5 | 8 | 3 | 10 | 4 | 7 | 10 | 8 | 7 | 4 | 4 | 9 | 7 | 9 | 10 | 10 | 7 | 8 | 10 | 10 | 10 | 7 | 3 | 5 | 8 | 10 | 3 |
| Cocklebur | 0 | 0 | 0 | 2 | 0 | 10 | 7 | — | — | 1 | 4 | 5 | — | 0 | — | 6 | 0 | 0 | 0 | 3 | 4 | 0 | 0 | 0 | 3 | 0 | 0 |
| Corn | 0 | 6 | 1 | 1 | 3 | 3 | 6 | 5 | 6 | 6 | 3 | 3 | 1 | 5 | 8 | 3 | 0 | 2 | 5 | 6 | 4 | 3 | 0 | 0 | 0 | 2 | 2 |
| Cotton | 0 | 0 | 0 | 1 | 1 | 0 | 2 | 0 | 0 | 3 | 3 | 4 | 6 | 3 | 0 | 2 | 0 | 4 | 0 | 1 | 0 | 0 | 0 | 0 | 0 | 0 | 0 |
| Crabgrass | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 7 | 10 | 10 | 10 | 10 |
| Downy brome | 0 | 0 | 0 | 3 | 3 | 3 | 10 | 3 | 0 | 10 | 3 | 3 | 4 | 6 | 3 | 3 | 0 | 4 | 3 | 4 | 3 | 0 | 2 | 0 | 0 | 0 | 0 |
| Giant foxtail | 10 | 10 | 7 | 10 | 10 | 10 | 10 | 10 | 10 | 10 | 10 | 7 | 5 | 10 | 10 | 10 | 10 | 10 | 10 | 10 | 8 | 9 | 9 | 10 | 10 | 10 | 10 |
| Green foxtail | 10 | 10 | 10 | 10 | 10 | 10 | 10 | 10 | 10 | 10 | 10 | 10 | 10 | 10 | 10 | 10 | 10 | 10 | 10 | 10 | 10 | 9 | 10 | 10 | 10 | 10 | 10 |
| Jimsonweed | 6 | 8 | 0 | 5 | 8 | 7 | 10 | 7 | 0 | 10 | 10 | 10 | 7 | 10 | 10 | 8 | 0 | 6 | 9 | 10 | 10 | 4 | 3 | 5 | 6 | 9 | 5 |
| Johnsongrass | 6 | 10 | 8 | 9 | 8 | 9 | 9 | 8 | 10 | 10 | 10 | 4 | 4 | 9 | 10 | 7 | 3 | 6 | 9 | 8 | 8 | 3 | 3 | 0 | 6 | 7 | 3 |
| Lambsquarters | 10 | 10 | 10 | 8 | 10 | 10 | 10 | 10 | 10 | 10 | 10 | 10 | 10 | 9 | 10 | 9 | 7 | 7 | 10 | 10 | 10 | 10 | 8 | 9 | 10 | 10 | 10 |
| Morningglory | 7 | 8 | 7 | 5 | 0 | 8 | 10 | 8 | 10 | 10 | 9 | 9 | 7 | 3 | 9 | 7 | 3 | 7 | 5 | 10 | 10 | 8 | 4 | 3 | 8 | 7 | 0 |
| Nutsedge | 0 | — | — | 2 | 0 | 3 | 3 | 0 | — | — | 8 | 0 | 2 | 3 | 5 | 3 | 3 | 3 | 2 | 0 | 5 | 0 | 0 | 3 | 0 | 0 | 0 |
| Rape | 6 | 8 | 0 | 8 | 8 | 10 | 10 | 10 | 10 | 10 | 10 | 10 | 9 | 8 | 10 | 10 | 5 | 10 | 5 | 10 | 10 | 7 | 4 | 4 | 5 | 10 | 8 |
| Rice | 0 | 8 | 0 | 1 | 5 | 0 | 3 | 2 | 0 | 7 | 7 | 2 | 3 | 2 | 3 | 0 | 3 | 0 | 2 | 6 | 6 | 2 | 0 | 0 | 3 | 0 | 0 |
| Sicklepod | 0 | 0 | 2 | 2 | 2 | 2 | 9 | 6 | 0 | 2 | 8 | 10 | 10 | 8 | 3 | 9 | 3 | 8 | 5 | 10 | 10 | 3 | 3 | 3 | 0 | 5 | 3 |
| Soybean | 0 | 5 | 0 | 2 | 3 | 2 | 5 | 3 | 9 | 5 | 3 | 5 | 2 | 7 | 8 | 6 | 0 | 3 | 1 | 7 | 6 | 3 | 2 | 3 | 2 | 5 | 2 |
| Sugar beet | 5 | 10 | 6 | 9 | 10 | 9 | 10 | 9 | 10 | 10 | 10 | 10 | 8 | 8 | 10 | 10 | 2 | 10 | 10 | 10 | 10 | 8 | 6 | 4 | 90 | 10 | 5 |
| Teaweed | 3 | 7 | 0 | 4 | 8 | 8 | 10 | 8 | 0 | 7 | 10 | 10 | 9 | 9 | 2 | 6 | 3 | 6 | 8 | 10 | 9 | 2 | 4 | 3 | 4 | 5 | 0 |
| Velvetleaf | 8 | 9 | 7 | 8 | 10 | 10 | 10 | 10 | 10 | 10 | 10 | 10 | 9 | 10 | 7 | 7 | 0 | 5 | 8 | 10 | 10 | 10 | 6 | 3 | 10 | 10 | 4 |
| Wheat | 0 | 0 | 0 | 0 | 1 | 0 | 0 | 0 | 0 | 0 | 0 | 0 | 0 | 2 | 0 | 2 | 0 | 2 | 0 | 0 | 0 | 0 | 0 | 0 | 0 | 0 | 0 |
| Wild buckwheat | 4 | 5 | 4 | 10 | 9 | 2 | 10 | 4 | 10 | 10 | 9 | 10 | — | 9 | — | 2 | 0 | 3 | 9 | 9 | 8 | 8 | 3 | 7 | 6 | 9 | 6 |
| Wild Oat | 2 | 0 | 0 | 5 | 6 | 5 | 10 | 7 | 4 | 10 | 8 | 5 | 4 | 7 | 9 | 3 | 0 | 6 | 7 | 9 | 3 | 2 | 4 | 3 | 0 | 0 | 0 |

COMPOUND
(125 g/ha)

TABLE B-continued

| | 15 | 16 | 17 | 23 | 25 | 28 | 32 | 33 | 34 | 35 | 36 | 37 | 40 | 43 | 44 | 45 | 46 | 48 | 50 | 53 | 55 | 56 | 57 | 61 | 68 | 69 | 71 | 73 |
|---|---|---|---|---|---|---|---|---|---|---|---|---|---|---|---|---|---|---|---|---|---|---|---|---|---|---|---|---|
| | | | | | | | | | | | | PREEMERGENCE | | | | | | | | | | | | | | | | |
| Barley | 10 | 0 | 0 | 0 | 0 | 0 | 0 | 0 | 0 | 0 | 0 | 0 | 0 | 0 | 2 | 0 | 0 | 2 | 0 | 3 | 2 | 0 | 1 | 0 | 3 | 0 | 3 | 3 |
| Barnyardgrass | 9 | 2 | 5 | 10 | 4 | 8 | 10 | 10 | 9 | 6 | 10 | 10 | 8 | 6 | 10 | 4 | 7 | 10 | 10 | 10 | 10 | 4 | 10 | 10 | 9 | 10 | 10 | 8 |
| Blackgrass | 9 | 2 | 5 | 9 | 10 | 2 | 10 | 8 | 1 | 2 | 8 | 10 | 4 | 6 | — | 0 | 9 | 9 | 8 | 10 | 8 | 7 | 3 | 5 | 2 | 5 | 10 | 9 |
| Chickweed | 6 | 0 | 10 | 5 | 8 | 0 | 5 | 8 | 0 | 5 | 9 | 2 | 3 | 3 | 4 | 0 | 9 | 3 | 5 | 9 | 7 | 2 | 2 | — | 7 | 6 | 5 | 10 |
| Cocklebur | 0 | 0 | 3 | 0 | 0 | 0 | 0 | 5 | 0 | 0 | 0 | 0 | — | — | — | 0 | 0 | 0 | 10 | 6 | 5 | 0 | 0 | 0 | 4 | — | 0 | — |
| Corn | 2 | 0 | 0 | 4 | 0 | 2 | 0 | 0 | 0 | 2 | 5 | 0 | 0 | 0 | 4 | 0 | 0 | 1 | 3 | 6 | 4 | 5 | 5 | 2 | 2 | 0 | 3 | 6 |
| Cotton | 0 | 0 | 0 | 0 | 0 | 0 | 0 | 0 | 10 | 0 | 0 | 0 | 0 | 0 | 0 | 0 | 0 | 1 | 0 | 2 | 0 | 0 | — | 3 | 0 | 5 | 2 | 0 |
| Crabgrass | 10 | 9 | 10 | 10 | 10 | 10 | 10 | 10 | 0 | 9 | 10 | 10 | 10 | 10 | 10 | 10 | 10 | 10 | 10 | 10 | 10 | 10 | 10 | 10 | 10 | — | 10 | 10 |
| Downy brome | 0 | 0 | 0 | 2 | 0 | 0 | 0 | 0 | 10 | 0 | 0 | 0 | 0 | 0 | 0 | 0 | 0 | 0 | 3 | 5 | 2 | 0 | 5 | 2 | 0 | 0 | 4 | 0 |
| Giant foxtail | 10 | 9 | 10 | 10 | 10 | 10 | 10 | 10 | 10 | 10 | 10 | 10 | 10 | 10 | 10 | 7 | 10 | 10 | 10 | 10 | 10 | 10 | 10 | 10 | — | 3 | 10 | 10 |
| Green foxtail | 10 | 9 | 10 | 10 | 10 | 10 | 10 | 10 | 8 | 10 | 10 | 10 | 10 | 10 | 10 | 10 | 10 | 10 | 10 | 10 | 10 | 10 | 10 | 10 | 10 | 10 | 10 | 10 |
| Jimsonweed | 9 | 0 | 7 | 10 | 7 | 2 | 5 | 3 | 8 | 2 | 9 | 6 | 5 | 3 | 0 | 0 | 2 | 4 | 6 | 10 | 6 | 0 | 8 | 8 | 9 | 7 | 8 | 9 |
| Johnsongrass | 9 | 0 | 3 | 10 | 10 | 6 | 9 | 10 | 10 | 9 | 10 | 8 | 7 | 5 | 10 | 8 | 7 | 5 | 8 | 9 | 7 | 8 | 8 | 7 | 2 | 0 | 9 | 8 |
| Lambsquarters | 9 | 8 | 10 | 9 | 10 | 5 | 10 | 10 | 2 | 9 | 10 | 10 | 10 | 10 | 10 | 10 | 8 | 8 | 10 | 10 | 10 | 10 | 10 | 10 | 10 | 10 | 9 | 10 |
| Morningglory | 5 | 0 | 2 | 9 | 3 | 4 | 4 | 2 | 0 | 7 | 8 | 8 | 8 | 4 | 4 | 0 | 2 | 0 | 7 | 10 | 7 | 7 | 9 | 8 | 8 | 3 | 3 | 5 |
| Nutsedge | 0 | 0 | 0 | 3 | 0 | 0 | 0 | 0 | 2 | 0 | 5 | 3 | 2 | 0 | — | — | 0 | 0 | 3 | 3 | 0 | — | — | 4 | 0 | 2 | 1 | 3 |
| Rape | 7 | 0 | 3 | 10 | 10 | 0 | 5 | 0 | 0 | 4 | 10 | 10 | 10 | 0 | 0 | 0 | 8 | 8 | 10 | 10 | 7 | 10 | 10 | 10 | 10 | 4 | 8 | 10 |
| Rice | 0 | 0 | 0 | 4 | 0 | 0 | 1 | 0 | 0 | 0 | 1 | 0 | 0 | 0 | 3 | 0 | 1 | 2 | 0 | 3 | 0 | 0 | 4 | 2 | 0 | 3 | 2 | 2 |
| Sicklepod | 0 | 0 | 0 | 2 | 0 | 0 | 0 | 5 | 0 | 3 | 5 | 0 | 3 | 0 | 0 | 0 | 0 | 0 | 2 | 7 | 3 | 0 | 0 | 3 | 5 | 10 | 7 | 0 |
| Soybean | 0 | 0 | 0 | 2 | 0 | 0 | 1 | 0 | 3 | 0 | 3 | 0 | 0 | 0 | 0 | 0 | 0 | 0 | 2 | 4 | 2 | 2 | 3 | 2 | 4 | 0 | 3 | 6 |
| Sugar beet | 10 | 0 | 10 | 10 | 10 | 0 | 8 | 8 | 0 | 9 | 10 | 10 | 10 | 3 | 4 | 2 | 6 | 9 | 8 | 10 | 9 | 10 | 10 | 10 | 6 | 8 | 5 | 10 |
| Teaweed | 3 | 0 | 2 | 2 | 3 | 0 | 2 | 3 | 0 | 3 | 3 | 9 | 8 | 3 | 0 | 0 | 2 | 7 | 5 | 9 | 5 | 0 | 6 | 6 | 9 | 8 | 7 | 0 |
| Velvetleaf | 9 | 3 | 9 | 9 | 5 | 5 | 10 | — | 0 | 2 | 10 | 8 | 10 | 6 | 9 | 6 | 4 | 9 | 10 | 10 | 10 | 4 | 10 | 10 | 7 | 9 | 10 | 3 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 10 | 0 | 7 | 7 | 8 | 0 | 3 | 0 | 0 | 0 | 8 | 5 | 2 | 3 | 5 | 3 | 9 | 8 | 0 | 10 | 3 | 6 | 3 | 8 | — | — | 9 | 9 |
| Wild Oat | 3 | 0 | 0 | 10 | 0 | 0 | 0 | 0 | 0 | 0 | 2 | 0 | 0 | 0 | 0 | 0 | 3 | 3 | 3 | 10 | 5 | 0 | 6 | 6 | 4 | 4 | 6 | 4 |

| | COMPOUND (125 g/ha) | | | | | | | | | | COMPOUND (62 g/ha) | | | | | | | | | | | | | | | | | | |
|---|---|---|---|---|---|---|---|---|---|---|---|---|---|---|---|---|---|---|---|---|---|---|---|---|---|---|---|---|---|
| | 74 | 75 | 76 | 82 | 84 | 87 | 90 | 104 | 107 | 117 | 5 | 8 | 15 | 16 | 17 | 23 | 25 | 32 | 33 | 34 | 35 | 36 | 37 | 40 | 44 | 45 | 46 | 48 | 50 |
| | | | | | | | | | | | PREEMERGENCE | | | | | | | | | | | | | | | | | | |
| Barley | 0 | 0 | 2 | 3 | 2 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 7 | 3 | 5 | 3 | 10 | 10 | 4 | 3 | 3 | 3 | 5 | 9 | 8 | 0 | 2 | 9 | 3 | 10 | 5 | 7 | 2 | 9 | 6 | 6 | 6 | 2 | 5 | 6 | 10 |
| Blackgrass | 9 | 6 | 7 | 9 | 5 | 7 | 4 | 3 | 6 | 7 | 3 | 4 | 3 | 0 | 3 | 7 | 8 | 3 | 0 | 0 | 0 | 3 | 5 | 2 | 9 | 0 | 9 | 0 | 8 |
| Chickweed | 9 | 3 | 7 | 8 | 9 | 8 | 7 | 3 | 0 | 5 | 8 | 10 | 4 | 0 | 6 | 3 | 5 | 4 | 0 | 0 | 5 | 4 | 0 | 0 | — | 0 | 7 | 0 | 3 |
| Cocklebur | 3 | 0 | 0 | 0 | 0 | 3 | 0 | 0 | 0 | 0 | 0 | 0 | 0 | 0 | 3 | 0 | — | 0 | 0 | 0 | 0 | — | 0 | — | — | — | 0 | 0 | 3 |
| Corn | 0 | 0 | 0 | 1 | 5 | 0 | 0 | 0 | 0 | 0 | 1 | 0 | 0 | 0 | 0 | 2 | 0 | 0 | 0 | 0 | 1 | 3 | 0 | 0 | 4 | 0 | 0 | 0 | 3 |
| Cotton | 0 | 0 | 4 | 0 | 0 | 0 | 0 | 0 | 0 | 0 | — | 0 | 0 | 0 | 0 | 0 | 0 | 0 | 0 | 0 | 0 | 0 | 0 | 0 | 0 | 0 | 0 | 0 | 0 |
| Crabgrass | 10 | 10 | 10 | 10 | 10 | 10 | 10 | 7 | 8 | 10 | 9 | 10 | 10 | 8 | 9 | 10 | 10 | 10 | 10 | 10 | 7 | 10 | 10 | 10 | 10 | 10 | 10 | 10 | 10 |
| Downy brome | 2 | 0 | 3 | 2 | 2 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Giant foxtail | 10 | 7 | 10 | 10 | 10 | 7 | 7 | 8 | 10 | 10 | 6 | 9 | 10 | 6 | 9 | 10 | 10 | 10 | 10 | 8 | 10 | 10 | 10 | 10 | 5 | 2 | 9 | 8 | 10 |
| Green foxtail | 10 | 10 | 9 | 10 | 10 | 10 | 9 | 7 | 10 | 10 | 3 | 10 | 10 | 8 | 7 | 10 | 10 | 10 | 10 | 10 | 10 | 10 | 10 | 10 | 6 | 3 | 10 | 10 | 10 |
| Jimsonweed | 7 | 0 | 4 | 3 | 10 | 10 | 2 | 3 | 3 | 4 | 3 | 5 | 2 | 0 | 3 | 4 | 1 | 2 | 0 | 0 | 2 | 7 | 2 | 4 | 0 | 0 | 2 | 3 | 5 |
| Johnsongrass | 6 | 0 | 5 | 3 | 7 | 7 | 0 | 0 | 0 | 0 | 0 | 3 | 8 | 0 | 0 | 8 | 5 | 9 | 0 | 7 | 7 | 8 | 5 | 6 | 8 | — | 7 | 0 | 7 |
| Lambsquarters | 9 | 4 | 5 | 9 | 10 | 10 | 10 | 7 | 6 | 10 | 9 | 10 | 9 | 8 | 9 | 9 | 10 | 9 | 7 | 9 | 9 | 10 | 8 | 10 | 10 | 6 | 8 | 3 | 9 |
| Morningglory | 6 | 0 | 4 | 2 | 10 | 10 | 2 | 0 | 3 | 6 | 3 | 2 | 2 | 0 | 0 | 5 | 2 | 3 | 1 | 0 | 0 | 2 | 5 | 3 | 0 | 0 | 2 | 0 | 5 |
| Nutsedge | 3 | 3 | 0 | 0 | 0 | 4 | 0 | 0 | 0 | 0 | — | 0 | 0 | 0 | 0 | — | 0 | 0 | 0 | 0 | 0 | 3 | 3 | 0 | — | — | 0 | 0 | 3 |
| Rape | 8 | 3 | 9 | 5 | 10 | 10 | 2 | 3 | 3 | 0 | 4 | 8 | 2 | 0 | 0 | 6 | 3 | 4 | 0 | 0 | 0 | 9 | 8 | 5 | — | 0 | 3 | 3 | 4 |
| Rice | 0 | 3 | 0 | 0 | 5 | 5 | 0 | 0 | 0 | 0 | 0 | 0 | 0 | 0 | 0 | 4 | 0 | 0 | 0 | 0 | 0 | 1 | 0 | 0 | 2 | 0 | 0 | 0 | 0 |
| Sicklepod | 8 | 3 | 7 | 2 | 3 | 10 | 2 | 2 | 0 | 0 | — | 3 | 0 | 0 | 0 | 0 | 0 | 0 | 0 | 0 | — | — | 0 | 3 | 0 | 0 | 0 | 0 | 0 |

TABLE B-continued

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Soybean | 4 | 0 | 2 | 1 | 3 | 5 | 0 | 2 | 3 | 0 | 1 | 2 | 0 | 0 | 0 | 0 | 0 | 0 | 0 | 0 | 0 | 0 | 0 | 0 | 0 | 0 | 0 | 0 | 0 |
| Sugar beet | 10 | 0 | 7 | 9 | 10 | 10 | 8 | 5 | 3 | 3 | 7 | 9 | 7 | 0 | 10 | 10 | 5 | 5 | 3 | 0 | 8 | 7 | 5 | 5 | 4 | 0 | 6 | 3 | 6 |
| Teaweed | 5 | 3 | 5 | 5 | 5 | 7 | 0 | 4 | 0 | 3 | 7 | 3 | 0 | 0 | 0 | 0 | 2 | 0 | 0 | 0 | 2 | 2 | 3 | 5 | 0 | 0 | 2 | 2 | 4 |
| Velvetleaf | 4 | 0 | 4 | 7 | 10 | 10 | 9 | 6 | 0 | 8 | 4 | 10 | 5 | 0 | 8 | 8 | 0 | 10 | 0 | — | 2 | 9 | 6 | 5 | 0 | 0 | 2 | 9 | 7 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | 0 | 2 | 9 | 9 | 7 | 7 | 0 | 6 | 5 | 7 | 5 | 3 | 0 | 3 | 5 | 5 | 0 | 0 | 0 | 0 | 3 | 2 | 0 | 4 | 0 | 7 | — | 0 |
| Wild Oat | 3 | 0 | 5 | 4 | 3 | 0 | 0 | 3 | 0 | 0 | 4 | 0 | 2 | 0 | 0 | 3 | 0 | 0 | 0 | 0 | 0 | 1 | 0 | 0 | 0 | 0 | 2 | 0 | 0 |

| | COMPOUND | | | | | | | | | | | | | | | | | | | | | | | | | | |
|---|---|---|---|---|---|---|---|---|---|---|---|---|---|---|---|---|---|---|---|---|---|---|---|---|---|---|---|
| | (62 g/ha) | | | | | | | | | | | | | | | | | | | (31 g/ha) | | | | | | | |
| | 53 | 55 | 56 | 57 | 61 | 68 | 69 | 71 | 73 | 74 | 75 | 76 | 82 | 84 | 87 | 90 | 104 | 107 | 117 | 8 | 17 | 23 | 25 | 32 | 33 | 34 | 35 |
| PREEMERGENCE | | | | | | | | | | | | | | | | | | | | | | | | | | | |
| Barley | 2 | 0 | 0 | 0 | 0 | 3 | 0 | 2 | 3 | 0 | 0 | 0 | 0 | 0 | 0 | 0 | 0 | 0 | 0 | 0 | 0 | 0 | 0 | 0 | 0 | 0 | 0 |
| Barnyardgrass | 7 | 9 | 4 | 10 | 9 | 5 | 8 | 10 | 8 | 5 | 0 | 2 | 2 | 7 | 5 | 3 | 2 | 0 | 0 | 3 | 0 | 4 | 0 | 8 | 0 | 0 | 0 |
| Blackgrass | 7 | 8 | 5 | 0 | 3 | 0 | 5 | 10 | 8 | 8 | 4 | 4 | 9 | 5 | 6 | 0 | 0 | 5 | 3 | 0 | 0 | 3 | 4 | 1 | 0 | 0 | 0 |
| Chickweed | 7 | 5 | 0 | 10 | 4 | 5 | 3 | 5 | 4 | 9 | 0 | 7 | 3 | 9 | 7 | 2 | 0 | 0 | 3 | 5 | 2 | 3 | 0 | 0 | 0 | 0 | 5 |
| Cocklebur | — | 2 | 0 | 0 | — | 0 | — | 0 | 0 | 3 | 0 | 0 | 0 | 0 | 2 | 0 | 0 | 0 | 0 | 0 | 0 | 0 | 0 | 0 | — | — | 0 |
| Corn | 5 | 0 | 3 | 4 | 2 | 0 | 0 | 0 | 4 | 0 | 0 | 0 | 0 | 3 | 0 | 0 | 0 | 0 | 0 | 0 | 0 | 0 | 0 | 0 | 0 | 0 | 0 |
| Cotton | 0 | 0 | 0 | 0 | 3 | 0 | 2 | 1 | 0 | 0 | 0 | 2 | 0 | 0 | 0 | 0 | 0 | 0 | 0 | 0 | 0 | 0 | 0 | 0 | 0 | 0 | 0 |
| Crabgrass | 10 | 10 | 10 | 10 | 10 | 10 | 10 | 10 | 10 | 10 | 10 | 10 | 10 | 10 | 10 | 9 | 7 | 5 | 6 | 9 | 8 | 9 | 10 | 10 | 8 | 10 | 3 |
| Downy brome | 3 | 0 | 0 | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Giant foxtail | 10 | 10 | 10 | 10 | 9 | 7 | 3 | 10 | 10 | 9 | 6 | 5 | 8 | 7 | 6 | 2 | 3 | 10 | 10 | 7 | 7 | 10 | 10 | 10 | 9 | 3 | 7 |
| Green foxtail | 10 | 10 | 10 | 10 | 10 | 10 | 10 | 10 | 10 | 10 | 7 | 9 | 10 | 10 | 9 | 5 | 4 | 9 | 8 | 10 | 7 | 12 | 10 | 10 | 10 | 10 | 10 |
| Jimsonweed | 8 | 5 | 0 | 2 | 8 | 8 | 6 | 5 | 7 | 5 | 0 | 3 | 2 | 5 | 6 | 0 | 1 | 0 | 0 | 2 | 0 | 2 | 0 | — | 0 | 0 | 0 |
| Johnsongrass | 6 | 6 | 0 | 8 | 7 | 0 | 0 | 3 | 2 | 6 | 0 | 0 | 3 | 6 | 5 | 0 | 0 | 0 | 0 | 0 | 0 | 4 | 0 | 8 | 0 | 0 | 0 |
| Lambsquarters | 10 | 10 | 9 | 10 | 10 | 10 | 10 | 8 | 9 | 9 | 4 | 5 | 7 | 10 | 10 | 10 | 4 | 3 | 7 | 10 | 8 | 8 | 8 | 7 | 0 | 7 | 0 |
| Morningglory | 9 | — | 3 | 4 | 5 | 3 | 2 | 2 | 3 | 5 | 0 | 3 | 0 | 5 | 6 | 0 | 0 | 3 | 0 | 0 | 0 | 2 | 0 | 0 | 0 | 0 | 0 |
| Nutsedge | 2 | 0 | — | — | 4 | 0 | 0 | 0 | 0 | 0 | 0 | 0 | 0 | 0 | 4 | 0 | 0 | 0 | 0 | 0 | 0 | 2 | 0 | 0 | 0 | 0 | 0 |
| Rape | 8 | 6 | 8 | 0 | 7 | 5 | 2 | 7 | 5 | 6 | 0 | 6 | 3 | 9 | 6 | 0 | 0 | 0 | 0 | 8 | 0 | 2 | 0 | 0 | 0 | 0 | 0 |
| Rice | 0 | 0 | 0 | 2 | 2 | 0 | 0 | 0 | 0 | 0 | 3 | 0 | 0 | 3 | 3 | 0 | 0 | 0 | 0 | 0 | 0 | 2 | 0 | 0 | 0 | 0 | 0 |
| Sicklepod | 5 | 3 | 0 | 0 | 2 | 4 | 8 | 0 | 0 | 8 | 3 | 5 | 0 | 3 | 7 | — | 2 | 0 | 0 | 3 | 0 | 0 | 0 | — | 0 | — | — |
| Soybean | 3 | 0 | 10 | 2 | 2 | 0 | 0 | 1 | 0 | 0 | 0 | 0 | 0 | 0 | 3 | 0 | 1 | 3 | 0 | 0 | 0 | 0 | 0 | 0 | 0 | 0 | 0 |
| Sugar beet | 10 | 8 | 4 | 10 | 10 | 0 | 7 | 2 | 5 | 10 | 0 | 6 | 8 | 10 | 10 | 8 | 3 | 0 | 0 | 9 | 3 | 5 | 4 | 5 | 3 | 5 | 7 |
| Teaweed | 8 | 3 | 0 | 6 | 6 | 9 | 8 | 3 | 0 | 3 | 3 | 3 | 3 | 3 | 3 | 0 | 3 | 0 | 0 | 0 | 0 | 0 | 0 | — | — | 0 | 2 |
| Velvetleaf | 10 | 10 | 3 | 10 | 8 | 6 | 7 | 8 | 0 | 3 | 0 | 3 | 3 | 8 | 8 | 8 | 3 | 0 | 3 | 3 | 3 | 5 | 0 | 10 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 3 | 0 | 3 | 0 | 7 | — | — | 8 | — | 0 | 0 | 0 | 8 | 8 | 5 | 4 | 0 | 3 | 3 | 3 | 0 | 2 | 2 | 0 | 0 | 0 | 0 |
| Wild Oat | 5 | 3 | 0 | 6 | 6 | 0 | 3 | 3 | 3 | 2 | 0 | 0 | 2 | 3 | 0 | 0 | 0 | 0 | 0 | 0 | 0 | 0 | 0 | 0 | 0 | 0 | 0 |

| | COMPOUND | | | | | | | | | | | | | | | | | | | | | |
|---|---|---|---|---|---|---|---|---|---|---|---|---|---|---|---|---|---|---|---|---|---|---|
| | (31 g/ha) | | | | | | | | | | | | | | | | | | | | | |
| | 36 | 37 | 40 | 44 | 45 | 46 | 48 | 50 | 53 | 55 | 56 | 57 | 61 | 68 | 69 | 71 | 73 | 74 | 76 | 82 | 84 | 117 |
| PREEMERGENCE | | | | | | | | | | | | | | | | | | | | | | |
| Barley | 0 | 0 | 0 | 0 | 0 | 0 | 0 | 0 | 0 | 0 | 0 | 0 | 0 | 2 | 0 | 0 | 0 | 0 | 0 | 0 | 0 | 0 |
| Barnyardgrass | 9 | 4 | 2 | 0 | 0 | 0 | 2 | 7 | 6 | 8 | 0 | 3 | 7 | 0 | 3 | 3 | 3 | 3 | 0 | 0 | 6 | 0 |
| Blackgrass | 1 | 3 | 0 | 5 | 0 | 4 | 0 | 7 | 6 | 7 | 0 | 0 | 3 | 0 | 3 | 8 | 2 | 7 | 0 | 3 | 2 | 3 |
| Chickweed | 0 | 0 | 0 | 3 | 0 | 4 | 0 | 0 | 6 | 3 | 0 | 1 | — | 5 | 2 | 0 | 2 | 8 | 7 | 0 | 3 | 3 |
| Cocklebur | 0 | 0 | — | 0 | — | 0 | 0 | — | — | 0 | — | — | — | — | 0 | 0 | 0 | 0 | 0 | 0 | 0 | 0 |
| Corn | 0 | 0 | 0 | 2 | 0 | 0 | 0 | 0 | 4 | 0 | 0 | 3 | 1 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 | 3 | 0 | 0 | 0 | 0 | 0 | 0 | 0 | 0 | 0 |
| Crabgrass | 8 | 8 | 8 | 10 | 9 | 10 | 9 | 10 | 10 | 10 | 8 | 10 | 10 | 10 | 10 | 10 | 9 | 10 | 9 | 9 | 1 | 6 |
| Downy brome | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE B-continued

| | | | | | | | | | | | | | | | | | | | | | |
|---|---|---|---|---|---|---|---|---|---|---|---|---|---|---|---|---|---|---|---|---|---|
| Giant foxtail | 10 | 10 | 8 | 0 | 0 | 8 | 7 | 10 | 10 | 10 | 3 | 5 | 6 | 3 | 1 | 10 | 5 | 6 | 5 | 7 | 4 | 10 |
| Green foxtail | 10 | 10 | 10 | 5 | 0 | 10 | 9 | 10 | 10 | 10 | 9 | 10 | 10 | 7 | 10 | 10 | 8 | 10 | 9 | 9 | 8 | 8 |
| Jimsonweed | 5 | 0 | 0 | 0 | 0 | 0 | 1 | 4 | 7 | 4 | 0 | 2 | 4 | 5 | 0 | 2 | 5 | 3 | 3 | 0 | 2 | 0 |
| Johnsongrass | 7 | 4 | 5 | 0 | 0 | 3 | 0 | 5 | 5 | 5 | 0 | 0 | 5 | 0 | 0 | 2 | 0 | 4 | 0 | 2 | 2 | 0 |
| Lambsquarters | 9 | 7 | 9 | 9 | 6 | 5 | 2 | 9 | 10 | 10 | 7 | 6 | 9 | 10 | 0 | 7 | — | 9 | 5 | 2 | 10 | 7 |
| Morningglory | 0 | 2 | 3 | 0 | 0 | 1 | 0 | 4 | 4 | 2 | 2 | 0 | 5 | 0 | 1 | 1 | 0 | 3 | 2 | 0 | 3 | 0 |
| Nutsedge | 0 | 0 | 0 | — | — | 0 | 0 | 3 | 0 | 0 | — | — | 0 | 0 | 0 | 0 | 0 | 0 | 0 | 0 | 0 | 0 |
| Rape | 9 | 5 | 3 | 0 | 0 | 0 | 3 | 0 | 4 | 6 | 3 | 0 | 7 | 0 | 0 | 0 | 2 | 3 | 4 | 0 | 3 | 0 |
| Rice | 0 | 0 | 0 | 0 | 0 | 0 | 0 | 0 | 0 | 0 | 0 | 10 | 2 | 0 | 0 | 0 | 0 | 0 | 0 | 0 | 0 | 0 |
| Sicklepod | 0 | 0 | 3 | 0 | 0 | 0 | 0 | 0 | 3 | 0 | 0 | 0 | 0 | 3 | 4 | 0 | 0 | 7 | 3 | 0 | 0 | 0 |
| Soybean | 0 | 0 | 0 | 0 | 0 | 0 | 0 | 0 | 2 | 0 | 1 | 0 | 2 | 0 | 0 | 0 | 0 | 0 | 0 | 0 | 0 | 0 |
| Sugar beet | 4 | 2 | 2 | — | 0 | 3 | 0 | 3 | 10 | 4 | 0 | 10 | 10 | 0 | 6 | 0 | 0 | 7 | 6 | 0 | 2 | 0 |
| Teaweed | 1 | 0 | 4 | 0 | 0 | 0 | 0 | 3 | 6 | 3 | 0 | 2 | 3 | — | 0 | 0 | 0 | 3 | 3 | 0 | 0 | 0 |
| Velvetleaf | 4 | 3 | 5 | 0 | — | 1 | 2 | 6 | 9 | 7 | 0 | 7 | 7 | 5 | 4 | 4 | 0 | 0 | 0 | 2 | 5 | 3 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 0 | 0 | 0 | 0 | 0 | 4 | — | 0 | 0 | 0 | 2 | 0 | 3 | — | — | — | 8 | 0 | 0 | 2 | 3 | 3 |
| Wild Oat | 1 | 0 | 0 | 0 | 0 | 1 | 0 | 0 | 3 | 3 | 0 | 0 | 5 | 0 | 2 | 2 | 0 | 0 | 0 | 0 | 0 | 0 |

TEST C

Plastic pots were partially filled with silt loam soil. The soil was then saturated with water. Japonica and Indica rice (*Oryza sativa*) seedlings at the 2.0 to 2.5 leaf stage, seeds selected from barnyardgrass (*Echinochloa crus-galli*), bulrush (*Scirpus mucronatus*), duck salad (*Heteranthera limosa*), and umbrella sedge (*Cyperus difformis*), and sprouted tubers of arrowhead (Sagittaria spp.) and/or waterchestnut (Eleocharis spp.) were planted into this soil. Several days after planting, water levels were raised to 3 cm above the soil surface and maintained at this level throughout the test. Chemical treatments were formulated in a non-phytotoxic solvent and applied directly to the paddy water. Treated plants and controls were maintained in a greenhouse for approximately 21 days, after which all species were compared to controls and visually evaluated. Plant response ratings, summarized in Table C, are based on a scale of 0 to 10 where 0 is no effect and 10 is complete control.

TABLE C

| | Rate | COMPOUND 5 | 13 | 15 | 23 | 25 | 28 | 32 | 33 | 34 | 35 | 36 | 37 | 40 | 43 | 44 | 46 | 48 | 50 | 53 | 55 | 56 | 60 | 69 | 71 | 74 | 76 | 82 | 103 |
|---|---|---|---|---|---|---|---|---|---|---|---|---|---|---|---|---|---|---|---|---|---|---|---|---|---|---|---|---|---|
| Arrowhead | 1000 | — | 6 | — | — | — | — | — | — | — | — | — | 9 | 0 | 6 | — | — | — | — | — | — | 8 | 9 | 6 | 7 | 9 | — | — | 0 |
| | 500 | 0 | 4 | 6 | — | — | — | — | — | — | — | 8 | 8 | 0 | 5 | 7 | 9 | 4 | 7 | 6 | 9 | 7 | 7 | 6 | 6 | 8 | 3 | 4 | 0 |
| | 250 | 0 | 0 | 4 | — | — | — | 7 | 4 | — | — | 6 | — | 0 | 0 | 4 | 6 | 0 | 7 | 6 | 9 | 8 | 7 | 5 | 4 | 6 | 3 | 5 | 0 |
| | 125 | 0 | 0 | 0 | — | — | — | 4 | 0 | — | — | 4 | 5 | 0 | 0 | 0 | 6 | 4 | 5 | 4 | 8 | 5 | 7 | 3 | 4 | 6 | 2 | 4 | 0 |
| | 64 | — | 0 | 0 | — | — | — | 3 | 0 | — | — | 0 | 5 | 0 | 0 | 0 | 0 | 0 | 3 | 3 | 8 | 0 | 6 | 0 | 0 | 4 | 0 | 3 | 0 |
| | 32 | — | — | 0 | — | — | — | 0 | 0 | — | — | 0 | — | — | — | 0 | 0 | 0 | 0 | 0 | 5 | — | — | — | — | — | 0 | 0 | — |
| | 16 | — | — | — | — | — | — | 0 | 0 | — | — | — | — | — | — | — | — | — | — | — | — | — | — | — | — | — | — | — | — |
| Barnyardgrass | 1000 | — | 10 | — | — | — | 9 | — | — | 10 | — | — | 10 | 10 | 10 | — | — | — | — | — | — | 10 | 10 | 10 | 10 | 10 | — | — | 10 |
| | 500 | 8 | 8 | 10 | 10 | 10 | 8 | — | — | 9 | 10 | 10 | 10 | 9 | 10 | 10 | 10 | 10 | 10 | 10 | 10 | 10 | 10 | 10 | 10 | 10 | 10 | 10 | 10 |
| | 250 | 5 | 6 | 10 | 9 | 7 | 6 | 10 | 10 | 9 | 9 | 10 | 10 | 10 | 9 | 10 | 10 | 10 | 10 | 10 | 10 | 9 | 9 | 10 | 10 | 10 | 10 | 10 | 10 |
| | 125 | 0 | 0 | 8 | 9 | 7 | 3 | 10 | 8 | 5 | 8 | 10 | 9 | 8 | 7 | 9 | 10 | 10 | 10 | 10 | 10 | 6 | 9 | 10 | 10 | 10 | 9 | 10 | 6 |
| | 64 | — | 0 | 5 | 6 | 4 | 0 | 10 | 7 | 0 | 5 | 10 | 8 | 6 | 6 | 6 | 9 | 10 | 10 | 10 | 10 | 4 | 6 | 9 | 10 | 9 | 9 | 8 | 4 |
| | 32 | — | — | 3 | 4 | 0 | — | 8 | 4 | — | 4 | 7 | — | — | — | 4 | 6 | 8 | 8 | 9 | 10 | — | — | — | — | — | 8 | 6 | — |
| | 16 | — | — | — | — | — | — | 6 | 0 | — | — | — | — | — | — | — | — | — | — | — | — | — | — | — | — | — | — | — | — |
| Bulrush | 1000 | — | 9 | — | — | — | 9 | — | — | 9 | — | — | 9 | 9 | 9 | — | — | — | — | — | — | 10 | 9 | 9 | 10 | 9 | — | — | 7 |
| | 500 | 7 | 9 | 10 | 10 | 10 | 9 | — | — | 9 | 9 | 10 | 9 | 9 | 9 | 9 | 9 | 9 | 10 | 10 | 9 | 9 | 9 | 9 | 10 | 9 | 10 | 8 | 7 |
| | 250 | 7 | 9 | 9 | 9 | 9 | 9 | 10 | 9 | 9 | 9 | 9 | 8 | 8 | 9 | 9 | 9 | 9 | 9 | 10 | 9 | 9 | 9 | 9 | 10 | 9 | 9 | 6 | 5 |
| | 125 | 0 | 8 | 8 | 9 | 9 | 0 | 9 | 6 | 4 | 9 | 9 | 7 | 8 | 9 | 7 | 8 | 8 | 9 | 9 | 9 | 4 | 9 | 9 | 10 | 9 | 8 | 5 | 4 |
| | 64 | — | 5 | 7 | 9 | 9 | 0 | 6 | 5 | 0 | 6 | 9 | 5 | 0 | 0 | 6 | 8 | 5 | 9 | 7 | 9 | 0 | 7 | 8 | 9 | 8 | 6 | 5 | 3 |
| | 32 | — | — | 0 | 6 | 0 | — | 5 | 0 | — | 0 | 6 | — | — | — | 0 | 6 | 4 | 9 | 7 | 9 | — | — | — | — | — | 0 | 4 | — |
| | 16 | — | — | — | — | — | — | 0 | 0 | — | — | — | — | — | — | — | — | — | — | — | — | — | — | — | — | — | — | — | — |
| Duck Salad | 1000 | — | — | — | — | — | — | — | — | 10 | — | — | 10 | — | — | — | — | — | — | — | — | — | — | 10 | 10 | 10 | — | — | 10 |
| | 500 | — | — | — | — | — | — | — | — | 10 | 10 | — | 10 | — | — | 2 | — | 10 | — | — | — | — | — | 10 | 10 | 10 | 10 | 10 | 10 |
| | 250 | — | — | — | — | — | — | — | — | 9 | 7 | — | 10 | — | — | 0 | — | 0 | — | — | — | — | — | 10 | 10 | 10 | 10 | 10 | 10 |
| | 125 | — | — | — | — | — | — | — | — | 0 | 6 | — | 10 | — | — | — | — | 0 | — | — | — | — | — | 10 | 10 | 10 | 10 | 10 | 10 |
| | 64 | — | — | — | — | — | — | — | — | 0 | 0 | — | 10 | — | — | — | — | 0 | — | — | — | — | — | 10 | 5 | 10 | 10 | 10 | 10 |
| | 32 | — | — | — | — | — | — | — | — | — | 0 | — | — | — | — | — | — | 0 | — | — | — | — | — | — | — | — | 9 | 0 | — |
| | 16 | — | — | — | — | — | — | — | — | — | — | — | — | — | — | — | — | — | — | — | — | — | — | — | — | — | — | — | — |
| Rice (Indica) | 1000 | — | 2 | — | — | — | 0 | — | — | 4 | — | — | 4 | 3 | 4 | — | — | — | — | — | — | 0 | 4 | 5 | 5 | 6 | — | — | 3 |
| | 500 | 0 | 1 | 2 | 4 | 3 | 0 | — | — | 3 | 4 | 3 | 2 | 0 | 2 | 2 | 3 | 3 | 5 | 5 | 7 | 0 | 3 | 3 | 4 | 3 | 0 | 2 | 2 |
| | 250 | 0 | 0 | 0 | 2 | 0 | 0 | 3 | 0 | 2 | 2 | 4 | 1 | 0 | 3 | 0 | 2 | 5 | 4 | 4 | 6 | 0 | 2 | 4 | 4 | 2 | 0 | 0 | 2 |
| | 125 | 0 | 0 | 0 | 0 | 0 | 0 | 2 | 0 | 0 | 2 | 4 | 0 | 0 | 0 | 0 | 0 | 0 | 3 | 2 | 5 | 0 | 0 | 2 | 2 | 0 | 0 | 0 | 0 |
| | 64 | — | 0 | 0 | 0 | 0 | 0 | 0 | 0 | 0 | 2 | 3 | 0 | 0 | 0 | 0 | 0 | 0 | 0 | 0 | 4 | 0 | 0 | 0 | 0 | 0 | 0 | 0 | 0 |
| | 32 | — | — | 0 | 0 | 0 | — | 0 | 0 | — | 0 | 0 | — | — | — | 0 | 0 | 0 | 0 | 2 | 3 | — | — | — | — | — | 0 | 0 | — |
| | 16 | — | — | — | — | — | — | 0 | 0 | — | — | — | — | — | — | — | — | — | — | — | — | — | — | — | — | — | — | — | — |
| Rice (Japonica) | 1000 | — | 0 | — | — | — | 3 | — | — | 6 | — | — | 5 | 4 | 4 | — | — | — | — | — | — | 0 | 5 | 6 | 5 | 8 | — | — | 3 |
| | 500 | 0 | 0 | 1 | 5 | 4 | 0 | — | — | 4 | 5 | 4 | 3 | 2 | 2 | 2 | 4 | 4 | 5 | 6 | 8 | 0 | 4 | 6 | 5 | 5 | 2 | 3 | 2 |
| | 250 | 0 | 0 | 0 | 4 | 2 | 0 | 4 | 0 | 0 | 4 | 4 | 1 | 0 | 3 | 0 | 3 | 3 | 4 | 5 | 8 | 0 | 3 | 4 | 4 | 4 | 0 | 0 | 1 |
| | 125 | 0 | 0 | 0 | 0 | 0 | 0 | 2 | 0 | 0 | 3 | 4 | 0 | 0 | 0 | 0 | 3 | 0 | 3 | 4 | 6 | 0 | 2 | 4 | 2 | 0 | 0 | 0 | 0 |
| | 64 | — | 0 | 0 | 0 | 0 | 0 | 2 | 0 | 0 | 3 | 3 | 0 | 0 | 0 | 0 | 0 | 0 | 0 | 2 | 5 | 0 | 0 | 2 | 0 | 0 | 0 | 0 | 0 |
| | 32 | — | — | 0 | 0 | 0 | — | 0 | 0 | — | 2 | 0 | — | — | — | 0 | 0 | 0 | 0 | 0 | 2 | — | — | — | — | — | 0 | 0 | — |
| | 16 | — | — | — | — | — | — | 0 | 0 | — | — | — | — | — | — | — | — | — | — | — | — | — | — | — | — | — | — | — | — |
| Umbrella Sedge | 1000 | — | 9 | — | — | — | 10 | — | — | 9 | — | — | 10 | 10 | 10 | — | — | — | — | — | — | 10 | 10 | 10 | 10 | 10 | — | — | 10 |
| | 500 | 9 | 9 | 10 | 10 | 10 | 9 | — | — | 9 | 10 | 10 | 10 | 9 | 10 | 10 | 10 | 10 | 10 | 10 | 10 | 10 | 10 | 10 | 10 | 9 | 10 | 10 | 10 |
| | 250 | 8 | 9 | 9 | 10 | 10 | 9 | 10 | 10 | 9 | 10 | 10 | 10 | 9 | 10 | 10 | 10 | 10 | 10 | 10 | 10 | 10 | 10 | 10 | 10 | 9 | 9 | 10 | 10 |
| | 125 | 0 | 8 | 9 | 10 | 10 | 0 | 10 | 10 | 9 | 9 | 10 | 10 | 9 | 10 | 9 | 10 | 10 | 10 | 10 | 10 | 10 | 10 | 10 | 10 | 9 | 9 | 9 | 9 |
| | 64 | — | 7 | 9 | 9 | 10 | 0 | 10 | 9 | 8 | 9 | 10 | 9 | 9 | 10 | 8 | 10 | 10 | 10 | 10 | 10 | 9 | 10 | 9 | 9 | 9 | 9 | 8 | 9 |
| | 32 | — | — | 6 | 6 | 5 | — | 10 | 7 | — | 8 | 10 | — | — | — | 5 | 10 | 9 | 10 | 9 | 10 | — | — | — | — | — | 9 | 5 | — |
| | 16 | — | — | — | — | — | — | 9 | 6 | — | — | — | — | — | — | — | — | — | — | — | — | — | — | — | — | — | — | — | — |
| Waterchestnut | 1000 | — | 8 | — | — | — | 5 | — | — | 7 | — | — | 9 | 6 | 9 | 10 | — | — | — | — | — | 9 | 7 | 4 | 9 | 9 | — | — | 3 |
| | 500 | 5 | 10 | 8 | 5 | 5 | 4 | — | — | 6 | 6 | 8 | 6 | 10 | 4 | 4 | 7 | 2 | 9 | 9 | 10 | 4 | 8 | 4 | 7 | 9 | 8 | 7 | 3 |

TABLE C-continued

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Rate | 5 | 13 | 15 | 23 | 25 | 28 | 32 | 33 | 34 | 35 | 36 | 37 | 40 | 43 | 44 | 46 | 48 | 50 | 53 | 55 | 56 | 60 | 69 | 71 | 74 | 76 | 82 | 103 |
| 250 | 0 | 10 | 5 | 5 | 5 | 0 | 5 | 4 | 5 | 5 | 5 | 5 | 8 | 0 | 0 | 5 | 0 | 9 | 10 | 9 | 3 | 7 | 7 | 9 | 8 | 7 | 2 | — |
| 125 | 0 | 8 | 0 | 5 | 4 | 0 | 4 | 0 | 0 | 5 | 0 | 0 | 0 | 0 | 0 | 0 | 0 | 9 | 8 | 9 | 0 | 7 | 0 | 9 | 7 | 4 | 0 | — |
| 64 | — | 0 | 0 | 3 | 0 | 0 | 0 | 0 | 0 | 0 | 0 | 0 | 0 | 0 | 0 | 0 | 0 | 10 | 4 | 9 | 0 | — | 0 | 0 | 5 | 0 | 0 | — |
| 32 | — | — | 0 | 0 | 0 | — | 0 | 0 | — | 0 | 0 | — | — | — | 0 | 0 | 0 | 10 | 4 | 9 | — | — | — | — | — | 0 | 0 | — |
| 16 | — | — | — | — | — | — | 0 | 0 | — | — | — | — | — | — | — | — | — | — | — | — | — | — | — | — | — | — | — | — |

TEST D

Seeds of spring and winter barley (*Hordeum vulgare*), black nightshade (*Solanum nigrum*), blackgrass (*Alopecurus myosuroides*), bluegrass (*Poa annua*), catchweed bedstraw (*Galium aparine*), cheatgrass (*Bromus secalinus*(), downy brome (*Bromus tectorum*), field pennycress (*Thlaspi arvense*), field violet (*Viola arvensis*), green foxtail (*Setaria viridis*), Italian ryegrass (*Lolium multiflorum*), ivyleaf speedwell (*Veronica hederaefolia*), jointed goatgrass (*Aegilops cylindrica*), kochia (*Kochia scroparia*), lambsquarters (*Chenopodium album*), Persian speedwell (*Veronica persica*), rape (*Brassica napus*), Russian thistle (*Salsola kali*), scentless chamomile (*Matricaria inordora*), sugar beet (*Beta vulgaris*), spring and winter wheat (*Triticum aestivum*), wild buckwheat (*Polygonum convolvulus*), and wild oat (*Avena fatua*) were planted and treated preemergence with test chemicals dissolved in a non-phytotoxic solvent. Postemergence applications of test chemicals were also applied to these same crop and weed species. Plants ranged in height from two to twenty-four cm (two to three leaf stage) for postemergence treatments. Blackgrass and wild oat were treated postemergence at two growth stages—the first stage being at two to three leaves and the second stage being approximately at four leaves or in the initial stages of tillering. Treated plants and controls were maintained in a greenhouse for approximately 21 days, after which all species were compared to controls and visually evaluated. Rates of application of each compound are listed in Table D. Plant response ratings, summarized in Table D, are based on a scale of 0 to 10 where 0 is no effect and 10 is complete control. A dash (-) response means no test result.

TABLE D

POSTEMERGENCE

| | COMPOUND (1000 g/ha) | | | | | | | | | | | | | | | |
|---|---|---|---|---|---|---|---|---|---|---|---|---|---|---|---|---|
| | 4 | 9 | 13 | 20 | 23 | 25 | 28 | 32 | 33 | 36 | 37 | 40 | 44 | 46 | 50 | 82 |
| Barley (Spring) | 0 | 0 | 0 | 1 | 4 | 2 | 1 | 2 | 3 | 6 | 2 | 1 | 2 | 2 | 8 | 1 |
| Barley (Winter) | 0 | 0 | 0 | 1 | 3 | 2 | 1 | 2 | 2 | 5 | 2 | 2 | 1 | 2 | 7 | 1 |
| Black nightshade | 0 | 1 | 0 | 10 | 10 | 10 | 7 | 10 | 10 | 10 | 10 | 8 | 10 | 9 | 10 | 10 |
| Blackgrass | 0 | 0 | 0 | 4 | 9 | 3 | 4 | 4 | 4 | 9 | 8 | 3 | 8 | 7 | 10 | 4 |
| Blackgrass (Stage 2) | 0 | 0 | 0 | 2 | 6 | 2 | 1 | 5 | 4 | 9 | 7 | 1 | 3 | 5 | 8 | 2 |
| Bluegrass | 0 | 1 | 0 | 4 | 9 | 8 | 3 | 9 | 9 | 10 | 9 | 9 | 9 | 10 | 10 | 10 |
| Catchweed bedstraw | 0 | 0 | 0 | 3 | 7 | 6 | 4 | 9 | 5 | 9 | 3 | 3 | 5 | 4 | 2 | 2 |
| Cheatgrass | 0 | 0 | 0 | 1 | 5 | 2 | 1 | 2 | 1 | 8 | 4 | 2 | 2 | 4 | 8 | 1 |
| Downy brome | 0 | 0 | 0 | 0 | 2 | 2 | 1 | 3 | 1 | 2 | 3 | 1 | 1 | 1 | 5 | 1 |
| Field pennycress | 0 | 4 | 8 | 10 | 10 | 10 | 8 | 10 | 10 | 10 | 10 | 10 | 10 | 10 | 10 | 10 |
| Field violet | 0 | 2 | 4 | 10 | 10 | 10 | 10 | 10 | 10 | 10 | 10 | 10 | 10 | 9 | 10 | 10 |
| Green foxtail | 2 | 2 | 1 | 7 | 10 | 9 | 10 | 10 | 10 | 10 | 10 | 9 | 10 | 10 | 10 | 10 |
| Italian ryegrass | 0 | 0 | 0 | 1 | 9 | 5 | 1 | 4 | 1 | 9 | 4 | 2 | 2 | 8 | 10 | 2 |
| Ivyleaf speedwell | 0 | 2 | 3 | 8 | 10 | 10 | 9 | 10 | 10 | 10 | 10 | 10 | 10 | 10 | 10 | 10 |
| Jointed goatgrass | 0 | 0 | 0 | 1 | 3 | 2 | 1 | 2 | 2 | 3 | 3 | 1 | 2 | 1 | 5 | 1 |
| Kochia | 0 | 2 | 10 | 9 | 9 | 9 | 10 | 10 | 10 | 10 | 10 | 10 | 10 | 10 | 10 | 10 |
| Lambsquarters | 0 | 2 | 2 | 5 | 10 | 10 | 3 | 10 | 10 | 10 | 10 | 10 | 8 | 10 | 10 | 10 |
| Persian speedwell | 0 | 1 | 5 | 9 | 10 | 10 | 10 | 10 | 10 | 10 | 10 | 4 | 10 | 9 | 9 | 9 |
| Rape | 3 | 6 | 7 | 7 | 10 | 10 | 9 | 10 | 10 | 10 | 10 | 9 | 8 | 9 | 10 | 10 |
| Russian thistle | 0 | 0 | 1 | 4 | 8 | 8 | 5 | 7 | 8 | 9 | 9 | 9 | 9 | 9 | 9 | 9 |
| Scentless chamomile | — | — | 0 | 0 | 0 | 0 | 1 | 1 | 1 | 2 | 2 | 1 | 1 | 1 | 2 | 1 |
| Sugar beet | 2 | 9 | 8 | 10 | 10 | 10 | 5 | 10 | 10 | 10 | 10 | 8 | 10 | 10 | 10 | 10 |
| Wheat (Spring) | 0 | 0 | 0 | 0 | 3 | 2 | 1 | 1 | 2 | 3 | 2 | 1 | 1 | 2 | 6 | 1 |
| Wheat (Winter) | 0 | 0 | 0 | 0 | 4 | 1 | 1 | 1 | 1 | 6 | 1 | 1 | 1 | 3 | 7 | 1 |
| Wild buckwheat | 0 | 1 | 1 | 3 | 9 | 10 | 5 | 10 | 9 | 9 | 9 | 2 | 7 | 9 | 10 | 7 |
| Wild oat | 0 | 0 | 0 | 2 | 6 | 4 | 1 | 4 | 3 | 9 | 8 | 3 | 2 | 5 | 8 | 2 |
| Wild oat (Stage 2) | 0 | 0 | 0 | 1 | 8 | 3 | 1 | 4 | 4 | 9 | 6 | 2 | 3 | 4 | 8 | 3 |

| | COMPOUND (750 g/ha) | | | | | | | | | | | | | | | | | | |
|---|---|---|---|---|---|---|---|---|---|---|---|---|---|---|---|---|---|---|---|
| | 4 | 9 | 13 | 15 | 20 | 23 | 25 | 28 | 32 | 36 | 37 | 40 | 44 | 46 | 49 | 50 | 53 | 55 | 82 |
| Barley (Spring) | 0 | 0 | 0 | 3 | 1 | 3 | 2 | 1 | 2 | 3 | 2 | 1 | 1 | 1 | 2 | 8 | 7 | 4 | 1 |
| Barley (Winter) | 0 | 0 | 0 | 2 | 1 | 3 | 1 | 0 | 2 | 2 | 2 | 1 | 1 | 1 | 2 | 6 | 6 | 2 | 1 |
| Black nightshade | 0 | 1 | 0 | 8 | 6 | 10 | 9 | 7 | 10 | 10 | 10 | 8 | 10 | 7 | 3 | 10 | 9 | 7 | 7 |
| Blackgrass | 0 | 0 | 0 | 8 | 4 | 9 | 3 | 1 | 4 | 9 | 8 | 3 | 5 | 7 | 2 | 10 | 9 | 8 | 1 |
| Blackgrass (Stage 2) | 0 | 0 | 0 | 2 | 2 | 4 | 2 | 1 | 2 | 8 | 3 | 1 | 3 | 4 | 2 | 8 | 9 | 7 | 2 |
| Bluegrass | 0 | 0 | 0 | 7 | 2 | 9 | 6 | 1 | 9 | 9 | 8 | 9 | 8 | 10 | 1 | 10 | 10 | 10 | 9 |
| Catchweed bedstraw | 0 | 0 | 0 | 3 | 3 | 5 | 4 | 4 | 6 | 4 | 3 | 3 | 5 | 2 | 2 | 2 | 7 | 3 | 1 |
| Cheatgrass | 0 | 0 | 0 | 1 | 0 | 3 | 1 | 0 | 2 | 7 | 2 | 1 | 2 | 4 | 0 | 8 | 8 | 4 | 0 |
| Downy brome | 0 | 0 | 0 | 1 | 0 | 2 | 1 | 0 | 1 | 2 | 3 | 1 | 0 | 1 | 0 | 4 | 8 | 2 | 0 |
| Field pennycress | 0 | 1 | 7 | 10 | 10 | 10 | 10 | 8 | 10 | 10 | 10 | 10 | 10 | 10 | 10 | 10 | 10 | 10 | 10 |
| Field violet | 0 | 2 | 1 | 10 | 8 | 10 | 10 | 6 | 10 | 10 | 10 | 10 | 10 | 9 | 3 | 10 | 10 | 10 | 10 |
| Green foxtail | 0 | 0 | 0 | 10 | 6 | 10 | 9 | 7 | 9 | 10 | 10 | 9 | 10 | 10 | 9 | 10 | 10 | 10 | 10 |
| Italian ryegrass | 0 | 0 | 0 | 2 | 1 | 8 | 2 | 0 | 3 | 8 | 3 | 2 | 2 | 4 | 1 | 9 | 9 | 8 | 2 |
| Ivyleaf speedwell | 0 | 2 | 3 | 8 | 7 | 10 | 10 | 7 | 10 | 10 | 10 | 10 | 10 | 10 | 2 | 10 | 8 | 10 | 10 |
| Jointed goatgrass | 0 | 0 | 0 | 2 | 1 | 2 | 2 | 0 | 1 | 3 | 2 | 1 | 1 | 1 | 1 | 4 | 5 | 4 | 0 |
| Kochia | 0 | 1 | 6 | 10 | 8 | 9 | 9 | 10 | 8 | 10 | 10 | 10 | 10 | 10 | 8 | 10 | — | 9 | 10 |
| Lambsquarters | 0 | 2 | 2 | 7 | 5 | 10 | 10 | 3 | 10 | 10 | 10 | 10 | 7 | 9 | 2 | 10 | 8 | 8 | 10 |
| Persian speedwell | 0 | 1 | 5 | 7 | 9 | 10 | 10 | 10 | 10 | 8 | 10 | 4 | 10 | 9 | 4 | 9 | 9 | 8 | 7 |
| Rape | 0 | 6 | 2 | 8 | 7 | 10 | 9 | 7 | 10 | 10 | 10 | 8 | 6 | 9 | 6 | 10 | 10 | 10 | 8 |
| Russian thistle | 0 | 0 | 0 | 5 | 2 | 8 | 8 | 2 | 7 | 9 | 9 | 9 | 8 | 9 | 4 | 9 | 9 | 9 | 8 |
| Scentless chamomile | — | — | 0 | 0 | 0 | 0 | 0 | 0 | 0 | 2 | 2 | 1 | 1 | 1 | — | 1 | 8 | 2 | 0 |
| Sugar beet | 1 | 8 | 8 | 10 | 10 | 10 | 10 | 5 | 10 | 10 | 10 | 7 | 10 | 10 | 9 | 10 | 10 | 10 | 10 |
| Wheat (Spring) | 0 | 0 | 0 | 2 | 0 | 3 | 2 | 1 | 1 | 3 | 1 | 1 | 1 | 2 | 2 | 2 | 6 | 3 | 1 |
| Wheat (Winter) | 0 | 0 | 0 | 2 | 0 | 3 | 1 | 1 | 1 | 3 | 1 | 1 | 1 | 2 | 2 | 3 | 6 | 3 | 1 |
| Wild buckwheat | 0 | 1 | 0 | 7 | 1 | 8 | 9 | 2 | 9 | 9 | 9 | 2 | 3 | 7 | 2 | 10 | 9 | 10 | 5 |
| Wild oat | 0 | 0 | 0 | 2 | 2 | 6 | 4 | 0 | 4 | 8 | 8 | 3 | 2 | 4 | 2 | 8 | 9 | 8 | 2 |
| Wild oat (Stage 2) | 0 | 0 | 0 | 2 | 1 | 6 | 2 | 0 | 3 | 7 | 6 | 2 | 2 | 3 | 1 | 8 | 8 | 8 | 1 |

| | COMPOUND (500 g/ha) | | | | | | | | | | | | | | | | | |
|---|---|---|---|---|---|---|---|---|---|---|---|---|---|---|---|---|---|---|
| | 4 | 5 | 9 | 13 | 15 | 20 | 23 | 25 | 28 | 32 | 33 | 36 | 37 | 40 | 44 | 46 | 48 | 49 |
| Barley (Spring) | 0 | 2 | 0 | 0 | 2 | 0 | 2 | 1 | 0 | 2 | 1 | 3 | 1 | 1 | 1 | 1 | 2 | 2 |
| Barley (Winter) | 0 | 1 | 0 | 0 | 2 | 1 | 2 | 1 | 0 | 1 | 1 | 2 | 1 | 1 | 0 | 1 | 2 | 1 |
| Black nightshade | 0 | 5 | 0 | 0 | 7 | 4 | 10 | 7 | 4 | 10 | 6 | 10 | 6 | 7 | 6 | 5 | 7 | 3 |
| Blackgrass | 0 | 0 | 0 | 0 | 6 | 2 | 3 | 1 | 1 | 4 | 1 | 8 | 7 | 2 | 3 | 5 | 4 | 2 |
| Blackgrass (Stage 2) | 0 | 0 | 0 | 0 | 2 | 1 | 2 | 1 | 0 | 1 | 2 | 4 | 3 | 1 | 1 | 2 | 2 | 2 |
| Bluegrass | 0 | 1 | 0 | 0 | 5 | 1 | 7 | 4 | 0 | 8 | 6 | 9 | 8 | 9 | 8 | 9 | 4 | 1 |
| Catchweed bedstraw | 0 | 0 | 0 | 0 | 1 | 2 | 5 | 3 | 4 | 6 | 2 | 4 | 2 | 2 | 4 | 2 | 5 | 1 |
| Cheatgrass | 0 | 1 | 0 | 0 | 0 | 0 | 1 | 0 | 0 | 1 | 1 | 3 | 1 | 1 | 1 | 2 | 2 | 0 |
| Downy brome | 0 | 1 | 0 | 0 | 0 | 0 | 1 | 0 | 0 | 1 | 1 | 1 | 1 | 1 | 0 | 0 | 2 | 0 |
| Field pennycress | 0 | 3 | 1 | 5 | 10 | 8 | 10 | 10 | 4 | 10 | 10 | 10 | 10 | 10 | 10 | 10 | 10 | 7 |
| Field violet | 0 | 10 | 2 | 0 | 10 | 7 | 10 | 10 | 5 | 7 | 10 | 9 | 10 | 10 | 8 | 9 | 9 | 2 |
| Green foxtail | 0 | 0 | 0 | 0 | 8 | 4 | 10 | 9 | 3 | 8 | 9 | 10 | 10 | 9 | 10 | 10 | 10 | 9 |
| Italian ryegrass | 0 | 1 | 0 | 0 | 2 | 0 | 7 | 1 | 0 | 1 | 1 | 3 | 1 | 1 | 1 | 4 | 2 | 0 |
| Ivyleaf speedwell | 0 | 7 | 1 | 1 | 8 | 6 | 10 | 10 | 9 | 10 | 9 | 10 | 10 | 7 | 10 | 7 | 8 | 1 |
| Jointed goatgrass | 0 | 0 | 0 | 0 | 2 | 0 | 2 | 1 | 0 | 0 | 2 | 3 | 1 | 1 | 1 | 1 | 1 | 0 |
| Kochia | 0 | 8 | 0 | — | 8 | 8 | 9 | 9 | 10 | 8 | 10 | 10 | 10 | 10 | 10 | 10 | 8 | 8 |
| Lambsquarters | 0 | 4 | 0 | 1 | 7 | 3 | 10 | 10 | 3 | 10 | 9 | 10 | 9 | 9 | 4 | 8 | 9 | 2 |
| Persian speedwell | 0 | 7 | 0 | 2 | 7 | 7 | 9 | 10 | 10 | 10 | 9 | 8 | 10 | 4 | 9 | 7 | 9 | 2 |
| Rape | 0 | 3 | 2 | 1 | 8 | 6 | 10 | 9 | 7 | 9 | 10 | 10 | 9 | 6 | 6 | 8 | 7 | 6 |

| | COMPOUND (500 g/ha) | | | | | | | | | | | COMPOUND (250 g/ha) | | | | | | |
|---|---|---|---|---|---|---|---|---|---|---|---|---|---|---|---|---|---|---|
| | 50 | 53 | 55 | 56 | 57 | 71 | 73 | 76 | 82 | 84 | 100 | 4 | 5 | 9 | 13 | 15 | 20 | 23 |
| Barley (Spring) | 4 | 3 | 3 | 2 | 5 | 4 | 3 | 3 | 1 | 3 | 3 | 0 | 1 | 0 | 0 | 2 | 0 | 2 |
| Barley (Winter) | 5 | 3 | 2 | 2 | 3 | 4 | 1 | 3 | 1 | 3 | 3 | 0 | 0 | 0 | 0 | 1 | 0 | 1 |
| Black nightshade | 10 | 9 | 7 | 8 | 10 | 6 | 10 | 10 | 7 | 10 | 10 | 0 | 2 | 0 | 0 | 5 | 2 | 6 |
| Blackgrass | 8 | 9 | 7 | 1 | 4 | 6 | 3 | 3 | 1 | 8 | 7 | 0 | 0 | 0 | 0 | 2 | 0 | 1 |
| Blackgrass (Stage 2) | 7 | 8 | 5 | 2 | 2 | 3 | 3 | 1 | 1 | 5 | 4 | 0 | 0 | 0 | 0 | 1 | 1 | 1 |
| Bluegrass | 10 | 10 | 9 | 2 | 10 | 10 | 9 | 10 | 8 | 10 | 2 | 0 | 0 | 0 | 0 | 2 | 0 | 3 |
| Catchweed bedstraw | 2 | 4 | 2 | 2 | 8 | 6 | 8 | 6 | 0 | 9 | 9 | 0 | 0 | 0 | 0 | 1 | 0 | 4 |
| Cheatgrass | 7 | 8 | 3 | 3 | 4 | 5 | 1 | 2 | 0 | 4 | 3 | 0 | 1 | 0 | 0 | 0 | 0 | 1 |
| Downy brome | 2 | 6 | 1 | 3 | 2 | 3 | 1 | 3 | 0 | 3 | 3 | 0 | 1 | 0 | 0 | 0 | 0 | 1 |
| Field pennycress | 10 | 10 | 10 | 9 | 10 | 8 | 10 | 10 | 10 | 10 | 10 | 0 | 1 | 1 | 2 | 9 | 3 | 10 |
| Field violet | 10 | 9 | 10 | 6 | 10 | 10 | 6 | 10 | 10 | 10 | 10 | 0 | 10 | 1 | 0 | 8 | 5 | 10 |
| Green foxtail | 10 | 10 | 10 | 7 | 10 | 10 | 10 | 10 | 8 | 10 | 9 | 0 | 0 | 0 | 0 | 8 | 4 | 10 |
| Italian ryegrass | 7 | 9 | 7 | 3 | 9 | 3 | 8 | 3 | 1 | 10 | 9 | 0 | 0 | 0 | 0 | 1 | 0 | 3 |
| Ivyleaf speedwell | 10 | 8 | 10 | 10 | 9 | 10 | 9 | 10 | 9 | 10 | 10 | 0 | 7 | 0 | 0 | 8 | 4 | 10 |
| Jointed goatgrass | 2 | 3 | 2 | 1 | 3 | 2 | 0 | 2 | 0 | 3 | 1 | 0 | 0 | 0 | 0 | 1 | 0 | 1 |
| Kochia | 7 | 8 | 9 | 7 | 9 | 7 | 7 | 8 | 10 | 9 | 9 | 0 | 7 | 0 | 2 | 5 | 6 | 8 |
| Lambsquarters | 8 | 8 | 7 | 4 | 10 | 6 | 2 | 9 | 9 | 10 | 10 | 0 | 4 | 0 | 1 | 7 | 1 | 9 |
| Persian speedwell | 9 | 9 | 7 | 8 | 9 | 10 | 9 | 10 | 7 | 10 | 10 | 0 | 7 | 0 | 0 | 6 | 6 | 9 |
| Rape | 10 | 10 | 9 | 8 | 10 | 7 | 8 | 9 | 8 | 9 | 8 | 0 | 3 | 2 | 1 | 7 | 5 | 8 |

TABLE D-continued

| | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|
| Russian thistle | 0 | 4 | 0 | 0 | 4 | 1 | 8 | 8 | 2 | 7 | 8 | 9 | 9 | 9 | 8 | 8 | 7 | 1 | 9 | 9 | 9 | 1 | 7 | 6 | 1 | 10 | 8 | 8 | 7 | 0 | 4 | 0 | 0 | 4 | 1 | 6 |
| Scentless chamomile | 0 | 0 | — | 0 | 1 | 0 | 0 | 0 | 0 | 0 | 0 | 1 | 1 | 1 | 1 | 0 | 0 | 0 | 1 | — | — | 1 | 1 | 2 | 0 | 5 | 0 | 1 | 2 | 0 | 0 | 0 | 0 | 0 | 0 | 0 |
| Sugar beet | 1 | 8 | 7 | 7 | 9 | 9 | 10 | 10 | 5 | 10 | 9 | 10 | 10 | 7 | 10 | 10 | 10 | 9 | 10 | 10 | 10 | 8 | 10 | 10 | 10 | 10 | 10 | 10 | 10 | 0 | 7 | 6 | 6 | 9 | 8 | 10 |
| Wheat (Spring) | 0 | 0 | 0 | 0 | 2 | 0 | 2 | 1 | 0 | 1 | 2 | 3 | 1 | 1 | 1 | 1 | 1 | 2 | 2 | 5 | 3 | 2 | 3 | 2 | 3 | 3 | 1 | 2 | 2 | 0 | 0 | 0 | 0 | 2 | 0 | 1 |
| Wheat (Winter) | 0 | 0 | 0 | 0 | 2 | 0 | 1 | 1 | 0 | 0 | 1 | 2 | 0 | 0 | 0 | 1 | 1 | 2 | 2 | 5 | 3 | 2 | 3 | 2 | 2 | 2 | 1 | 2 | 2 | 0 | 0 | 0 | 0 | 2 | 0 | 1 |
| Wild buckwheat | 0 | 6 | 0 | 0 | 7 | 1 | 7 | 8 | 1 | 9 | 8 | 8 | 9 | 2 | 2 | 6 | 2 | 2 | 10 | 7 | 8 | 6 | 3 | 4 | 2 | 6 | 2 | 8 | 8 | 0 | 5 | 0 | 0 | 2 | 0 | 3 |
| Wild oat | 0 | 1 | 0 | 0 | 1 | 1 | 5 | 3 | 0 | 3 | 1 | 8 | 4 | 2 | 2 | 1 | 3 | 1 | 5 | 8 | 6 | 3 | 4 | 3 | 4 | 4 | 1 | 7 | 5 | 0 | 1 | 0 | 0 | 1 | 1 | 3 |
| Wild oat (Stage 2) | 0 | 1 | 0 | 0 | 2 | 1 | 5 | 2 | 0 | 3 | 4 | 6 | 3 | 2 | 1 | 2 | 2 | 1 | 7 | 7 | 4 | 2 | 4 | 3 | 4 | 3 | 0 | 8 | 2 | 0 | 1 | 0 | 0 | 1 | 0 | 2 |

| | COMPOUND (250 g/ha) | | | | | | | | | | | | | | | | | | | | | | | | COMPOUND (125 g/ha) | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| | 25 | 28 | 32 | 33 | 36 | 37 | 40 | 44 | 45 | 46 | 48 | 49 | 50 | 53 | 55 | 56 | 57 | 71 | 73 | 74 | 76 | 82 | 84 | 100 | 4 | 5 | 9 | 13 | 15 | 20 | 23 | 25 | 28 | 32 | 33 | 36 |
| Barley (Spring) | 1 | 0 | 1 | 1 | 1 | 1 | 1 | 1 | 0 | 0 | 2 | 1 | 1 | 3 | 3 | 2 | 3 | 3 | 2 | 2 | 2 | 1 | 3 | 2 | 0 | 0 | 0 | 0 | 2 | 0 | 1 | 0 | 0 | 0 | 0 | 0 |
| Barley (Winter) | 0 | 0 | 1 | 1 | 1 | 1 | 1 | 0 | 0 | 0 | 2 | 0 | 2 | 2 | 2 | 1 | 3 | 2 | 1 | 1 | 2 | 0 | 1 | 2 | 0 | 0 | 0 | 0 | 1 | 0 | 1 | 0 | 0 | 0 | 1 | 0 |
| Black nightshade | 7 | 2 | 7 | 6 | 10 | 6 | 5 | 6 | 2 | 4 | 5 | 3 | 8 | 6 | 6 | 5 | 10 | 4 | 7 | 10 | 7 | 2 | 10 | 10 | 0 | 1 | 0 | 0 | 5 | 1 | 5 | 3 | 0 | 7 | 3 | 10 |
| Blackgrass | 1 | 0 | 2 | 1 | 6 | 5 | 1 | 1 | 2 | 5 | 2 | 1 | 6 | 8 | 7 | 0 | 4 | 2 | 2 | 3 | 2 | 0 | 8 | 5 | 0 | 0 | 0 | 0 | 1 | 0 | 1 | 0 | 0 | 1 | 0 | 3 |
| Blackgrass (Stage 2) | 0 | 0 | 1 | 1 | 2 | 1 | 1 | 1 | 1 | 1 | 1 | 1 | 2 | 5 | 2 | 2 | 2 | 2 | 1 | 2 | 1 | 0 | 2 | 2 | 0 | 0 | 0 | 0 | 1 | 0 | 1 | 0 | 0 | 0 | 0 | 1 |
| Bluegrass | 2 | 0 | 3 | 3 | 8 | 3 | 7 | 2 | 1 | 8 | 4 | 0 | 9 | 10 | 8 | 1 | 9 | 9 | 7 | 2 | 8 | 3 | 9 | 1 | 0 | 0 | 0 | 0 | 1 | 0 | 1 | 0 | 0 | 1 | 2 | 6 |
| Catchweed bedstraw | 1 | 1 | 6 | 1 | 4 | 2 | 2 | 4 | 0 | 1 | 5 | 0 | 1 | 3 | 1 | 2 | 8 | 4 | 7 | 3 | 6 | 0 | 9 | 9 | 0 | 0 | 0 | 0 | 1 | 0 | 4 | 0 | 0 | 5 | 0 | 4 |
| Cheatgrass | 0 | 0 | 0 | 0 | 1 | 1 | 1 | 1 | 0 | 2 | 2 | 0 | 4 | 3 | 3 | 3 | 4 | 3 | 1 | 1 | 2 | 0 | 2 | 1 | 0 | 0 | 0 | 0 | 0 | 0 | 0 | 0 | 0 | 0 | 0 | 0 |
| Downy brome | 0 | 0 | 0 | 0 | 0 | 0 | 1 | 0 | 0 | 0 | 2 | 0 | 1 | 2 | 1 | 3 | 2 | 1 | 0 | 1 | 1 | 0 | 2 | 1 | 0 | 0 | 0 | 0 | 0 | 0 | 1 | 0 | 0 | 0 | 0 | 0 |
| Field pennycress | 10 | 1 | 10 | 8 | 10 | 10 | 10 | 8 | 8 | 8 | 6 | 7 | 9 | 10 | 10 | 3 | 8 | 7 | 4 | 8 | 7 | 7 | 10 | 7 | 0 | 0 | 1 | 0 | 8 | 0 | 3 | 6 | 0 | 9 | 5 | 10 |
| Field violet | 10 | 4 | 5 | 9 | 9 | 10 | 8 | 7 | 3 | 7 | 7 | 2 | 8 | 9 | 7 | 6 | 10 | 6 | 3 | 10 | 10 | 9 | 10 | 10 | 0 | 6 | 0 | 0 | 2 | 2 | 4 | 2 | 1 | 3 | 8 | 3 |
| Green foxtail | 8 | 1 | 6 | 8 | 8 | 7 | 7 | 8 | 7 | 6 | 7 | 7 | 9 | 10 | 10 | 4 | 10 | 10 | 9 | 7 | 7 | 4 | 10 | 9 | 0 | 0 | 0 | 0 | 6 | 1 | 7 | 5 | 0 | 5 | 5 | 8 |
| Italian ryegrass | 0 | 0 | 1 | 0 | 3 | 0 | 1 | 1 | 0 | 1 | 1 | 0 | 2 | 8 | 2 | 3 | 7 | 1 | 2 | 4 | 1 | 0 | 9 | 7 | 0 | 0 | 0 | 0 | 1 | 0 | 1 | 0 | 0 | 0 | 0 | 1 |
| Ivyleaf speedwell | 10 | 6 | 10 | 9 | 10 | 10 | 7 | 10 | 2 | 4 | 8 | 1 | 9 | 8 | 9 | 10 | 9 | 10 | 9 | 10 | 10 | 7 | 10 | 10 | 0 | 7 | 0 | 0 | 7 | 2 | 9 | 3 | 2 | 9 | 8 | 9 |
| Jointed goatgrass | 0 | 0 | 0 | 0 | 1 | 0 | 0 | 0 | 0 | 1 | 1 | 0 | 0 | 1 | 2 | 1 | 1 | 2 | 0 | 1 | 1 | 0 | 1 | 1 | 0 | 0 | 0 | 0 | 1 | 0 | 1 | 0 | 0 | 0 | 0 | 0 |
| Kochia | 9 | 10 | 8 | 10 | 10 | 9 | 9 | 10 | — | 9 | 7 | 8 | 5 | — | 6 | 4 | 8 | 7 | 6 | 8 | 7 | 10 | 9 | 9 | 0 | 4 | 0 | 0 | 5 | 5 | 8 | 7 | 6 | 7 | 8 | 10 |
| Lambsquarters | 8 | 1 | 10 | 5 | 10 | 6 | 8 | 4 | 2 | 7 | 4 | 1 | 2 | 8 | 4 | 4 | 10 | 3 | 2 | 3 | 7 | 8 | 9 | 9 | 0 | 2 | 0 | 0 | 5 | 0 | 4 | 2 | 0 | 10 | 5 | 6 |
| Persian speedwell | 10 | 9 | 10 | 4 | 7 | 9 | 2 | 7 | 2 | 6 | 8 | 2 | 7 | 8 | 7 | 8 | 9 | 9 | 9 | 8 | 10 | 6 | 10 | 10 | 0 | 7 | 0 | 0 | 3 | 3 | 7 | 5 | 1 | 9 | 3 | 6 |
| Rape | 7 | 5 | 9 | 8 | 10 | 8 | 6 | 5 | 4 | 8 | 6 | 4 | 7 | 9 | 8 | 6 | 9 | 4 | 8 | 6 | 7 | 7 | 8 | 8 | 0 | 1 | 1 | 0 | 7 | 3 | 5 | 5 | 2 | 8 | 6 | 4 |
| Russian thistle | 6 | 1 | 6 | 7 | 9 | 8 | 9 | 6 | 2 | 8 | 7 | 1 | 4 | 8 | 7 | 0 | 5 | 4 | 0 | 2 | 10 | 7 | 5 | 7 | 0 | 4 | 0 | 0 | 3 | 0 | 4 | 2 | 0 | 6 | 5 | 9 |
| Scentless chamomile | 0 | 0 | 0 | 0 | 1 | 1 | 1 | 0 | 2 | 0 | 0 | — | 0 | 5 | — | 0 | 1 | 0 | 0 | 5 | 1 | 0 | 0 | 0 | 0 | 0 | 0 | 0 | 0 | 0 | 0 | 0 | 0 | 0 | 0 | 0 |
| Sugar beet | 10 | 5 | 10 | 9 | 10 | 10 | 7 | 9 | 9 | 10 | 8 | 7 | 10 | 10 | 9 | 4 | 10 | 9 | 8 | 9 | 10 | 10 | 10 | 9 | 0 | 5 | 6 | 2 | 8 | 7 | 8 | 8 | 4 | 9 | 9 | 9 |
| Wheat (Spring) | 0 | 0 | 0 | 1 | 1 | 0 | 1 | 1 | 1 | 0 | 1 | 1 | 1 | 5 | 3 | 1 | 1 | 2 | 3 | 2 | 2 | 1 | 2 | 2 | 0 | 0 | 0 | 0 | 2 | 0 | 1 | 0 | 0 | 0 | 1 | 1 |
| Wheat (Winter) | 0 | 0 | 0 | 0 | 1 | 0 | 0 | 0 | 1 | 1 | 1 | 1 | 1 | 3 | 2 | 1 | 2 | 2 | 2 | 1 | 2 | 0 | 2 | 2 | 0 | 0 | 0 | 0 | 2 | 0 | 1 | 0 | 0 | 0 | 0 | 1 |
| Wild buckwheat | 4 | 0 | 7 | 6 | 4 | 9 | 2 | 2 | 1 | 5 | 1 | 1 | 10 | 3 | 3 | 2 | 0 | 4 | 2 | 5 | 4 | 1 | 7 | 7 | 0 | 3 | 0 | 0 | 2 | 0 | 1 | 2 | 0 | 7 | 6 | 2 |
| Wild oat | 1 | 0 | 1 | 1 | 6 | 4 | 2 | 1 | 1 | 1 | 3 | 0 | 3 | 5 | 4 | 2 | 2 | 3 | 2 | 1 | 3 | 1 | 7 | 4 | 0 | 1 | 0 | 0 | 1 | 0 | 1 | 0 | 0 | 0 | 1 | 3 |
| Wild oat (Stage 2) | 1 | 0 | 1 | 2 | 2 | 2 | 1 | 1 | 2 | 1 | 2 | 0 | 4 | 4 | 2 | 2 | 3 | 3 | 2 | 2 | 3 | 0 | 6 | 1 | 0 | 1 | 0 | 0 | 1 | 0 | 1 | 0 | 0 | 0 | 1 | 2 |

| | COMPOUND (125 g/ha) | | | | | | | | | | | | | | | | | | | COMPOUND (64 g/ha) | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| | 37 | 40 | 44 | 45 | 46 | 48 | 49 | 50 | 53 | 55 | 56 | 57 | 71 | 73 | 74 | 76 | 82 | 84 | 100 | 4 | 5 | 9 | 13 | 15 | 20 | 23 | 32 | 33 | 36 | 37 | 40 | 44 | 45 | 46 | 48 | 49 |
| Barley (Spring) | 1 | 0 | 0 | 0 | 0 | 2 | 0 | 0 | 2 | 2 | 1 | 3 | 3 | 2 | 1 | 2 | 0 | 2 | 2 | 0 | 0 | 0 | 0 | 1 | 0 | 1 | 0 | 0 | 0 | 0 | 0 | 0 | 0 | 0 | 1 | 0 |
| Barley (Winter) | 0 | 1 | 0 | 0 | 0 | 2 | 0 | 1 | 2 | 2 | 0 | 3 | 2 | 0 | 1 | 0 | 0 | 1 | 2 | 0 | 0 | 0 | 0 | 0 | 0 | 1 | 0 | 0 | 0 | 0 | 0 | 0 | 0 | 0 | 1 | 0 |
| Black nightshade | 6 | 5 | 3 | 2 | 4 | 2 | 1 | 3 | 5 | 5 | 1 | 2 | 2 | 7 | 7 | 3 | 1 | 10 | 7 | 0 | 0 | 0 | 0 | 3 | 0 | 5 | 1 | 1 | 2 | 2 | 5 | 2 | 1 | 2 | 0 | 0 |
| Blackgrass | 2 | 1 | 1 | 0 | 2 | 2 | 0 | 3 | 6 | 6 | 0 | 2 | 0 | 0 | 1 | 1 | 0 | 1 | 5 | 0 | 0 | 0 | 0 | 0 | 0 | 0 | 0 | 0 | 1 | 0 | 0 | 0 | 0 | 1 | 1 | 0 |
| Blackgrass (Stage 2) | 0 | 0 | 0 | 1 | 0 | 1 | 1 | 1 | 1 | 2 | 1 | 2 | 1 | 1 | 0 | 0 | 0 | 1 | 1 | 0 | 0 | 0 | 0 | 0 | 0 | 0 | 0 | 0 | 0 | 0 | 0 | 0 | 0 | 0 | 0 | 0 |
| Bluegrass | 2 | 3 | 1 | 0 | 8 | 2 | 0 | 6 | 7 | 5 | 0 | 3 | 2 | 2 | 1 | 5 | 1 | 2 | 1 | 0 | 0 | 0 | 0 | 0 | 0 | 1 | 0 | 0 | 2 | 0 | 0 | 0 | 0 | 6 | 1 | 0 |
| Catchweed bedstraw | 1 | 2 | 2 | 0 | 0 | 3 | 0 | 0 | 1 | 1 | 1 | 7 | 3 | 5 | 1 | 4 | 0 | 6 | 8 | 0 | 0 | 0 | 0 | 0 | 0 | 3 | 1 | 0 | 1 | 0 | 1 | 0 | 0 | 0 | 2 | 0 |
| Cheatgrass | 0 | 1 | 1 | 0 | 1 | 2 | 0 | 2 | 3 | 1 | 1 | 2 | 1 | 0 | 0 | 1 | 0 | 1 | 0 | 0 | 0 | 0 | 0 | 0 | 0 | 0 | 0 | 0 | 0 | 0 | 0 | 1 | 0 | 0 | 1 | 0 |
| Downy brome | 0 | 0 | 0 | 0 | 0 | 1 | 0 | 0 | 2 | 0 | 1 | 2 | 1 | 0 | 0 | 0 | 0 | 1 | 1 | 0 | 0 | 0 | 0 | 0 | 0 | 0 | 0 | 0 | 0 | 0 | 0 | 0 | 0 | 0 | 0 | 0 |
| Field pennycress | 9 | 10 | 3 | 2 | 6 | 2 | 3 | 6 | 9 | 8 | 0 | 5 | 3 | 2 | 8 | 5 | 4 | 10 | 3 | 0 | 0 | 1 | 0 | 2 | 0 | 2 | 3 | 2 | 4 | 4 | 3 | 3 | 0 | 2 | 0 | 3 |
| Field violet | 4 | 7 | 3 | 2 | 5 | 7 | 1 | 4 | 9 | 2 | 5 | 7 | 6 | 2 | 7 | 9 | 7 | 6 | 4 | 0 | 4 | 0 | 0 | 1 | 0 | 2 | 0 | 3 | 2 | 2 | 4 | 1 | 2 | 2 | 4 | 1 |
| Green foxtail | 7 | 5 | 2 | 7 | 3 | 6 | 6 | 9 | 9 | 10 | 1 | 8 | 8 | 5 | 2 | 2 | 2 | 10 | 8 | 0 | 0 | 0 | 0 | 2 | 0 | 6 | 2 | 2 | 5 | 0 | 2 | 1 | 5 | 2 | 3 | 2 |

TABLE D-continued

| | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| Italian ryegrass | 0 | 0 | 1 | 0 | 0 | 1 | 0 | 1 | 7 | 1 | 1 | 4 | 1 | 1 | 1 | 1 | 0 | 3 | 2 | 0 | 0 | 0 | 0 | 0 | 0 | 1 | 0 | 0 | 0 | 0 | 0 | 0 | 0 | 0 | 0 | 0 |
| Ivyleaf speedwell | 5 | 6 | 10 | 2 | 2 | 6 | 0 | 7 | 7 | 8 | 5 | 7 | 10 | 7 | 9 | 9 | 5 | 10 | 10 | 0 | 7 | 0 | 0 | 2 | 0 | 9 | 5 | 8 | 8 | 3 | 2 | 1 | 1 | 0 | 6 | 0 |
| Jointed goatgrass | 0 | 0 | 0 | 0 | 0 | 0 | 0 | 0 | 1 | 1 | 0 | 0 | 1 | 0 | 0 | 1 | 0 | 1 | 0 | 0 | 0 | 0 | 0 | 0 | 0 | 1 | 0 | 0 | 0 | 0 | 0 | 0 | 0 | 0 | 0 | 0 |
| Kochia | 9 | 9 | 10 | 0 | 7 | 7 | 2 | 1 | 2 | — | 2 | 6 | 5 | 6 | 8 | 7 | 10 | 8 | 6 | 0 | 4 | 0 | 0 | 0 | 5 | 7 | 6 | 6 | 8 | 7 | 8 | 8 | 0 | 5 | 5 | 0 |
| Lambsquarters | 3 | 6 | 2 | 2 | 5 | 2 | 0 | 0 | 7 | 3 | 1 | 6 | 2 | 0 | 3 | 7 | 5 | 7 | 6 | 0 | 2 | 0 | 0 | 2 | 0 | 4 | 2 | 0 | 3 | 1 | 3 | 1 | 1 | 3 | 1 | 0 |
| Persian speedwell | 3 | 2 | 4 | 2 | 3 | 6 | 2 | 7 | 8 | 6 | 7 | 8 | 8 | 7 | 7 | 9 | 3 | 10 | 8 | 0 | 6 | 0 | 0 | 2 | 0 | 5 | 3 | 0 | 3 | 2 | 1 | 2 | 2 | 1 | 3 | 2 |
| Rape | 8 | 2 | 2 | 2 | 7 | 4 | 3 | 6 | 8 | 7 | 3 | 7 | 2 | 4 | 3 | 7 | 3 | 7 | 7 | 0 | 0 | 0 | 0 | 5 | 1 | 5 | 6 | 3 | 1 | 2 | 1 | 0 | 1 | 5 | 3 | 1 |
| Russian thistle | 8 | 8 | 3 | 1 | 7 | 3 | 0 | — | 6 | 5 | 0 | 4 | 2 | 0 | 2 | 7 | 4 | 3 | 4 | 0 | 1 | 0 | 0 | 1 | 0 | 2 | 4 | 3 | 8 | 5 | 5 | 1 | 0 | 5 | 1 | 0 |
| Scentless chamomile | 0 | 1 | 0 | 0 | 0 | 0 | — | 0 | 5 | — | 0 | 0 | 0 | 0 | 2 | 0 | 0 | 0 | 0 | 0 | 0 | — | 0 | 0 | 0 | 0 | 0 | 0 | 0 | 0 | 0 | 0 | — | 0 | 0 | — |
| Sugar beet | 10 | 7 | 9 | 8 | 9 | 7 | 7 | 7 | 9 | 9 | 3 | 9 | 8 | 7 | 9 | 9 | 9 | 10 | 9 | 0 | 2 | 2 | 0 | 7 | 4 | 7 | 6 | 8 | 9 | 8 | 6 | 7 | 6 | 7 | 5 | 6 |
| Wheat (Spring) | 0 | 0 | 0 | 0 | 0 | 1 | 1 | 0 | 4 | 2 | 0 | 1 | 1 | 1 | 1 | 1 | 0 | 1 | 2 | 0 | 0 | 0 | 0 | 1 | 0 | 1 | 0 | 0 | 1 | 0 | 0 | 1 | 0 | 0 | 0 | 0 |
| Wheat (Winter) | 0 | 0 | 0 | 0 | 0 | 1 | 0 | 0 | 2 | 2 | 1 | 1 | 1 | 1 | 1 | 1 | 0 | 1 | 1 | 0 | 0 | 0 | 0 | 1 | 0 | 1 | 0 | 0 | 0 | 0 | 0 | 0 | 0 | 0 | 0 | 0 |
| Wild buckwheat | 2 | 2 | 0 | 0 | 3 | 0 | 1 | 4 | 1 | 1 | 1 | 0 | 2 | 1 | 2 | 0 | 0 | 6 | 2 | 0 | 0 | 0 | 0 | 0 | 0 | 0 | 2 | 4 | 0 | 0 | 0 | 0 | 0 | 1 | 0 | 0 |
| Wild oat | 2 | 1 | 1 | 0 | 0 | 2 | 0 | 1 | 2 | 2 | 2 | 2 | 3 | 2 | 1 | 2 | 0 | 3 | 2 | 0 | 1 | 0 | 0 | 1 | 0 | 1 | 0 | 0 | 2 | 1 | 1 | 0 | 0 | 0 | 1 | 0 |
| Wild oat (Stage 2) | 1 | 1 | 1 | 1 | 1 | 2 | 0 | 1 | 3 | 2 | 1 | 2 | 1 | 2 | 1 | 2 | 0 | 2 | 1 | 0 | 0 | 0 | 0 | 0 | 0 | 1 | 0 | 0 | 1 | 1 | 0 | 0 | 0 | 0 | 1 | 0 |

| | COMPOUND (64 g/ha) | | | | | | | | | | | | COMPOUND (32 g/ha) | | | | | | | | | | | | |
|---|---|---|---|---|---|---|---|---|---|---|---|---|---|---|---|---|---|---|---|---|---|---|---|---|---|
| | 50 | 53 | 55 | 56 | 57 | 71 | 73 | 74 | 76 | 82 | 84 | 100 | 5 | 13 | 23 | 46 | 48 | 56 | 57 | 71 | 73 | 74 | 76 | 82 | 100 |
| Barley (Spring) | 0 | 1 | 1 | 0 | 2 | 3 | 1 | 0 | 1 | 0 | 2 | 1 | 0 | 0 | 1 | 0 | 0 | 0 | 2 | 3 | 0 | 0 | 1 | 0 | 1 |
| Barley (Winter) | 0 | 1 | 1 | 0 | 2 | 2 | 0 | 0 | 0 | 0 | 1 | 1 | 0 | 0 | 1 | 0 | 0 | 0 | 1 | 1 | 0 | 0 | 0 | 0 | 1 |
| Black nightshade | 0 | 4 | 2 | 0 | 2 | 2 | 5 | 5 | 3 | 0 | 6 | 7 | 0 | 0 | 2 | 0 | 0 | 0 | 1 | 0 | 1 | 2 | 2 | 0 | 3 |
| Blackgrass | 0 | 2 | 4 | 0 | 2 | 0 | 0 | 0 | 1 | 0 | 1 | 2 | 0 | 0 | 0 | 0 | 0 | 0 | 1 | 0 | 0 | 0 | 0 | 0 | 0 |
| Blackgrass (Stage 2) | 0 | 0 | 1 | 0 | 0 | 1 | 0 | 0 | 0 | 0 | 0 | 0 | 0 | 0 | 0 | 0 | 0 | 0 | 0 | 0 | 0 | 0 | 0 | 0 | 0 |
| Bluegrass | 1 | 2 | 2 | 0 | 3 | 2 | 1 | 0 | 3 | 0 | 1 | 0 | 0 | 0 | 0 | 2 | 0 | 0 | 1 | 0 | 0 | 0 | 1 | 0 | 0 |
| Catchweed bedstraw | 0 | 0 | 0 | 0 | 2 | 3 | 2 | 0 | 2 | 0 | 3 | 7 | 0 | 0 | 1 | 0 | 0 | 0 | 0 | 1 | 1 | 0 | 0 | 0 | 3 |
| Cheatgrass | 0 | 1 | 0 | 0 | 1 | 0 | 0 | 0 | 0 | 0 | 1 | 0 | 0 | 0 | 0 | 0 | 0 | 0 | 0 | 0 | 0 | 0 | 0 | 0 | 0 |
| Downy brome | 0 | 1 | 0 | 0 | 2 | 0 | 0 | 0 | 0 | 0 | 0 | 0 | 0 | 0 | 0 | 0 | 0 | 0 | 0 | 0 | 0 | 0 | 0 | 0 | 0 |
| Field pennycress | 1 | 3 | 7 | 0 | 2 | 1 | 0 | 2 | 5 | 2 | 4 | 3 | 0 | 0 | 0 | 0 | 0 | 0 | 0 | 0 | 0 | 0 | 3 | 0 | 0 |
| Field violet | 0 | 6 | 2 | 3 | 7 | 3 | 2 | 4 | 9 | 3 | 4 | 2 | 2 | 0 | 1 | 0 | 1 | 0 | 3 | 1 | 1 | 1 | 3 | 1 | 0 |
| Green foxtail | 6 | 9 | 7 | 0 | 6 | 5 | 1 | 0 | 2 | 0 | 8 | 6 | 0 | 0 | 4 | 0 | 2 | 0 | 2 | 2 | 0 | 0 | 0 | 0 | 2 |
| Italian ryegrass | 0 | 2 | 1 | 0 | 2 | 0 | 1 | 0 | 0 | 0 | 0 | 1 | 0 | 0 | 0 | 0 | 0 | 0 | 0 | 0 | 0 | 0 | 0 | 0 | 0 |
| Ivyleaf speedwell | 2 | 5 | 8 | 0 | 7 | 8 | 7 | 7 | 8 | 3 | 9 | 10 | 3 | 0 | 8 | 0 | 2 | 0 | 5 | 5 | 6 | 4 | 5 | 0 | 8 |
| Jointed goatgrass | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Kochia | 0 | 0 | 1 | 2 | 3 | 3 | 4 | 7 | 5 | 8 | 8 | 4 | 1 | 0 | 4 | 2 | 2 | 1 | 1 | 1 | 2 | 3 | 3 | 5 | 3 |
| Lambsquarters | 0 | 2 | 2 | 0 | 2 | 2 | 0 | 0 | 3 | 2 | 4 | 4 | 0 | 0 | 2 | 0 | 0 | 0 | 0 | 0 | 0 | 0 | 2 | 0 | 3 |
| Persian speedwell | 3 | 4 | 5 | 4 | 6 | 5 | 6 | 3 | 7 | 1 | 6 | 8 | 1 | 0 | 4 | 0 | 0 | 2 | 4 | 2 | 3 | 0 | 4 | 0 | 6 |
| Rape | 2 | 6 | 7 | 1 | 4 | 2 | 2 | 1 | 5 | 2 | 6 | 7 | 0 | 0 | 2 | 0 | 0 | 0 | 4 | 1 | 1 | 0 | 3 | 0 | 4 |
| Russian thistle | 1 | 1 | 4 | 0 | 2 | 0 | 0 | 1 | 3 | 2 | 2 | 2 | 0 | 0 | 1 | 2 | 0 | 0 | 1 | 0 | 0 | 0 | 1 | 0 | 1 |
| Scentless chamomile | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 4 | 8 | 8 | 3 | 8 | 7 | 6 | 8 | 9 | 8 | 9 | 7 | 2 | 0 | 5 | 3 | 5 | 0 | 6 | 7 | 2 | 7 | 8 | 4 | 5 |
| Wheat (Spring) | 0 | 1 | 2 | 0 | 1 | 1 | 1 | 0 | 1 | 0 | 1 | 1 | 0 | 0 | 1 | 0 | 0 | 0 | 0 | 0 | 0 | 0 | 0 | 0 | 1 |
| Wheat (Winter) | 0 | 2 | 2 | 0 | 1 | 1 | 0 | 0 | 1 | 0 | 1 | 1 | 0 | 0 | 1 | 0 | 0 | 0 | 1 | 0 | 0 | 0 | 0 | 0 | 1 |
| Wild buckwheat | 1 | 0 | 1 | 0 | 0 | 1 | 0 | 0 | 0 | 0 | 1 | 0 | 0 | 0 | 0 | 0 | 0 | 0 | 0 | 0 | 0 | 0 | 0 | 0 | 0 |
| Wild oat | 0 | 1 | 1 | 1 | 2 | 2 | 1 | 0 | 2 | 0 | 2 | 2 | 0 | 0 | 1 | 0 | 0 | 0 | 2 | 2 | 1 | 0 | 1 | 0 | 1 |
| Wild oat (Stage 2) | 0 | 1 | 1 | 1 | 2 | 1 | 1 | 1 | 2 | 0 | 1 | 1 | 0 | 0 | 0 | 0 | 1 | 0 | 1 | 1 | 1 | 0 | 0 | 0 | 1 |

PREEMERGENCE

| | COMPOUND (1000 g/ha) | | | | | | | | | | | | | | | | COMPOUND (750 g/ha) | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|
| | 4 | 9 | 13 | 20 | 23 | 25 | 28 | 32 | 33 | 36 | 37 | 40 | 44 | 46 | 50 | 82 | 4 | 9 | 13 | 15 | 20 | 23 | 25 | 28 | 32 | 36 | 37 | 40 | 44 | 46 | 49 | 50 | 53 | 55 | 82 |
| Barley (Spring) | 0 | 1 | 3 | 2 | 4 | 2 | 1 | 3 | 1 | 5 | 3 | 2 | 5 | 3 | 6 | 3 | 0 | 0 | 2 | 1 | 1 | 3 | 2 | 1 | 2 | 5 | 3 | 2 | 4 | 3 | 2 | 6 | 10 | 7 | 3 |
| Barley (Winter) | 0 | 1 | 2 | 2 | 2 | 3 | 1 | 1 | 1 | 4 | 2 | 1 | 3 | 4 | 6 | 2 | 0 | 0 | 0 | 0 | 1 | 2 | 2 | 1 | 1 | 3 | 2 | 0 | 3 | 4 | 2 | 6 | 7 | 5 | 1 |
| Black nightshade | 0 | 7 | 10 | 10 | 10 | 10 | 8 | 10 | 10 | 10 | 9 | 10 | 10 | 10 | 10 | 10 | 0 | 7 | 10 | 10 | 10 | 10 | 10 | 8 | 10 | 10 | 9 | 10 | 10 | 10 | 9 | 10 | 10 | 10 | 10 |
| Blackgrass | 1 | 3 | 10 | 10 | 10 | 10 | 9 | 10 | 10 | 10 | 10 | 10 | 10 | 10 | 10 | 10 | 1 | 3 | 10 | 10 | 10 | 10 | 10 | 7 | 10 | 10 | 10 | 10 | 10 | 10 | 7 | 10 | 10 | 10 | 10 |

TABLE D-continued

| | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|
| Bluegrass | 0 | 1 | 10 | 10 | 10 | 10 | 10 | 10 | 10 | 10 | 10 | 10 | 10 | 10 | 10 | 10 | 0 | 1 | 10 | 10 | 10 | 10 | 10 | 10 | 10 | 10 | 10 | 9 | 10 | 10 | 9 | 10 | 10 | 10 | 10 |
| Catchweed bedstraw | 0 | 2 | 0 | 4 | 10 | 10 | 3 | 10 | 7 | 10 | 8 | 9 | 8 | 10 | 10 | 3 | 0 | 1 | 0 | 7 | 2 | 10 | 7 | 1 | 10 | 10 | 8 | 9 | 8 | 4 | 2 | 10 | 10 | 7 | 3 |
| Cheatgrass | 0 | 0 | 3 | 2 | 10 | 6 | 1 | 5 | 1 | 10 | 10 | 3 | 7 | 9 | 10 | 2 | 0 | 0 | 2 | 8 | 2 | 8 | 5 | 0 | 2 | 10 | 9 | 3 | 4 | 9 | 3 | 10 | 10 | 10 | 2 |
| Downy brome | 0 | 0 | 8 | 2 | 10 | 6 | 1 | 3 | 1 | 9 | 7 | 2 | 6 | 6 | 10 | 4 | 0 | 0 | 5 | 7 | 2 | 8 | 3 | 1 | 3 | 8 | 5 | 2 | 3 | 4 | 0 | 7 | 10 | 7 | 2 |
| Field pennycress | 2 | 10 | 10 | 10 | 10 | 10 | 10 | 10 | 10 | 10 | 10 | 10 | 10 | 10 | 10 | 10 | 1 | 10 | 10 | 10 | 10 | 10 | 10 | 10 | 10 | 10 | 10 | 10 | 10 | 10 | 10 | 10 | 10 | 10 | 10 |
| Field violet | 1 | 10 | 10 | 10 | 10 | 10 | 10 | 10 | 10 | 10 | 10 | 10 | 10 | 10 | 10 | 10 | 0 | 10 | 10 | 10 | 10 | 10 | 10 | 9 | 10 | 10 | 10 | 10 | 10 | 10 | 10 | 10 | 10 | 10 | 10 |
| Green foxtail | 2 | 10 | 10 | 10 | 10 | 10 | 10 | 10 | 10 | 10 | 10 | 10 | 10 | 10 | 10 | 10 | 1 | 10 | 10 | 10 | 10 | 10 | 10 | 10 | 10 | 10 | 10 | 10 | 10 | 10 | 10 | 10 | 10 | 10 | 10 |
| Italian ryegrass | 0 | 3 | 9 | 9 | 10 | 6 | 3 | 10 | 6 | 10 | 10 | 9 | 9 | 10 | 10 | 9 | 0 | 2 | 7 | 9 | 7 | 10 | 2 | 3 | 3 | 10 | 10 | 9 | 9 | 10 | 4 | 10 | 10 | 10 | 9 |
| Ivyleaf speedwell | 0 | 8 | 10 | 10 | 10 | 10 | 10 | 10 | 10 | 10 | 10 | 10 | 10 | 10 | 10 | 10 | 0 | 4 | 10 | 10 | 10 | 10 | 10 | 10 | 10 | 10 | 10 | 8 | 10 | 10 | 9 | 10 | 10 | 10 | 10 |
| Jointed goatgrass | 0 | 0 | 2 | 2 | 2 | 3 | 1 | 3 | 2 | 4 | 4 | 4 | 2 | 3 | 7 | 1 | 0 | 0 | 1 | 2 | 0 | 1 | 1 | 0 | 3 | 4 | 4 | 1 | 2 | 2 | 3 | 4 | 6 | 8 | 1 |
| Kochia | 0 | 10 | 10 | 10 | 10 | 10 | 10 | 10 | 10 | 10 | 10 | 10 | 10 | 10 | 10 | 10 | 0 | 9 | 10 | 10 | 9 | 10 | 10 | 10 | 10 | 10 | 10 | 10 | 10 | 10 | 10 | 10 | 10 | 10 | 10 |
| Lambsquarters | 1 | 9 | 10 | 10 | 10 | 10 | 10 | 10 | 10 | 10 | 10 | 10 | 10 | 10 | 10 | 10 | 0 | 9 | 10 | 10 | 10 | 10 | 10 | 10 | 10 | 10 | 10 | 10 | 10 | 10 | 10 | 10 | 10 | 10 | 10 |
| Persian speedwell | 0 | 8 | 10 | 10 | 10 | 10 | 10 | 10 | 10 | 10 | 10 | 10 | 10 | 10 | 10 | 10 | 0 | 8 | 10 | 10 | 10 | 10 | 10 | 10 | 10 | 10 | 10 | 10 | 10 | 10 | 9 | 10 | 10 | 10 | 10 |
| Rape | 1 | 9 | 10 | 10 | 10 | 10 | 10 | 10 | 10 | 10 | 10 | 10 | 10 | 10 | 10 | 10 | 1 | 6 | 10 | 10 | 10 | 10 | 10 | 10 | 10 | 10 | 10 | 10 | 10 | 10 | 10 | 10 | 10 | 10 | 10 |
| Russian thistle | 0 | 4 | 10 | 8 | 10 | 10 | 2 | 9 | 10 | 10 | 8 | 8 | 9 | 10 | 10 | 10 | 0 | 2 | 10 | 10 | 3 | 10 | 10 | 2 | 9 | 10 | 8 | 8 | 9 | 8 | 2 | 10 | 10 | 10 | 7 |
| Scentless chamomile | 1 | 3 | 10 | 10 | 8 | 10 | 10 | 10 | 8 | 10 | 10 | 9 | 9 | 10 | 10 | 10 | — | 3 | 8 | 10 | 9 | 6 | 9 | 9 | 9 | 9 | 9 | 9 | 9 | 10 | 10 | 10 | 10 | 10 | 10 |
| Sugar beet | 2 | 10 | 10 | 10 | 10 | 10 | 10 | 10 | 10 | 10 | 10 | 10 | 10 | 10 | 10 | 10 | 1 | 10 | 10 | 10 | 10 | 10 | 10 | 9 | 10 | 10 | 10 | 10 | 10 | 10 | 10 | 10 | 10 | 10 | 10 |
| Wheat (Spring) | 0 | 1 | 3 | 2 | 4 | 2 | 1 | 2 | 1 | 4 | 3 | 0 | 3 | 3 | 5 | 2 | 0 | 0 | 1 | 3 | 2 | 3 | 1 | 0 | 2 | 2 | 3 | 0 | 3 | 2 | 3 | 5 | 8 | 6 | 2 |
| Wheat (Winter) | 0 | 1 | 1 | 2 | 4 | 1 | 1 | 4 | 1 | 4 | 2 | 0 | 2 | 5 | 6 | 3 | 0 | 0 | 1 | 4 | 1 | 3 | 1 | 0 | 1 | 4 | 1 | 0 | 2 | 2 | 2 | 5 | 9 | 4 | 1 |
| Wild buckwheat | 0 | 9 | 10 | 4 | 10 | 10 | 10 | 10 | 10 | 10 | 10 | 8 | 10 | 10 | 10 | 5 | 0 | 9 | 10 | 10 | 3 | 10 | 10 | 10 | 10 | 10 | 10 | 8 | 10 | 10 | 8 | 10 | 10 | 10 | 5 |
| Wild oat | 0 | 2 | 8 | 3 | 10 | 4 | 2 | 7 | 3 | 10 | 9 | 7 | 7 | 10 | 10 | 10 | 0 | 0 | 2 | 9 | 3 | 9 | 4 | 1 | 6 | 10 | 9 | 7 | 7 | 10 | 4 | 9 | 10 | 10 | 9 |

| | COMPOUND (500 g/ha) | | | | | | | | | | | | | | | | | | | | | | | | | | | | | COMPOUND (250 g/ha) | | | | | | |
|---|---|---|---|---|---|---|---|---|---|---|---|---|---|---|---|---|---|---|---|---|---|---|---|---|---|---|---|---|---|---|---|---|---|---|---|---|
| | 4 | 5 | 9 | 13 | 15 | 20 | 23 | 25 | 28 | 32 | 33 | 36 | 37 | 40 | 44 | 46 | 48 | 49 | 50 | 53 | 55 | 56 | 57 | 71 | 73 | 76 | 82 | 84 | 100 | 4 | 5 | 9 | 13 | 15 | 20 | 23 |
| Barley (Spring) | 0 | 0 | 0 | 1 | 0 | 1 | 1 | 1 | 0 | 1 | 1 | 4 | 2 | 1 | 1 | 3 | 2 | 0 | 5 | 7 | 3 | 2 | 5 | 2 | 5 | 3 | 1 | 6 | 1 | 0 | 0 | 0 | 1 | 0 | 0 | 1 |
| Barley (Winter) | 0 | 0 | 0 | 0 | 0 | 0 | 1 | 1 | 0 | 0 | 0 | 2 | 1 | 0 | 1 | 2 | 1 | 0 | 4 | 4 | 4 | 1 | 4 | 2 | 7 | 2 | 1 | 4 | 1 | 0 | 0 | 0 | 0 | 0 | 0 | 1 |
| Black nightshade | 0 | 10 | 7 | 5 | 10 | 10 | 10 | 10 | 7 | 10 | 10 | 10 | 9 | 10 | 10 | 7 | 7 | 9 | 10 | 10 | 10 | 10 | 10 | 10 | 10 | 8 | 10 | 10 | 10 | 0 | 9 | 2 | 5 | 10 | 10 | 10 |
| Blackgrass | 0 | 6 | 1 | 8 | 10 | 10 | 10 | 9 | 2 | 8 | 9 | 10 | 10 | 10 | 8 | 10 | 8 | 7 | 10 | 10 | 10 | 10 | 10 | 10 | 10 | 10 | 10 | 10 | 8 | 0 | 6 | 0 | 6 | 9 | 9 | 9 |
| Bluegrass | 0 | 8 | 1 | 10 | 10 | 10 | 9 | 10 | 9 | 10 | 10 | 10 | 10 | 9 | 10 | 10 | 10 | 9 | 10 | 10 | 10 | 8 | 10 | 10 | 10 | 10 | 10 | 9 | 10 | 0 | 2 | 0 | 10 | 8 | 9 | 9 |
| Catchweed bedstraw | 0 | 0 | 0 | 0 | 3 | 1 | 10 | 4 | 1 | 7 | 3 | 10 | 7 | 9 | 5 | 4 | 10 | 1 | 3 | 10 | 5 | 10 | 10 | 10 | 10 | 10 | 2 | 10 | 10 | 0 | 0 | 0 | 0 | 1 | 1 | 8 |
| Cheatgrass | 0 | 2 | 0 | 1 | 6 | 1 | 7 | 1 | 0 | 2 | 1 | 9 | 9 | 2 | 2 | 4 | 5 | 2 | 10 | 10 | 8 | 5 | 10 | 10 | 10 | 2 | 1 | 9 | 2 | 0 | 0 | 0 | 0 | 5 | 0 | 2 |
| Downy brome | 0 | 0 | 0 | 2 | 4 | 1 | 7 | 3 | 0 | 1 | 0 | 8 | 5 | 2 | 1 | 2 | 2 | 0 | 7 | 9 | 7 | 5 | 10 | 10 | 7 | 7 | 1 | 6 | 2 | 0 | 0 | 0 | 1 | 1 | 0 | 2 |
| Field pennycress | 0 | 10 | 1 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 0 | 10 | 10 | 10 | 10 | 10 | 10 |
| Field violet | 0 | 10 | 9 | 10 | 10 | 10 | 10 | 9 | 9 | 9 | 10 | 10 | 10 | 10 | 10 | 10 | 10 | 10 | 10 | 10 | 10 | 10 | 10 | 10 | 10 | 10 | 10 | 10 | 10 | 0 | 10 | 8 | 10 | 10 | 9 | 10 |
| Green foxtail | 0 | 6 | 8 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 0 | 2 | 3 | 10 | 10 | 10 | 10 |
| Italian ryegrass | 0 | 2 | 0 | 6 | 8 | 7 | 10 | 2 | 1 | 3 | 2 | 9 | 10 | 5 | 8 | 8 | 9 | 3 | 10 | 10 | 10 | 6 | 10 | 10 | 10 | 8 | 6 | 10 | 5 | 0 | 1 | 0 | 3 | 6 | 6 | 3 |
| Ivyleaf speedwell | 0 | 10 | 2 | 10 | 10 | 10 | 10 | 10 | 10 | 9 | 9 | 10 | 10 | 8 | 10 | 10 | 10 | 7 | 10 | 10 | 10 | 10 | 10 | 10 | 10 | 10 | 10 | 10 | 10 | 0 | 9 | 0 | 5 | 10 | 9 | 10 |
| Jointed goatgrass | 0 | 0 | 0 | 0 | 1 | 0 | 1 | 0 | 0 | 1 | 0 | 2 | 2 | 1 | 1 | 1 | 1 | 3 | 2 | 6 | 5 | 0 | 8 | 3 | 3 | 1 | 0 | 3 | 2 | 0 | 0 | 0 | 0 | 0 | 0 | 0 |
| Kochia | 0 | 9 | 1 | 10 | 10 | 9 | 10 | 10 | 9 | 10 | 10 | 10 | 10 | 10 | 10 | 10 | 10 | 10 | 10 | 10 | 10 | 10 | 10 | 9 | 9 | 10 | 10 | 10 | 10 | 0 | 9 | 0 | 10 | 10 | 8 | 10 |
| Lambsquarters | 0 | 10 | 8 | 10 | 10 | 9 | 10 | 10 | 9 | 10 | 10 | 10 | 9 | 9 | 10 | 10 | 10 | 10 | 10 | 10 | 10 | 10 | 10 | 10 | 10 | 10 | 10 | 10 | 10 | 0 | 8 | 8 | 10 | 10 | 7 | 10 |
| Persian speedwell | 0 | 10 | 7 | 10 | 10 | 10 | 10 | 10 | 10 | 10 | 10 | 10 | 10 | 10 | 10 | 10 | 10 | 7 | 10 | 10 | 10 | 10 | 10 | 10 | 10 | 10 | 10 | 10 | 10 | 0 | 10 | 5 | 10 | 10 | 8 | 10 |
| Rape | 0 | 10 | 6 | 8 | 10 | 9 | 10 | 10 | 9 | 10 | 10 | 10 | 10 | 10 | 10 | 10 | 10 | 10 | 10 | 10 | 10 | 9 | 10 | 10 | 10 | 10 | 9 | 10 | 10 | 0 | 8 | 4 | 6 | 10 | 8 | 10 |
| Russian thistle | 0 | 7 | 1 | 10 | 9 | 2 | 10 | 10 | 1 | 9 | 5 | 8 | 5 | 5 | 9 | 8 | 9 | — | 8 | 10 | 9 | 7 | 6 | 3 | 9 | 10 | 3 | 10 | 10 | 0 | 2 | 1 | 10 | 7 | 1 | 10 |
| Scentless chamomile | 0 | 7 | 1 | 6 | 8 | 8 | 6 | 9 | 2 | 7 | 4 | 9 | 9 | 9 | 9 | 10 | 7 | 10 | 10 | 10 | 10 | 10 | 10 | 10 | 10 | 10 | 9 | 10 | 9 | 0 | 3 | 0 | 1 | 7 | 7 | 4 |
| Sugar beet | 0 | 10 | 10 | 10 | 10 | 10 | 10 | 10 | 9 | 10 | 10 | 10 | 10 | 10 | 10 | 10 | 10 | 10 | 10 | 10 | 10 | 10 | 10 | 10 | 10 | 10 | 10 | 10 | 10 | 0 | 10 | 8 | 10 | 10 | 9 | 10 |
| Wheat (Spring) | 0 | — | 0 | 1 | 1 | 1 | 3 | 1 | 0 | 1 | 0 | 2 | 1 | 0 | 1 | 2 | 2 | 2 | 5 | 8 | 3 | 2 | 5 | 2 | 7 | 1 | 1 | 5 | 1 | 0 | 0 | 0 | 0 | 0 | 0 | 2 |
| Wheat (Winter) | 0 | 0 | 0 | 1 | 0 | 0 | 1 | 0 | 0 | 1 | 0 | 3 | 1 | 0 | 2 | 1 | 2 | 2 | 3 | 9 | 3 | 2 | 4 | 2 | 6 | 0 | 1 | 4 | 0 | 0 | 0 | 0 | 0 | 0 | 0 | 1 |
| Wild buckwheat | 0 | 7 | 8 | 10 | 10 | 1 | 10 | 10 | 9 | 10 | 10 | 10 | 9 | 8 | 2 | 10 | 10 | 3 | 10 | 10 | 10 | 10 | 10 | 10 | 10 | 10 | 5 | 10 | 10 | 0 | 7 | 2 | 6 | 10 | 0 | 10 |
| Wild oat | 0 | 2 | 0 | 2 | 4 | 2 | 8 | 4 | 0 | 6 | 3 | 10 | 9 | 7 | 4 | 8 | 8 | 3 | 9 | 10 | 9 | 5 | 6 | 6 | 7 | 8 | 7 | 9 | 7 | 0 | 0 | 0 | 1 | 3 | 1 | 8 |

| | COMPOUND (250 g/ha) | | | | | | | | | | | | | | | | | | | | | | | | COMPOUND (125 g/ha) | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| | 25 | 28 | 32 | 33 | 36 | 37 | 40 | 44 | 45 | 46 | 48 | 49 | 50 | 53 | 55 | 56 | 57 | 71 | 73 | 74 | 76 | 82 | 84 | 100 | 4 | 5 | 9 | 13 | 15 | 20 | 23 | 25 | 28 | 32 | 33 | 36 |
| Barley (Spring) | 1 | 0 | 0 | 0 | 1 | 1 | 1 | 0 | 1 | 1 | 1 | 0 | 3 | 2 | 1 | 0 | 4 | 2 | 4 | 3 | 1 | 0 | 3 | 1 | 0 | 0 | 0 | 0 | 0 | 0 | 0 | 0 | 0 | 0 | 0 | 0 |

TABLE D-continued

| | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| Barley (Winter) | 0 | 0 | 0 | 0 | 1 | 1 | 0 | 0 | 0 | 1 | 0 | 0 | 2 | 4 | 1 | 1 | 4 | 2 | 5 | 4 | 1 | 0 | 2 | 0 | 0 | 0 | 0 | 0 | 0 | 0 | 0 | 0 | 0 | 0 | 0 | 0 |
| Black nightshade | 10 | 4 | 10 | 8 | 9 | 8 | 10 | 9 | 2 | 5 | 7 | 4 | 10 | 10 | 10 | 10 | 10 | 8 | 10 | 10 | 8 | 4 | 10 | 10 | 0 | 2 | 0 | 4 | 7 | 9 | 9 | 4 | 0 | 10 | 3 | 9 |
| Blackgrass | 7 | 2 | 5 | 6 | 10 | 10 | 9 | 8 | 4 | 8 | 8 | 6 | 10 | 10 | 10 | 8 | 10 | 10 | 10 | 9 | 7 | 10 | 10 | 7 | 0 | 1 | 0 | 6 | 8 | 3 | 9 | 3 | 0 | 5 | 5 | 10 |
| Bluegrass | 10 | 3 | 10 | 9 | 10 | 10 | 9 | 9 | 2 | 10 | 8 | 3 | 10 | 10 | 10 | 3 | 10 | 10 | 10 | 10 | 10 | 8 | 9 | 7 | 0 | 0 | 0 | 9 | 6 | 6 | 9 | 8 | 10 | 10 | 8 | 10 |
| Catchweed bedstraw | 1 | 0 | 7 | 1 | 9 | 2 | 2 | 3 | 0 | 4 | 8 | 0 | 2 | 10 | 5 | 2 | 10 | 9 | 10 | 7 | 7 | 1 | 10 | 10 | 0 | 0 | 0 | 0 | 0 | 0 | 4 | 0 | 0 | 3 | 0 | 9 |
| Cheatgrass | 1 | 0 | 1 | 0 | 7 | 7 | 2 | 1 | 0 | 2 | 2 | 0 | 6 | 8 | 5 | 2 | 7 | 7 | 10 | 5 | 0 | 1 | 6 | 1 | 0 | 0 | 0 | 0 | 1 | 0 | 1 | 0 | 0 | 0 | 0 | 3 |
| Downy brome | 1 | 0 | 0 | 0 | 4 | 2 | 1 | 1 | 0 | 1 | 1 | 0 | 3 | 9 | 3 | 2 | 6 | 3 | 7 | 5 | 3 | 0 | 3 | 1 | 0 | 0 | 0 | 0 | 0 | 0 | 1 | 0 | 0 | 0 | 0 | 1 |
| Field pennycress | 10 | 7 | 10 | 10 | 10 | 10 | 10 | 10 | 10 | 10 | 9 | 10 | 10 | 10 | 10 | 10 | 10 | 10 | 10 | 10 | 9 | 10 | 10 | 10 | 0 | 9 | 10 | 7 | 10 | 10 | 10 | 9 | 5 | 9 | 10 | 10 |
| Field violet | 9 | 9 | 9 | 10 | 10 | 9 | 10 | 10 | 10 | 10 | 9 | 10 | 10 | 10 | 10 | 10 | 10 | 10 | 10 | 10 | 10 | 10 | 10 | 10 | 0 | 10 | 4 | 8 | 10 | 9 | 10 | 8 | 6 | 9 | 10 | 10 |
| Green foxtail | 10 | 10 | 10 | 10 | 10 | 10 | 10 | 10 | 10 | 10 | 10 | 9 | 10 | 10 | 10 | 10 | 10 | 10 | 10 | 10 | 10 | 10 | 10 | 10 | 0 | 0 | 3 | 10 | 10 | 9 | 10 | 9 | 10 | 10 | 10 | 10 |
| Italian ryegrass | 2 | 0 | 2 | 1 | 9 | 9 | 4 | 6 | 1 | 8 | 6 | 1 | 80 | 10 | 10 | 3 | 9 | 8 | 9 | 9 | 7 | 2 | 8 | 5 | 0 | 0 | 0 | 1 | 3 | 2 | 3 | 2 | 0 | 1 | 0 | 9 |
| Ivyleaf speedwell | 9 | 3 | 9 | 9 | 10 | 9 | 8 | 10 | 3 | 10 | 10 | 3 | 10 | 10 | 10 | 10 | 10 | 10 | 10 | 10 | 10 | 5 | 10 | 10 | 0 | 0 | 0 | 2 | 4 | 3 | 10 | 8 | 0 | 9 | 8 | 10 |
| Jointed goatgrass | 0 | 0 | 1 | 0 | 1 | 1 | 0 | 0 | 0 | 0 | 1 | 1 | 1 | 4 | 4 | 0 | 3 | 1 | 1 | 2 | 0 | 0 | 3 | 1 | 0 | 0 | 0 | 0 | 0 | 0 | 0 | 0 | 0 | 0 | 0 | 1 |
| Kochia | 9 | 9 | 10 | 10 | 10 | 10 | 8 | 10 | 0 | 10 | 7 | 10 | 10 | 10 | 10 | 9 | 9 | 7 | 6 | 9 | 10 | 8 | 10 | 10 | 0 | 3 | 0 | 10 | 9 | 8 | 4 | 8 | 8 | 9 | 9 | 10 |
| Lambsquarters | 10 | 9 | 10 | 10 | 9 | 9 | 9 | 10 | 9 | 10 | 10 | 10 | 10 | 10 | 10 | 10 | 10 | 9 | 10 | 10 | 10 | 10 | 10 | 10 | 0 | 8 | 5 | 8 | 9 | 4 | 10 | 9 | 2 | 10 | 9 | 9 |
| Persian speedwell | 10 | 8 | 10 | 10 | 9 | 10 | 8 | 9 | 10 | 10 | 10 | 3 | 10 | 10 | 10 | 10 | 10 | 10 | 10 | 10 | 10 | 10 | 10 | 10 | 0 | 10 | 2 | 10 | 9 | 8 | 10 | 10 | 2 | 10 | 5 | 9 |
| Rape | 10 | 6 | 10 | 10 | 10 | 9 | 8 | 10 | 7 | 9 | 9 | 3 | 10 | 10 | 10 | 7 | 10 | 5 | 10 | 10 | 9 | 6 | 10 | 10 | 0 | 8 | 0 | 3 | 10 | 3 | 6 | 2 | 1 | 10 | 9 | 10 |
| Russian thistle | 7 | 0 | 8 | 4 | 8 | 5 | 5 | 5 | 5 | 4 | 3 | 0 | 4 | 8 | 8 | 2 | 3 | 1 | 3 | 9 | 10 | 1 | 10 | 10 | 0 | 0 | 0 | 7 | 3 | 0 | 9 | 6 | 0 | 7 | 3 | 4 |
| Scentless chamomile | 6 | 2 | 6 | 2 | 8 | 8 | 8 | 7 | 9 | 10 | 7 | 10 | 10 | 10 | 10 | 10 | 8 | 10 | 10 | 10 | 10 | 9 | 10 | 7 | 0 | 0 | 0 | 0 | 0 | 7 | 1 | 1 | 0 | 6 | 1 | 8 |
| Sugar beet | 10 | 7 | 10 | 10 | 10 | 10 | 10 | 10 | 10 | 9 | 10 | 10 | 10 | 10 | 10 | 10 | 10 | 10 | 10 | 10 | 10 | 9 | 10 | 10 | 0 | 10 | 5 | 6 | 10 | 9 | 10 | 6 | 5 | 10 | 9 | 10 |
| Wheat (Spring) | 0 | 0 | 1 | 0 | 1 | 1 | 0 | 1 | 0 | 1 | 0 | 0 | 5 | 5 | 1 | 0 | 4 | 2 | 6 | 3 | 0 | 0 | 4 | 0 | 0 | 0 | 0 | 0 | 0 | 0 | 0 | 0 | 0 | 0 | 0 | 0 |
| Wheat (Winter) | 0 | 0 | 0 | 0 | 1 | 0 | 0 | 0 | 0 | 0 | 1 | 0 | 3 | 8 | 2 | 1 | 4 | 0 | 6 | 4 | 0 | 0 | 2 | 0 | 0 | 0 | 0 | 0 | 0 | 0 | 0 | 0 | 0 | 0 | 0 | 0 |
| Wild buckwheat | 9 | 9 | 10 | 10 | 10 | 9 | 7 | 2 | 1 | 4 | 9 | 0 | 9 | 10 | 9 | 10 | 10 | 10 | 7 | 10 | 7 | 2 | 10 | 10 | 0 | 2 | 1 | 1 | 8 | 0 | 9 | 9 | 5 | 9 | 9 | 4 |
| Wild oat | 2 | 0 | 2 | 1 | 9 | 8 | 3 | 2 | 1 | 6 | 5 | 1 | 8 | 10 | 6 | 2 | 6 | 6 | 7 | 3 | 4 | 4 | 8 | 5 | 0 | 0 | 0 | 0 | 2 | 1 | 2 | 1 | 0 | 1 | 0 | 8 |

| | COMPOUND (125 g/ha) | | | | | | | | | | | | | | | | | | | COMPOUND (64 g/ha) | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| | 37 | 40 | 44 | 45 | 46 | 48 | 49 | 50 | 53 | 55 | 56 | 57 | 71 | 73 | 74 | 76 | 82 | 84 | 100 | 4 | 5 | 9 | 13 | 15 | 20 | 23 | 32 | 33 | 36 | 37 | 40 | 44 | 45 | 46 | 48 | 49 |
| Barley (Spring) | 0 | 0 | 0 | 0 | 1 | 0 | 0 | 1 | 2 | 0 | 0 | 2 | 1 | 3 | 1 | 1 | 0 | 1 | 0 | 0 | 0 | 0 | 0 | 0 | 0 | 0 | 0 | 0 | 0 | 0 | 0 | 0 | 0 | 0 | 0 | 0 |
| Barley (Winter) | 0 | 0 | 0 | 0 | 1 | 0 | 0 | 0 | 2 | 0 | 0 | 1 | 1 | 3 | 1 | 0 | 0 | 1 | 0 | 0 | 0 | 0 | 0 | 0 | 0 | 0 | 0 | 0 | 0 | 0 | 0 | 0 | 0 | 0 | 0 | 0 |
| Black nightshade | 4 | 8 | 9 | 0 | — | 7 | 3 | 7 | 10 | 9 | 9 | 5 | 7 | 10 | 10 | 5 | 1 | 10 | 7 | 0 | 0 | 0 | 0 | 5 | 6 | 7 | 2 | 2 | 1 | 2 | 6 | 7 | 0 | 1 | — | 0 |
| Blackgrass | 9 | 2 | 8 | 2 | 6 | 7 | 2 | 10 | 10 | 10 | 5 | 9 | 8 | 7 | 9 | 7 | 9 | 10 | 7 | 0 | 0 | 0 | 5 | 6 | 1 | 5 | 1 | 0 | 8 | 8 | 0 | 4 | 0 | 2 | 3 | 0 |
| Bluegrass | 9 | 9 | 9 | 0 | 7 | 4 | 2 | 9 | 10 | 10 | 1 | 10 | 9 | 9 | 8 | 7 | 3 | 8 | 2 | 0 | 0 | 0 | 8 | 2 | 4 | 2 | 7 | 5 | 9 | 8 | 7 | 6 | 0 | 3 | 1 | 0 |
| Catchweed bedstraw | 1 | 2 | 1 | 0 | 0 | 4 | 0 | 0 | 7 | 3 | 0 | 10 | 9 | 10 | 7 | 6 | 0 | 3 | 6 | 0 | 0 | 0 | 0 | 0 | 0 | 0 | 1 | 0 | 7 | 0 | 1 | 1 | 0 | 0 | 1 | 0 |
| Cheatgrass | 3 | 1 | 0 | 0 | 1 | 0 | 0 | 5 | 7 | 2 | 0 | 7 | 6 | 5 | 4 | 0 | 0 | 5 | 0 | 0 | 0 | 0 | 0 | 0 | 0 | 1 | 0 | 0 | 0 | 2 | 0 | 0 | 0 | 0 | 0 | 0 |
| Downy brome | 1 | 0 | 0 | 0 | 0 | 1 | 0 | 2 | 6 | 2 | 1 | 6 | 2 | 4 | 1 | 1 | 0 | 2 | 0 | 0 | 0 | 0 | 0 | 0 | 0 | 1 | 0 | 0 | 0 | 0 | 0 | 0 | 0 | 0 | 0 | 0 |
| Field pennycress | 10 | 10 | 10 | 10 | 9 | 8 | 10 | 10 | 10 | 10 | 10 | 9 | 10 | 10 | 10 | 9 | 10 | 10 | 10 | 0 | 7 | 10 | 6 | 10 | 7 | 10 | 9 | 8 | 10 | 10 | 10 | 10 | 10 | 7 | 8 | 10 |
| Field violet | 9 | 10 | 9 | 10 | 10 | 9 | 9 | 10 | 10 | 7 | 10 | 10 | 10 | 10 | 10 | 9 | 10 | 10 | 9 | 0 | 2 | 2 | 3 | 10 | 3 | 10 | 7 | 7 | 8 | 9 | 7 | 8 | 3 | 10 | 8 | 3 |
| Green foxtail | 10 | 10 | 10 | 8 | 9 | 10 | 5 | 10 | 10 | 10 | 8 | 10 | 10 | 10 | 10 | 8 | 10 | 10 | 8 | 0 | 0 | 1 | 10 | 10 | 8 | 10 | 8 | 10 | 10 | 10 | 10 | 10 | 2 | 8 | 10 | 2 |
| Italian ryegrass | 7 | 4 | 6 | 0 | 3 | 3 | 0 | 5 | 9 | 9 | 1 | 8 | 7 | 7 | 7 | 3 | 1 | 6 | 4 | 0 | 0 | 0 | 0 | 1 | 0 | 2 | 0 | 0 | 5 | 4 | 1 | 1 | 0 | 1 | 1 | 0 |
| Ivyleaf speedwell | 9 | 8 | 10 | 1 | 3 | 8 | 0 | 10 | 10 | 10 | 3 | 9 | 10 | 10 | 10 | 10 | 1 | 10 | 10 | 0 | 0 | 0 | 0 | 2 | 1 | 9 | 8 | 6 | 10 | 7 | 7 | 4 | 0 | 1 | 7 | 0 |
| Jointed goatgrass | 0 | 0 | 0 | 0 | 0 | 0 | 0 | 0 | 1 | 1 | 0 | 0 | 0 | 0 | 0 | 0 | 0 | 1 | 1 | 0 | 0 | 0 | 0 | 0 | 0 | 0 | 0 | 0 | 0 | 0 | 0 | 0 | 0 | 0 | 0 | 0 |
| Kochia | 10 | 8 | 10 | 0 | 8 | 5 | 9 | 9 | 10 | 10 | 8 | 7 | 6 | 3 | 9 | 6 | 3 | 9 | 9 | 0 | 0 | 0 | 7 | 7 | 7 | 1 | 7 | 9 | 8 | 10 | 5 | 10 | 0 | 4 | 4 | 6 |
| Lambsquarters | 5 | 8 | 9 | 9 | 8 | 10 | 10 | 8 | 10 | 10 | 10 | 10 | 7 | 10 | 10 | 7 | 7 | 10 | 9 | 0 | 3 | 2 | 6 | 8 | 3 | 9 | 9 | 7 | 2 | 2 | 1 | 8 | 6 | 2 | 5 | 8 |
| Persian speedwell | 7 | 8 | 8 | 10 | 10 | 10 | 1 | 10 | 10 | 10 | 9 | 10 | 10 | 10 | 10 | 10 | 10 | 10 | 10 | 0 | 2 | 0 | 10 | 8 | 3 | 10 | 9 | 2 | 8 | 7 | 7 | 2 | 7 | 10 | 7 | 0 |
| Rape | 9 | 8 | 9 | 1 | 3 | 5 | 1 | 8 | 10 | 9 | 5 | 10 | 5 | 7 | 10 | 7 | 6 | 7 | 10 | 0 | 8 | 0 | 1 | 7 | 0 | 6 | 7 | 5 | 9 | 8 | 3 | 1 | 0 | 1 | 3 | 0 |
| Russian thistle | 3 | 2 | 2 | 4 | 2 | 1 | 0 | 3 | 8 | 6 | 2 | 2 | 0 | 1 | 6 | 6 | 1 | 9 | 7 | 0 | 0 | 0 | 2 | 1 | 0 | 2 | 4 | 1 | 2 | 1 | 1 | 1 | 0 | 0 | 0 | 0 |
| Scentless chamomile | 2 | 6 | 3 | 2 | 10 | 3 | 9 | 10 | 10 | 10 | 7 | 6 | 10 | 9 | 10 | 7 | 8 | 10 | 4 | 0 | 0 | 0 | 0 | 0 | 4 | 0 | 3 | 0 | 2 | 1 | 1 | 2 | 0 | 3 | 3 | 0 |
| Sugar beet | 10 | 9 | 8 | 1 | 9 | 10 | 9 | 10 | 10 | 10 | 10 | 10 | 10 | 10 | 10 | 10 | 6 | 10 | 10 | 0 | 10 | 2 | 6 | 10 | 8 | 10 | 9 | 8 | 9 | 4 | 8 | 7 | 1 | 8 | 8 | 7 |
| Wheat (Spring) | 0 | 0 | 0 | 0 | 0 | 0 | 0 | 2 | 5 | 0 | 0 | 2 | 0 | 2 | 3 | 0 | 0 | 2 | 0 | 0 | 0 | 0 | 0 | 0 | 0 | 0 | 0 | 0 | 0 | 0 | 0 | 0 | 0 | 0 | 0 | 0 |
| Wheat (Winter) | 0 | 0 | 0 | 0 | 0 | 0 | 0 | 1 | 5 | 0 | 0 | 1 | 0 | 4 | 2 | 0 | 0 | 1 | 0 | 0 | 0 | 0 | 0 | 0 | 0 | 0 | 0 | 0 | 0 | 0 | 0 | 0 | 0 | 0 | 0 | 0 |
| Wild buckwheat | 6 | 3 | 1 | 0 | 1 | 2 | 0 | 3 | 10 | 3 | 5 | 10 | 8 | 7 | 9 | 6 | 1 | 10 | 8 | 0 | 0 | 0 | 0 | 7 | 0 | 5 | 2 | 3 | 2 | 6 | 0 | 0 | 0 | 1 | 0 | 0 |
| Wild oat | 7 | 2 | 2 | 0 | 2 | 3 | 0 | 4 | 9 | 5 | 1 | 6 | 5 | 5 | 2 | 2 | 1 | 8 | 5 | 0 | 0 | 0 | 0 | 1 | 0 | 1 | 0 | 0 | 5 | 2 | 1 | 1 | 0 | 0 | 1 | 0 |

TABLE D-continued

| | COMPOUND (64 g/ha) | | | | | | | | | | | | COMPOUND (32 g/ha) | | | | | | | | | | | | |
|---|---|---|---|---|---|---|---|---|---|---|---|---|---|---|---|---|---|---|---|---|---|---|---|---|---|
| | 50 | 53 | 55 | 56 | 57 | 71 | 73 | 74 | 76 | 82 | 84 | 100 | 5 | 13 | 23 | 46 | 48 | 56 | 57 | 71 | 73 | 74 | 76 | 82 | 100 |
| Barley (Spring) | 0 | 0 | 0 | 0 | 2 | 0 | 1 | 1 | 0 | 0 | 0 | 0 | 0 | 0 | 0 | 0 | 0 | 0 | 0 | 0 | 0 | 0 | 0 | 0 | 0 |
| Barley (Winter) | 0 | 0 | 0 | 0 | 0 | 0 | 1 | 1 | 0 | 0 | 0 | 0 | 0 | 0 | 0 | 0 | 0 | 0 | 0 | 0 | 0 | 0 | 0 | 0 | 0 |
| Black nightshade | 3 | 5 | 5 | 7 | 2 | 6 | 7 | 10 | 4 | 0 | 10 | 5 | 0 | 0 | 5 | 0 | 0 | 2 | 2 | 2 | 2 | 4 | 1 | 0 | 1 |
| Blackgrass | 8 | 9 | 8 | 1 | 5 | 5 | 7 | 7 | 4 | 4 | 7 | 6 | 0 | 4 | 1 | 0 | 1 | 0 | 2 | 3 | 1 | 4 | 2 | 0 | 4 |
| Bluegrass | 4 | 10 | 5 | 0 | 7 | 9 | 5 | 4 | 5 | 1 | 7 | 1 | 0 | 8 | 0 | 1 | 0 | 0 | 3 | 2 | 2 | 1 | 2 | 0 | 0 |
| Catchweed bedstraw | 0 | 2 | 0 | 0 | 8 | 1 | 10 | 4 | 2 | 0 | 0 | 1 | 0 | 0 | 0 | 0 | 0 | 0 | 7 | 0 | 7 | 1 | 0 | 0 | 0 |
| Cheatgrass | 1 | 3 | 1 | 0 | 3 | 2 | 2 | 2 | 0 | 0 | 2 | 0 | 0 | 0 | 0 | 0 | 0 | 0 | 1 | 0 | 1 | 0 | 0 | 0 | 0 |
| Downy brome | 0 | 2 | 0 | 0 | 1 | 0 | 3 | 0 | 0 | 0 | 0 | 0 | 0 | 0 | 0 | 0 | 0 | 0 | 0 | 0 | 0 | 0 | 0 | 0 | 0 |
| Field pennycress | 10 | 10 | 10 | 7 | 7 | 9 | 10 | 10 | 9 | 8 | 9 | 10 | 3 | 6 | 7 | 2 | 2 | 5 | 7 | 4 | 10 | 10 | 8 | 5 | 9 |
| Field violet | 5 | 10 | 7 | 10 | 10 | 10 | 8 | 9 | 9 | 10 | 10 | 9 | 1 | 0 | 9 | 0 | 8 | 7 | 8 | 8 | 7 | 4 | 8 | 3 | 8 |
| Green foxtail | 5 | 10 | 10 | 6 | 10 | 10 | 10 | 9 | 8 | 9 | 10 | 6 | 0 | 5 | 2 | 8 | 8 | 2 | 9 | 7 | 7 | 7 | 5 | 2 | 4 |
| Italian ryegrass | 3 | 6 | 6 | 0 | 5 | 2 | 6 | 5 | 1 | 0 | 4 | 2 | 0 | 0 | 0 | 0 | 0 | 0 | 2 | 0 | 1 | 1 | 0 | 0 | 0 |
| Ivyleaf speedwell | 2 | 10 | 9 | 3 | 9 | 4 | 10 | 10 | 8 | 0 | 10 | 10 | 0 | 0 | 7 | 0 | 3 | 0 | 3 | 2 | 4 | 8 | 3 | 0 | 9 |
| Jointed goatgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Kochia | 7 | 10 | 9 | 3 | 5 | 2 | 3 | 7 | 4 | 0 | 7 | 7 | 0 | 6 | 0 | 0 | 0 | 0 | 2 | 0 | 1 | 5 | 1 | 0 | 3 |
| Lambsquarters | 8 | 9 | 9 | 9 | 9 | 7 | 10 | 10 | 7 | 2 | 10 | 8 | 0 | 0 | 7 | 0 | 2 | 6 | 6 | 2 | 9 | 9 | 4 | 0 | 4 |
| Persian speedwell | 9 | 10 | 10 | 9 | 10 | 7 | 10 | 10 | 10 | 10 | 10 | 9 | 0 | 0 | 8 | 3 | 2 | 7 | 8 | 7 | 8 | 10 | 6 | 0 | 8 |
| Rape | 4 | 9 | 9 | 3 | 5 | 3 | 4 | 10 | 7 | 3 | 6 | 8 | 3 | 0 | 2 | 0 | 0 | 1 | 2 | 0 | 1 | 2 | 5 | 0 | 6 |
| Russian thistle | 1 | 5 | 2 | 1 | 2 | 0 | 0 | 4 | 4 | 0 | 5 | 3 | 0 | 0 | 0 | 0 | 0 | 0 | 0 | 0 | 0 | 2 | 1 | 0 | 0 |
| Scentless chamomile | 10 | 4 | 3 | 3 | 6 | 5 | 7 | 10 | 4 | 5 | 7 | 4 | 0 | 0 | 0 | 1 | 0 | 1 | 2 | 2 | 2 | 7 | 1 | 2 | 0 |
| Sugar beet | 9 | 10 | 10 | 9 | 9 | 9 | 10 | 10 | 10 | 5 | 10 | 8 | 6 | 6 | 10 | 6 | 3 | 6 | 8 | 6 | 7 | 10 | 7 | 3 | 4 |
| Wheat (Spring) | 0 | 3 | 0 | 0 | 1 | 0 | 2 | 1 | 0 | 0 | 0 | 0 | 0 | 0 | 0 | 0 | 0 | 0 | 0 | 0 | 0 | 0 | 0 | 0 | 0 |
| Wheat (Winter) | 0 | 2 | 0 | 0 | 0 | 0 | 3 | 1 | 0 | 0 | 0 | 0 | 0 | 0 | 0 | 0 | 0 | 0 | 0 | 0 | 1 | 0 | 0 | 0 | 0 |
| Wild buckwheat | 0 | 8 | 2 | 2 | 7 | 3 | 2 | 9 | 4 | 0 | 8 | 7 | 0 | 0 | 2 | 0 | 0 | 0 | 1 | 0 | 0 | 3 | 2 | 0 | 2 |
| Wild oat | 2 | 7 | 2 | 0 | 5 | 4 | 2 | 2 | 1 | 0 | 5 | 1 | 0 | 0 | 0 | 0 | 0 | 0 | 2 | 2 | 1 | 0 | 0 | 0 | 0 |

TEST E

Seeds selected from barnyardgrass (*Echinochloa crus-galli*), bermudagrass (*Cynodon dactylon*), cocklebur (*Xanthium pensylvanicum*), cotton (*Gossypium hirsutum*), fall panicum (*Panicum dichotomiflorum*), goosegrass (*Eleusine indica*), ground cherry (*Physalis heterophylla*), johnsongrass (*Sorghum halepense*), lambsquarters (*Chenopodium album*), large crabgrass (*Digitaria sanguinalis*), morningglory (*Ipomoea hederacea*), purslane (*Portulaca oleracea*), redroot pigweed (*Amaranthus retroflexus*), sicklepod (*Cassia obtusifolia*), signalgrass (Brachiaria platyphylla), smartweed (*Polygonum pericaria*), teaweed (*Sida spinosa*), and velvetleaf (*Abutilon theophrasti*) and purple nutsedge (*Cyperus rotundus*) tubers were planted and treated preemergence with test chemicals dissolved in a non-phytotoxic solvent. Treated plants and controls were maintained in a greenhouse for approximately 21 days, after which all species were compared to controls and visually elevated. Response ratings, summarized in Table E, are based on a scale of 0 to 100 where 0 is no effect and 100 is complete control. A dash (-) response means no test result.

TABLE E

PREEMERGENCE

| | Cmpd 13 | | | | | | Cmpd 15 | | | | | | Cmpd 23 | | | | |
|---|---|---|---|---|---|---|---|---|---|---|---|---|---|---|---|---|---|
| RATE (g/ha) | 1000 | 500 | 250 | 125 | 64 | 32 | 1000 | 500 | 250 | 125 | 64 | 32 | 1000 | 500 | 250 | 125 | 64 |
| Barnyardgrass | 100 | 100 | 98 | 40 | 20 | 10 | 100 | 100 | 60 | 90 | 20 | 10 | 100 | 100 | 100 | 70 | 30 |
| Bermudagrass | 100 | 100 | 0 | 0 | 0 | 0 | 90 | 40 | 30 | 20 | 0 | 0 | 100 | 100 | 100 | 60 | 20 |
| Cocklebur | 40 | 0 | 0 | 0 | 0 | 0 | 0 | 0 | 0 | 0 | 0 | 0 | 0 | 0 | 0 | 0 | 0 |
| Cotton | 5 | 0 | 0 | 0 | 0 | 0 | 10 | 0 | 0 | 0 | 0 | 0 | 10 | 0 | 0 | 0 | 0 |
| Fall Panicum | — | — | — | — | — | — | — | — | — | — | — | — | 100 | 100 | 100 | 100 | 100 |
| Goosegrass | 100 | 98 | 70 | 60 | 50 | 30 | 100 | 100 | 100 | 98 | 70 | 50 | 100 | 100 | 100 | 80 | 40 |
| Ground cherry | 100 | 100 | 40 | 20 | 0 | 0 | 100 | 98 | 50 | 40 | 20 | 10 | 100 | 100 | 60 | 30 | 20 |
| Johnsongrass | 100 | 60 | 30 | 0 | 0 | 0 | 100 | 100 | 50 | 0 | 0 | 0 | 80 | 60 | 30 | 20 | 0 |
| Lambsquarters | 100 | 100 | 100 | 90 | 70 | 0 | 100 | 100 | 100 | 100 | 90 | 0 | — | — | — | — | — |
| Large crabgrass | 100 | 100 | 100 | 95 | 70 | 60 | 100 | 100 | 100 | 100 | 70 | 30 | 100 | 100 | 100 | 100 | 90 |
| Morningglory | 100 | 100 | 70 | 20 | 0 | 0 | 100 | 100 | 40 | 20 | 0 | 0 | 100 | 90 | 100 | 20 | 0 |
| Nutsedge | 100 | 50 | 50 | 20 | 0 | 0 | 90 | 50 | 50 | 0 | — | — | 30 | 40 | 30 | 20 | 10 |
| Purslane | 100 | 100 | 100 | 100 | 90 | 0 | 100 | 100 | 100 | 100 | 100 | 20 | 100 | 100 | 100 | 100 | 100 |
| Redroot pigweed | 100 | 100 | 100 | 100 | 100 | 100 | 100 | 100 | 100 | 100 | 100 | 95 | 100 | 100 | 100 | 100 | 100 |
| Sicklepod | 60 | 20 | 0 | 0 | 0 | 0 | 100 | 70 | 0 | 0 | 0 | 0 | 100 | 100 | 80 | 30 | 0 |
| Signalgrass | — | — | — | — | — | — | — | — | — | — | — | — | 100 | 100 | 100 | 90 | 20 |
| Smartweed | 100 | 20 | 10 | 0 | 0 | 0 | 100 | 30 | 0 | 0 | 0 | 0 | 100 | 50 | 0 | 0 | 0 |
| Teaweed | 100 | 100 | 50 | 0 | 0 | 0 | 100 | 100 | 30 | 0 | 0 | 0 | 100 | 100 | 100 | 60 | 0 |
| Velvetleaf | 100 | 100 | 50 | 0 | 0 | 0 | 100 | 100 | 60 | 10 | 0 | 0 | 100 | 100 | 98 | 98 | 30 |

| | Cmpd 25 | | | | | Cmpd 32 | | | | |
|---|---|---|---|---|---|---|---|---|---|---|
| RATE (g/ha) | 1000 | 500 | 250 | 125 | 64 | 1000 | 500 | 250 | 125 | 64 |
| Barnyardgrass | 100 | 100 | 100 | 20 | 10 | 100 | 100 | 100 | 100 | 0 |
| Bermudagrass | 100 | 100 | 60 | 20 | 20 | 100 | 100 | 95 | 95 | 20 |
| Cocklebur | 0 | 0 | 0 | 0 | 0 | 0 | 0 | 0 | 0 | 0 |
| Cotton | 5 | 5 | 0 | 0 | 0 | 0 | 0 | 0 | 0 | 0 |
| Fall Panicum | 100 | 100 | 100 | 100 | 30 | — | — | — | — | — |
| Goosegrass | 100 | 100 | 100 | 80 | 50 | 100 | 100 | 100 | 100 | 50 |
| Ground cherry | 95 | 70 | 20 | 10 | 0 | 100 | 100 | 60 | 50 | 0 |
| Johnsongrass | 70 | 30 | 20 | 0 | 0 | 30 | 30 | 30 | 20 | 0 |
| Lambsquarters | — | — | — | — | — | — | — | — | — | — |
| Large crabgrass | 100 | 100 | 100 | 95 | 85 | 100 | 100 | 100 | 100 | 50 |
| Morningglory | 100 | 95 | 30 | 30 | 0 | 100 | 70 | 60 | 0 | 0 |
| Nutsedge | 30 | 10 | 0 | 0 | 0 | 10 | 10 | 0 | 0 | 0 |
| Purslane | 100 | 100 | 100 | 100 | 90 | — | — | — | — | — |
| Redroot pigweed | 100 | 100 | 100 | 100 | 100 | 100 | 100 | 100 | 100 | 70 |
| Sicklepod | 100 | 70 | 20 | 10 | 0 | — | — | — | — | — |
| Signalgrass | 100 | 100 | 60 | 60 | 20 | 100 | 100 | 100 | 100 | 0 |
| Smartweed | 70 | 20 | 0 | 0 | 0 | 100 | 20 | 20 | 0 | 0 |
| Teaweed | 100 | 70 | 40 | 20 | 0 | 100 | 100 | 100 | 90 | 90 |
| Velvetleaf | 100 | 80 | 50 | 30 | 20 | 90 | 60 | 60 | 30 | 0 |

| | Cmpd 50 | | | | | | Cmpd 53 | | | | | |
|---|---|---|---|---|---|---|---|---|---|---|---|---|
| RATE (g/ha) | 500 | 250 | 125 | 64 | 32 | 16 | 500 | 250 | 125 | 64 | 32 | 16 |
| Barnyardgrass | 100 | 90 | 80 | 30 | 0 | 0 | 100 | 70 | 60 | 30 | 20 | 0 |
| Bermudagrass | 100 | 60 | 60 | 30 | 30 | 30 | 100 | 100 | 100 | 95 | 30 | 10 |
| Cocklebur | 0 | 0 | 0 | 0 | 0 | 0 | 50 | 0 | 0 | 0 | 0 | 0 |
| Cotton | 20 | 20 | 10 | 0 | 0 | 0 | 20 | 10 | 0 | 0 | 0 | 0 |
| Fall Panicum | 100 | 100 | 100 | 90 | 90 | 0 | 100 | 100 | 100 | 50 | 50 | 0 |
| Goosegrass | 100 | 100 | 100 | 70 | 40 | 40 | 100 | 90 | 80 | 50 | 10 | 10 |
| Ground cherry | 100 | 90 | 80 | 30 | 10 | 0 | 100 | 100 | 40 | 40 | 10 | 0 |
| Johnsongrass | 100 | 100 | 60 | 10 | 10 | 0 | 100 | 100 | 100 | 95 | 80 | 0 |
| Lambsquarters | 100 | 100 | 100 | 50 | 50 | 0 | 100 | 100 | 100 | 100 | 100 | 0 |
| Large crabgrass | 100 | 100 | 100 | 100 | 95 | 95 | 100 | 100 | 100 | 100 | 70 | 40 |
| Morningglory | 90 | 70 | 20 | 0 | 0 | 0 | 100 | 100 | 30 | 0 | 0 | 0 |
| Nutsedge | 30 | 20 | 10 | 0 | 0 | 0 | 20 | 20 | 20 | 10 | 0 | 0 |
| Purslane | — | — | — | — | — | — | — | — | — | — | — | — |
| Redroot pigweed | 100 | 100 | 100 | 100 | 20 | 0 | 100 | 100 | 100 | 100 | 100 | 30 |
| Sicklepod | 100 | 0 | 60 | 0 | 0 | 0 | 100 | 100 | 100 | 50 | — | — |
| Signalgrass | 100 | 100 | 100 | 100 | 100 | 90 | 100 | 100 | 100 | 95 | 60 | 20 |
| Smartweed | 100 | 60 | 0 | 0 | 0 | 0 | 100 | 100 | 70 | 100 | 0 | — |
| Teaweed | 80 | 100 | 70 | 50 | 50 | 50 | 100 | 100 | 100 | 100 | 0 | 0 |

TABLE E-continued

| PREEMERGENCE | | | | | | | | | | | | |
|---|---|---|---|---|---|---|---|---|---|---|---|---|
| Velvetleaf | 90 | 70 | 40 | 0 | 0 | 0 | 100 | 80 | 70 | 40 | 0 | 0 |

TEST F

Seeds of barnyardgrass (*Echinochloa crus-galli*), black nightshade (*Solanum nigrum*), cocklebur (*Xanthium pensylvanicum*), corn (*Zea mays*), fall panicum (*Panicum dichotomiflorum*), giant foxtail (*Setaria faberi*), green foxtail (*Setaria viridis*), hemp sesbania (*Sesbania exaltata*), jimsonweed (*Datura stramonium*), johnsongrass (*Sorghum halepense*), lambsquarters (*Chenopodium album*), large crabgrass. (*Digitaria sanguinalis*), morningglory (*Ipomoea hederacea*), redroot pigweed (*Amaranthus retroflexus*), sicklepod (*Cassia obtusifolia*), signalgrass (*Brachiaria platyphylla*), smartweed (*Polygonum persicaria*), soybean (*Glycine max*), teaweed (*Sida spinosa*), and velvetleaf (*Abutilon theophrasti*) and purple nutsedge (*Cyperus rotundus*) tubers were planted in a silt loam soil and treated preemergence with test chemicals dissolved in a non-phytotoxic solvent. Treated plants and controls were maintained in a greenhouse for approximately 21 days, after which all species were compared to controls and visually evaluated. Response ratings, summarized in Table F, are based on a scale of 0 to 100 where 0 is no effect and 100 is complete control. A dash (-) response means no test result.

TABLE F

PREEMERGENCE

| | Cmpd 13 | | | | | Cmpd 15 | | | | |
|---|---|---|---|---|---|---|---|---|---|---|
| RATE (g/ha) | 1000 | 500 | 250 | 125 | 64 | 1000 | 500 | 250 | 125 | 64 |
| Barnyardgrass | 100 | 70 | 20 | 0 | 0 | 100 | 95 | 70 | 0 | 0 |
| Black nightshade | 100 | 20 | 0 | 0 | 0 | 100 | 75 | 60 | 40 | 20 |
| Cocklebur | 30 | 20 | 0 | 0 | 0 | 50 | 30 | 0 | 0 | 0 |
| Corn | 40 | 15 | 10 | 0 | 0 | 45 | 45 | 0 | 0 | 0 |
| Fall panicum | — | — | — | — | — | — | — | — | — | — |
| Giant foxtail | 100 | 100 | 100 | 100 | 20 | 100 | 100 | 100 | 85 | 85 |
| Green foxtail | 100 | 100 | 100 | 70 | 30 | 100 | 100 | 100 | 95 | 80 |
| Hemp sesbania | 100 | 70 | 30 | 0 | 0 | 100 | 85 | 40 | 40 | 20 |
| Jimsonweed | 100 | 20 | 0 | 0 | 0 | 100 | 80 | 40 | 0 | 0 |
| Johnsongrass | 45 | 20 | 0 | 0 | 0 | 80 | 45 | 20 | 0 | 0 |
| Lambsquarters | 100 | 100 | 98 | 98 | 30 | 100 | 100 | 100 | 100 | 98 |
| Large crabgrass | 100 | 100 | 100 | 70 | 0 | 100 | 100 | 100 | 85 | 70 |
| Morningglory | 100 | 70 | 0 | 0 | 0 | 100 | 75 | 75 | 0 | 0 |
| Nutsedge | 75 | 50 | 0 | 0 | 0 | 80 | 80 | 80 | 0 | 0 |
| Redrood pigweed | 100 | 100 | 100 | 100 | 95 | 100 | 100 | 100 | 100 | 100 |
| Sicklepod | 30 | 0 | 0 | 0 | 0 | 20 | 0 | 0 | 0 | 0 |
| Signalgrass | 100 | 100 | 100 | 80 | 70 | 100 | 100 | 100 | 80 | 70 |
| Smartweed | 30 | 0 | 0 | 0 | 0 | 60 | 50 | 40 | 0 | 0 |
| Soybean | 90 | 30 | 10 | 0 | 0 | 65 | 65 | 0 | 0 | 0 |
| Teaweed | 30 | 0 | 0 | 0 | 0 | 30 | 0 | 0 | 0 | 0 |
| Velvetleaf | 100 | 80 | 30 | 0 | 0 | 100 | 100 | 60 | 30 | 0 |
| | Cmpd 23 | | | | | Cmpd 25 | | | | |
| RATE (g/ha) | 1000 | 500 | 250 | 125 | 64 | 1000 | 500 | 250 | 125 | 64 |
| Barnyardgrass | 100 | 100 | 80 | 60 | 40 | 100 | 100 | 70 | 40 | 0 |
| Black nightshade | 100 | 100 | 85 | 40 | 0 | 100 | 100 | 100 | 70 | 0 |
| Cocklebur | 50 | 50 | 20 | 0 | 0 | 100 | 40 | 20 | 0 | 0 |
| Corn | 75 | 60 | 40 | 20 | 0 | 50 | 30 | 0 | 0 | 0 |
| Fall panicum | — | — | — | — | — | 100 | 100 | 100 | 100 | 0 |
| Giant foxtail | 100 | 100 | 100 | 100 | 90 | 100 | 100 | 100 | 100 | 0 |
| Green foxtail | 100 | 100 | 100 | 100 | 70 | 100 | 100 | 100 | 98 | 0 |
| Hemp sesbania | 100 | 100 | 80 | 40 | 20 | 100 | 100 | 100 | 70 | 0 |
| Jimsonweed | 100 | 100 | 70 | 30 | 0 | 100 | 100 | 40 | 20 | 0 |
| Johnsongrass | 100 | 75 | 60 | 40 | 0 | 98 | 75 | 50 | 30 | 0 |
| Lambsquarters | 100 | 100 | 100 | 100 | 98 | 100 | 100 | 100 | 100 | 0 |
| Large crabgrass | 100 | 100 | 100 | 100 | 100 | 100 | 100 | 100 | 100 | 0 |
| Morningglory | 100 | 100 | 75 | 50 | 0 | 100 | 100 | 30 | 0 | 0 |
| Nutsedge | 90 | 50 | 50 | 50 | 0 | 0 | 0 | 0 | 0 | 0 |
| Redrood pigweed | 100 | 100 | 100 | 100 | 100 | 100 | 100 | 100 | 100 | 30 |
| Sicklepod | 85 | 40 | 0 | 0 | 0 | 40 | 20 | 0 | 0 | 0 |
| Signalgrass | 100 | 100 | 100 | 100 | 90 | 100 | 100 | 95 | 70 | 0 |
| Smartweed | 75 | 50 | 20 | 0 | 0 | 100 | 60 | 30 | 0 | 0 |
| Soybean | 100 | 75 | 40 | 20 | 0 | 45 | 20 | 0 | 0 | 0 |
| Teaweed | 100 | 85 | 30 | 0 | 0 | 80 | 80 | 30 | 0 | 0 |
| Velvetleaf | 100 | 100 | 100 | 70 | 50 | 100 | 98 | 50 | 40 | 0 |

TEST G

Seeds of barnyardgrass (*Echinochloa crus-galli*), cocklebur (*Xanthium pensylvanicum*), corn (*Zea mays*), crabgrass (Digitaria spp.), fall panicum (*Panicum dichotomiflorum*), giant foxtail (*Setaria faberi*), green foxtail (Setaria viridis), jimsonweed (*Datura stramonium*), johnsongrass (*Sorghum halepense*), lambsquarters (*Chenopodium album*), morningglory (*Ipomoea hederacea*), redroot pigweed (*Amaranthus retroflexus*), smartweed (*Polygonum persicaria*), sorghum (*Sorghum bicolor*), soybean (*Glycine max*), and velvetleaf (*Abutilon theophrasti*) and purple nutsedge (*Cyperus rotundus*) tubers were planted and treated preemergence with test chemicals dissolved in a non-phytotoxic solvent. Several of the test compounds were also applied postemergence to these crop and weed species. For postemergence applications, plants were from two to twenty-five cm tall.

The soil surface of an additional container of corn (Corn, Perlite) to be treated postemergence was covered with the absorbent, perlite, before postemergence treatments were applied. After application of test compounds, the perlite was removed from the soil surface to remove chemical sorbed onto the perlite. This procedure would therefore allow only that portion of chemical sorbed onto the plant foliage to cause corn injury response.

Treated plants and controls were maintained in a greenhouse for approximately 24 days, after which all species were compared to controls and visually evaluated. Test rates for each compound are listed in Table G. The ratings, summarized in Table G, are based on a scale of 0 to 100 where 0 is no effect and 100 is complete control. A dash (-) response means no test result.

TABLE G

POSTEMERGENCE

| | Cmpd 5 | | | | | Cmpd 13 | | | | Cmpd 15 | | | | | | |
|---|---|---|---|---|---|---|---|---|---|---|---|---|---|---|---|---|
| RATE (g/ha) | 1000 | 500 | 250 | 125 | 64 | 500 | 250 | 125 | 64 | 1000 | 500 | 250 | 125 | 64 | 32 | 16 |
| Barnyardgrass | 70 | 35 | 20 | 0 | 0 | 20 | 0 | 0 | | | 65 | 50 | 45 | 40 | 30 | 25 |
| Cocklebur | 35 | 25 | 0 | 0 | 0 | 45 | 25 | 0 | | | 45 | 40 | 30 | 25 | 0 | 0 |
| Corn | 40 | 20 | 0 | 0 | 0 | 0 | 0 | 0 | | | 40 | 0 | 0 | 0 | 0 | 0 |
| Corn (Perlite) | 25 | 0 | 0 | 0 | 0 | 0 | 0 | 0 | | | 30 | 0 | 0 | 0 | 0 | 0 |
| Crabgrass | 80 | 50 | 35 | 0 | 0 | 0 | 0 | 0 | | | 70 | 55 | 45 | 40 | 30 | 20 |
| Fall panicum | 45 | 20 | 0 | 0 | 0 | 0 | 0 | 0 | | | 60 | 45 | 40 | 35 | 25 | 0 |
| Giant foxtail | 35 | 0 | 0 | 0 | 0 | 25 | 0 | 0 | | | 60 | 45 | 40 | 30 | 25 | 20 |
| Green foxtail | 60 | 25 | 0 | 0 | 0 | 35 | 0 | 0 | | | — | — | — | — | — | — |
| Jimsonweed | 100 | 95 | 85 | 45 | 0 | — | 25 | 0 | | | 85 | 75 | 50 | 45 | 40 | 25 |
| Johnsongrass | 40 | 25 | 0 | 0 | 0 | 20 | 0 | 0 | | | 65 | 55 | 50 | 45 | 40 | 30 |
| Lambsquarters | — | — | — | — | — | — | — | — | | | 95 | 80 | 65 | 55 | 45 | 30 |
| Morningglory | 65 | 40 | 35 | 20 | 0 | 45 | 20 | 0 | | | 60 | 50 | 40 | 35 | 25 | 0 |
| Nutsedge | 0 | 0 | 0 | 0 | 0 | 0 | 0 | 0 | | | 20 | 0 | 0 | 0 | 0 | 0 |
| Redroot pigweed | 100 | 100 | 95 | 75 | 35 | — | 50 | 0 | | | 95 | 80 | 55 | 40 | 40 | 25 |
| Smartweed | 40 | 25 | 0 | 0 | 0 | — | — | — | | | 65 | 50 | 35 | 30 | 20 | 0 |
| Sorghum | 45 | 20 | 0 | 0 | 0 | 20 | 0 | 0 | | | 65 | 55 | 50 | 45 | 35 | 25 |
| Soybean | 85 | 65 | 40 | 20 | 0 | 50 | 35 | 0 | | | 60 | 40 | 35 | 30 | 20 | 0 |
| Velvetleaf | 55 | 25 | 20 | 0 | 0 | 50 | 35 | 0 | | | 60 | 50 | 40 | 30 | 20 | 0 |

PREEMERGENCE

| | Cmpd 5 | | | | | Cmpd 13 | | | | Cmpd 15 | | | | | | |
|---|---|---|---|---|---|---|---|---|---|---|---|---|---|---|---|---|
| RATE (g/ha) | 1000 | 500 | 250 | 125 | 64 | 500 | 250 | 125 | 64 | 1000 | 500 | 250 | 125 | 64 | 32 | 16 |
| Barnyardgrass | 75 | 45 | 25 | 0 | | 100 | 85 | 45 | 20 | 100 | 100 | 55 | 25 | 0 | 0 | 0 |
| Cocklebur | 0 | 0 | 0 | 0 | | 0 | 0 | 0 | 0 | 25 | 0 | 0 | 0 | 0 | 0 | 0 |
| Corn | 25 | 0 | 0 | 0 | | 0 | 0 | 0 | 0 | 40 | 20 | 0 | 0 | 0 | 0 | 0 |
| Corn (Perlite) | | | | | | | | | | | | | | | | |
| Crabgrass | 65 | 40 | 20 | 0 | | 100 | 100 | 65 | 20 | 100 | 100 | 85 | 40 | 0 | 0 | 0 |
| Fall panicum | 50 | 35 | 0 | 0 | | 100 | 80 | 35 | 0 | 100 | 100 | 65 | 35 | 0 | 0 | 0 |
| Giant foxtail | 20 | 0 | 0 | 0 | | 100 | 95 | 60 | 30 | 95 | 90 | 60 | 25 | 0 | 0 | 0 |
| Green foxtail | 45 | 25 | 0 | 0 | | 100 | 90 | 65 | 30 | 100 | 100 | 70 | 35 | 0 | 0 | 0 |
| Jimsonweed | 100 | 75 | 35 | 0 | | 25 | 0 | 0 | 0 | 100 | 100 | 70 | 35 | 0 | 0 | 0 |
| Johnsongrass | 55 | 40 | 20 | 0 | | 95 | 85 | 50 | 20 | 95 | 75 | 40 | 20 | 0 | 0 | 0 |
| Lambsquarters | 100 | 100 | 65 | 40 | | — | — | — | — | 100 | 100 | 90 | 45 | 0 | 0 | 0 |
| Morningglory | 40 | 0 | 0 | 0 | | 0 | 0 | 0 | 0 | 95 | 90 | 50 | 20 | 0 | 0 | 0 |
| Nutsedge | 0 | 0 | 0 | 0 | | 0 | 0 | 0 | 0 | 25 | 0 | 0 | 0 | 0 | 0 | 0 |
| Redroot pigweed | 100 | 100 | 70 | 40 | | 100 | 100 | 60 | 20 | 100 | 100 | 90 | 40 | 0 | 0 | 0 |
| Smartweed | 55 | 35 | 20 | 0 | | — | — | — | — | 100 | 95 | 65 | 30 | 0 | 0 | 0 |
| Sorghum | 20 | 0 | 0 | 0 | | 20 | 0 | 0 | 0 | 50 | 25 | 0 | 0 | 0 | 0 | 0 |
| Soybean | 40 | 0 | 0 | 0 | | 50 | 20 | 0 | 0 | 55 | 30 | 0 | 0 | 0 | 0 | 0 |
| Velvetleaf | 100 | 60 | 25 | 0 | | 40 | 25 | 0 | 0 | 100 | 90 | 50 | 20 | 0 | 0 | 0 |

PREEMERGENCE

| | Cmpd 23 | | | | | | | Cmpd 32 | | | | | |
|---|---|---|---|---|---|---|---|---|---|---|---|---|---|
| RATE (g/ha) | 1000 | 500 | 250 | 125 | 64 | 32 | 16 | 1000 | 500 | 250 | 125 | 64 | 32 |
| Barnyardgrass | 100 | 100 | 100 | 100 | 65 | 35 | 0 | 100 | 95 | 65 | 40 | 20 | 0 |
| Cocklebur | 20 | 0 | 0 | 0 | 0 | 0 | 0 | 0 | 0 | 0 | 0 | 0 | 0 |
| Corn | 65 | 50 | 30 | 0 | 0 | 0 | 0 | 65 | 45 | 20 | 0 | 0 | 0 |
| Corn (Perlite) | | | | | | | | | | | | | |
| Crabgrass | 100 | 100 | 100 | 100 | 100 | 75 | 25 | 100 | 100 | 90 | 60 | 30 | 0 |
| Fall panicum | 100 | 100 | 100 | 100 | 45 | 20 | 0 | 100 | 70 | 55 | 30 | 20 | 0 |
| Giant foxtail | 100 | 100 | 100 | 100 | 100 | 50 | 20 | 100 | 85 | 60 | 20 | 0 | 0 |
| Green foxtail | 100 | 100 | 100 | 100 | 90 | 35 | 0 | 100 | 90 | 70 | 40 | 25 | 0 |
| Jimsonweed | 100 | 100 | 100 | 100 | 75 | 30 | 0 | 100 | 85 | 35 | 20 | 0 | 0 |
| Johnsongrass | 100 | 100 | 90 | 70 | 50 | 20 | 0 | 95 | 90 | 65 | 35 | 25 | 0 |
| Lambsquarters | — | — | — | — | — | — | — | 100 | 100 | 100 | 100 | 95 | 55 |
| Morningglory | 100 | 100 | 85 | 40 | 0 | 0 | 0 | 100 | 90 | 60 | 35 | 0 | 0 |
| Nutsedge | 45 | 35 | 20 | 0 | 0 | 0 | 0 | 25 | 0 | 0 | 0 | 0 | 0 |
| Redroot pigweed | 100 | 100 | 100 | 100 | 100 | 90 | 40 | 100 | 100 | 100 | 100 | 100 | 60 |
| Smartweed | 100 | 100 | 95 | 75 | 60 | 25 | 0 | 80 | 65 | 50 | 45 | 35 | 25 |
| Sorghum | 75 | 60 | 30 | 0 | 0 | 0 | 0 | 60 | 35 | 20 | 0 | 0 | 0 |
| Soybean | 100 | 80 | 65 | 25 | 0 | 0 | 0 | 85 | 65 | 35 | 20 | 0 | 0 |
| Velvetleaf | 100 | 100 | 85 | 65 | 20 | 0 | 0 | 95 | 65 | 25 | 0 | 0 | 0 |

PREEMERGENCE

| | Cmpd 36 | | | | | Cmpd 50 | | | |
|---|---|---|---|---|---|---|---|---|---|
| RATE (g/ha) | 500 | 250 | 125 | 64 | 32 | 250 | 125 | 64 | 32 |

TABLE G-continued

| | | | | | | | | | |
|---|---|---|---|---|---|---|---|---|---|
| Barnyardgrass | 100 | 100 | 70 | 30 | 0 | 100 | 85 | 75 | 30 |
| Cocklebur | 0 | 0 | 0 | 0 | 0 | 0 | 0 | 0 | 0 |
| Corn | 65 | 40 | 30 | 0 | 0 | 45 | 25 | 0 | 0 |
| Corn (Perlite) | | | | | | | | | |
| Crabgrass | 100 | 100 | 95 | 65 | 35 | 100 | 100 | 80 | 35 |
| Fall panicum | 100 | 100 | 40 | 20 | 0 | 95 | 70 | 50 | 0 |
| Giant foxtail | 100 | 85 | 35 | 0 | 0 | 100 | 80 | 55 | 20 |
| Green foxtail | 100 | 100 | 65 | 30 | 0 | 100 | 95 | 65 | 35 |
| Jimsonweed | 100 | 90 | 35 | 0 | 0 | 65 | 40 | 0 | 0 |
| Johnsongrass | 80 | 75 | 40 | 0 | 0 | 85 | 80 | 50 | 20 |
| Lambsquarters | 100 | 100 | 100 | 70 | 40 | 100 | 90 | 85 | 60 |
| Morningglory | 100 | 40 | 30 | 0 | 0 | 65 | 45 | 20 | 0 |
| Nutsedge | 40 | 20 | 0 | 0 | 0 | 20 | 0 | 0 | 0 |
| Redroot pigweed | 100 | 100 | 100 | 90 | 60 | 100 | 100 | 100 | 70 |
| Smartweed | 60 | 55 | 40 | 20 | 0 | 60 | 40 | 25 | 0 |
| Sorghum | 60 | 40 | 0 | 0 | 0 | 55 | 35 | 0 | 0 |
| Soybean | 65 | 35 | 25 | 0 | 0 | 40 | 20 | 0 | 0 |
| Velvetleaf | 90 | 45 | 25 | 0 | 0 | 60 | 40 | 0 | 0 |

TEST H

Seeds of blackgrass (*Alopercurus myosuroides*), catchweed bedstraw (*Galium aparine*) , chickweed (*Stellaria media*), knotweed (*Polygonum aviculare*), lambsquarters (*Chenopodium album*(, Persian speedwell (*Veronica persica*), scentless chamomile (*Viola arvensis*), sugar beet (*Beta vulgaris*), viola (*Viola arvensis*), wheat (*Triticum aestivum*), wild buckwheat (*Polygonum convolvulus*), and wild oat (*Avena fatua*), were planted and treated preemergence with test chemicals dissolved in a non-Phytotoxic solvent. These crop and weed species were also treated with postemergence applications of test chemicals. Plants ranged in height from two to twenty cm (two to three leaf stage) for postemergence treatments. Treated plants and controls were maintained in a greenhouse for approximately 24 days, after which all species were compared to controls and visually evaluated. Application rates for each test chemical are shown in Table H. Plant response ratings, summarized in Table H, are based on a scale of 0 to 100 where 0 is no effect and 100 is complete control. A dash (-) response means no test result.

TABLE H

POSTEMERGENCE

| | Cmpd 28 | | | | | Cmpd 36 | | | | | Cmpd 71 | | | | |
|---|---|---|---|---|---|---|---|---|---|---|---|---|---|---|---|
| RATE (g/ha) | 1000 | 750 | 500 | 250 | 125 | 2000 | 1500 | 1000 | 500 | 250 | 250 | 125 | 64 | 32 | 16 |
| Blackgrass | | 20 | 20 | 0 | 0 | 100 | 100 | 100 | 80 | 20 | | | | 30 | 0 |
| Catchweed bedstraw | | 30 | 30 | 0 | 0 | 100 | 100 | 100 | 100 | 100 | | | | 0 | 0 |
| Chickweed | | 0 | 0 | 0 | 0 | 100 | 90 | 80 | 80 | 80 | | | | 30 | 20 |
| Knotweed | | 100 | 100 | 100 | 70 | — | — | — | — | — | | | | — | — |
| Lambsquarters | | 90 | 90 | 50 | 50 | 100 | 100 | 100 | 100 | 100 | | | | 60 | 50 |
| Persian speedwell | | 100 | 100 | 100 | 70 | 100 | 100 | 100 | 80 | 80 | | | | 80 | 60 |
| Scentless chamomille | | 30 | 0 | 0 | 0 | 80 | 80 | 70 | 50 | 30 | | | | 0 | 0 |
| Sugar beet | | 20 | 20 | 0 | 0 | 100 | 100 | 100 | 90 | 80 | | | | 50 | 35 |
| Viola | | 80 | 50 | 50 | 0 | 100 | 100 | 100 | 100 | 100 | | | | 80 | 50 |
| Wheat | | 0 | 0 | 0 | 0 | 10 | 10 | 10 | 10 | 10 | | | | 30 | 0 |
| Wild buckwheat | | 50 | 50 | 20 | 0 | 100 | 100 | 100 | 90 | 80 | | | | 20 | 0 |
| Wild oat | | 0 | 0 | 0 | 0 | 50 | 50 | 50 | 30 | 30 | | | | 0 | 0 |

PREEMERGENCE

| | Cmpd 28 | | | | | Cmpd 36 | | | | | Cmpd 68 | | | | | |
|---|---|---|---|---|---|---|---|---|---|---|---|---|---|---|---|---|
| RATE (g/ha) | 1000 | 750 | 500 | 250 | 125 | 2000 | 1500 | 1000 | 500 | 250 | 125 | 64 | 32 | 16 | 8 | 4 |
| Blackgrass | 50 | 50 | 30 | 30 | 0 | | | | 100 | 80 | 40 | 20 | 20 | 20 | 0 | 0 |
| Catchweed bedstraw | 90 | 70 | 70 | 30 | 0 | | | | 95 | 70 | 0 | 0 | 0 | 0 | 0 | 0 |
| Chickweed | 20 | 20 | 0 | 0 | 0 | | | | 100 | 100 | 100 | 60 | 50 | 0 | 0 | 0 |
| Knotweed | 100 | 100 | 100 | 30 | 0 | | | | — | — | — | — | — | — | — | — |
| Lambsquarters | 100 | 80 | 80 | 80 | 0 | | | | 100 | 100 | 100 | 100 | 90 | 60 | 50 | 30 |
| Persian speedwell | 90 | 80 | 50 | 50 | 0 | | | | 100 | 100 | 100 | 90 | 30 | 0 | 0 | 0 |
| Scentless chamomille | 80 | 70 | 70 | 70 | 30 | | | | — | — | — | — | — | — | — | — |
| Sugar beet | 0 | 0 | 0 | 0 | 0 | | | | 100 | 100 | 100 | 50 | 50 | 40 | 20 | 10 |
| Viola | 90 | 50 | 30 | 20 | 0 | | | | 100 | 100 | 30 | 20 | 20 | 0 | 0 | 0 |
| Wheat | 20 | 0 | 0 | 0 | 0 | | | | 30 | 20 | 30 | 20 | 20 | 10 | 0 | 0 |
| Wild buckwheat | 80 | 80 | 40 | 40 | 20 | | | | 100 | 100 | 90 | 50 | 30 | 20 | 0 | 0 |
| Wild oat | 30 | 30 | 30 | 30 | 0 | | | | 70 | 50 | 0 | 0 | 0 | 0 | 0 | 0 |

PREEMERGENCE

| | Cmpd 71 | | | | |
|---|---|---|---|---|---|
| RATE (g/ha) | 250 | 125 | 64 | 32 | 16 |
| Blackgrass | 80 | 80 | 75 | 0 | 0 |
| Catchweed bedstraw | 0 | 0 | 0 | 0 | 0 |
| Chickweed | 100 | 90 | 0 | 0 | 0 |
| Knotweed | — | — | — | — | — |
| Lambsquarters | 100 | 70 | 70 | 50 | 30 |
| Persian speedwell | 50 | 40 | 30 | 20 | 0 |
| Scentless chamomille | — | — | — | 0 | 0 |
| Sugar beet | 100 | 90 | 60 | 50 | 30 |
| Viola | 90 | 60 | 50 | 20 | 20 |

TABLE H-continued

| | | | | | |
|---|---|---|---|---|---|
| Wheat | 30 | 30 | 20 | 0 | 0 |
| Wild buckwheat | 100 | 70 | 30 | 20 | 0 |
| Wild oat | 20 | 20 | 0 | 0 | 0 |

TEST I

Seeds of alfalfa (*Medicago sativa*), barley (*Hordeum vulgare*), bluegrass (*Poa pratensis*), corn (*Zea mays*), cotton (*Gossypium hirsutum*), flax (*Linum usitatissimum*), oat (*Avena sativa*), pea (sativum), peanut (*Arachis hypogaea*), rape (*Brassica napus*), rice (*Oryza sativa*), sorghum (*Sorghum bicolor*), soybean (*Glycine max*), sugar beet (*Beta vulgaris*), sunflower (*Helianthus annuus*), tomato (*Lycopersicon esculentum*), and wheat (*Triticum aeastivum*), were planted and treated preemergence with a test chemical dissolved in a non-phytotoxic solvent. These crop species were also treated with postemergence applications of the test chemical. Plants ranged in height from four to twenty cm (two to three leaf stage) when post-emergence applications were applied. Treated plants and controls were grown under greenhouse conditions for approximately twenty-four days, after which all plants treated with the test chemical were compared to untreated controls and visually evaluated for injury response. Application rates for the test chemical are shown in Table I. Plant response ratings, summarized in Table I, are from 0 to 100 where 0 is no injury and 100 is complete control. A dash (-) response means no test result.

TABLE I

| POSTEMERGENCE | Cmpd 15 | | | | | | Cmpd 23 | | | | |
|---|---|---|---|---|---|---|---|---|---|---|---|
| RATE (g/ha) | 1000 | 500 | 250 | 125 | 64 | 32 | 2000 | 1000 | 500 | 250 | 125 |
| Alfalfa | 100 | 95 | 60 | 30 | 0 | | | 95 | 70 | 50 | 25 |
| Barley | 80 | 35 | 20 | 0 | 0 | | | 80 | 40 | 25 | 0 |
| Bluegrass | 90 | 75 | 30 | 0 | 0 | | | 95 | 60 | 35 | 0 |
| Corn | 75 | 40 | 20 | 0 | 0 | | | 90 | 65 | 40 | 20 |
| Cotton | 100 | 85 | 60 | 30 | 0 | | | 60 | 40 | 20 | 0 |
| Flax | 70 | 50 | 40 | 20 | 0 | | | — | — | — | — |
| Oat | 80 | 40 | 20 | 0 | 0 | | | 95 | 60 | 30 | 0 |
| Pea | 100 | 100 | 80 | 70 | 35 | | | 80 | 55 | 35 | 20 |
| Peanut | 100 | 85 | 70 | 40 | 20 | | | 100 | 70 | 40 | 20 |
| Rape | 100 | 95 | 70 | 50 | 25 | | | 100 | 90 | 55 | 20 |
| Rice | 95 | 70 | 20 | 0 | 0 | | | 85 | 65 | 40 | 0 |
| Sorghum | 75 | 40 | 20 | 0 | 0 | | | 85 | 65 | 40 | 15 |
| Soybean | 95 | 85 | 65 | 40 | 25 | | | 95 | 75 | 55 | 25 |
| Sugar beet | 100 | 100 | 75 | 60 | 35 | | | 100 | 100 | 65 | 35 |
| Sunflower | 100 | 90 | 75 | 50 | 35 | | | — | — | — | — |
| Tomato | 100 | 100 | 80 | 65 | 25 | | | 100 | 85 | 60 | 20 |
| Wheat | 80 | 40 | 25 | 0 | 0 | | | 85 | 50 | 25 | 0 |

| PREEMERGENCE | Cmpd 15 | | | | | | Cmpd 23 | | | | |
|---|---|---|---|---|---|---|---|---|---|---|---|
| RATE (g/ha) | 1000 | 500 | 250 | 125 | 64 | 32 | 2000 | 1000 | 500 | 250 | 125 |
| Alfalfa | 100 | 100 | 70 | 45 | 25 | 0 | 100 | 100 | 100 | 70 | 35 |
| Barley | 85 | 40 | 0 | 0 | 0 | 0 | 100 | 100 | 90 | 40 | 20 |
| Bluegrass | 100 | 100 | 80 | 45 | 25 | 0 | 100 | 100 | 100 | 95 | 65 |
| Corn | 90 | 65 | 30 | 0 | 0 | 0 | 100 | 100 | 95 | 65 | 30 |
| Cotton | 35 | 0 | 0 | 0 | 0 | 0 | 30 | 20 | 0 | 0 | 0 |
| Flax | 100 | 85 | 50 | 35 | 0 | 0 | 100 | 100 | 100 | 80 | 40 |
| Oat | 95 | 85 | 60 | 40 | 25 | 0 | 100 | 100 | 95 | 45 | 25 |
| Pea | 100 | 70 | 35 | 0 | 0 | 0 | 100 | 100 | 75 | 30 | 0 |
| Peanut | 85 | 55 | 30 | 0 | 0 | 0 | 95 | 65 | 50 | 20 | 0 |
| Rape | 100 | 100 | 100 | 75 | 40 | 20 | 100 | 100 | 100 | 100 | 100 |
| Rice | 60 | 30 | 0 | 0 | 0 | 0 | 100 | 100 | 90 | 60 | 35 |
| Sorghum | 100 | 95 | 80 | 40 | 20 | 0 | 100 | 100 | 95 | 65 | 35 |
| Soybean | 95 | 70 | 35 | 0 | 0 | 0 | 100 | 95 | 85 | 50 | 25 |
| Sugar beet | 100 | 100 | 100 | 75 | 45 | 20 | 100 | 100 | 100 | 100 | 100 |
| Sunflower | 80 | 50 | 30 | 0 | 0 | 0 | 95 | 60 | 50 | 20 | 0 |
| Tomato | 100 | 100 | 65 | 25 | 0 | 0 | 100 | 100 | 100 | 100 | 70 |
| Wheat | 85 | 40 | 0 | 0 | 0 | 0 | 100 | 100 | 85 | 40 | 25 |

What is claimed is:

1. A compound of the formula

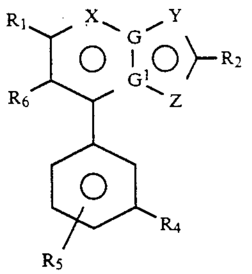

I wherein

G is C;

$G^1$ is N;

$R_1$ is $C_1$–$C_4$ alkyl, $C_1$–$C_4$ haloalkyl, $C_2$–$C_4$ alkoxyalkyl, $C_2$–$C_4$ alkenyl, $C_2$–$C_4$ alkynyl, $C_1$–$C_4$ alkoxy, $C_1$–$C_4$ alkylthio, halogen, $C_2$–$C_4$ alkylcarbonyl, $C_1$–$C_4$ alkylamino, $C_2$–$C_4$ dialkylamino or $C_2$–$C_4$ alkylthioalkyl;

$R_2$ is halogen, $NO_2$, $OR_3$, $S(O)_nR_3$, $OSO_2R_3$, $C_1$–$C_4$ haloalkyl, $C_3$–$C_4$ halocycloalkyl, $C_3$–$C_4$ haloalkynyl or $C_2$–$C_4$ haloalkenyl;

$R_3$ is $C_1$–$C_4$ alkyl, $C_1$–$C_4$ haloalkyl, $C_2$–$C_4$ alkenyl, $C_2$–$C_4$ haloalkenyl, $C_3$–$C_4$ alkynyl, $C_3$–$C_4$ haloalkynyl, or $C_3C$–$_4$ halocycloalkyl;

$R_4$ is H, halogen, $C_1$–$C_3$ alkoxy, $C_1$–$C_3$ alkyl or $CF_3$;

$R_5$ is H, halogen, $C_1$–$C_4$ alkyl, $C_1$–$C_4$ haloalkyl, $C_2$–$C_4$ alkoxyalkyl, $C_2$–$C_4$ alkenyl, $C_2$–$C_4$ alkynyl, $NO_2$, $OR_3$, $S(O)_nR_3$, $OSO_2R_3$, phenyl, phenoxy, $C_2$–$C_4$ alkoxycarbonyl, $C_2$–$C_4$ alkylcarbonyl, CN, $NHSO_2CF_3$, $C_2$–$C_4$ haloalkenyl, $C_3$–$C_4$ haloalkynyl, $C_2$–$C_4$ dialkylamino or $C_3$–$C_4$ halocycloalkyl;

n is 0, 1 or 2;

$R_6$ is H or F;

X, Y and Z are N; and $R_7$ is H, CN, halogen, $NO_2$, $CO_2R_3$, $C_1$–$C_3$ alkyl, $C_1$–$C_3$ haloalkyl or $CONH_2$.

2. A compound of claim 1 wherein

Formula I is Ia;

X is N;

Y is N; and

Z is N.

3. A compound of claim 2 wherein $R_6$ is H; and $R_1$ is $C_1$–$C_3$ alkyl, $SCH_3$, $NHCH_3$, $CH_2OCH_3$ or $CH_2SCH_3$.

4. Compounds of claim 3 wherein $R_2$ is $CF_3$, $SCF_3$, $SCF_2H$, $OCF_3$,$OCH_2CHF_2$, $OCH_2CF_3$, $OCF_2H$, $CF_2CF_3$, $CF_2Cl$, $CHF_2$, $CH{=}CF_2$ or 2, 2-difluorocyclopropane;

5. Compounds of claim 4 wherein $R_3$ is $CH_2CH_2F$, $CH_2CF_3$, $CH(CH_3)CF_3$, $CH_2CH_2CF_3$, $CH_2CHF_2$, $CF_3$ or $CF_2H$; and $R_4$ is H.

6. Compounds of claim 5 wherein $R_5$ is H, halogen, $OCH_3$, $OCF_2H$, $OCH_2CF_3$, $SCF_3$, $C_1$–$C_3$ alkyl, $OCF_3$, $OCH_2CHF_2$, $OCH_2CF_3$, $OCH_2CH_2F$, $SCHF_2$, $CF_3$, $CHF_2$, $CF_2Cl$, $CH_2CF_3$, $CH_2F$, $CCl_3$, $CH_2Cl$ or CN and $R_5$ is in the meta position.

7. Compounds of claim 6 wherein $R_1$ is $C_1$–$C_3$ alkyl.

8. An agriculturally suitable composition for controlling the growth of undesired vegetation comprising an effective amount of a compound of any one of claim 1, 2 and 3 through 7 and at least one of the following: surfactant, solid diluent or liquid diluent.

9. A method for controlling the growth of undesired vegetation which comprises applying to the locus to be protected an effective amount of a compound of any one of claim 1, 2 and 3 through 7.

10. The method of claim 9 wherein the undesired vegetation is present in wheat or barley.

* * * * *